United States Patent
Chu et al.

(10) Patent No.: US 11,312,769 B2
(45) Date of Patent: Apr. 26, 2022

(54) ANTI-TMEFF1 ANTIBODIES AND ANTIBODY DRUG CONJUGATES

(71) Applicant: Bluefin BioMedicine, Inc., Beverly, MA (US)

(72) Inventors: Isabel Milan Chu, Lexington, MA (US); Scott Michael Lonning, Westford, MA (US); Nels Eric Pederson, Mansfield, MA (US); Klarisa Rikova, Reading, MA (US); Aleksandr Tkachev, Cambridge, MA (US); Jason G. Beaudet, Beverly, MA (US)

(73) Assignee: Bluefin BioMedicine, Inc., Beverly, MA (US)

( * ) Notice: Subject to any disclaimer, the term of this patent is extended or adjusted under 35 U.S.C. 154(b) by 97 days.

(21) Appl. No.: 16/495,633

(22) PCT Filed: Mar. 22, 2018

(86) PCT No.: PCT/US2018/023795
§ 371 (c)(1),
(2) Date: Sep. 19, 2019

(87) PCT Pub. No.: WO2018/175740
PCT Pub. Date: Sep. 27, 2018

(65) Prior Publication Data
US 2020/0109194 A1    Apr. 9, 2020

Related U.S. Application Data

(60) Provisional application No. 62/474,873, filed on Mar. 22, 2017.

(51) Int. Cl.
| | | |
|---|---|---|
| *C07K 16/28* | (2006.01) | |
| *A61K 39/395* | (2006.01) | |
| *A61P 35/00* | (2006.01) | |
| *A61K 47/68* | (2017.01) | |
| *A61K 33/243* | (2019.01) | |
| *A61K 31/454* | (2006.01) | |
| *A61K 31/7048* | (2006.01) | |
| *A61K 45/06* | (2006.01) | |
| *C12N 15/09* | (2006.01) | |
| *C07K 14/705* | (2006.01) | |
| *A61K 39/00* | (2006.01) | |

(52) U.S. Cl.
CPC ............ *C07K 16/28* (2013.01); *A61K 31/454* (2013.01); *A61K 31/7048* (2013.01); *A61K 33/243* (2019.01); *A61K 39/3955* (2013.01); *A61K 45/06* (2013.01); *A61K 47/6803* (2017.08); *A61K 47/6811* (2017.08); *A61K 47/6849* (2017.08); *A61P 35/00* (2018.01); *C12N 15/09* (2013.01); *A61K 2039/505* (2013.01); *C07K 14/705* (2013.01); *C07K 2317/21* (2013.01); *C07K 2317/33* (2013.01); *C07K 2317/565* (2013.01); *C07K 2317/77* (2013.01); *C07K 2317/92* (2013.01)

(58) Field of Classification Search
CPC ...... C07K 16/28; A61K 39/3955; A61P 35/00
See application file for complete search history.

(56) References Cited

U.S. PATENT DOCUMENTS

| | | |
|---|---|---|
| 2004/0018198 A1 | 1/2004 | Gudas et al. |
| 2006/0286112 A1 | 12/2006 | Kellermann et al. |
| 2006/0292074 A1 | 12/2006 | Heitner et al. |
| 2016/0024195 A1 | 1/2016 | Economides et al. |

FOREIGN PATENT DOCUMENTS

WO    2004/064612 A2    8/2004

OTHER PUBLICATIONS

Benjamini et al, 1991. Immunology: A Short Course, 2nd edition, p. 40 only).*
Ferrara et al (2015. mAbs. 7(1): 32-41).*
Noelker et al., Differentially expressed gene profile in the 6-hydroxy-dopamine-induced cell culture model of Parkinson's disease Neurosci Lett. Jan. 17, 2012;507(1):10-5.
Penning et al., Induction of apoptosis in hematopoietic cells with an antibody against tomoregulin-1. Anticancer Res. Jan.-Feb. 2006;26(1A):339-46.
Extended European Search Report for Application No. 18771883.8, dated Dec. 11, 2020, 8 pages.
International Search Report and Written Opinion for Application No. PCT/US2018/023795, dated Jul. 31, 2018, 13 pages.
International Preliminary Report on Patentability for Application No. PCT/US2018/023795, dated Oct. 3, 2019, 9 pages.

* cited by examiner

*Primary Examiner* — Zachary C Howard
(74) *Attorney, Agent, or Firm* — McCarter & English, LLP; Marcie B. Clarke

(57) ABSTRACT

Disclosed herein are transmembrane protein with EGF-like and two-follistatin-like domains 1 (TMEFF1) antibodies and antibody drug conjugates (ADCs), including compositions and methods of using said antibodies and ADCs.

14 Claims, 16 Drawing Sheets
Specification includes a Sequence Listing.

Internalization of Anti-TMEFF1 antibodies in 293-hTMEFF1 cells.

- hIgG-HBV-MMAE (3.46)
- 24F10-MMAE (3.30)
- 30C10-MMAE (4.81)
- 36H6-MMAE (4.93)
- M1F1-MMAE (5.20)
- M3-MMAE (5.20)
- 31B7-MMAE (4.26)
- 34B7-MMAE (4.79)

- ─○─ hIgG-HBV-MMAE (3.46)
- ─□─ 24F10-MMAE (3.30)
- ─△─ 30C10-MMAE (4.81)
- ─▼─ 36H6-MMAE (4.93)
- ─▽─ M1F1-MMAE (5.20)
- ─✳─ M3-MMAE (5.20)
- ─☆─ 31B7-MMAE (4.26)
- ─+─ 34B7-MMAE (4.79)

- hIgG-HBV-MMAE (3.46)
- 24F10-MMAE (3.30)
- 30C10-MMAE (4.81)
- 36H6-MMAE (4.93)
- M1F1-MMAE (5.20)
- M3-MMAE (5.20)
- 31B7-MMAE (4.26)
- 34B7-MMAE (4.79)

1

ANTI-TMEFF1 ANTIBODIES AND ANTIBODY DRUG CONJUGATES

RELATED APPLICATIONS

The instant application is a 35 U.S.C. § 371 national stage filing of International Application No. PCT/US2018/023795, filed on Mar. 22, 2018, which in turn claims priority to U.S. Provisional Application No. 62/474,873, filed on Mar. 22, 2017, the entire contents of each of which are expressly incorporated by reference herein in their entirety.

SEQUENCE LISTING

The instant application contains a Sequence Listing which has been submitted electronically in ASCII format and is hereby incorporated by reference in its entirety. Said ASCII copy, created on Mar. 21, 2018, is named 127913-00520_SL.txt and is 147,493 bytes in size.

BACKGROUND

TMEFF1 is also known as "transmembrane protein with EGF-like and two-follistatin-like domains 1," "tomoregulin-1," "C9orf2," "H7365," "CT120.1," and "cancer/testis antigen family 120, member 1." TMEFF1 is a type I transmembrane glycoprotein belonging to the tomoregulin family. TMEFF1 contains two follistatin domains and an epidermal growth factor (EGF) domain in its extracellular domain, which suggest a potential role for TMEFF1 in growth factor signaling (Gery et al. (2003) *Oncogene* 22:2723-2727). TMEFF1 also contains a transmembrane domain and a short cytoplasmic tail. TMEFF1 selectively regulates nodal but not activin signaling through direct binding to the nodal co-receptor, Cripto, and regulates BMP activities, during neural patterning. Thus, TMEFF1 has been identified as a regulator of nodal and BMP signaling during early vertebrate embryogenesis (Chang et al. (2003) *Dev. Biol. March* 1; 255(1):1-11).

TMEFF1 has been found to be predominantly expressed in the brain, and also in the heart, placenta and skeletal muscle. Weaker levels of expression were found in the liver, kidney and pancreas. In addition, TMEFF1 was found to be expressed in certain cancer cell lines from various tissues, including brain cancer, prostate cancer, breast cancer, small cell lung cancer, nonsmall lung cancer, pancreatic cancer, hepatoma, and leukemia cell lines (Gery et al. (2003) *Oncogene* 22:2723-2727).

Antibody drug conjugates (ADC) represent a new class of therapeutics comprising an antibody conjugated to a cytotoxic drug via a chemical linker. The therapeutic concept of ADCs is to combine binding capabilities of an antibody with a drug, where the antibody is used to deliver the drug to a tumor cell by means of binding to a target surface antigen.

Accordingly, there remains a need in the art for anti-TMEFF1 antibodies and ADCs that can be used for therapeutic purposes in the treatment of cancer.

SUMMARY

In certain aspects, the present invention provides for anti-TMEFF1 antibodies and antibody drug conjugates (ADCs), and antigen binding portions thereof.

In certain embodiments of the invention, the antibodies, ADCs, or antigen binding portions thereof, bind to TMEFF1 (SEQ ID NO: 229) or the extracellular domain of TMEFF1. In one embodiment, the antibodies, ADCs, or antigen binding portions thereof, of the invention, bind to TMEFF1 with a $K_d$ of about 2,000 nM or less, about 1,000 nM or less, about 500 nM or less, about 200 nM or less, about 100 nM or less, about 75 nM or less, about 50 nM or less, about 43 nM or less, about 25 nM or less, about 20 nM or less, about 19 nM or less, about 18 nM or less, about 17 nM or less, about 16 nM or less, about 15 nM or less, about 14 nM or less, about 13 nM or less, about 12 nM or less, about 11 nM or less, about 10 nM or less, about 9 nM or less, about 8 nM or less, about 7 nM or less, about 6 nM or less, about 5 nM or less, about 4 nM or less, about 3 nM or less, about 2 nM or less, about 1 nM or less, about 0.5 nM or less, about 0.3 nM or less, about 0.1 nM or less, or about 0.01 nM or less, or about 0.001 nM or less.

In one embodiment, the anti-TMEFF1 antibodies, ADCs, or antigen binding portions thereof, bind to the follistatin 1 (FS1) domain of TMEFF1. In another embodiment, the anti-TMEFF1 antibodies, ADCs, or antigen binding portions thereof, bind to the follistatin 2 (FS2) domain of TMEFF1. In still another embodiment, the anti-TMEFF1 antibodies, ADCs, or antigen binding portions thereof, do not bind to the FS1 domain or the FS2 domain of TMEFF1.

In some embodiments, the antibodies, or antigen binding portions thereof, comprise a heavy chain variable region comprising a CDR3 having the amino acid sequence of SEQ ID NO: 4 and a light chain variable region comprising a CDR3 having the amino acid sequence of SEQ ID NO: 8; a heavy chain variable region comprising a CDR3 having the amino acid sequence of SEQ ID NO: 12 and a light chain variable region comprising a CDR3 having the amino acid sequence of SEQ ID NO: 16; a heavy chain variable region comprising a CDR3 having the amino acid sequence of SEQ ID NO: 20 and a light chain variable region comprising a CDR3 having the amino acid sequence of SEQ ID NO: 24; a heavy chain variable region comprising a CDR3 having the amino acid sequence of SEQ ID NO: 28 and a light chain variable region comprising a CDR3 having the amino acid sequence of SEQ ID NO: 32; a heavy chain variable region comprising a CDR3 having the amino acid sequence of SEQ ID NO: 35 and a light chain variable region comprising a CDR3 having the amino acid sequence of SEQ ID NO: 37; a heavy chain variable region comprising a CDR3 having the amino acid sequence of SEQ ID NO: 40 and a light chain variable region comprising a CDR3 having the amino acid sequence of SEQ ID NO: 42; a heavy chain variable region comprising a CDR3 having the amino acid sequence of SEQ ID NO: 46 and a light chain variable region comprising a CDR3 having the amino acid sequence of SEQ ID NO: 48; a heavy chain variable region comprising a CDR3 having the amino acid sequence of SEQ ID NO: 52 and a light chain variable region comprising a CDR3 having the amino acid sequence of SEQ ID NO: 55; a heavy chain variable region comprising a CDR3 having the amino acid sequence of SEQ ID NO: 59 and a light chain variable region comprising a CDR3 having the amino acid sequence of SEQ ID NO: 24; a heavy chain variable region comprising a CDR3 having the amino acid sequence of SEQ ID NO: 69 and a light chain variable region comprising a CDR3 having the amino acid sequence of SEQ ID NO: 8; a heavy chain variable region comprising a CDR3 having the amino acid sequence of SEQ ID NO: 81 and a light chain variable region comprising a CDR3 having the amino acid sequence of SEQ ID NO: 84; a heavy chain variable region comprising a CDR3 having the amino acid sequence of SEQ ID NO: 87 and a light chain variable region comprising a CDR3 having the amino acid sequence of SEQ ID NO: 8; a heavy chain variable region comprising a CDR3 having the amino acid sequence of SEQ ID NO: 92 and a light chain variable region comprising a CDR3 having the amino acid sequence of SEQ ID NO: 95; a heavy chain variable region comprising a CDR3 having the amino acid sequence of SEQ ID NO: 98 and a light chain variable region comprising a CDR3 having the amino acid sequence of SEQ ID NO: 95; a heavy chain variable region comprising a CDR3 having the amino acid sequence of SEQ ID NO: 105 and a light chain variable region comprising a CDR3 having the amino acid sequence of SEQ ID NO: 95; a heavy chain variable region comprising a CDR3 having the amino acid sequence of SEQ ID NO: 109 and a light chain variable region comprising a CDR3 having the amino acid sequence of SEQ ID NO: 113; a heavy chain variable region comprising a CDR3 having the amino acid sequence of SEQ ID NO: 74 and a light chain variable region comprising a CDR3 having the amino acid sequence of SEQ ID NO: 77; a heavy chain variable region comprising a CDR3 having the amino acid sequence of SEQ ID NO: 127 and a light chain variable region comprising a CDR3 having the amino acid sequence of SEQ ID NO: 42; a heavy chain variable region comprising a CDR3 having the amino acid sequence of SEQ ID NO: 132 and a light chain variable region comprising a CDR3 having the amino acid sequence of SEQ ID NO: 16; a heavy chain variable region comprising a CDR3 having the amino acid sequence of SEQ ID NO: 137 and a light chain variable region comprising a CDR3 having the amino acid sequence of SEQ ID NO: 140; a heavy chain variable region comprising a CDR3 having the amino acid sequence of SEQ ID NO: 121 and a light chain variable region comprising a CDR3 having the amino acid sequence of SEQ ID NO: 123; a heavy chain variable region comprising a CDR3 having the amino acid sequence of SEQ ID NO: 132 and a light chain variable region comprising a CDR3 having the amino acid sequence of SEQ ID NO: 16; a heavy chain variable region comprising a CDR3 having the amino acid sequence of SEQ ID NO: 59 and a light chain variable region comprising a CDR3 having the amino acid sequence of SEQ ID NO: 150; a heavy chain variable region comprising a CDR3 having the amino acid sequence of SEQ ID NO: 153 and a light chain variable region comprising a CDR3 having the amino acid sequence of SEQ ID NO: 156; a heavy chain variable region comprising a CDR3 having the amino acid sequence of SEQ ID NO: 20 and a light chain variable region comprising a CDR3 having the amino acid sequence of SEQ ID NO: 24; or a heavy chain variable region comprising a CDR3 having the amino acid sequence of SEQ ID NO: 162 and a light chain variable region comprising a CDR3 having the amino acid sequence of SEQ ID NO: 164.

In other embodiments, the antibodies, or antigen binding portions thereof, comprise a heavy chain variable region comprising a CDR2 having the amino acid sequence of SEQ ID NO: 3 and a light chain variable region comprising a CDR2 having the amino acid sequence of SEQ ID NO: 7; a heavy chain variable region comprising a CDR2 having the amino acid sequence of SEQ ID NO: 11 and a light chain variable region comprising a CDR2 having the amino acid sequence of SEQ ID NO: 15; a heavy chain variable region comprising a CDR2 having the amino acid sequence of SEQ ID NO: 19 and a light chain variable region comprising a CDR2 having the amino acid sequence of SEQ ID NO: 23; a heavy chain variable region comprising a CDR2 having the amino acid sequence of SEQ ID NO: 27 and a light chain variable region comprising a CDR2 having the amino acid sequence of SEQ ID NO: 31; a heavy chain variable region comprising a CDR2 having the amino acid sequence of SEQ ID NO: 34 and a light chain variable region comprising a CDR2 having the amino acid sequence of SEQ ID NO: 15; a heavy chain variable region comprising a CDR2 having the amino acid sequence of SEQ ID NO: 39 and a light chain variable region comprising a CDR2 having the amino acid sequence of SEQ ID NO: 15; a heavy chain variable region comprising a CDR2 having the amino acid sequence of SEQ ID NO: 45 and a light chain variable region comprising a CDR2 having the amino acid sequence of SEQ ID NO: 7; a heavy chain variable region comprising a CDR2 having the amino acid sequence of SEQ ID NO: 51 and a light chain variable region comprising a CDR2 having the amino acid sequence of SEQ ID NO: 7; a heavy chain variable region comprising a CDR2 having the amino acid sequence of SEQ ID NO: 58 and a light chain variable region comprising a CDR2 having the amino acid sequence of SEQ ID NO: 23; a heavy chain variable region comprising a CDR2 having the amino acid sequence of SEQ ID NO: 63 and a light chain variable region comprising a CDR2 having the amino acid sequence of SEQ ID NO: 23; a heavy chain variable region comprising a CDR2 having the amino acid sequence of SEQ ID NO: 68 and a light chain variable region comprising a CDR2 having the amino acid sequence of SEQ ID NO: 7; a heavy chain variable region comprising a CDR2 having the amino acid sequence of SEQ ID NO: 11 and a light chain variable region comprising a CDR2 having the amino acid sequence of SEQ ID NO: 7; a heavy chain variable region comprising a CDR2 having the amino acid sequence of SEQ ID NO: 80 and a light chain variable region comprising a CDR2 having the amino acid sequence of SEQ ID NO: 7; a heavy chain variable region comprising a CDR2 having the amino acid sequence of SEQ ID NO: 86 and a light chain variable region comprising a CDR2 having the amino acid sequence of SEQ ID NO: 7; a heavy chain variable region comprising a CDR2 having the amino acid sequence of SEQ ID NO: 91 and a light chain variable region comprising a CDR2 having the amino acid sequence of SEQ ID NO: 7; a heavy chain variable region comprising a CDR2 having the amino acid sequence of SEQ ID NO: 97 and a light chain variable region comprising a CDR2 having the amino acid sequence of SEQ ID NO: 7; a heavy chain variable region comprising a CDR2 having the amino acid sequence of SEQ ID NO: 100 and a light chain variable region comprising a CDR2 having the amino acid sequence of SEQ ID NO: 102; a heavy chain variable region comprising a CDR2 having the amino acid sequence of SEQ ID NO: 104 and a light chain variable region comprising a CDR2 having the amino acid sequence of SEQ ID NO: 7; a heavy chain variable region comprising a CDR2 having the amino acid sequence of SEQ ID NO: 108 and a light chain variable region comprising a CDR2 having the amino acid sequence of SEQ ID NO: 112; a heavy chain variable region comprising a CDR2 having the amino acid sequence of SEQ ID NO: 73 and a light chain variable region comprising a CDR2 having the amino acid sequence of SEQ ID NO: 112; a heavy chain variable region comprising a CDR2 having the amino acid sequence of SEQ ID NO: 126 and a light chain variable region comprising a CDR2 having the amino acid sequence of SEQ ID NO: 15; a heavy chain variable region comprising a CDR2 having the amino acid sequence of SEQ ID NO: 131 and a light chain variable region comprising a CDR2 having the amino acid sequence of SEQ ID NO: 15; a heavy chain variable region comprising a CDR2 having the amino acid sequence of SEQ ID NO: 116 and a light chain variable region comprising a CDR2 having the amino acid sequence of SEQ ID NO: 112; a heavy chain variable region comprising a CDR2 having the amino acid sequence of SEQ ID NO: 136 and a light chain variable region comprising a CDR2 having the amino acid sequence of SEQ ID NO: 23; a heavy chain variable region comprising a CDR2 having the amino acid sequence of SEQ ID NO: 120 and a light chain variable region comprising a CDR2 having the amino acid sequence of SEQ ID NO: 7; a heavy chain variable region comprising a CDR2 having the amino acid sequence of SEQ ID NO: 143 and a light chain variable region comprising a CDR2 having the amino acid sequence of SEQ ID NO: 15; a heavy chain variable region comprising a CDR2 having the amino acid sequence of SEQ ID NO: 145 and a light chain variable region comprising a CDR2 having the amino acid sequence of SEQ ID NO: 15; a heavy chain variable region comprising a CDR2 having the amino acid sequence of SEQ ID NO: 58 and a light chain variable region comprising a CDR2 having the amino acid sequence of SEQ ID NO: 23; a heavy chain variable region comprising a CDR2 having the amino acid sequence of SEQ ID NO: 152 and a light chain variable region comprising a CDR2 having the amino acid sequence of SEQ ID NO: 155; a heavy chain variable region comprising a CDR2 having the amino acid sequence of SEQ ID NO: 108 and a light chain variable region comprising a CDR2 having the amino acid sequence of SEQ ID NO: 23; or a heavy chain variable region comprising a CDR2 having the amino acid sequence of SEQ ID NO: 11 and a light chain variable region comprising a CDR2 having the amino acid sequence of SEQ ID NO: 7.

In other embodiments, the antibodies, or antigen binding portions thereof, comprise a heavy chain variable region comprising a CDR1 having the amino acid sequence of SEQ ID NO: 2 and a light chain variable region comprising a CDR1 having the amino acid sequence of SEQ ID NO: 6; a heavy chain variable region comprising a CDR1 having the amino acid sequence of SEQ ID NO: 10 and a light chain variable region comprising a CDR1 having the amino acid sequence of SEQ ID NO: 14; a heavy chain variable region comprising a CDR1 having the amino acid sequence of SEQ ID NO: 18 and a light chain variable region comprising a CDR1 having the amino acid sequence of SEQ ID NO: 22; a heavy chain variable region comprising a CDR1 having the amino acid sequence of SEQ ID NO: 26 and a light chain variable region comprising a CDR1 having the amino acid sequence of SEQ ID NO: 30; a heavy chain variable region comprising a CDR1 having the amino acid sequence of SEQ ID NO: 18 and a light chain variable region comprising a CDR1 having the amino acid sequence of SEQ ID NO: 14; a heavy chain variable region comprising a CDR1 having the amino acid sequence of SEQ ID NO: 44 and a light chain variable region comprising a CDR1 having the amino acid sequence of SEQ ID NO: 6; a heavy chain variable region comprising a CDR1 having the amino acid sequence of SEQ ID NO: 50 and a light chain variable region comprising a CDR1 having the amino acid sequence of SEQ ID NO: 54; a heavy chain variable region comprising a CDR1 having the amino acid sequence of SEQ ID NO: 57 and a light chain variable region comprising a CDR1 having the amino acid sequence of SEQ ID NO: 61; a heavy chain variable region comprising a CDR1 having the amino acid sequence of SEQ ID NO: 57 and a light chain variable region comprising a CDR1 having the amino acid sequence of SEQ ID NO: 65; a heavy chain variable region comprising a CDR1 having the amino acid sequence of SEQ ID NO: 67 and a light chain variable region comprising a CDR1 having the amino acid sequence of SEQ ID NO: 6; a heavy chain variable region comprising a CDR1 having the amino acid sequence of SEQ ID NO: 50 and a light chain variable region comprising a CDR1 having the amino acid sequence of SEQ ID NO: 83; a heavy chain variable region comprising a CDR1 having the amino acid sequence of SEQ ID NO: 90 and a light chain variable region comprising a CDR1 having the amino acid sequence of SEQ ID NO: 94; a heavy chain variable region comprising a CDR1 having the amino acid sequence of SEQ ID NO: 18 and a light chain variable region comprising a CDR1 having the amino acid sequence of SEQ ID NO: 111; a heavy chain variable region comprising a CDR1 having the amino acid sequence of SEQ ID NO: 10 and a light chain variable region comprising a CDR1 having the amino acid sequence of SEQ ID NO: 6; a heavy chain variable region comprising a CDR1 having the amino acid sequence of SEQ ID NO: 72 and a light chain variable region comprising a CDR1 having the amino acid sequence of SEQ ID NO: 76; a heavy chain variable region comprising a CDR1 having the amino acid sequence of SEQ ID NO: 125 and a light chain variable region comprising a CDR1 having the amino acid sequence of SEQ ID NO: 14; a heavy chain variable region comprising a CDR1 having the amino acid sequence of SEQ ID NO: 130 and a light chain variable region comprising a CDR1 having the amino acid sequence of SEQ ID NO: 14; a heavy chain variable region comprising a CDR1 having the amino acid sequence of SEQ ID NO: 115 and a light chain variable region comprising a CDR1 having the amino acid sequence of SEQ ID NO: 76; a heavy chain variable region comprising a CDR1 having the amino acid sequence of SEQ ID NO: 135 and a light chain variable region comprising a CDR1 having the amino acid sequence of SEQ ID NO: 139; a heavy chain variable region comprising a CDR1 having the amino acid sequence of SEQ ID NO: 119 and a light chain variable region comprising a CDR1 having the amino acid sequence of SEQ ID NO: 6; a heavy chain variable region comprising a CDR1 having the amino acid sequence of SEQ ID NO: 130 and a light chain variable region comprising a CDR1 having the amino acid sequence of SEQ ID NO: 14; a heavy chain variable region comprising a CDR1 having the amino acid sequence of SEQ ID NO: 148 and a light chain variable region comprising a CDR1 having the amino acid sequence of SEQ ID NO: 65; a heavy chain variable region comprising a CDR1 having the amino acid sequence of SEQ ID NO: 18 and a light chain variable region comprising a CDR1 having the amino acid sequence of SEQ ID NO: 94; a heavy chain variable region comprising a CDR1 having the amino acid sequence of SEQ ID NO: 158 and a light chain variable region comprising a CDR1 having the amino acid sequence of SEQ ID NO: 22; or a heavy chain variable region comprising a CDR1 having the amino acid sequence of SEQ ID NO: 161 and a light chain variable region comprising a CDR1 having the amino acid sequence of SEQ ID NO: 54.

In some embodiments, the antibodies, or antigen binding portions thereof, comprise the antibody, or antigen binding portion thereof, is an IgG isotype.

In some embodiments, the antibodies, or antigen binding portions thereof, comprise a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6; a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14; a heavy chain variable region comprising a CDR3 domain comprising the amino acid sequence of SEQ ID NO: 20, a CDR2 domain comprising the amino acid sequence of SEQ ID NO: 19, and a CDR1 domain comprising the amino acid sequence of SEQ ID NO: 18, and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 22; a heavy chain variable region comprising a CDR3 domain comprising the amino acid sequence of SEQ ID NO: 28, a CDR2 domain comprising the amino acid sequence of SEQ ID NO: 27, and a CDR1 domain comprising the amino acid sequence of SEQ ID NO: 26 and a light chain variable region comprising a CDR3 domain comprising the amino acid sequence of SEQ ID NO: 32, a CDR2 domain comprising the amino acid sequence of SEQ ID NO: 31, and a CDR1 domain comprising the amino acid sequence of SEQ ID NO: 30; a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 18 and a light chain variable region comprising a CDR3 domain comprising the amino acid sequence of SEQ ID NO: 37, a CDR2 domain comprising the amino acid sequence of SEQ ID NO: 15, and a CDR1 domain comprising the amino acid sequence of SEQ ID NO: 14; a heavy chain variable region comprising a CDR3 domain comprising the amino acid sequence of SEQ ID NO: 40, a CDR2 domain comprising the amino acid sequence of SEQ ID NO: 39, and a CDR1 domain comprising the amino acid sequence of SEQ ID NO: 18 and a light chain variable region comprising a CDR3 domain comprising the amino acid sequence of SEQ ID NO: 42, a CDR2 domain comprising the amino acid sequence of SEQ ID NO: 15, and a CDR1 domain comprising the amino acid sequence of SEQ ID NO: 14; a heavy chain variable region comprising a CDR3 domain comprising the amino acid sequence of SEQ ID NO: 46, a CDR2 domain comprising the amino acid sequence of SEQ ID NO: 45, and a CDR1 domain comprising the amino acid sequence of SEQ ID NO: 44 and a light chain variable region comprising a CDR3 domain comprising the amino acid sequence of SEQ ID NO: 48, a CDR2 domain comprising the amino acid sequence of SEQ ID NO: 7, and a CDR1 domain comprising the amino acid sequence of SEQ ID NO: 6; a heavy chain variable region comprising a CDR3 domain comprising the amino acid sequence of SEQ ID NO: 52, a CDR2 domain comprising the amino acid sequence of SEQ ID NO: 51, and a CDR1 domain comprising the amino acid sequence of SEQ ID NO: 50 and a light chain variable region comprising a CDR3 domain comprising the amino acid sequence of SEQ ID NO: 55, a CDR2 domain comprising the amino acid sequence of SEQ ID NO: 7, and a CDR1 domain comprising the amino acid sequence of SEQ ID NO: 54; a heavy chain variable region comprising a CDR3 domain comprising the amino acid sequence of SEQ ID NO: 59, a CDR2 domain comprising the amino acid sequence of SEQ ID NO: 58, and a CDR1 domain comprising the amino acid sequence of SEQ ID NO: 57 and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 61; a heavy chain variable region comprising a CDR3 domain comprising the amino acid sequence of SEQ ID NO: 59, a CDR2 domain comprising the amino acid sequence of SEQ ID NO: 63, and a CDR1 domain comprising the amino acid sequence of SEQ ID NO: 57 and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 65; a heavy chain variable region comprising a CDR3 domain comprising the amino acid sequence of SEQ ID NO: 69, a CDR2 domain comprising the amino acid sequence of SEQ ID NO: 68, and a CDR1 domain comprising the amino acid sequence of SEQ ID NO: 67 and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6; a heavy chain variable region comprising a CDR3 domain comprising the amino acid sequence of SEQ ID NO: 81, a CDR2 domain comprising the amino acid sequence of SEQ ID NO: 80, and a CDR1 domain comprising the amino acid sequence of SEQ ID NO: 50 and a light chain variable region comprising a CDR3 domain comprising the amino acid sequence of SEQ ID NO: 84, a CDR2 domain comprising the amino acid sequence of SEQ ID NO: 7, and a CDR1 domain comprising the amino acid sequence of SEQ ID NO: 83; a heavy chain variable region comprising a CDR3 domain comprising the amino acid sequence of SEQ ID NO: 87, a CDR2 domain comprising the amino acid sequence of SEQ ID NO: 86, and a CDR1 domain comprising the amino acid sequence of SEQ ID NO: 2 and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6; a heavy chain variable region comprising a CDR3 domain comprising the amino acid sequence of SEQ ID NO: 92, a CDR2 domain comprising the amino acid sequence of SEQ ID NO: 91, and a CDR1 domain comprising the amino acid sequence of SEQ ID NO: 90 and a light chain variable region comprising a CDR3 domain comprising the amino acid sequence of SEQ ID NO: 95, a CDR2 domain comprising the amino acid sequence of SEQ ID NO: 7, and a CDR1 domain comprising the amino acid sequence of SEQ ID NO: 94; a heavy chain variable region comprising a CDR3 domain comprising the amino acid sequence of SEQ ID NO: 98, a CDR2 domain comprising the amino acid sequence of SEQ ID NO: 97, and a CDR1 domain comprising the amino acid sequence of SEQ ID NO: 90 and a light chain variable region comprising a CDR3 domain comprising the amino acid sequence of SEQ ID NO: 95, a CDR2 domain comprising the amino acid sequence of SEQ ID NO: 7, and a CDR1 domain comprising the amino acid sequence of SEQ ID NO: 94; a heavy chain variable region comprising a CDR3 domain comprising the amino acid sequence of SEQ ID NO: 98, a CDR2 domain comprising the amino acid sequence of SEQ ID NO: 100, and a CDR1 domain comprising the amino acid sequence of SEQ ID NO: 90 and a light chain variable region comprising a CDR3 domain comprising the amino acid sequence of SEQ ID NO: 95, a CDR2 domain comprising the amino acid sequence of SEQ ID NO: 102, and a CDR1 domain comprising the amino acid sequence of SEQ ID NO: 94; a heavy chain variable region comprising a CDR3 domain comprising the amino acid sequence of SEQ ID NO: 105, a CDR2 domain comprising the amino acid sequence of SEQ ID NO: 104, and a CDR1 domain comprising the amino acid sequence of SEQ ID NO: 90 and a light chain variable region comprising a CDR3 domain comprising the amino acid sequence of SEQ ID NO: 95, a CDR2 domain comprising the amino acid sequence of SEQ ID NO: 7, and a CDR1 domain comprising the amino acid sequence of SEQ ID NO: 94; a heavy chain variable region comprising a CDR3 domain comprising the amino acid sequence of SEQ ID NO: 109, a CDR2 domain comprising the amino acid sequence of SEQ ID NO: 108, and a CDR1 domain comprising the amino acid sequence of SEQ ID NO: 18 and a light chain variable region comprising a CDR3 domain comprising the amino acid sequence of SEQ ID NO: 113, a CDR2 domain comprising the amino acid sequence of SEQ ID NO: 112, and a CDR1 domain comprising the amino acid sequence of SEQ ID NO: 111; a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10 and a light chain variable region comprising a CDR3 domain comprising the amino acid sequence of SEQ ID NO: 16, a CDR2 domain comprising the amino acid sequence of SEQ ID NO: 7, and a CDR1 domain comprising the amino acid sequence of SEQ ID NO: 6; a heavy chain variable region comprising a CDR3 domain comprising the amino acid sequence of SEQ ID NO: 74, a CDR2 domain comprising the amino acid sequence of SEQ ID NO: 73, and a CDR1 domain comprising the amino acid sequence of SEQ ID NO: 72 and a light chain variable region comprising a CDR3 domain comprising the amino acid sequence of SEQ ID NO: 77, a CDR2 domain comprising the amino acid sequence of SEQ ID NO: 112, and a CDR1 domain comprising the amino acid sequence of SEQ ID NO: 76; a heavy chain variable region comprising a CDR3 domain comprising the amino acid sequence of SEQ ID NO: 74, a CDR2 domain comprising the amino acid sequence of SEQ ID NO: 116, and a CDR1 domain comprising the amino acid sequence of SEQ ID NO: 115 and a light chain variable region comprising a CDR3 domain comprising the amino acid sequence of SEQ ID NO: 77, a CDR2 domain comprising the amino acid sequence of SEQ ID NO: 112, and a CDR1 domain comprising the amino acid sequence of SEQ ID NO: 76; a heavy chain variable region comprising a CDR3 domain comprising the amino acid sequence of SEQ ID NO: 127, a CDR2 domain comprising the amino acid sequence of SEQ ID NO: 126, and a CDR1 domain comprising the amino acid sequence of SEQ ID NO: 125 and a light chain variable region comprising a CDR3 domain comprising the amino acid sequence of SEQ ID NO: 42, a CDR2 domain comprising the amino acid sequence of SEQ ID NO: 15, and a CDR1 domain comprising the amino acid sequence of SEQ ID NO: 14; a heavy chain variable region comprising a CDR3 domain comprising the amino acid sequence of SEQ ID NO: 132, a CDR2 domain comprising the amino acid sequence of SEQ ID NO: 131, and a CDR1 domain comprising the amino acid sequence of SEQ ID NO: 130 and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14; a heavy chain variable region comprising a CDR3 domain comprising the amino acid sequence of SEQ ID NO: 137, a CDR2 domain comprising the amino acid sequence of SEQ ID NO: 136, and a CDR1 domain comprising the amino acid sequence of SEQ ID NO: 135 and a light chain variable region comprising a CDR3 domain comprising the amino acid sequence of SEQ ID NO: 140, a CDR2 domain comprising the amino acid sequence of SEQ ID NO: 23, and a CDR1 domain comprising the amino acid sequence of SEQ ID NO: 139; a heavy chain variable region comprising a CDR3 domain comprising the amino acid sequence of SEQ ID NO: 121, a CDR2 domain comprising the amino acid sequence of SEQ ID NO: 120, and a CDR1 domain comprising the amino acid sequence of SEQ ID NO: 119 and a light chain variable region comprising a CDR3 domain comprising the amino acid sequence of SEQ ID NO: 123, a CDR2 domain comprising the amino acid sequence of SEQ ID NO: 7, and a CDR1 domain comprising the amino acid sequence of SEQ ID NO: 6; a heavy chain variable region comprising a CDR3 domain comprising the amino acid sequence of SEQ ID NO: 132, a CDR2 domain comprising the amino acid sequence of SEQ ID NO: 143, and a CDR1 domain comprising the amino acid sequence of SEQ ID NO: 130 and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14; a heavy chain variable region comprising a CDR3 domain comprising the amino acid sequence of SEQ ID NO: 132, a CDR2 domain comprising the amino acid sequence of SEQ ID NO: 145, and a CDR1 domain comprising the amino acid sequence of SEQ ID NO: 130 and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14; a heavy chain variable region comprising a CDR3 domain comprising the amino acid sequence of SEQ ID NO: 59, a CDR2 domain comprising the amino acid sequence of SEQ ID NO: 58, and a CDR1 domain comprising the amino acid sequence of SEQ ID NO: 148 and a light chain variable region comprising a CDR3 domain comprising the amino acid sequence of SEQ ID NO: 150, a CDR2 domain comprising the amino acid sequence of SEQ ID NO: 23, and a CDR1 domain comprising the amino acid sequence of SEQ ID NO: 65; a heavy chain variable region comprising a CDR3 domain comprising the amino acid sequence of SEQ ID NO: 153, a CDR2 domain comprising the amino acid sequence of SEQ ID NO: 152, and a CDR1 domain comprising the amino acid sequence of SEQ ID NO: 18 and a light chain variable region comprising a CDR3 domain comprising the amino acid sequence of SEQ ID NO: 156, a CDR2 domain comprising the amino acid sequence of SEQ ID NO: 155, and a CDR1 domain comprising the amino acid sequence of SEQ ID NO: 94; a heavy chain variable region comprising a CDR3 domain comprising the amino acid sequence of SEQ ID NO: 20, a CDR2 domain comprising the amino acid sequence of SEQ ID NO: 108, and a CDR1 domain comprising the amino acid sequence of SEQ ID NO: 158 and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 22; or a heavy chain variable region comprising a CDR3 domain comprising the amino acid sequence of SEQ ID NO: 162, a CDR2 domain comprising the amino acid sequence of SEQ ID NO: 11, and a CDR1 domain comprising the amino acid sequence of SEQ ID NO: 161 and a light chain variable region comprising a CDR3 domain comprising the amino acid sequence of SEQ ID NO: 164, a CDR2 domain comprising the amino acid sequence of SEQ ID NO: 7, and a CDR1 domain comprising the amino acid sequence of SEQ ID NO: 54.

In still other embodiments, the antibodies, or antigen binding portions thereof, comprise a heavy chain variable domain comprising an amino acid sequence set forth in SEQ ID NO: 1 and a light chain variable domain comprising an amino acid sequence set forth in SEQ ID NO: 5; a heavy chain variable region comprising the amino acid sequence of SEQ ID NO: 9 and a light chain variable region comprising the amino acid sequence of SEQ ID NO: 13; a heavy chain variable region comprising the amino acid sequence of SEQ ID NO: 17 and a light chain variable region comprising the amino acid sequence of SEQ ID NO: 21; a heavy chain variable region comprising the amino acid sequence of SEQ ID NO: 25 and a light chain variable region comprising the amino acid sequence of SEQ ID NO: 29; a heavy chain variable region comprising the amino acid sequence of SEQ ID NO: 33 and a light chain variable region comprising the amino acid sequence of SEQ ID NO: 36; a heavy chain variable region comprising the amino acid sequence of SEQ ID NO: 38 and a light chain variable region comprising the amino acid sequence of SEQ ID NO: 41; a heavy chain variable region comprising the amino acid sequence of SEQ ID NO: 43 and a light chain variable region comprising the amino acid sequence of SEQ ID NO: 47; a heavy chain variable region comprising the amino acid sequence of SEQ ID NO: 49 and a light chain variable region comprising the amino acid sequence of SEQ ID NO: 53; a heavy chain variable region comprising the amino acid sequence of SEQ ID NO: 56 and a light chain variable region comprising the amino acid sequence of SEQ ID NO: 60; a heavy chain variable region comprising the amino acid sequence of SEQ ID NO: 62 and a light chain variable region comprising the amino acid sequence of SEQ ID NO: 64; a heavy chain variable region comprising the amino acid sequence of SEQ ID NO: 66 and a light chain variable region comprising the amino acid sequence of SEQ ID NO: 70; a heavy chain variable region comprising the amino acid sequence of SEQ ID NO: 71 and a light chain variable region comprising the amino acid sequence of SEQ ID NO: 75; a heavy chain variable region comprising the amino acid sequence of SEQ ID NO: 79 and a light chain variable region comprising the amino acid sequence of SEQ ID NO: 82; a heavy chain variable region comprising the amino acid sequence of SEQ ID NO: 85 and a light chain variable region comprising the amino acid sequence of SEQ ID NO: 88; a heavy chain variable region comprising the amino acid sequence of SEQ ID NO: 89 and a light chain variable region comprising the amino acid sequence of SEQ ID NO: 93; a heavy chain variable region comprising the amino acid sequence of SEQ ID NO: 96 and a light chain variable region comprising the amino acid sequence of SEQ ID NO: 93; a heavy chain variable region comprising the amino acid sequence of SEQ ID NO: 99 and a light chain variable region comprising the amino acid sequence of SEQ ID NO: 101; a heavy chain variable region comprising the amino acid sequence of SEQ ID NO: 103 and a light chain variable region comprising the amino acid sequence of SEQ ID NO: 106; a heavy chain variable region comprising the amino acid sequence of SEQ ID NO: 107 and a light chain variable region comprising the amino acid sequence of SEQ ID NO: 110; a heavy chain variable region comprising the amino acid sequence of SEQ ID NO: 9 and a light chain variable region comprising the amino acid sequence of SEQ ID NO: 78; a heavy chain variable region comprising the amino acid sequence of SEQ ID NO: 9 and a light chain variable region comprising the amino acid sequence of SEQ ID NO: 141; a heavy chain variable region comprising the amino acid sequence of SEQ ID NO: 124 and a light chain variable region comprising the amino acid sequence of SEQ ID NO: 128; a heavy chain variable region comprising the amino acid sequence of SEQ ID NO: 129 and a light chain variable region comprising the amino acid sequence of SEQ ID NO: 133; a heavy chain variable region comprising the amino acid sequence of SEQ ID NO: 114 and a light chain variable region comprising the amino acid sequence of SEQ ID NO: 117; a heavy chain variable region comprising the amino acid sequence of SEQ ID NO: 134 and a light chain variable region comprising the amino acid sequence of SEQ ID NO: 138; a heavy chain variable region comprising the amino acid sequence of SEQ ID NO: 118 and a light chain variable region comprising the amino acid sequence of SEQ ID NO: 122; a heavy chain variable region comprising the amino acid sequence of SEQ ID NO: 142 and a light chain variable region comprising the amino acid sequence of SEQ ID NO: 133; a heavy chain variable region comprising the amino acid sequence of SEQ ID NO: 144 and a light chain variable region comprising the amino acid sequence of SEQ ID NO: 146; a heavy chain variable region comprising the amino acid sequence of SEQ ID NO: 147 and a light chain variable region comprising the amino acid sequence of SEQ ID NO: 149; a heavy chain variable region comprising the amino acid sequence of SEQ ID NO: 151 and a light chain variable region comprising the amino acid sequence of SEQ ID NO: 154; a heavy chain variable region comprising the amino acid sequence of SEQ ID NO: 157 and a light chain variable region comprising the amino acid sequence of SEQ ID NO: 159; or a heavy chain variable region comprising the amino acid sequence of SEQ ID NO: 160 and a light chain variable region comprising the amino acid sequence of SEQ ID NO: 163.

In some embodiments, the antibodies, or antigen binding portions thereof, comprise a heavy chain comprising an amino acid sequence set forth in SEQ ID NO: 1, or a sequence having at least 90%, 95%, 96%, 97%, 98%, or 99% identity to SEQ ID NO: 1, and/or a light chain comprising an amino acid sequence set forth in SEQ ID NO: 5, or a sequence having at least 90%, 95%, 96%, 97%, 98%, or 99% identity to SEQ ID NO: 5; a heavy chain comprising an amino acid sequence set forth in SEQ ID NO: 9, or a sequence having at least 90%, 95%, 96%, 97%, 98%, or 99% identity to SEQ ID NO: 9, and/or a light chain comprising an amino acid sequence set forth in SEQ ID NO: 13, or a sequence having at least 90%, 95%, 96%, 97%, 98%, or 99% identity to SEQ ID NO: 13; a heavy chain comprising an amino acid sequence set forth in SEQ ID NO: 17, or a sequence having at least 90%, 95%, 96%, 97%, 98%, or 99% identity to SEQ ID NO: 17, and/or a light chain comprising an amino acid sequence set forth in SEQ ID NO: 21, or a sequence having at least 90%, 95%, 96%, 97%, 98%, or 99% identity to SEQ ID NO: 21; a heavy chain comprising an amino acid sequence set forth in SEQ ID NO: 25, or a sequence having at least 90%, 95%, 96%, 97%, 98%, or 99% identity to SEQ ID NO: 25, and/or a light chain comprising an amino acid sequence set forth in SEQ ID NO: 29, or a sequence having at least 90%, 95%, 96%, 97%, 98%, or 99% identity to SEQ ID NO: 29; a heavy chain comprising an amino acid sequence set forth in SEQ ID NO: 33, or a sequence having at least 90%, 95%, 96%, 97%, 98%, or 99% identity to SEQ ID NO: 33, and/or a light chain comprising an amino acid sequence set forth in SEQ ID NO: 36, or a sequence having at least 90%, 95%, 96%, 97%, 98%, or 99% identity to SEQ ID NO: 36; a heavy chain comprising an amino acid sequence set forth in SEQ ID NO: 38, or a sequence having at least 90%, 95%, 96%, 97%, 98%, or 99% identity to SEQ ID NO: 38, and/or a light chain comprising an amino acid sequence set forth in SEQ ID NO: 41, or a sequence having at least 90%, 95%, 96%, 97%, 98%, or 99% identity to SEQ ID NO: 41; a heavy chain comprising an amino acid sequence set forth in SEQ ID NO: 43, or a sequence having at least 90%, 95%, 96%, 97%, 98%, or 99% identity to SEQ ID NO: 43, and/or a light chain comprising an amino acid sequence set forth in SEQ ID NO: 47, or a sequence having at least 90%, 95%, 96%, 97%, 98%, or 99% identity to SEQ ID NO: 47; a heavy chain comprising an amino acid sequence set forth in SEQ ID NO: 49, or a sequence having at least 90%, 95%, 96%, 97%, 98%, or 99% identity to SEQ ID NO: 49, and/or a light chain comprising an amino acid sequence set forth in SEQ ID NO: 53, or a sequence having at least 90%, 95%, 96%, 97%, 98%, or 99% identity to SEQ ID NO: 53; a heavy chain comprising an amino acid sequence set forth in SEQ ID NO: 56, or a sequence having at least 90%, 95%, 96%, 97%, 98%, or 99% identity to SEQ ID NO: 56, and/or a light chain comprising an amino acid sequence set forth in SEQ ID NO: 60, or a sequence having at least 90%, 95%, 96%, 97%, 98%, or 99% identity to SEQ ID NO: 60; a heavy chain comprising an amino acid sequence set forth in SEQ ID NO: 62, or a sequence having at least 90%, 95%, 96%, 97%, 98%, or 99% identity to SEQ ID NO: 62, and/or a light chain comprising an amino acid sequence set forth in SEQ ID NO: 64, or a sequence having at least 90%, 95%, 96%, 97%, 98%, or 99% identity to SEQ ID NO: 64; a heavy chain comprising an amino acid sequence set forth in SEQ ID NO: 66, or a sequence having at least 90%, 95%, 96%, 97%, 98%, or 99% identity to SEQ ID NO: 66, and/or a light chain comprising an amino acid sequence set forth in SEQ ID NO: 70, or a sequence having at least 90%, 95%, 96%, 97%, 98%, or 99% identity to SEQ ID NO: 70; a heavy chain comprising an amino acid sequence set forth in SEQ ID NO: 71, or a sequence having at least 90%, 95%, 96%, 97%, 98%, or 99% identity to SEQ ID NO: 71, and/or a light chain comprising an amino acid sequence set forth in SEQ ID NO: 75, or a sequence having at least 90%, 95%, 96%, 97%, 98%, or 99% identity to SEQ ID NO: 75; a heavy chain comprising an amino acid sequence set forth in SEQ ID NO: 79, or a sequence having at least 90%, 95%, 96%, 97%, 98%, or 99% identity to SEQ ID NO: 79, and/or a light chain comprising an amino acid sequence set forth in SEQ ID NO: 82, or a sequence having at least 90%, 95%, 96%, 97%, 98%, or 99% identity to SEQ ID NO: 82; a heavy chain comprising an amino acid sequence set forth in SEQ ID NO: 85, or a sequence having at least 90%, 95%, 96%, 97%, 98%, or 99% identity to SEQ ID NO: 85, and/or a light chain comprising an amino acid sequence set forth in SEQ ID NO: 88, or a sequence having at least 90%, 95%, 96%, 97%, 98%, or 99% identity to SEQ ID NO: 88; a heavy chain comprising an amino acid sequence set forth in SEQ ID NO: 89, or a sequence having at least 90%, 95%, 96%, 97%, 98%, or 99% identity to SEQ ID NO: 89, and/or a light chain comprising an amino acid sequence set forth in SEQ ID NO: 93, or a sequence having at least 90%, 95%, 96%, 97%, 98%, or 99% identity to SEQ ID NO: 93; a heavy chain comprising an amino acid sequence set forth in SEQ ID NO: 96, or a sequence having at least 90%, 95%, 96%, 97%, 98%, or 99% identity to SEQ ID NO: 96, and/or a light chain comprising an amino acid sequence set forth in SEQ ID NO: 93, or a sequence having at least 90%, 95%, 96%, 97%, 98%, or 99% identity to SEQ ID NO: 93; a heavy chain comprising an amino acid sequence set forth in SEQ ID NO: 99, or a sequence having at least 90%, 95%, 96%, 97%, 98%, or 99% identity to SEQ ID NO: 99, and/or a light chain comprising an amino acid sequence set forth in SEQ ID NO: 101, or a sequence having at least 90%, 95%, 96%, 97%, 98%, or 99% identity to SEQ ID NO: 101; a heavy chain comprising an amino acid sequence set forth in SEQ ID NO: 103, or a sequence having at least 90%, 95%, 96%, 97%, 98%, or 99% identity to SEQ ID NO: 103, and/or a light chain comprising an amino acid sequence set forth in SEQ ID NO: 106, or a sequence having at least 90%, 95%, 96%, 97%, 98%, or 99% identity to SEQ ID NO: 106; a heavy chain comprising an amino acid sequence set forth in SEQ ID NO: 107, or a sequence having at least 90%, 95%, 96%, 97%, 98%, or 99% identity to SEQ ID NO: 107, and/or a light chain comprising an amino acid sequence set forth in SEQ ID NO: 110, or a sequence having at least 90%, 95%, 96%, 97%, 98%, or 99% identity to SEQ ID NO: 110; a heavy chain comprising an amino acid sequence set forth in SEQ ID NO: 9, or a sequence having at least 90%, 95%, 96%, 97%, 98%, or 99% identity to SEQ ID NO: 9, and/or a light chain comprising an amino acid sequence set forth in SEQ ID NO: 78, or a sequence having at least 90%, 95%, 96%, 97%, 98%, or 99% identity to SEQ ID NO: 78; a heavy chain comprising an amino acid sequence set forth in SEQ ID NO: 9, or a sequence having at least 90%, 95%, 96%, 97%, 98%, or 99% identity to SEQ ID NO: 9, and/or a light chain comprising an amino acid sequence set forth in SEQ ID NO: 141, or a sequence having at least 90%, 95%, 96%, 97%, 98%, or 99% identity to SEQ ID NO: 141; a heavy chain comprising an amino acid sequence set forth in SEQ ID NO: 124, or a sequence having at least 90%, 95%, 96%, 97%, 98%, or 99% identity to SEQ ID NO: 124, and/or a light chain comprising an amino acid sequence set forth in SEQ ID NO: 128, or a sequence having at least 90%, 95%, 96%, 97%, 98%, or 99% identity to SEQ ID NO: 128; a heavy chain comprising an amino acid sequence set forth in SEQ ID NO: 129, or a sequence having at least 90%, 95%, 96%, 97%, 98%, or 99% identity to SEQ ID NO: 129, and/or a light chain comprising an amino acid sequence set forth in SEQ ID NO: 133, or a sequence having at least 90%, 95%, 96%, 97%, 98%, or 99% identity to SEQ ID NO: 133; a heavy chain comprising an amino acid sequence set forth in SEQ ID NO: 114, or a sequence having at least 90%, 95%, 96%, 97%, 98%, or 99% identity to SEQ ID NO: 114, and/or a light chain comprising an amino acid sequence set forth in SEQ ID NO: 117, or a sequence having at least 90%, 95%, 96%, 97%, 98%, or 99% identity to SEQ ID NO: 117; a heavy chain comprising an amino acid sequence set forth in SEQ ID NO: 134, or a sequence having at least 90%, 95%, 96%, 97%, 98%, or 99% identity to SEQ ID NO: 134, and/or a light chain comprising an amino acid sequence set forth in SEQ ID NO: 138, or a sequence having at least 90%, 95%, 96%, 97%, 98%, or 99% identity to SEQ ID NO: 138; or a heavy chain comprising an amino acid sequence set forth in SEQ ID NO: 118, a sequence having at least 90%, 95%, 96%, 97%, 98%, or 99% identity to SEQ ID NO: 118, and/or a light chain comprising an amino acid sequence set forth in SEQ ID NO: 122, or a sequence having at least 90%, 95%, 96%, 97%, 98%, or 99% identity to SEQ ID NO: 122; a heavy chain comprising an amino acid sequence set forth in SEQ ID NO: 142, or a sequence having at least 90%, 95%, 96%, 97%, 98%, or 99% identity to SEQ ID NO: 142, and/or a light chain comprising an amino acid sequence set forth in SEQ ID NO: 133, or a sequence having at least 90%, 95%, 96%, 97%, 98%, or 99% identity to SEQ ID NO: 133; a heavy chain comprising an amino acid sequence set forth in SEQ ID NO: 144, or a sequence having at least 90%, 95%, 96%, 97%, 98%, or 99% identity to SEQ ID NO: 144, and/or a light chain comprising an amino acid sequence set forth in SEQ ID NO: 146, or a sequence having at least 90%, 95%, 96%, 97%, 98%, or 99% identity to SEQ ID NO: 146; a heavy chain comprising an amino acid sequence set forth in SEQ ID NO: 147, or a sequence having at least 90%, 95%, 96%, 97%, 98%, or 99% identity to SEQ ID NO: 147, and/or a light chain comprising an amino acid sequence set forth in SEQ ID NO: 149, or a sequence having at least 90%, 95%, 96%, 97%, 98%, or 99% identity to SEQ ID NO: 149; a heavy chain comprising an amino acid sequence set forth in SEQ ID NO: 151, or a sequence having at least 90%, 95%, 96%, 97%, 98%, or 99% identity to SEQ ID NO: 151, and/or a light chain comprising an amino acid sequence set forth in SEQ ID NO: 154, or a sequence having at least 90%, 95%, 96%, 97%, 98%, or 99% identity to SEQ ID NO: 154; a heavy chain comprising an amino acid sequence set forth in SEQ ID NO: 157, or a sequence having at least 90%, 95%, 96%, 97%, 98%, or 99% identity to SEQ ID NO: 157, and/or a light chain comprising an amino acid sequence set forth in SEQ ID NO: 159, or a sequence having at least 90%, 95%, 96%, 97%, 98%, or 99% identity to SEQ ID NO: 159; or a heavy chain comprising an amino acid sequence set forth in SEQ ID NO: 160, or a sequence having at least 90%, 95%, 96%, 97%, 98%, or 99% identity to SEQ ID NO: 160, and/or a light chain comprising an amino acid sequence set forth in SEQ ID NO: 163, or a sequence having at least 90%, 95%, 96%, 97%, 98%, or 99% identity to SEQ ID NO: 163.

In other embodiments, the antibodies, or antigen binding portions thereof binds to the same epitope as an antibody, or antigen-binding portion thereof described herein.

The invention also provides, in certain embodiments, isolated nucleic acids encoding the antibodies, or antigen binding portions thereof of the invention.

In some embodiments of the invention, the antibodies, or antigen binding portions thereof, comprise a heavy chain immunoglobulin constant domain selected from the group consisting of a human IgG constant domain, a human IgM constant domain, a human IgE constant domain, and a human IgA constant domain. In some embodiments, the IgG constant domain is selected from the group consisting of an IgG1 constant domain, an IgG2 constant domain, an IgG3 constant domain, and an IgG4 constant domain. In other embodiments, the antibody is a multispecific antibody.

In other embodiments of the invention, the antibodies, or antigen binding portions thereof, comprise a Fab, a Fab', a F(ab')2, a Fv, a disulfide linked Fv, an scFv, a single domain antibody, and a diabody.

In other embodiments the invention provides a pharmaceutical composition comprising the antibody, or antigen binding portion thereof, as described herein, and a pharmaceutically acceptable carrier.

In other embodiments the invention provides an antibody, or antigen binding portion thereof, as described herein, conjugated to at least one drug. In some embodiments, the at least one drug is selected from the group consisting of an anti-apoptotic agent, a mitotic inhibitor, an anti-tumor antibiotic, an immunomodulating agent, a nucleic acid for gene therapy, an anti-angiogenic agent, an anti-metabolite, a boron-containing agent, a chemoprotective agent, a hormone agent, an anti-hormone agent, a corticosteroid, a photoactive therapeutic agent, an oligonucleotide, a radionuclide agent, a radiosensitizer, a topoisomerase inhibitor, and a tyrosine kinase inhibitor. In one embodiment, the drug is a pyrrolobenzodiazepine (PBD).

In some embodiments, the at least one drug is conjugated to the antibody, or antigen-binding portion thereof, via a linker, e.g., a cleavable linker or a non-cleavable linker.

In other aspects, the invention provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6; a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14; a heavy chain variable region comprising a CDR3 domain comprising the amino acid sequence of SEQ ID NO: 20, a CDR2 domain comprising the amino acid sequence of SEQ ID NO: 19, and a CDR1 domain comprising the amino acid sequence of SEQ ID NO: 18, and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 22; a heavy chain variable region comprising a CDR3 domain comprising the amino acid sequence of SEQ ID NO: 28, a CDR2 domain comprising the amino acid sequence of SEQ ID NO: 27, and a CDR1 domain comprising the amino acid sequence of SEQ ID NO: 26 and a light chain variable region comprising a CDR3 domain comprising the amino acid sequence of SEQ ID NO: 32, a CDR2 domain comprising the amino acid sequence of SEQ ID NO: 31, and a CDR1 domain comprising the amino acid sequence of SEQ ID NO: 30; a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 18 and a light chain variable region comprising a CDR3 domain comprising the amino acid sequence of SEQ ID NO: 37, a CDR2 domain comprising the amino acid sequence of SEQ ID NO: 15, and a CDR1 domain comprising the amino acid sequence of SEQ ID NO: 14; a heavy chain variable region comprising a CDR3 domain comprising the amino acid sequence of SEQ ID NO: 40, a CDR2 domain comprising the amino acid sequence of SEQ ID NO: 39, and a CDR1 domain comprising the amino acid sequence of SEQ ID NO: 18 and a light chain variable region comprising a CDR3 domain comprising the amino acid sequence of SEQ ID NO: 42, a CDR2 domain comprising the amino acid sequence of SEQ ID NO: 15, and a CDR1 domain comprising the amino acid sequence of SEQ ID NO: 14; a heavy chain variable region comprising a CDR3 domain comprising the amino acid sequence of SEQ ID NO: 46, a CDR2 domain comprising the amino acid sequence of SEQ ID NO: 45, and a CDR1 domain comprising the amino acid sequence of SEQ ID NO: 44 and a light chain variable region comprising a CDR3 domain comprising the amino acid sequence of SEQ ID NO: 48, a CDR2 domain comprising the amino acid sequence of SEQ ID NO: 7, and a CDR1 domain comprising the amino acid sequence of SEQ ID NO: 6; a heavy chain variable region comprising a CDR3 domain comprising the amino acid sequence of SEQ ID NO: 52, a CDR2 domain comprising the amino acid sequence of SEQ ID NO: 51, and a CDR1 domain comprising the amino acid sequence of SEQ ID NO: 50 and a light chain variable region comprising a CDR3 domain comprising the amino acid sequence of SEQ ID NO: 55, a CDR2 domain comprising the amino acid sequence of SEQ ID NO: 7, and a CDR1 domain comprising the amino acid sequence of SEQ ID NO: 54; a heavy chain variable region comprising a CDR3 domain comprising the amino acid sequence of SEQ ID NO: 59, a CDR2 domain comprising the amino acid sequence of SEQ ID NO: 58, and a CDR1 domain comprising the amino acid sequence of SEQ ID NO: 57 and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 61; a heavy chain variable region comprising a CDR3 domain comprising the amino acid sequence of SEQ ID NO: 59, a CDR2 domain comprising the amino acid sequence of SEQ ID NO: 63, and a CDR1 domain comprising the amino acid sequence of SEQ ID NO: 57 and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 65; a heavy chain variable region comprising a CDR3 domain comprising the amino acid sequence of SEQ ID NO: 69, a CDR2 domain comprising the amino acid sequence of SEQ ID NO: 68, and a CDR1 domain comprising the amino acid sequence of SEQ ID NO: 67 and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6; a heavy chain variable region comprising a CDR3 domain comprising the amino acid sequence of SEQ ID NO: 81, a CDR2 domain comprising the amino acid sequence of SEQ ID NO: 80, and a CDR1 domain comprising the amino acid sequence of SEQ ID NO: 50 and a light chain variable region comprising a CDR3 domain comprising the amino acid sequence of SEQ ID NO: 84, a CDR2 domain comprising the amino acid sequence of SEQ ID NO: 7, and a CDR1 domain comprising the amino acid sequence of SEQ ID NO: 83; a heavy chain variable region comprising a CDR3 domain comprising the amino acid sequence of SEQ ID NO: 87, a CDR2 domain comprising the amino acid sequence of SEQ ID NO: 86, and a CDR1 domain comprising the amino acid sequence of SEQ ID NO: 2 and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6; a heavy chain variable region comprising a CDR3 domain comprising the amino acid sequence of SEQ ID NO: 92, a CDR2 domain comprising the amino acid sequence of SEQ ID NO: 91, and a CDR1 domain comprising the amino acid sequence of SEQ ID NO: 90 and a light chain variable region comprising a CDR3 domain comprising the amino acid sequence of SEQ ID NO: 95, a CDR2 domain comprising the amino acid sequence of SEQ ID NO: 7, and a CDR1 domain comprising the amino acid sequence of SEQ ID NO: 94; a heavy chain variable region comprising a CDR3 domain comprising the amino acid sequence of SEQ ID NO: 98, a CDR2 domain comprising the amino acid sequence of SEQ ID NO: 97, and a CDR1 domain comprising the amino acid sequence of SEQ ID NO: 90 and a light chain variable region comprising a CDR3 domain comprising the amino acid sequence of SEQ ID NO: 95, a CDR2 domain comprising the amino acid sequence of SEQ ID NO: 7, and a CDR1 domain comprising the amino acid sequence of SEQ ID NO: 94; a heavy chain variable region comprising a CDR3 domain comprising the amino acid sequence of SEQ ID NO: 98, a CDR2 domain comprising the amino acid sequence of SEQ ID NO: 100, and a CDR1 domain comprising the amino acid sequence of SEQ ID NO: 90 and a light chain variable region comprising a CDR3 domain comprising the amino acid sequence of SEQ ID NO: 95, a CDR2 domain comprising the amino acid sequence of SEQ ID NO: 102, and a CDR1 domain comprising the amino acid sequence of SEQ ID NO: 94; a heavy chain variable region comprising a CDR3 domain comprising the amino acid sequence of SEQ ID NO: 105, a CDR2 domain comprising the amino acid sequence of SEQ ID NO: 104, and a CDR1 domain comprising the amino acid sequence of SEQ ID NO: 90 and a light chain variable region comprising a CDR3 domain comprising the amino acid sequence of SEQ ID NO: 95, a CDR2 domain comprising the amino acid sequence of SEQ ID NO: 7, and a CDR1 domain comprising the amino acid sequence of SEQ ID NO: 94; a heavy chain variable region comprising a CDR3 domain comprising the amino acid sequence of SEQ ID NO: 109, a CDR2 domain comprising the amino acid sequence of SEQ ID NO: 108, and a CDR1 domain comprising the amino acid sequence of SEQ ID NO: 18 and a light chain variable region comprising a CDR3 domain comprising the amino acid sequence of SEQ ID NO: 113, a CDR2 domain comprising the amino acid sequence of SEQ ID NO: 112, and a CDR1 domain comprising the amino acid sequence of SEQ ID NO: 111; a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10 and a light chain variable region comprising a CDR3 domain comprising the amino acid sequence of SEQ ID NO: 16, a CDR2 domain comprising the amino acid sequence of SEQ ID NO: 7, and a CDR1 domain comprising the amino acid sequence of SEQ ID NO: 6; a heavy chain variable region comprising a CDR3 domain comprising the amino acid sequence of SEQ ID NO: 121, a CDR2 domain comprising the amino acid sequence of SEQ ID NO: 120, and a CDR1 domain comprising the amino acid sequence of SEQ ID NO: 119 and a light chain variable region comprising a CDR3 domain comprising the amino acid sequence of SEQ ID NO: 123, a CDR2 domain comprising the amino acid sequence of SEQ ID NO: 7, and a CDR1 domain comprising the amino acid sequence of SEQ ID NO: 6; a heavy chain variable region comprising a CDR3 domain comprising the amino acid sequence of SEQ ID NO: 127, a CDR2 domain comprising the amino acid sequence of SEQ ID NO: 126, and a CDR1 domain comprising the amino acid sequence of SEQ ID NO: 125 and a light chain variable region comprising a CDR3 domain comprising the amino acid sequence of SEQ ID NO: 42, a CDR2 domain comprising the amino acid sequence of SEQ ID NO: 15, and a CDR1 domain comprising the amino acid sequence of SEQ ID NO: 14; a heavy chain variable region comprising a CDR3 domain comprising the amino acid sequence of SEQ ID NO: 132, a CDR2 domain comprising the amino acid sequence of SEQ ID NO: 131, and a CDR1 domain comprising the amino acid sequence of SEQ ID NO: 130 and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14; a heavy chain variable region comprising a CDR3 domain comprising the amino acid sequence of SEQ ID NO: 74, a CDR2 domain comprising the amino acid sequence of SEQ ID NO: 73, and a CDR1 domain comprising the amino acid sequence of SEQ ID NO: 72 and a light chain variable region comprising a CDR3 domain comprising the amino acid sequence of SEQ ID NO: 77, a CDR2 domain comprising the amino acid sequence of SEQ ID NO: 112, and a CDR1 domain comprising the amino acid sequence of SEQ ID NO: 76; a heavy chain variable region comprising a CDR3 domain comprising the amino acid sequence of SEQ ID NO: 74, a CDR2 domain comprising the amino acid sequence of SEQ ID NO: 116, and a CDR1 domain comprising the amino acid sequence of SEQ ID NO: 115 and a light chain variable region comprising a CDR3 domain comprising the amino acid sequence of SEQ ID NO: 77, a CDR2 domain comprising the amino acid sequence of SEQ ID NO: 112, and a CDR1 domain comprising the amino acid sequence of SEQ ID NO: 76; a heavy chain variable region comprising a CDR3 domain comprising the amino acid sequence of SEQ ID NO: 137, a CDR2 domain comprising the amino acid sequence of SEQ ID NO: 136, and a CDR1 domain comprising the amino acid sequence of SEQ ID NO: 135 and a light chain variable region comprising a CDR3 domain comprising the amino acid sequence of SEQ ID NO: 140, a CDR2 domain comprising the amino acid sequence of SEQ ID NO: 23, and a CDR1 domain comprising the amino acid sequence of SEQ ID NO: 139; a heavy chain variable region comprising a CDR3 domain comprising the amino acid sequence of SEQ ID NO: 132, a CDR2 domain comprising the amino acid sequence of SEQ ID NO: 143, and a CDR1 domain comprising the amino acid sequence of SEQ ID NO: 130 and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14; a heavy chain variable region comprising a CDR3 domain comprising the amino acid sequence of SEQ ID NO: 132, a CDR2 domain comprising the amino acid sequence of SEQ ID NO: 145, and a CDR1 domain comprising the amino acid sequence of SEQ ID NO: 130 and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14; a heavy chain variable region comprising a CDR3 domain comprising the amino acid sequence of SEQ ID NO: 59, a CDR2 domain comprising the amino acid sequence of SEQ ID NO: 58, and a CDR1 domain comprising the amino acid sequence of SEQ ID NO: 148 and a light chain variable region comprising a CDR3 domain comprising the amino acid sequence of SEQ ID NO: 150, a CDR2 domain comprising the amino acid sequence of SEQ ID NO: 23, and a CDR1 domain comprising the amino acid sequence of SEQ ID NO: 65; a heavy chain variable region comprising a CDR3 domain comprising the amino acid sequence of SEQ ID NO: 153, a CDR2 domain comprising the amino acid sequence of SEQ ID NO: 152, and a CDR1 domain comprising the amino acid sequence of SEQ ID NO: 18 and a light chain variable region comprising a CDR3 domain comprising the amino acid sequence of SEQ ID NO: 156, a CDR2 domain comprising the amino acid sequence of SEQ ID NO: 155, and a CDR1 domain comprising the amino acid sequence of SEQ ID NO: 94; a heavy chain variable region comprising a CDR3 domain comprising the amino acid sequence of SEQ ID NO: 20, a CDR2 domain comprising the amino acid sequence of SEQ ID NO: 108, and a CDR1 domain comprising the amino acid sequence of SEQ ID NO: 158 and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 22; or a heavy chain variable region comprising a CDR3 domain comprising the amino acid sequence of SEQ ID NO: 162, a CDR2 domain comprising the amino acid sequence of SEQ ID NO: 11, and a CDR1 domain comprising the amino acid sequence of SEQ ID NO: 161 and a light chain variable region comprising a CDR3 domain comprising the amino acid sequence of SEQ ID NO: 164, a CDR2 domain comprising the amino acid sequence of SEQ ID NO: 7, and a CDR1 domain comprising the amino acid sequence of SEQ ID NO: 54.

In some embodiments, the at least one drug is conjugated to the antibody, or antigen-binding portion thereof, via a linker, e.g., a cleavable linker or a non-cleavable linker.

In other embodiments, the invention provides a pharmaceutical composition comprising an ADC mixture comprising a plurality of the ADC described herein, and a pharmaceutically acceptable carrier. In some embodiments, the ADC mixture has an average drug to antibody ratio (DAR) of 0 to 8.

In other aspects, the invention provides a method for treating cancer, comprising administering a therapeutically effective amount of an antibody or antigen binding portion thereof or an ADC described herein, to a subject in need thereof.

In one embodiment, the cancer is small cell lung cancer. In another embodiment, the cancer is triple negative breast cancer. In another embodiment, the cancer is ovarian cancer.

In other aspects, the invention provides a method for inhibiting or decreasing solid tumor growth in a subject having a solid tumor, said method comprising administering an effective amount of an antibody or antigen binding portion thereof or an ADC described herein, to the subject having the solid tumor, such that the solid tumor growth is inhibited or decreased.

In one embodiment, the cancer is small cell lung cancer. In another embodiment, the cancer is triple negative breast cancer. In another embodiment, the cancer is ovarian cancer.

In some embodiments, the cancer or tumor is characterized as having TMEFF1 expression or overexpression.

In some embodiments, the antibody, ADC, or antigen binding portion thereof is administered in combination with an additional agent or an additional therapy. In one embodiment, the additional agent is an immune checkpoint inhibitor. In some embodiments, the checkpoint inhibitor is an antibody, such as an antibody selected from the group consisting of an anti-PD1 antibody, an anti-PD-L1 antibody, a CD38 antibody, an anti-CTLA-4 antibody, or a combination thereof. In other embodiments, the additional agent is PARP inhibitor. In other embodiments, the additional agent is a DNA alkylating agent. In other embodiments, the additional agent is a topoisomerase inhibitor. In other embodiments, the additional agent is etoposide, cisplatin, carboplatin, topotecan, irinotecan, or niraparib.

In other embodiments, the additional agent is radiation. In still other embodiments, the additional agent is a chemotherapeutic agent.

In one aspect, the present invention provides a method for treating cancer, comprising administering a combination of (i) a therapeutically effective amount of an anti-TMEFF1 antibody or antigen binding portion thereof or an anti-TMEFF1 ADC and (ii) a PARP inhibitor, to a subject in need thereof. In one embodiment, the PARP inhibitor is niraparib.

In another aspect, the present invention provides a methods for treating cancer, comprising administering a combination of (i) a therapeutically effective amount of an anti-TMEFF1 antibody or antigen binding portion thereof or an anti-TMEFF1 ADC and (ii) a DNA alkylating agent, to a subject in need thereof. In one embodiment, the DNA alkylating agent is cisplatin.

In another aspect, the present invention provides a methods for treating cancer, comprising administering a combination of (i) a therapeutically effective amount of an anti-TMEFF1 antibody or antigen binding portion thereof or an anti-TMEFF1 ADC and (ii) a topoisomerase inhibitor, to a subject in need thereof. In one embodiment, the topoisomerase inhibitor agent is etoposide.

In one embodiment, the combination of an anti-TMEFF1 antibody or antigen binding portion thereof or an anti-TMEFF1 ADC, a PARP inhibitor or a DNA alkylating agent, or a topoisomerase inhibitor has a synergistic effect on decreasing or inhibiting cancer, tumor cellular proliferation or tumor growth, or tumor invasion or metastasis in the subject.

BRIEF DESCRIPTION OF THE DRAWINGS

FIG. 1A shows that four antibodies tested, 24F10, 36H6, 31B7 and 30C10 show consistent cell surface binding in fix cells for the duration of the assay. FIG. 1B shows that antibodies tested show about a 50% internalization by 30 minutes of treatment in live cells.

DETAILED DESCRIPTION

Figure 1A:
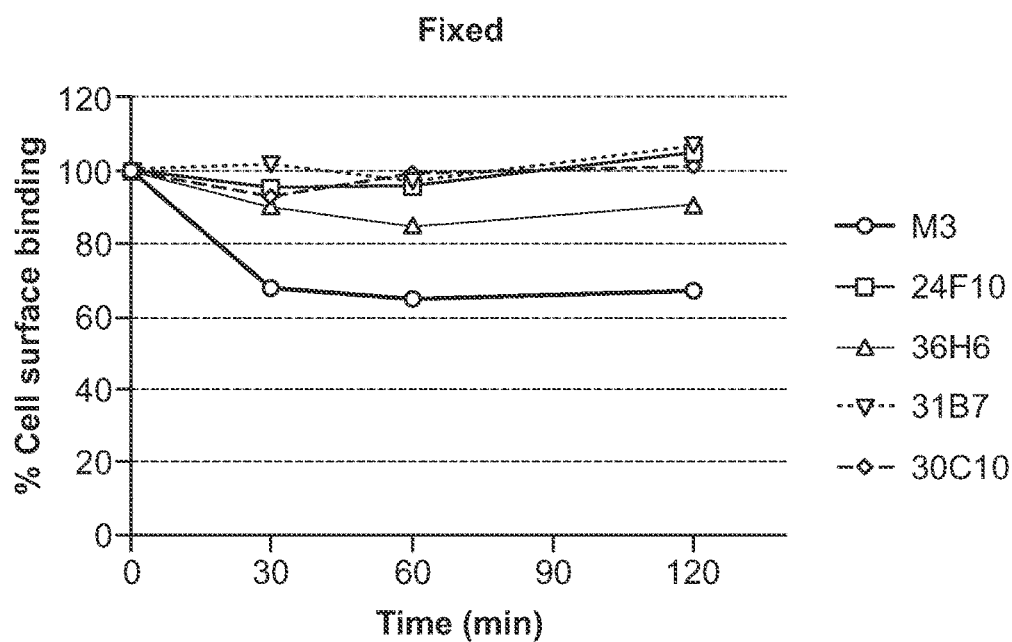
FIGS. 1A-1B illustrate internalization of anti-TMEFF1 antibodies in 293-hTMEFF1 cells.

Various aspects of the disclosure relate to anti-TMEFF1 antibodies and antibody fragments, anti-TMEFF1 ADCs, and pharmaceutical compositions thereof, as well as nucleic acids, recombinant expression vectors and host cells for making such antibodies and fragments. Methods of using the antibodies and ADCs described herein to detect human TMEFF1, to bind to and inhibit human TMEFF1 on TMEFF1 expressing cells. In one embodiment, the anti-TMEFF1 antibodies or ADCs of the invention are administered to a subject for the treatment of a cancer. In another embodiment, the anti-TMEFF1 antibody drug conjugates (ADCs) of the invention are administered to a subject for the treatment of a cancer in combination with an anti cancer agent such as a PARP inhibitor, a DNA alkylating agent, or a topoisomerase inhibitor, wherein the combination has a synergistic effect on decreasing or inhibiting cancer, tumor cellular proliferation or tumor growth, or tumor invasion or metastasis, in the subject. In another embodiment of the invention, anti-TMEFF1 antibody drug conjugates (ADCs) of the invention (e.g., the TMEFF1 antibodies of the invention conjugated to a toxin) are internalized and/or induce cell death of cells endogenously expressing TMEFF1.

I. Definitions

In order that the invention may be more readily understood, certain terms are first defined. In addition, it should be noted that whenever a value or range of values of a parameter are recited, it is intended that values and ranges intermediate to the recited values are also intended to be part of this invention.

The terms "anti-tomoregulin-1 antibody," or "anti-TMEFF1 antibody", used interchangeably herein, refer to an antibody that specifically binds to TMEFF1, e.g., human TMEFF1. An antibody "which binds" an antigen of interest, i.e., TMEFF1, is one capable of binding that antigen with sufficient affinity such that the antibody is useful in targeting a cell expressing the antigen. In a preferred embodiment, the antibody specifically binds to human TMEFF1 (hTMEFF1). Examples of human anti-TMEFF1 antibodies are disclosed in Example 2, below. Unless otherwise indicated, the term "anti-TMEFF1 antibody" is meant to refer to an antibody which binds to wild type TMEFF1, a variant, or an isoform of TMEFF1.

Two different isoforms of TMEFF1 produced by alternative splicing have been identified. An exemplary amino acid sequence of wild type human TMEFF1, which contains 380 amino acids, is provided below as SEQ ID NO: 229, where the signal peptide (amino acid residues 1-39) are underlined. The mature form of wild type TMEFF1 corresponds to the protein without the signal peptide, i.e., amino acid residues 40 to 380 of SEQ ID NO: 229. The extracellular domain (ECD) of TMEFF1 comprises amino acid residues 40-330 of SEQ ID NO: 229.

```
         10         20         30         40
MGAAAAEAPL RLPAAPPLAF CCYTSVLLLF AFSLPGSRAS 50         60         70         80
NQPPGGGGGS GGDCPGGKGK SINCSELNVR ESDVRVCDES 90        100        110        120
SCKYGGVCKE DGDGLKCACQ FQCHTNYIPV CGSNGDTYQN 130        140        150        160
ECFLRRAACK HQKEITVIAR GPCYSDNGSG SGEGEEEGSG 170        180        190        200
AEVHRKHSKC GPCKYKAECD EDAENVGCVC NIDCSGYSFN 210        220        230        240
PVCASDGSSY NNPCFVREAS CIKQEQIDIR HLGHCTDTDD 250        260        270        280
TSLLGKKDDG LQYRPDVKDA SDQREDVYIG NHMPCPENLN 290        300        310        320
GYCIHGKCEF IYSTQKASCR CESGYTGQHC EKTDFSILYV 330        340        350        360
VPSRQKLTHV LIAAIIGAVQ IAIIVAIVMC ITRKCPKNNR 370        380
GRRQKQNLGH FTSDTSSRMV
```

TMEFF1 is a member of the tomoregulin family. The protein contains two follistatin domains at amino acid residues C103-C143 and S198-C235 and an EGF-like domain at amino acid residues N271-E311.

The terms "specific binding" or "specifically binding", as used herein, in reference to the interaction of an TMEFF1 antibody or an ADC with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody or ADC is specific for epitope "A", the presence of a molecule containing epitope A (or free, unlabeled A), in a reaction containing labeled "A" and the antibody, will reduce the amount of labeled A bound to the antibody or ADC.

In one embodiment, the phrase "specifically binds to TMEFF1" or "specific binding to TMEFF1", as used herein, refers to the ability of an anti-TMEFF1 antibody or ADC to interact with TMEFF1 (including human, mouse, and/or monkey TMEFF1) with a dissociation constant ($K_D$) of about 2,000 nM or less, about 1,000 nM or less, about 500 nM or less, about 200 nM or less, about 100 nM or less, about 75 nM or less, about 50 nM or less, about 43 nM or less, about 25 nM or less, about 20 nM or less, about 19 nM or less, about 18 nM or less, about 17 nM or less, about 16 nM or less, about 15 nM or less, about 14 nM or less, about 13 nM or less, about 12 nM or less, about 11 nM or less, about 10 nM or less, about 9 nM or less, about 8 nM or less, about 7 nM or less, about 6 nM or less, about 5 nM or less, about 4 nM or less, about 3 nM or less, about 2 nM or less, about 1 nM or less, about 0.5 nM or less, about 0.3 nM or less, about 0.1 nM or less, or about 0.01 nM or less, or about 0.001 nM or less.

In another embodiment, the phrase "specifically binds to TMEFF1" or "specific binding to TMEFF1", as used herein, refers to the ability of an anti-TMEFF1 antibody or ADC to interact with TMEFF1 with a dissociation constant ($K_D$) of between about 1 pM (0.001 nM) to 2,000 nM, between about 500 pM (0.5 nM) to 1,000 nM, between about 500 pM (0.5 nM) to 500 nM, between about 1 nM) to 200 nM, between about 1 nM to 100 nM, between about 1 nM to 50 nM, between about 1 nM to 20 nM, or between about 1 nM to 5 nM. In one embodiment, $K_D$ is determined by surface plasmon resonance.

The term "antibody" broadly refers to an immunoglobulin (Ig) molecule, generally comprised of four polypeptide chains, two heavy (H) chains and two light (L) chains, or any functional fragment, mutant, variant, or derivative thereof, that retains the essential target binding features of an Ig molecule. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY) and class (e.g., IgG1, IgG2, IgG 3, IgG4, IgA1 and IgA2) or subclass.

The term "antigen binding portion" of an antibody (or simply "antibody portion"), as used herein, refers to one or more fragments of an antibody that retain the ability to specifically bind to an antigen (e.g., hTMEFF1). It has been shown that the antigen binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen binding portion" of an antibody include (i) a Fab fragment, a monovalent fragment consisting of the VL, VH, CL and CH1 domains; (ii) a F(ab')₂ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen binding portion" of an antibody. In certain embodiments, scFv molecules may be incorporated into a fusion protein. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5).

The term "antibody construct" as used herein refers to a polypeptide comprising one or more the antigen binding portions disclosed herein linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) *Proc. Natl. Acad. Sci. USA* 90:6444-6448; Poljak, R. J., et al. (1994) *Structure* 2:1121-1123). An immunoglobulin constant domain refers to a heavy or light chain constant domain. Antibody portions, such as Fab and F(ab')₂ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds TMEFF1 is substantially free of antibodies that specifically bind antigens other than TMEFF1). An isolated antibody that specifically binds TMEFF1 may, however, have cross-reactivity to other antigens, such as TMEFF1 molecules from other species. Moreover, an isolated antibody may be substantially free of other cellular material and/or chemicals.

The term "humanized antibody" refers to antibodies which comprise heavy and light chain variable region sequences from a nonhuman species (e.g., a mouse) but in which at least a portion of the VH and/or VL sequence has been altered to be more "human-like", i.e., more similar to human germline variable sequences. In particular, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')₂, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In other embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG1, IgG2, IgG3 and IgG4. The humanized antibody may comprise sequences from more than one class or isotype, and particular constant domains may be selected to optimize desired effector functions using techniques well-known in the art.

The terms "Kabat numbering," "Kabat definitions," and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) *Ann. NY Acad, Sci.* 190:382-391 and, Kabat, E. A., et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the term "CDR" refers to the complementarity determining region within antibody variable sequences. There are three CDRs in each of the variable regions of the heavy chain (HC) and the light chain (LC), which are designated CDR1, CDR2 and CDR3 (or specifically HC CDR1, HC CDR2, HC CDR3, LC CDR1, LC CDR2, and LC CDR3), for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia &Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. In one embodiment, the disclosure includes an amino acid sequence having at least 80%, at least 85%, at least 90%, at least 95%, at least 96%, at least 97%, at least 98%, or at least 99% identity to an amino acid sequence set forth in any one of SEQ ID NOs: 1 to 164.

The term "multivalent antibody" is used herein to denote an antibody comprising two or more antigen binding sites. In certain embodiments, the multivalent antibody may be engineered to have the three or more antigen binding sites, and is generally not a naturally occurring antibody.

The term "multispecific antibody" refers to an antibody capable of binding two or more unrelated antigens.

The term "dual variable domain" or "DVD," as used interchangeably herein, are antigen binding proteins that comprise two or more antigen binding sites and are tetravalent or multivalent binding proteins. Such DVDs may be monospecific, i.e., capable of binding one antigen or multispecific, i.e. capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. In one embodiment, the CDRs described herein are used in an anti-TMEFF1 DVD.

The term "activity" includes activities such as the binding specificity/affinity of an antibody or ADC for an antigen, for example, an anti-hTMEFF1 antibody that binds to an TMEFF1 antigen. In one embodiment, an anti-TMEFF1 antibody or anti-TMEFF1 ADC activity includes, but it not limited to, binding to TMEFF1 in vitro; binding to TMEFF1 on cells expressing TMEFF1 in vivo; inducing cell death in cells expressing TMEFF1, including cancer cells; inhibiting cancer cell invasion and metastasis; decreasing or inhibiting cancer; and decreasing or inhibiting tumor cellular proliferation or tumor growth in vivo. In one embodiment, an anti-TMEFF1 antibody or ADC, is capable of being internalized into a cell expressing TMEFF1.

The term "epitope" refers to a region of an antigen that is bound by an antibody, antibody portion, or ADC. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) *Ann. Biol. Clin.* 51:19-26; Jonsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$k_{on}$" or "$k_a$", as used herein, is intended to refer to the on rate constant for association of an antibody to the antigen to form the antibody/antigen complex.

The term "$k_{of}$" or "$k_d$", as used herein, is intended to refer to the off rate constant for dissociation of an antibody from the antibody/antigen complex.

The term "$K_D$", as used herein, is intended to refer to the equilibrium dissociation constant of a particular antibody-antigen interaction. $K_D$ is calculated by $k_a/k_d$. In one embodiment, the antibodies of the invention have a $K_D$ of about 2,000 nM or less, about 1,000 nM or less, about 500 nM or less, about 200 nM or less, about 100 nM or less, about 75 nM or less, about 50 nM or less, about 43 nM or less, about 25 nM or less, about 20 nM or less, about 19 nM or less, about 18 nM or less, about 17 nM or less, about 16 nM or less, about 15 nM or less, about 14 nM or less, about 13 nM or less, about 12 nM or less, about 11 nM or less, about 10 nM or less, about 9 nM or less, about 8 nM or less, about 7 nM or less, about 6 nM or less, about 5 nM or less, about 4 nM or less, about 3 nM or less, about 2 nM or less, about 1 nM or less, about 0.5 nM or less, about 0.3 nM or less, about 0.1 nM or less, or about 0.01 nM or less, or about 0.001 nM or less. In one embodiment, the antibodies of the invention have a $K_D$ of between about 1 pM (0.001 nM) to 2,000 nM, between about 500 pM (0.5 nM) to 1,000 nM, between about 500 pM (0.5 nM) to 500 nM, between about 1 nM) to 200 nM, between about 1 nM to 100 nM, between about 1 nM to 50 nM, between about 1 nM to 20 nM, or between about 1 nM to 5 nM.

The term "competitive binding", as used herein, refers to a situation in which a first antibody competes with a second antibody, for a binding site on a third molecule, e.g., an antigen. In one embodiment, competitive binding between two antibodies is determined using FACS analysis.

The term "competitive binding assay" is an assay used to determine whether two or more antibodies bind to the same epitope. In one embodiment, a competitive binding assay is a competition fluorescent activated cell sorting (FACS) assay which is used to determine whether two or more antibodies bind to the same epitope by determining whether the fluorescent signal of a labeled antibody is reduced due to the introduction of a non-labeled antibody, where competition for the same epitope will lower the level of fluorescence.

The term "labeled antibody" as used herein, refers to an antibody, or an antigen binding portion thereof, with a label incorporated that provides for the identification of the binding protein, e.g., an antibody. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody-drug-conjugate" or "ADC" refers to a binding protein, such as an antibody or antigen binding portion thereof, chemically linked to one or more chemical drug(s) (also referred to herein as agent(s)) that may optionally be therapeutic or cytotoxic agents. In a preferred embodiment, an ADC includes an antibody, a cytotoxic or therapeutic drug, and a linker that enables attachment or conjugation of the drug to the antibody. An ADC typically has anywhere from 1 to 8 drugs conjugated to the antibody, including drug loaded species of 2, 4, 6, or 8. Non-limiting examples of drugs that may be included in the ADCs are mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, and radiosensitizers.

The terms "tomoregulin-1 antibody drug conjugate," "anti-TMEFF1 antibody drug conjugate," or "anti-TMEFF1 ADC", used interchangeably herein, refer to an ADC comprising an antibody that specifically binds to TMEFF1, whereby the antibody is conjugated to one or more chemical agent(s) or payloads. In one embodiment, the chemical agent is linked to the antibody via a linker.

The term "drug-to-antibody ratio" or "DAR" refers to the number of drugs, e.g., IGN, auristatin, or maytansinoid, attached to the antibody of the ADC. The DAR of an ADC can range from 1 to 8, although higher loads, e.g., 10, are also possible depending on the number of linkage site on an antibody. The term DAR may be used in reference to the number of drugs loaded onto an individual antibody, or, alternatively, may be used in reference to the average or mean DAR of a group of ADCs.

The term "TMEFF1 associated disorder," as used herein, includes any disorder or disease (including proliferative disorders, e.g., cancer) that is marked, diagnosed, detected or identified by a phenotypic or genotypic aberration of TMEFF1 genetic components or expression during the course or etiology of the disease or disorder. In this regard an TMEFF1 phenotypic aberration or determinant may, for example, comprise increased or decreased levels of TMEFF1 protein expression on one cell population, e.g., a cancer cell population, as compared to another cell population, e.g., a normal cell population, or increased or decreased TMEFF1 protein expression on certain definable cell populations, or increased or decreased TMEFF1 protein expression at an inappropriate phase or stage of a cell lifecycle. It will be appreciated that similar expression patterns of genotypic determinants (e.g., mRNA transcription levels) of TMEFF1 may also be used to classify or detect TMEFF1 associated disorders. In one embodiment, an TMEFF1 associated disorder is cancer, including, but not limited to lung cancer, e.g., small cell lung cancer, ovarian cancer or triple negative breast cancer (TNBC).

The term "cancer," as used herein, is meant to refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include, but are not limited to, lung cancer, small cell lung cancer, non-small cell lung cancer, breast cancer (Luminal A, TNBC, Ductal), ovarian cancer, prostate cancer, squamous cell tumors, squamous cell carcinoma (e.g., squamous cell lung cancer or squamous cell head and neck cancer), neuroendocrine tumors, urothelial cancer, vulvar cancer, mesothelioma, liver cancer, bone cancer, pancreatic cancer, skin cancer, cancer of the head or neck, cutaneous or intraocular malignant melanoma, renal cancer, uterine cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, environmentally induced cancers including those induced by asbestos, hematologic malignancies including, for example, multiple myeloma, B-cell lymphoma, Hodgkin lyimphomia/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, imirunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers. PVNS, acute myeloid leukemia, adrenocortico carcinoma, bladder urothelial carcinoma, cervical squamous cell carcinoma, endocervical adenocarcinoma, diffuse large B cell lymphoma, glioblastoma multiforme, chronic lymphocytic leukemia, brain lower grade glioma, head and neck squamous cell carcinoma, hepatocellular carcinoma, lung adenocarcinoma, large squamous cell carcinoma, cutaneous melanoma, ovarial serous cystadenocarcinoma, gastric cancer, soft tissue sarcoma, testicular germ cell cancer, thymoma, thyroid carcinoma, uterine corpus endometrial carcinoma, uterine carcinosarcoma, kidney renal clear cell carcinoma, and kidney renal papillary cell carcinoma. The present invention is also applicable to treatment of metastatic cancers.

In one embodiment, the antibodies or ADCs of the invention are administered to a patient having a solid tumor, including an advanced solid tumor, e.g., a breast tumor, an ovarian tumor, or a lung tumor. In another embodiment, administration of ADCs of the invention induce cell death of TMEFF1 expressing cells.

The term "TMEFF1 expressing tumor," as used herein, refers to a tumor which expresses TMEFF1 protein, such as a small cell lung cancer tumor, an ovarian cancer tumor, or a breast cancer (e.g., TNBC) tumor. In one embodiment, TMEFF1 expression in a tumor is determined using immunohistochemical staining of tumor cell membranes, where any immunohistochemical staining above background level in a tumor sample indicates that the tumor is an TMEFF1 expressing tumor. In another embodiment, an TMEFF1 expressing tumor is identified in a patient when greater than 1%, greater than 2%, greater than 3%, greater than 4%, greater than 5%, greater than 6%, greater than 7%, greater than 8%, greater than 9%, greater than 10%, greater than 15%, greater than 20%, greater than 25%, or greater than 30%, greater than 40%, greater than 50%, greater than 60%, greater than 70%, greater than 80%, greater than 90%, or more of the cells in a tumor sample are positive for TMEFF1 expression. In another embodiment, TMEFF1 positive expression is determined based on membrane staining as determined by, e.g., immunohistochemistry (IHC) analysis.

An TMEFF1 expressing tumor is identified as having an "elevated level of TMEFF1" or "expressing TMEFF1 at an elevated level" when the level of TMEFF1 is higher than in tissue surrounding the cancer. In some embodiments, an "elevated level of TMEFF1" is one in which 5% or more of the cells in a tumor sample have membrane staining. In some embodiments a "high level" in regard to TMEFF1 is 5% or more staining. for example, 5, 10, 20, 30, 40, 50, 60, 70, 80, 90, or 100% of the cells in the tumor sample are stained. In some embodiments, the protein expression levels can be measured by IHC analysis.

An TMEFF1 expressing tumor is identified as having a "low level of TMEFF1" or "expressing TMEFF1 at a low level" is one in which 5% or less of the cells in a tumor sample have membrane staining. In some embodiments a "low level" in regard to TMEFF1 is 5% or less staining, for example, 4.9, 4.5, 4, 3, 2, 1, 0.9, 0.8, 0.7, 0.6, 0.5, 0.4, 0.3, 0.2, 0.1% or less of the cells in the tumor sample are stained. In some embodiments, the protein expression levels can be measured by IHC analysis.

A cell that expresses no TMEFF1 can also be described as expressing a "low level of TMEFF1". Thus, the phrase "expresses a low level of TMEFF1" encompasses no TMEFF1 expression. In some embodiments, a low level of TMEFF1 is within the background staining levels. In some embodiments, a sample that is TMEFF1 "negative" has no TMEFF1 expression or a low level of TMEFF1. In some embodiments, TMEFF1 staining is negative when no or less than 5%, 4%, 3%, 2%, or 1% of the cells have membrane staining for TMEFF1.

As used herein, the term "non-cancer sample" or "normal sample" refers to a sample from a normal tissue (e.g., a lung, breast, or ovarian tissue sample). In some embodiments, the non-cancer sample comes from the same subject, but is from a different part of the subject than that being tested. In some embodiments, the non-cancer sample is from a tissue area surrounding or adjacent to the cancer, e.g., small cell lung cancer, TNBC, or ovarian cancer. In some embodiments, the non-cancer sample is not from the subject being tested, but is a sample from a subject known to have, or not to have, a disorder in question (for example, a particular cancer such as small cell lung cancer, ovarian cancer, TNBC or another TMEFF1 related disorder). In some embodiments, the non-cancer sample is from the same subject, but from a point in time before the subject developed cancer. In some embodiments, the reference sample is from a benign cancer sample (for example, benign lung cancer, benign breast tumor or a benign ovarian tumor sample), from the same or a different subject. Methods for detecting expression of TMEFF1 in a tumor are known in the art.

The terms "overexpress," "overexpression," or "overexpressed" interchangeably refer to a gene that is transcribed or translated at a detectably greater level, usually in a cancer cell, in comparison to a normal cell. Overexpression therefore refers to both overexpression of protein and RNA (due to increased transcription, post transcriptional processing, translation, post translational processing, altered stability, and altered protein degradation), as well as local overexpression due to altered protein traffic patterns (increased nuclear localization), and augmented functional activity, e.g., as in an increased enzyme hydrolysis of substrate. Thus, overexpression refers to either protein or RNA levels. Overexpression can also be by 5%, 10%, 20%, 30%, 40%, 50%, 60%, 70%, 80%, 90% or more in comparison to a normal cell or comparison cell. In certain embodiments, the anti-TMEFF1 antibodies or ADCs are used to treat solid tumors likely to overexpress TMEFF1.

The term "administering" as used herein is meant to refer to the delivery of a substance (e.g., an anti-TMEFF1 antibody or ADC) to achieve a therapeutic objective (e.g., the treatment of an TMEFF1-associated disorder or the inhibition or reduction of a tumor). Modes of administration may be parenteral, enteral and topical. Parenteral administration is usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "combination therapy", as used herein, refers to the administration of two or more therapeutic substances, e.g., an anti-TMEFF1 antibody or ADC and an additional therapeutic agent. The additional therapeutic agent may be administered concomitant with, prior to, or following the administration of the anti-TMEFF1 antibody or ADC. In one embodiment, the combination therapy has a synergistic effect on decreasing or inhibiting cancer, tumor cellular proliferation or tumor growth, or tumor invasion or metastasis.

As used herein, the term "effective amount" or "therapeutically effective amount" refers to the amount of a drug, e.g., an antibody or ADC, which is sufficient to reduce or ameliorate the severity and/or duration of a disorder, e.g., cancer, or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent). The effective amount of an antibody or ADC may, for example, inhibit tumor growth (e.g., inhibit an increase in tumor volume), decrease tumor growth (e.g., decrease tumor volume), reduce the number of cancer cells, and/or relieve to some extent one or more of the symptoms associated with the cancer. The effective amount may, for example, improve disease free survival (DFS), improve overall survival (OS), or decrease likelihood of recurrence.

Various aspects of the invention are described in further detail in the following subsections.

II. Anti-TMEFF1 Antibodies

One aspect disclosed herein provides humanized anti-TMEFF1 antibodies, or antigen binding portions thereof. Another aspect disclosed herein provides human anti-TMEFF1 antibodies, or antigen binding portions thereof. In one embodiment, the antibodies disclosed herein bind human TMEFF1. In another embodiment, the antibodies disclosed herein bind monkey TMEFF1. In another embodiment, the antibodies disclosed herein bind human TMEFF1 expressed on tumor cells.

Another aspect disclosed herein features antibody drug conjugates (ADCs) comprising an anti-TMEFF1 antibody described herein and at least one drug(s). The antibodies or ADCs disclosed herein have characteristics including, but not limited to, binding to human TMEFF1 in vitro, binding human TMEFF1 expressed on tumor cells, and decreasing or inhibiting cancer, tumor cellular proliferation or tumor growth, or tumor invasion and metastasis. ADCs disclosed herein, in particular, have characteristics including, but not limited to, inducing cell death in cells expressing TMEFF1, e.g., cancer cells expressing TMEFF1. In one embodiment, an anti-TMEFF1 antibody or ADC disclosed herein is capable of being internalized into a cell expressing TMEFF1.

In one embodiment, the anti-TMEFF1 antibodies, ADCs, or antigen binding portions thereof, bind to the follistatin 1 domain of TMEFF1. In another embodiment, the anti-TMEFF1 antibodies, ADCs, or antigen binding portions thereof, bind to the follistatin 2 domain of TMEFF1. In still another embodiment, the anti-TMEFF1 antibodies, ADCs, or antigen binding portions thereof, do not bind to the follistatin 1 domain or the follistatin 2 domain of TMEFF1.

In one embodiment, anti-TMEFF1 antibodies are disclosed which have the ability to bind to TMEFF1, as described in the Examples below. Collectively, the novel antibodies are referred to herein as "TMEFF1 antibodies." The anti-TMEFF1 antibodies, ADCs, or antigen binding portions thereof, are able to inhibit or decrease tumor growth in vivo. In various embodiments, anti-TMEFF1 antibodies, ADCs, or antigen binding portions thereof, are capable of modulating a biological function of TMEFF1, e.g., modulating growth factor signaling. In other embodiments of the foregoing aspects, the anti-TMEFF1 antibodies, ADCs, or antigen binding portions thereof, bind TMEFF1 on cells expressing TMEFF1. Thus, the disclosure includes anti-TMEFF1 antibodies, ADCs, or antigen binding portions thereof, that are effective at inhibiting or decreasing tumor growth.

Antibodies having combinations of any of the aforementioned characteristics are contemplated as aspects of the disclosure. ADCs, described in more detail below, may also have any of the foregoing characteristics.

One aspect of the disclosure features an anti-human TMEFF1 (anti-hTMEFF1) Antibody Drug Conjugate (ADC) comprising an anti-hTMEFF1 antibody conjugated to a drug via a linker. Exemplary anti-TMEFF1 antibodies (and sequences thereof) that can be used in the ADCs are described herein.

The anti-TMEFF1 antibodies described herein provide the ADCs with the ability to bind to TMEFF1 such that the cytotoxic molecule attached to the antibody may be delivered to the TMEFF1-expressing cell, particularly a TMEFF1 expressing cancer cell.

While the term "antibody" is used throughout, it should be noted that antibody portions (i.e., antigen-binding portions of an anti-TMEFF1 antibody) are also included in the disclosure and may be included in the embodiments (methods and compositions) described throughout. For example, an anti-TMEFF1 antibody portion may be conjugated to the drugs, as described herein. In certain embodiments, an anti-TMEFF1 antibody binding portion is a Fab, a Fab', a F(ab')2, a Fv, a disulfide linked Fv, an scFv, a single domain antibody, or a diabody.

Example 2 describes the generation of 32 human recombinant TMEFF1 antibodies against the extracellular domain of human TMEFF1. The heavy and light chain variable region amino acid sequences for these human antibodies are set forth in Table 6, below.

Thus, in one embodiment, the disclosure includes human anti-hTMEFF1 antibodies, or antigen binding portions thereof, comprising a heavy chain variable region comprising an amino acid sequence selected from the group consisting of SEQ ID NOs:1, 9, 17, 25, 33, 38, 43, 49, 56, 62, 66, 71, 79, 85, 89, 96, 99, 103, 107, 114, 116, 118, 124, 129, 134, 142, 144, 147, 151, 157, and 160; and a light chain variable region comprising an amino acid sequence selected from the group consisting of 5, 13, 21, 29, 36, 41, 47, 53, 60, 64, 70, 75, 78, 82, 88, 93, 101, 106, 110, 117, 122, 128, 133, 138, 141, 133, 146, 149, 154, 159, and 163.

In one embodiment, the disclosure includes a human anti-hTMEFF1 antibody, or antigen binding portion thereof, comprising an HC CDR set (CDR1, CDR2, and CDR3) selected from those set forth in Table 6; and an LC CDR set (CDR1, CDR2, and CDR3) selected from those set forth in Table 6.

In one embodiment, an anti-TMEFF1 antibody, or antigen binding portion thereof, is the human antibody 34B7. The 34B7 antibody comprises a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6. In further embodiments, disclosed herein is an antibody having a heavy chain variable region comprising the amino acid sequence of SEQ ID NO: 1 and a light chain variable region comprising the amino acid sequence of SEQ ID NO: 5.

In some embodiments, an anti-TMEFF1 antibody, or antigen-binding portion thereof, comprises a heavy chain comprising an amino acid sequence set forth in SEQ ID NO: 1, or a sequence having at least 90%, 95%, 96%, 97%, 98%, or 99% identity to SEQ ID NO: 1, and/or a light chain comprising an amino acid sequence set forth in SEQ ID NO: 5, or a sequence having at least 90%, 95%, 96%, 97%, 98%, or 99% identity to SEQ ID NO: 5.

In one embodiment, the disclosure features an anti-TMEFF1 antibody, or antigen binding portion thereof, which is the human antibody M1F1. The M1F1 antibody comprises a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14. In further embodiments, the disclosure provides an antibody having a heavy chain variable region comprising the amino acid sequence of SEQ ID NO: 9 and a light chain variable region comprising the amino acid sequence of SEQ ID NO: 13.

In some embodiments, an anti-TMEFF1 antibody, or antigen-binding portion thereof, comprises a heavy chain comprising an amino acid sequence set forth in SEQ ID NO: 9, or a sequence having at least 90%, 95%, 96%, 97%, 98%, or 99% identity to SEQ ID NO: 9, and/or a light chain comprising an amino acid sequence set forth in SEQ ID NO: 13, or a sequence having at least 90%, 95%, 96%, 97%, 98%, or 99% identity to SEQ ID NO: 13.

In one embodiment, the disclosure features an anti-TMEFF1 antibody, or antigen binding portion thereof, which is the human antibody 31B7. The 31B7 antibody comprises a heavy chain variable region comprising a CDR3 domain comprising the amino acid sequence of SEQ ID NO: 20, a CDR2 domain comprising the amino acid sequence of SEQ ID NO: 19, and a CDR1 domain comprising the amino acid sequence of SEQ ID NO: 18, and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 22. In further embodiments, the disclosure provides an antibody having a heavy chain variable region comprising the amino acid sequence of SEQ ID NO: 17 and a light chain variable region comprising the amino acid sequence of SEQ ID NO: 21.

In some embodiments, an anti-TMEFF1 antibody, or antigen-binding portion thereof, comprises a heavy chain comprising an amino acid sequence set forth in SEQ ID NO: 17, or a sequence having at least 90%, 95%, 96%, 97%, 98%, or 99% identity to SEQ ID NO: 17, and/or a light chain comprising an amino acid sequence set forth in SEQ ID NO: 21, or a sequence having at least 90%, 95%, 96%, 97%, 98%, or 99% identity to SEQ ID NO: 21.

In one embodiment, the disclosure features an anti-TMEFF1 antibody, or antigen binding portion thereof, which is the human antibody M3. The M3 antibody comprises a heavy chain variable region comprising a CDR3 domain comprising the amino acid sequence of SEQ ID NO: 28, a CDR2 domain comprising the amino acid sequence of SEQ ID NO: 27, and a CDR1 domain comprising the amino acid sequence of SEQ ID NO: 26 and a light chain variable region comprising a CDR3 domain comprising the amino acid sequence of SEQ ID NO: 32, a CDR2 domain comprising the amino acid sequence of SEQ ID NO: 31, and a CDR1 domain comprising the amino acid sequence of SEQ ID NO: 30. In further embodiments, the disclosure provides an antibody having a heavy chain variable region comprising the amino acid sequence of SEQ ID NO: 25 and a light chain variable region comprising the amino acid sequence of SEQ ID NO: 29.

In some embodiments, an anti-TMEFF1 antibody, or antigen-binding portion thereof, comprises a heavy chain comprising an amino acid sequence set forth in SEQ ID NO: 25, or a sequence having at least 90%, 95%, 96%, 97%, 98%, or 99% identity to SEQ ID NO: 25, and/or a light chain comprising an amino acid sequence set forth in SEQ ID NO: 29, or a sequence having at least 90%, 95%, 96%, 97%, 98%, or 99% identity to SEQ ID NO: 29.

In one embodiment, the disclosure features an anti-TMEFF1 antibody, or antigen binding portion thereof, which is the human antibody 24F10. The 24F10 antibody comprises a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 18 and a light chain variable region comprising a CDR3 domain comprising the amino acid sequence of SEQ ID NO: 37, a CDR2 domain comprising the amino acid sequence of SEQ ID NO: 15, and a CDR1 domain comprising the amino acid sequence of SEQ ID NO: 14. In further embodiments, the disclosure provides an antibody having a heavy chain variable region comprising the amino acid sequence of SEQ ID NO: 33 and a light chain variable region comprising the amino acid sequence of SEQ ID NO: 36.

In some embodiments, an anti-TMEFF1 antibody, or antigen-binding portion thereof, comprises a heavy chain comprising an amino acid sequence set forth in SEQ ID NO: 33, or a sequence having at least 90%, 95%, 96%, 97%, 98%, or 99% identity to SEQ ID NO: 33, and/or a light chain comprising an amino acid sequence set forth in SEQ ID NO: 36, or a sequence having at least 90%, 95%, 96%, 97%, 98%, or 99% identity to SEQ ID NO: 36.

In one embodiment, the disclosure features an anti-TMEFF1 antibody, or antigen binding portion thereof, which is the human antibody 30C10. The 30C10 antibody comprises a heavy chain variable region comprising a CDR3 domain comprising the amino acid sequence of SEQ ID NO: 40, a CDR2 domain comprising the amino acid sequence of SEQ ID NO: 39, and a CDR1 domain comprising the amino acid sequence of SEQ ID NO: 18 and a light chain variable region comprising a CDR3 domain comprising the amino acid sequence of SEQ ID NO: 42, a CDR2 domain comprising the amino acid sequence of SEQ ID NO: 15, and a CDR1 domain comprising the amino acid sequence of SEQ ID NO: 14. In further embodiments, the disclosure provides an antibody having a heavy chain variable region comprising the amino acid sequence of SEQ ID NO: 38 and a light chain variable region comprising the amino acid sequence of SEQ ID NO: 41.

In some embodiments, an anti-TMEFF1 antibody, or antigen-binding portion thereof, comprises a heavy chain comprising an amino acid sequence set forth in SEQ ID NO: 38, or a sequence having at least 90%, 95%, 96%, 97%, 98%, or 99% identity to SEQ ID NO: 38, and/or a light chain comprising an amino acid sequence set forth in SEQ ID NO: 41, or a sequence having at least 90%, 95%, 96%, 97%, 98%, or 99% identity to SEQ ID NO: 41.

In one embodiment, the disclosure features an anti-TMEFF1 antibody, or antigen binding portion thereof, which is the human antibody 36H6. The 36H6 antibody comprises a heavy chain variable region comprising a CDR3 domain comprising the amino acid sequence of SEQ ID NO: 46, a CDR2 domain comprising the amino acid sequence of SEQ ID NO: 45, and a CDR1 domain comprising the amino acid sequence of SEQ ID NO: 44 and a light chain variable region comprising a CDR3 domain comprising the amino acid sequence of SEQ ID NO: 48, a CDR2 domain comprising the amino acid sequence of SEQ ID NO: 7, and a CDR1 domain comprising the amino acid sequence of SEQ ID NO: 6. In further embodiments, the disclosure provides an antibody having a heavy chain variable region comprising the amino acid sequence of SEQ ID NO: 43 and a light chain variable region comprising the amino acid sequence of SEQ ID NO: 47.

In some embodiments, an anti-TMEFF1 antibody, or antigen-binding portion thereof, comprises a heavy chain comprising an amino acid sequence set forth in SEQ ID NO: 43, or a sequence having at least 90%, 95%, 96%, 97%, 98%, or 99% identity to SEQ ID NO: 43, and/or a light chain comprising an amino acid sequence set forth in SEQ ID NO: 47, or a sequence having at least 90%, 95%, 96%, 97%, 98%, or 99% identity to SEQ ID NO: 47.

In one embodiment, the disclosure features an anti-TMEFF1 antibody, or antigen binding portion thereof, which is the human antibody 43A12H8. The 43A12H8 antibody comprises a heavy chain variable region comprising a CDR3 domain comprising the amino acid sequence of SEQ ID NO: 52, a CDR2 domain comprising the amino acid sequence of SEQ ID NO: 51, and a CDR1 domain comprising the amino acid sequence of SEQ ID NO: 50 and a light chain variable region comprising a CDR3 domain comprising the amino acid sequence of SEQ ID NO: 55, a CDR2 domain comprising the amino acid sequence of SEQ ID NO: 7, and a CDR1 domain comprising the amino acid sequence of SEQ ID NO: 54. In further embodiments, the disclosure provides an antibody having a heavy chain variable region comprising the amino acid sequence of SEQ ID NO: 49 and a light chain variable region comprising the amino acid sequence of SEQ ID NO: 53.

In some embodiments, an anti-TMEFF1 antibody, or antigen-binding portion thereof, comprises a heavy chain comprising an amino acid sequence set forth in SEQ ID NO: 49, or a sequence having at least 90%, 95%, 96%, 97%, 98%, or 99% identity to SEQ ID NO: 49, and/or a light chain comprising an amino acid sequence set forth in SEQ ID NO: 53, or a sequence having at least 90%, 95%, 96%, 97%, 98%, or 99% identity to SEQ ID NO: 53.

In one embodiment, the disclosure features an anti-TMEFF1 antibody, or antigen binding portion thereof, which is the human antibody 6C11. The 6C11 antibody comprises a heavy chain variable region comprising a CDR3 domain comprising the amino acid sequence of SEQ ID NO: 59, a CDR2 domain comprising the amino acid sequence of SEQ ID NO: 58, and a CDR1 domain comprising the amino acid sequence of SEQ ID NO: 57 and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 61. In further embodiments, the disclosure provides an antibody having a heavy chain variable region comprising the amino acid sequence of SEQ ID NO: 56 and a light chain variable region comprising the amino acid sequence of SEQ ID NO: 60.

In some embodiments, an anti-TMEFF1 antibody, or antigen-binding portion thereof, comprises a heavy chain comprising an amino acid sequence set forth in SEQ ID NO: 56, or a sequence having at least 90%, 95%, 96%, 97%, 98%, or 99% identity to SEQ ID NO: 56, and/or a light chain comprising an amino acid sequence set forth in SEQ ID NO: 60, or a sequence having at least 90%, 95%, 96%, 97%, 98%, or 99% identity to SEQ ID NO: 60.

In one embodiment, the disclosure features an anti-TMEFF1 antibody, or antigen binding portion thereof, which is the human antibody 19H1. The 19H1 antibody comprises a heavy chain variable region comprising a CDR3 domain comprising the amino acid sequence of SEQ ID NO: 59, a CDR2 domain comprising the amino acid sequence of SEQ ID NO: 63, and a CDR1 domain comprising the amino acid sequence of SEQ ID NO: 57 and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 65. In further embodiments, the disclosure provides an antibody having a heavy chain variable region comprising the amino acid sequence of SEQ ID NO: 62 and a light chain variable region comprising the amino acid sequence of SEQ ID NO: 64.

In some embodiments, an anti-TMEFF1 antibody, or antigen-binding portion thereof, comprises a heavy chain comprising an amino acid sequence set forth in SEQ ID NO: 62, or a sequence having at least 90%, 95%, 96%, 97%, 98%, or 99% identity to SEQ ID NO: 62, and/or a light chain comprising an amino acid sequence set forth in SEQ ID NO: 64, or a sequence having at least 90%, 95%, 96%, 97%, 98%, or 99% identity to SEQ ID NO: 64.

In one embodiment, the disclosure features an anti-TMEFF1 antibody, or antigen binding portion thereof, which is the human antibody 35B1. The 35B1 antibody comprises a heavy chain variable region comprising a CDR3 domain comprising the amino acid sequence of SEQ ID NO: 69, a CDR2 domain comprising the amino acid sequence of SEQ ID NO: 68, and a CDR1 domain comprising the amino acid sequence of SEQ ID NO: 67 and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6. In further embodiments, the disclosure provides an antibody having a heavy chain variable region comprising the amino acid sequence of SEQ ID NO: 66 and a light chain variable region comprising the amino acid sequence of SEQ ID NO: 70.

In some embodiments, an anti-TMEFF1 antibody, or antigen-binding portion thereof, comprises a heavy chain comprising an amino acid sequence set forth in SEQ ID NO: 66, or a sequence having at least 90%, 95%, 96%, 97%, 98%, or 99% identity to SEQ ID NO: 66, and/or a light chain comprising an amino acid sequence set forth in SEQ ID NO:

70, or a sequence having at least 90%, 95%, 96%, 97%, 98%, or 99% identity to SEQ ID NO: 70.

In one embodiment, the disclosure features an anti-TMEFF1 antibody, or antigen binding portion thereof, which is the human antibody M17. The M17 antibody comprises a heavy chain variable region comprising a CDR3 domain comprising the amino acid sequence of SEQ ID NO: 81, a CDR2 domain comprising the amino acid sequence of SEQ ID NO: 80, and a CDR1 domain comprising the amino acid sequence of SEQ ID NO: 50 and a light chain variable region comprising a CDR3 domain comprising the amino acid sequence of SEQ ID NO: 84, a CDR2 domain comprising the amino acid sequence of SEQ ID NO: 7, and a CDR1 domain comprising the amino acid sequence of SEQ ID NO: 83. In further embodiments, the disclosure provides an antibody having a heavy chain variable region comprising the amino acid sequence of SEQ ID NO: 79 and a light chain variable region comprising the amino acid sequence of SEQ ID NO: 82.

In some embodiments, an anti-TMEFF1 antibody, or antigen-binding portion thereof, comprises a heavy chain comprising an amino acid sequence set forth in SEQ ID NO: 79, or a sequence having at least 90%, 95%, 96%, 97%, 98%, or 99% identity to SEQ ID NO: 79, and/or a light chain comprising an amino acid sequence set forth in SEQ ID NO: 82, or a sequence having at least 90%, 95%, 96%, 97%, 98%, or 99% identity to SEQ ID NO: 82.

In one embodiment, the disclosure features an anti-TMEFF1 antibody, or antigen binding portion thereof, which is the human antibody 37G7. The 37G7 antibody comprises a heavy chain variable region comprising a CDR3 domain comprising the amino acid sequence of SEQ ID NO: 87, a CDR2 domain comprising the amino acid sequence of SEQ ID NO: 86, and a CDR1 domain comprising the amino acid sequence of SEQ ID NO: 2 and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6. In further embodiments, the disclosure provides an antibody having a heavy chain variable region comprising the amino acid sequence of SEQ ID NO: 85 and a light chain variable region comprising the amino acid sequence of SEQ ID NO: 88.

In some embodiments, an anti-TMEFF1 antibody, or antigen-binding portion thereof, comprises a heavy chain comprising an amino acid sequence set forth in SEQ ID NO: 85, or a sequence having at least 90%, 95%, 96%, 97%, 98%, or 99% identity to SEQ ID NO: 85, and/or a light chain comprising an amino acid sequence set forth in SEQ ID NO: 88, or a sequence having at least 90%, 95%, 96%, 97%, 98%, or 99% identity to SEQ ID NO: 88.

In one embodiment, the disclosure features an anti-TMEFF1 antibody, or antigen binding portion thereof, which is the human antibody 18C2. The 18C2 antibody comprises a heavy chain variable region comprising a CDR3 domain comprising the amino acid sequence of SEQ ID NO: 92, a CDR2 domain comprising the amino acid sequence of SEQ ID NO: 91, and a CDR1 domain comprising the amino acid sequence of SEQ ID NO: 90 and a light chain variable region comprising a CDR3 domain comprising the amino acid sequence of SEQ ID NO: 95, a CDR2 domain comprising the amino acid sequence of SEQ ID NO: 7, and a CDR1 domain comprising the amino acid sequence of SEQ ID NO: 94. In further embodiments, the disclosure provides an antibody having a heavy chain variable region comprising the amino acid sequence of SEQ ID NO: 89 and a light chain variable region comprising the amino acid sequence of SEQ ID NO: 93.

In some embodiments, an anti-TMEFF1 antibody, or antigen-binding portion thereof, comprises a heavy chain comprising an amino acid sequence set forth in SEQ ID NO: 89, or a sequence having at least 90%, 95%, 96%, 97%, 98%, or 99% identity to SEQ ID NO: 89, and/or a light chain comprising an amino acid sequence set forth in SEQ ID NO: 93, or a sequence having at least 90%, 95%, 96%, 97%, 98%, or 99% identity to SEQ ID NO: 93.

In one embodiment, the disclosure features an anti-TMEFF1 antibody, or antigen binding portion thereof, which is the human antibody 10C10. The 10C10 antibody comprises a heavy chain variable region comprising a CDR3 domain comprising the amino acid sequence of SEQ ID NO: 98, a CDR2 domain comprising the amino acid sequence of SEQ ID NO: 97, and a CDR1 domain comprising the amino acid sequence of SEQ ID NO: 90 and a light chain variable region comprising a CDR3 domain comprising the amino acid sequence of SEQ ID NO: 95, a CDR2 domain comprising the amino acid sequence of SEQ ID NO: 7, and a CDR1 domain comprising the amino acid sequence of SEQ ID NO: 94. In further embodiments, the disclosure provides an antibody having a heavy chain variable region comprising the amino acid sequence of SEQ ID NO: 96 and a light chain variable region comprising the amino acid sequence of SEQ ID NO: 93.

In some embodiments, an anti-TMEFF1 antibody, or antigen-binding portion thereof, comprises a heavy chain comprising an amino acid sequence set forth in SEQ ID NO: 96, or a sequence having at least 90%, 95%, 96%, 97%, 98%, or 99% identity to SEQ ID NO: 96, and/or a light chain comprising an amino acid sequence set forth in SEQ ID NO: 93, or a sequence having at least 90%, 95%, 96%, 97%, 98%, or 99% identity to SEQ ID NO: 93.

In one embodiment, the disclosure features an anti-TMEFF1 antibody, or antigen binding portion thereof, which is the human antibody 19D9. The 19D9 antibody comprises a heavy chain variable region comprising a CDR3 domain comprising the amino acid sequence of SEQ ID NO: 98, a CDR2 domain comprising the amino acid sequence of SEQ ID NO: 100, and a CDR1 domain comprising the amino acid sequence of SEQ ID NO: 90 and a light chain variable region comprising a CDR3 domain comprising the amino acid sequence of SEQ ID NO: 95, a CDR2 domain comprising the amino acid sequence of SEQ ID NO: 102, and a CDR1 domain comprising the amino acid sequence of SEQ ID NO: 94. In further embodiments, the disclosure provides an antibody having a heavy chain variable region comprising the amino acid sequence of SEQ ID NO: 99 and a light chain variable region comprising the amino acid sequence of SEQ ID NO: 101.

In some embodiments, an anti-TMEFF1 antibody, or antigen-binding portion thereof, comprises a heavy chain comprising an amino acid sequence set forth in SEQ ID NO: 99, or a sequence having at least 90%, 95%, 96%, 97%, 98%, or 99% identity to SEQ ID NO: 99, and/or a light chain comprising an amino acid sequence set forth in SEQ ID NO: 101, or a sequence having at least 90%, 95%, 96%, 97%, 98%, or 99% identity to SEQ ID NO: 101.

In one embodiment, the disclosure features an anti-TMEFF1 antibody, or antigen binding portion thereof, which is the human antibody 7F12. The 7F12 antibody comprises a heavy chain variable region comprising a CDR3 domain comprising the amino acid sequence of SEQ ID NO: 105, a CDR2 domain comprising the amino acid sequence of SEQ ID NO: 104, and a CDR1 domain comprising the amino acid sequence of SEQ ID NO: 90 and a light chain variable region comprising a CDR3 domain comprising the amino acid sequence of SEQ ID NO: 95, a CDR2 domain comprising the amino acid sequence of SEQ ID NO: 7, and a CDR1 domain comprising the amino acid sequence of SEQ ID NO: 94. In further embodiments, the disclosure provides an antibody having a heavy chain variable region comprising the amino acid sequence of SEQ ID NO: 103 and a light chain variable region comprising the amino acid sequence of SEQ ID NO: 106.

In some embodiments, an anti-TMEFF1 antibody, or antigen-binding portion thereof, comprises a heavy chain comprising an amino acid sequence set forth in SEQ ID NO: 103, or a sequence having at least 90%, 95%, 96%, 97%, 98%, or 99% identity to SEQ ID NO: 103, and/or a light chain comprising an amino acid sequence set forth in SEQ ID NO: 106, or a sequence having at least 90%, 95%, 96%, 97%, 98%, or 99% identity to SEQ ID NO: 106.

In one embodiment, the disclosure features an anti-TMEFF1 antibody, or antigen binding portion thereof, which is the human antibody 9D1. The 9D1 antibody comprises a heavy chain variable region comprising a CDR3 domain comprising the amino acid sequence of SEQ ID NO: 109, a CDR2 domain comprising the amino acid sequence of SEQ ID NO: 108, and a CDR1 domain comprising the amino acid sequence of SEQ ID NO: 18 and a light chain variable region comprising a CDR3 domain comprising the amino acid sequence of SEQ ID NO: 113, a CDR2 domain comprising the amino acid sequence of SEQ ID NO: 112, and a CDR1 domain comprising the amino acid sequence of SEQ ID NO: 111. In further embodiments, the disclosure provides an antibody having a heavy chain variable region comprising the amino acid sequence of SEQ ID NO: 107 and a light chain variable region comprising the amino acid sequence of SEQ ID NO: 110.

In some embodiments, an anti-TMEFF1 antibody, or antigen-binding portion thereof, comprises a heavy chain comprising an amino acid sequence set forth in SEQ ID NO: 107, or a sequence having at least 90%, 95%, 96%, 97%, 98%, or 99% identity to SEQ ID NO: 107, and/or a light chain comprising an amino acid sequence set forth in SEQ ID NO: 110, or a sequence having at least 90%, 95%, 96%, 97%, 98%, or 99% identity to SEQ ID NO: 110.

In one embodiment, the disclosure features an anti-TMEFF1 antibody, or antigen binding portion thereof, which is the human antibody M1H1. The M1H1 antibody comprises a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10 and a light chain variable region comprising a CDR3 domain comprising the amino acid sequence of SEQ ID NO: 16, a CDR2 domain comprising the amino acid sequence of SEQ ID NO: 7, and a CDR1 domain comprising the amino acid sequence of SEQ ID NO: 6. In further embodiments, the disclosure provides an antibody having a heavy chain variable region comprising the amino acid sequence of SEQ ID NO: 9 and a light chain variable region comprising the amino acid sequence of SEQ ID NO: 78.

In some embodiments, an anti-TMEFF1 antibody, or antigen-binding portion thereof, comprises a heavy chain comprising an amino acid sequence set forth in SEQ ID NO: 9, or a sequence having at least 90%, 95%, 96%, 97%, 98%, or 99% identity to SEQ ID NO: 9, and/or a light chain comprising an amino acid sequence set forth in SEQ ID NO: 78, or a sequence having at least 90%, 95%, 96%, 97%, 98%, or 99% identity to SEQ ID NO: 78.

In one embodiment, the disclosure features an anti-TMEFF1 antibody, or antigen binding portion thereof, which is the human antibody M33F. The M33F antibody comprises a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10 and a light chain variable region comprising a CDR3 domain comprising the amino acid sequence of SEQ ID NO: 16, a CDR2 domain comprising the amino acid sequence of SEQ ID NO: 7, and a CDR1 domain comprising the amino acid sequence of SEQ ID NO: 6. In further embodiments, the disclosure provides an antibody having a heavy chain variable region comprising the amino acid sequence of SEQ ID NO: 9 and a light chain variable region comprising the amino acid sequence of SEQ ID NO: 141.

In some embodiments, an anti-TMEFF1 antibody, or antigen-binding portion thereof, comprises a heavy chain comprising an amino acid sequence set forth in SEQ ID NO: 9, or a sequence having at least 90%, 95%, 96%, 97%, 98%, or 99% identity to SEQ ID NO: 9, and/or a light chain comprising an amino acid sequence set forth in SEQ ID NO: 141, or a sequence having at least 90%, 95%, 96%, 97%, 98%, or 99% identity to SEQ ID NO: 141.

In one embodiment, the disclosure features an anti-TMEFF1 antibody, or antigen binding portion thereof, which is the human antibody M10. The M10 antibody comprises a heavy chain variable region comprising a CDR3 domain comprising the amino acid sequence of SEQ ID NO: 127, a CDR2 domain comprising the amino acid sequence of SEQ ID NO: 126, and a CDR1 domain comprising the amino acid sequence of SEQ ID NO: 125 and a light chain variable region comprising a CDR3 domain comprising the amino acid sequence of SEQ ID NO: 42, a CDR2 domain comprising the amino acid sequence of SEQ ID NO: 15, and a CDR1 domain comprising the amino acid sequence of SEQ ID NO: 14. In further embodiments, the disclosure provides an antibody having a heavy chain variable region comprising the amino acid sequence of SEQ ID NO: 124 and a light chain variable region comprising the amino acid sequence of SEQ ID NO: 128.

In some embodiments, an anti-TMEFF1 antibody, or antigen-binding portion thereof, comprises a heavy chain comprising an amino acid sequence set forth in SEQ ID NO: 124, or a sequence having at least 90%, 95%, 96%, 97%, 98%, or 99% identity to SEQ ID NO: 124, and/or a light chain comprising an amino acid sequence set forth in SEQ ID NO: 128, or a sequence having at least 90%, 95%, 96%, 97%, 98%, or 99% identity to SEQ ID NO: 128.

In one embodiment, the disclosure features an anti-TMEFF1 antibody, or antigen binding portion thereof, which is the human antibody 45D8. The 45D8 antibody comprises a heavy chain variable region comprising a CDR3 domain comprising the amino acid sequence of SEQ ID NO: 132, a CDR2 domain comprising the amino acid sequence of SEQ ID NO: 131, and a CDR1 domain comprising the amino acid sequence of SEQ ID NO: 130 and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14. In further embodiments, the disclosure provides an antibody having a heavy chain variable region comprising the amino acid sequence of SEQ ID NO: 129 and a light chain variable region comprising the amino acid sequence of SEQ ID NO: 133.

In some embodiments, an anti-TMEFF1 antibody, or antigen-binding portion thereof, comprises a heavy chain comprising an amino acid sequence set forth in SEQ ID NO: 129, or a sequence having at least 90%, 95%, 96%, 97%, 98%, or 99% identity to SEQ ID NO: 129, and/or a light chain comprising an amino acid sequence set forth in SEQ ID NO: 133, or a sequence having at least 90%, 95%, 96%, 97%, 98%, or 99% identity to SEQ ID NO: 133.

In one embodiment, the disclosure features an anti-TMEFF1 antibody, or antigen binding portion thereof, which is the human antibody 11F9. The 11F9 antibody comprises a heavy chain variable region comprising a CDR3 domain comprising the amino acid sequence of SEQ ID NO: 74, a CDR2 domain comprising the amino acid sequence of SEQ ID NO: 73, and a CDR1 domain comprising the amino acid sequence of SEQ ID NO: 72 and a light chain variable region comprising a CDR3 domain comprising the amino acid sequence of SEQ ID NO: 77, a CDR2 domain comprising the amino acid sequence of SEQ ID NO: 112, and a CDR1 domain comprising the amino acid sequence of SEQ ID NO: 76. In further embodiments, the disclosure provides an antibody having a heavy chain variable region comprising the amino acid sequence of SEQ ID NO: 71 and a light chain variable region comprising the amino acid sequence of SEQ ID NO: 75.

In some embodiments, an anti-TMEFF1 antibody, or antigen-binding portion thereof, comprises a heavy chain comprising an amino acid sequence set forth in SEQ ID NO: 71, or a sequence having at least 90%, 95%, 96%, 97%, 98%, or 99% identity to SEQ ID NO: 71, and/or a light chain comprising an amino acid sequence set forth in SEQ ID NO: 75, or a sequence having at least 90%, 95%, 96%, 97%, 98%, or 99% identity to SEQ ID NO: 75.

In one embodiment, the disclosure features an anti-TMEFF1 antibody, or antigen binding portion thereof, which is the human antibody 3H9. The 3H9 antibody comprises a heavy chain variable region comprising a CDR3 domain comprising the amino acid sequence of SEQ ID NO: 74, a CDR2 domain comprising the amino acid sequence of SEQ ID NO: 116, and a CDR1 domain comprising the amino acid sequence of SEQ ID NO: 115 and a light chain variable region comprising a CDR3 domain comprising the amino acid sequence of SEQ ID NO: 77, a CDR2 domain comprising the amino acid sequence of SEQ ID NO: 112, and a CDR1 domain comprising the amino acid sequence of SEQ ID NO: 76. In further embodiments, the disclosure provides an antibody having a heavy chain variable region comprising the amino acid sequence of SEQ ID NO: 114 and a light chain variable region comprising the amino acid sequence of SEQ ID NO: 117.

In some embodiments, an anti-TMEFF1 antibody, or antigen-binding portion thereof, comprises a heavy chain comprising an amino acid sequence set forth in SEQ ID NO: 114, or a sequence having at least 90%, 95%, 96%, 97%, 98%, or 99% identity to SEQ ID NO: 114, and/or a light chain comprising an amino acid sequence set forth in SEQ ID NO: 117, or a sequence having at least 90%, 95%, 96%, 97%, 98%, or 99% identity to SEQ ID NO: 117.

In one embodiment, the disclosure features an anti-TMEFF1 antibody, or antigen binding portion thereof, which is the human antibody M35hA10. The M35hA10 antibody comprises a heavy chain variable region comprising a CDR3 domain comprising the amino acid sequence of SEQ ID NO: 137, a CDR2 domain comprising the amino acid sequence of SEQ ID NO: 136, and a CDR1 domain comprising the amino acid sequence of SEQ ID NO: 135 and a light chain variable region comprising a CDR3 domain comprising the amino acid sequence of SEQ ID NO: 140, a CDR2 domain comprising the amino acid sequence of SEQ ID NO: 23, and a CDR1 domain comprising the amino acid sequence of SEQ ID NO: 139. In further embodiments, the disclosure provides an antibody having a heavy chain variable region comprising the amino acid sequence of SEQ ID NO: 134 and a light chain variable region comprising the amino acid sequence of SEQ ID NO: 138.

In some embodiments, an anti-TMEFF1 antibody, or antigen-binding portion thereof, comprises a heavy chain comprising an amino acid sequence set forth in SEQ ID NO: 134, or a sequence having at least 90%, 95%, 96%, 97%, 98%, or 99% identity to SEQ ID NO: 134, and/or a light chain comprising an amino acid sequence set forth in SEQ ID NO: 138, or a sequence having at least 90%, 95%, 96%, 97%, 98%, or 99% identity to SEQ ID NO: 138.

In one embodiment, the disclosure features an anti-TMEFF1 antibody, or antigen binding portion thereof, which is the human antibody 29C4. The 29C4 antibody comprises a heavy chain variable region comprising a CDR3 domain comprising the amino acid sequence of SEQ ID NO: 121, a CDR2 domain comprising the amino acid sequence of SEQ ID NO: 120, and a CDR1 domain comprising the amino acid sequence of SEQ ID NO: 119 and a light chain variable region comprising a CDR3 domain comprising the amino acid sequence of SEQ ID NO: 123, a CDR2 domain comprising the amino acid sequence of SEQ ID NO: 7, and a CDR1 domain comprising the amino acid sequence of SEQ ID NO: 6. In further embodiments, the disclosure provides an antibody having a heavy chain variable region comprising the amino acid sequence of SEQ ID NO: 118 and a light chain variable region comprising the amino acid sequence of SEQ ID NO: 122.

In some embodiments, an anti-TMEFF1 antibody, or antigen-binding portion thereof, comprises a heavy chain comprising an amino acid sequence set forth in SEQ ID NO: 118, or a sequence having at least 90%, 95%, 96%, 97%, 98%, or 99% identity to SEQ ID NO: 118, and/or a light chain comprising an amino acid sequence set forth in SEQ ID NO: 122, or a sequence having at least 90%, 95%, 96%, 97%, 98%, or 99% identity to SEQ ID NO: 122.

In one embodiment, the disclosure features an anti-TMEFF1 antibody, or antigen binding portion thereof, which is the human antibody 43B2_56A6. The 43B2_56A6 antibody comprises a heavy chain variable region comprising a CDR3 domain comprising the amino acid sequence of SEQ ID NO: 132, a CDR2 domain comprising the amino acid sequence of SEQ ID NO: 143, and a CDR1 domain comprising the amino acid sequence of SEQ ID NO: 130 and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14. In further embodiments, the disclosure provides an antibody having a heavy chain variable region comprising the amino acid sequence of SEQ ID NO: 142 and a light chain variable region comprising the amino acid sequence of SEQ ID NO: 133.

In some embodiments, an anti-TMEFF1 antibody, or antigen-binding portion thereof, comprises a heavy chain comprising an amino acid sequence set forth in SEQ ID NO: 142, or a sequence having at least 90%, 95%, 96%, 97%, 98%, or 99% identity to SEQ ID NO: 142, and/or a light chain comprising an amino acid sequence set forth in SEQ ID NO: 133, or a sequence having at least 90%, 95%, 96%, 97%, 98%, or 99% identity to SEQ ID NO: 133.

In one embodiment, the disclosure features an anti-TMEFF1 antibody, or antigen binding portion thereof, which is the human antibody 50B4_56B2. The 50B4_56B2 antibody comprises a heavy chain variable region comprising a CDR3 domain comprising the amino acid sequence of SEQ ID NO: 132, a CDR2 domain comprising the amino acid sequence of SEQ ID NO: 145, and a CDR1 domain comprising the amino acid sequence of SEQ ID NO: 130 and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14. In further embodiments, the disclosure provides an antibody having a heavy chain variable region comprising the amino acid sequence of SEQ ID NO: 144 and a light chain variable region comprising the amino acid sequence of SEQ ID NO: 146.

In some embodiments, an anti-TMEFF1 antibody, or antigen-binding portion thereof, comprises a heavy chain comprising an amino acid sequence set forth in SEQ ID NO: 144, or a sequence having at least 90%, 95%, 96%, 97%, 98%, or 99% identity to SEQ ID NO: 144, and/or a light chain comprising an amino acid sequence set forth in SEQ ID NO: 146, or a sequence having at least 90%, 95%, 96%, 97%, 98%, or 99% identity to SEQ ID NO: 146.

In one embodiment, the disclosure features an anti-TMEFF1 antibody, or antigen binding portion thereof, which is the human antibody 3A6_56A1. The 3A6_56A1 antibody comprises a heavy chain variable region comprising a CDR3 domain comprising the amino acid sequence of SEQ ID NO: 59, a CDR2 domain comprising the amino acid sequence of SEQ ID NO: 58, and a CDR1 domain comprising the amino acid sequence of SEQ ID NO: 148 and a light chain variable region comprising a CDR3 domain comprising the amino acid sequence of SEQ ID NO: 150, a CDR2 domain comprising the amino acid sequence of SEQ ID NO: 23, and a CDR1 domain comprising the amino acid sequence of SEQ ID NO: 65. In further embodiments, the disclosure provides an antibody having a heavy chain variable region comprising the amino acid sequence of SEQ ID NO: 147 and a light chain variable region comprising the amino acid sequence of SEQ ID NO: 149.

In some embodiments, an anti-TMEFF1 antibody, or antigen-binding portion thereof, comprises a heavy chain comprising an amino acid sequence set forth in SEQ ID NO: 147, or a sequence having at least 90%, 95%, 96%, 97%, 98%, or 99% identity to SEQ ID NO: 147, and/or a light chain comprising an amino acid sequence set forth in SEQ ID NO: 149, or a sequence having at least 90%, 95%, 96%, 97%, 98%, or 99% identity to SEQ ID NO: 149.

In one embodiment, the disclosure features an anti-TMEFF1 antibody, or antigen binding portion thereof, which is the human antibody 46G4_60A5. The 46G4_60A5 antibody comprises a heavy chain variable region comprising a CDR3 domain comprising the amino acid sequence of SEQ ID NO: 153, a CDR2 domain comprising the amino acid sequence of SEQ ID NO: 152, and a CDR1 domain comprising the amino acid sequence of SEQ ID NO: 18 and a light chain variable region comprising a CDR3 domain comprising the amino acid sequence of SEQ ID NO: 156, a CDR2 domain comprising the amino acid sequence of SEQ ID NO: 155, and a CDR1 domain comprising the amino acid sequence of SEQ ID NO: 94. In further embodiments, the disclosure provides an antibody having a heavy chain variable region comprising the amino acid sequence of SEQ ID NO: 151 and a light chain variable region comprising the amino acid sequence of SEQ ID NO: 154.

In some embodiments, an anti-TMEFF1 antibody, or antigen-binding portion thereof, comprises a heavy chain comprising an amino acid sequence set forth in SEQ ID NO: 151, or a sequence having at least 90%, 95%, 96%, 97%, 98%, or 99% identity to SEQ ID NO: 151, and/or a light chain comprising an amino acid sequence set forth in SEQ ID NO: 154, or a sequence having at least 90%, 95%, 96%, 97%, 98%, or 99% identity to SEQ ID NO: 154.

In one embodiment, the disclosure features an anti-TMEFF1 antibody, or antigen binding portion thereof, which is the human antibody 34E1_56A4. The 34E1_56A4 antibody comprises a heavy chain variable region comprising a CDR3 domain comprising the amino acid sequence of SEQ ID NO: 20, a CDR2 domain comprising the amino acid sequence of SEQ ID NO: 108, and a CDR1 domain comprising the amino acid sequence of SEQ ID NO: 158 and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 22. In further embodiments, the disclosure provides an antibody having a heavy chain variable region comprising the amino acid sequence of SEQ ID NO: 157 and a light chain variable region comprising the amino acid sequence of SEQ ID NO: 159.

In some embodiments, an anti-TMEFF1 antibody, or antigen-binding portion thereof, comprises a heavy chain comprising an amino acid sequence set forth in SEQ ID NO: 157, or a sequence having at least 90%, 95%, 96%, 97%, 98%, or 99% identity to SEQ ID NO: 157, and/or a light chain comprising an amino acid sequence set forth in SEQ ID NO: 159, or a sequence having at least 90%, 95%, 96%, 97%, 98%, or 99% identity to SEQ ID NO: 159.

In one embodiment, the disclosure features an anti-TMEFF1 antibody, or antigen binding portion thereof, which is the human antibody 27G5_56A2. The 27G5_56A2 antibody comprises a heavy chain variable region comprising a CDR3 domain comprising the amino acid sequence of SEQ ID NO: 162, a CDR2 domain comprising the amino acid sequence of SEQ ID NO: 11, and a CDR1 domain comprising the amino acid sequence of SEQ ID NO: 161 and a light chain variable region comprising a CDR3 domain comprising the amino acid sequence of SEQ ID NO: 164, a CDR2 domain comprising the amino acid sequence of SEQ ID NO: 7, and a CDR1 domain comprising the amino acid sequence of SEQ ID NO: 54. In further embodiments, the disclosure provides an antibody having a heavy chain variable region comprising the amino acid sequence of SEQ ID NO: 160 and a light chain variable region comprising the amino acid sequence of SEQ ID NO: 163.

In some embodiments, an anti-TMEFF1 antibody, or antigen-binding portion thereof, comprises a heavy chain comprising an amino acid sequence set forth in SEQ ID NO: 160, or a sequence having at least 90%, 95%, 96%, 97%, 98%, or 99% identity to SEQ ID NO: 160, and/or a light chain comprising an amino acid sequence set forth in SEQ ID NO: 163, or a sequence having at least 90%, 95%, 96%, 97%, 98%, or 99% identity to SEQ ID NO: 163.

The foregoing anti-TMEFF1 antibody CDR sequences establish a novel family of TMEFF1 binding proteins, isolated in accordance with this disclosure, and comprising antigen binding polypeptides that include the CDR sequences listed in Table 6, as well as the Sequence Summary.

To generate and to select CDRs having preferred TMEFF1 binding and/or neutralizing activity with respect to hTMEFF1, standard methods known in the art for generating antibodies, or antigen binding portions thereof, and assessing the TMEFF1 binding and/or neutralizing characteristics of those antibodies, or antigen binding portions thereof, may be used, including but not limited to those specifically described herein (see, e.g., Example 2).

In certain embodiments, the antibody comprises a heavy chain constant region, such as an IgG1, IgG2, IgG3, IgG4, IgA, IgE, IgM, or IgD constant region. In certain embodiments, the anti-TMEFF1 antibody, or antigen binding portion thereof, comprises a heavy chain immunoglobulin constant domain selected from the group consisting of a human IgG constant domain, a human IgM constant domain, a human IgE constant domain, and a human IgA constant domain. In further embodiments, the antibody, or antigen binding portion thereof, has an IgG1 heavy chain constant region, an IgG2 heavy chain constant region, an IgG3 constant region, or an IgG4 heavy chain constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In certain embodiments, the anti-TMEFF1 antibody binding portion is a Fab, a Fab', a F(ab')2, a Fv, a disulfide linked Fv, an scFv, a single domain antibody, or a diabody.

In certain embodiments, the anti-TMEFF1 antibody, or antigen binding portion thereof, is a multispecific antibody, e.g. a bispecific antibody.

In certain embodiments, the anti-TMEFF1 antibody, or antigen binding portion thereof, comprises a heavy chain constant region comprising the amino acid sequence set forth in SEQ ID NO: 1 and/or a light chain constant region comprising the amino acid sequence set forth in SEQ ID NO: 5.

In certain embodiments, the anti-TMEFF1 antibody, or antigen binding portion thereof, comprises a heavy chain constant region comprising the amino acid sequence set forth in SEQ ID NO: 9 and/or a light chain constant region comprising the amino acid sequence set forth in SEQ ID NO: 13.

In certain embodiments, the anti-TMEFF1 antibody, or antigen binding portion thereof, comprises a heavy chain constant region comprising the amino acid sequence set forth in SEQ ID NO: 17 and/or a light chain constant region comprising the amino acid sequence set forth in SEQ ID NO: 21.

In certain embodiments, the anti-TMEFF1 antibody, or antigen binding portion thereof, comprises a heavy chain constant region comprising the amino acid sequence set forth in SEQ ID NO: 25 and/or a light chain constant region comprising the amino acid sequence set forth in SEQ ID NO: 29.

In certain embodiments, the anti-TMEFF1 antibody, or antigen binding portion thereof, comprises a heavy chain constant region comprising the amino acid sequence set forth in SEQ ID NO: 33 and/or a light chain constant region comprising the amino acid sequence set forth in SEQ ID NO: 36.

In certain embodiments, the anti-TMEFF1 antibody, or antigen binding portion thereof, comprises a heavy chain constant region comprising the amino acid sequence set forth in SEQ ID NO: 38 and/or a light chain constant region comprising the amino acid sequence set forth in SEQ ID NO: 41.

In certain embodiments, the anti-TMEFF1 antibody, or antigen binding portion thereof, comprises a heavy chain constant region comprising the amino acid sequence set forth in SEQ ID NO: 43 and/or a light chain constant region comprising the amino acid sequence set forth in SEQ ID NO: 47.

In certain embodiments, the anti-TMEFF1 antibody, or antigen binding portion thereof, comprises a heavy chain constant region comprising the amino acid sequence set forth in SEQ ID NO: 49 and/or a light chain constant region comprising the amino acid sequence set forth in SEQ ID NO: 53.

In certain embodiments, the anti-TMEFF1 antibody, or antigen binding portion thereof, comprises a heavy chain constant region comprising the amino acid sequence set forth in SEQ ID NO: 56 and/or a light chain constant region comprising the amino acid sequence set forth in SEQ ID NO: 60.

In certain embodiments, the anti-TMEFF1 antibody, or antigen binding portion thereof, comprises a heavy chain constant region comprising the amino acid sequence set forth in SEQ ID NO: 62 and/or a light chain constant region comprising the amino acid sequence set forth in SEQ ID NO: 64.

In certain embodiments, the anti-TMEFF1 antibody, or antigen binding portion thereof, comprises a heavy chain constant region comprising the amino acid sequence set forth in SEQ ID NO: 66 and/or a light chain constant region comprising the amino acid sequence set forth in SEQ ID NO: 70.

In certain embodiments, the anti-TMEFF1 antibody, or antigen binding portion thereof, comprises a heavy chain constant region comprising the amino acid sequence set forth in SEQ ID NO: 79 and/or a light chain constant region comprising the amino acid sequence set forth in SEQ ID NO: 82.

In certain embodiments, the anti-TMEFF1 antibody, or antigen binding portion thereof, comprises a heavy chain constant region comprising the amino acid sequence set forth in SEQ ID NO: 85 and/or a light chain constant region comprising the amino acid sequence set forth in SEQ ID NO: 88.

In certain embodiments, the anti-TMEFF1 antibody, or antigen binding portion thereof, comprises a heavy chain constant region comprising the amino acid sequence set forth in SEQ ID NO: 89 and/or a light chain constant region comprising the amino acid sequence set forth in SEQ ID NO: 93.

In certain embodiments, the anti-TMEFF1 antibody, or antigen binding portion thereof, comprises a heavy chain constant region comprising the amino acid sequence set forth in SEQ ID NO: 96 and/or a light chain constant region comprising the amino acid sequence set forth in SEQ ID NO: 93.

In certain embodiments, the anti-TMEFF1 antibody, or antigen binding portion thereof, comprises a heavy chain constant region comprising the amino acid sequence set forth in SEQ ID NO: 99 and/or a light chain constant region comprising the amino acid sequence set forth in SEQ ID NO: 101.

In certain embodiments, the anti-TMEFF1 antibody, or antigen binding portion thereof, comprises a heavy chain constant region comprising the amino acid sequence set forth in SEQ ID NO: 103 and/or a light chain constant region comprising the amino acid sequence set forth in SEQ ID NO: 106.

In certain embodiments, the anti-TMEFF1 antibody, or antigen binding portion thereof, comprises a heavy chain constant region comprising the amino acid sequence set forth in SEQ ID NO: 107 and/or a light chain constant region comprising the amino acid sequence set forth in SEQ ID NO: 110.

In certain embodiments, the anti-TMEFF1 antibody, or antigen binding portion thereof, comprises a heavy chain constant region comprising the amino acid sequence set forth in SEQ ID NO: 9 and/or a light chain constant region comprising the amino acid sequence set forth in SEQ ID NO: 78.

In certain embodiments, the anti-TMEFF1 antibody, or antigen binding portion thereof, comprises a heavy chain constant region comprising the amino acid sequence set forth in SEQ ID NO: 9 and/or a light chain constant region comprising the amino acid sequence set forth in SEQ ID NO: 141.

In certain embodiments, the anti-TMEFF1 antibody, or antigen binding portion thereof, comprises a heavy chain constant region comprising the amino acid sequence set forth in SEQ ID NO: 124 and/or a light chain constant region comprising the amino acid sequence set forth in SEQ ID NO: 128.

In certain embodiments, the anti-TMEFF1 antibody, or antigen binding portion thereof, comprises a heavy chain constant region comprising the amino acid sequence set forth in SEQ ID NO: 129 and/or a light chain constant region comprising the amino acid sequence set forth in SEQ ID NO: 133.

In certain embodiments, the anti-TMEFF1 antibody, or antigen binding portion thereof, comprises a heavy chain constant region comprising the amino acid sequence set forth in SEQ ID NO: 71 and/or a light chain constant region comprising the amino acid sequence set forth in SEQ ID NO: 75.

In certain embodiments, the anti-TMEFF1 antibody, or antigen binding portion thereof, comprises a heavy chain constant region comprising the amino acid sequence set forth in SEQ ID NO: 114 and/or a light chain constant region comprising the amino acid sequence set forth in SEQ ID NO: 117.

In certain embodiments, the anti-TMEFF1 antibody, or antigen binding portion thereof, comprises a heavy chain constant region comprising the amino acid sequence set forth in SEQ ID NO: 134 and/or a light chain constant region comprising the amino acid sequence set forth in SEQ ID NO: 138.

In certain embodiments, the anti-TMEFF1 antibody, or antigen binding portion thereof, comprises a heavy chain constant region comprising the amino acid sequence set forth in SEQ ID NO: 118 and/or a light chain constant region comprising the amino acid sequence set forth in SEQ ID NO: 122.

In certain embodiments, the anti-TMEFF1 antibody, or antigen binding portion thereof, comprises a heavy chain constant region comprising the amino acid sequence set forth in SEQ ID NO: 142 and/or a light chain constant region comprising the amino acid sequence set forth in SEQ ID NO: 133.

In certain embodiments, the anti-TMEFF1 antibody, or antigen binding portion thereof, comprises a heavy chain constant region comprising the amino acid sequence set forth in SEQ ID NO: 144 and/or a light chain constant region comprising the amino acid sequence set forth in SEQ ID NO: 146.

In certain embodiments, the anti-TMEFF1 antibody, or antigen binding portion thereof, comprises a heavy chain constant region comprising the amino acid sequence set forth in SEQ ID NO: 147 and/or a light chain constant region comprising the amino acid sequence set forth in SEQ ID NO: 149.

In certain embodiments, the anti-TMEFF1 antibody, or antigen binding portion thereof, comprises a heavy chain constant region comprising the amino acid sequence set forth in SEQ ID NO: 151 and/or a light chain constant region comprising the amino acid sequence set forth in SEQ ID NO: 154.

In certain embodiments, the anti-TMEFF1 antibody, or antigen binding portion thereof, comprises a heavy chain constant region comprising the amino acid sequence set forth in SEQ ID NO: 157 and/or a light chain constant region comprising the amino acid sequence set forth in SEQ ID NO: 159.

In certain embodiments, the anti-TMEFF1 antibody, or antigen binding portion thereof, comprises a heavy chain constant region comprising the amino acid sequence set forth in SEQ ID NO: 160 and/or a light chain constant region comprising the amino acid sequence set forth in SEQ ID NO: 163.

Replacements of amino acid residues in the Fc portion to alter antibody effector function have been described (Winter, et al. U.S. Pat. Nos. 5,648,260 and 5,624,821, incorporated by reference herein). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to Fc Rs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment includes a labeled anti-TMEFF1 antibody, or antibody portion thereof, where the antibody is derivatized or linked to one or more functional molecule(s) (e.g., another peptide or protein). For example, a labeled antibody can be derived by functionally linking an antibody or antibody portion of the disclosure (by chemical coupling, genetic fusion, noncovalent association or otherwise) to one or more other molecular entities, such as another antibody (e.g., a bispecific antibody or a diabody), a detectable agent, a pharmaceutical agent, a protein or peptide that can mediate the association of the antibody or antibody portion with another molecule (such as a streptavidin core region or a polyhistidine tag), and/or a cytotoxic or therapeutic agent selected from the group consisting of a mitotic inhibitor, an antitumor antibiotic, an immunomodulating agent, a vector for gene therapy, an alkylating agent, an antiangiogenic agent, an antimetabolite, a boron-containing agent, a chemoprotective agent, a hormone, an antihormone agent, a corticosteroid, a photoactive therapeutic agent, an oligonucleotide, a radionuclide agent, a topoisomerase inhibitor, a tyrosine kinase inhibitor, a radiosensitizer, and a combination thereof.

Useful detectable agents with which an antibody or antibody portion thereof, may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present the addition of hydrogen peroxide and diaminobenzidine leads to a colored reaction product, which is detectable. An antibody may also be derivatized with biotin, and detected through indirect measurement of avidin or streptavidin binding.

In one embodiment, the antibody is conjugated to an imaging agent. Examples of imaging agents that may be used in the compositions and methods described herein include, but are not limited to, a radiolabel (e.g., indium), an enzyme, a fluorescent label, a luminescent label, a bioluminescent label, a magnetic label, and biotin.

In one embodiment, the antibodies or ADCs are linked to a radiolabel, such as, but not limited to, indium ($^{111}$In). $^{111}$Indium may be used to label the antibodies and ADCs described herein for use in identifying TMEFF1 positive tumors. In a certain embodiment, anti-TMEFF1 antibodies (or ADCs) described herein are labeled with $^{111}$I via a bifunctional chelator which is a bifunctional cyclohexyl diethylenetriaminepentaacetic acid (DTPA) chelate (see U.S. Pat. Nos. 5,124,471; 5,434,287; and 5,286,850, each of which is incorporated herein by reference).

Another embodiment of the disclosure provides a glycosylated binding protein wherein the anti-TMEFF1 antibody or antigen binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, *Biotechnol. Prog.* 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., *Mol. Immunol.* (1993) 30:1361-1367), or result in increased affinity for the antigen (Wallick, S. C., et al., *Exp. Med.* (1988) 168:1099-1109; Wright, A., et al., *EMBO J.* (1991) 10:2717-2723).

One aspect of the disclosure is directed to generating glycosylation site mutants in which the O- or N-linked glycosylation site of the binding protein has been mutated. One skilled in the art can generate such mutants using standard well-known technologies. Glycosylation site mutants that retain the biological activity, but have increased or decreased binding activity, are another object of the disclosure.

In still another embodiment, the glycosylation of the anti-TMEFF1 antibody or antigen binding portion is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication WO2003016466A2, and U.S. Pat. Nos. 5,714,350 and 6,350,861, each of which is incorporated herein by reference in its entirety.

Additionally or alternatively, a modified anti-TMEFF1 antibody can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176,195; PCT Publications WO 03/035835; WO 99/54342 80, each of which is incorporated herein by reference in its entirety.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful may include, but are not limited to, glucose, galactose, mannose, fucose, n-acetylglucosamine and sialic acid. Preferably the glycosylated binding protein comprises glycosyl residues such that the glycosylation pattern is human.

Differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using recombinant techniques, a practitioner may generate antibodies or antigen binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. patent Publication Nos. 20040018590 and 20020137134 and PCT publication WO2005100584 A2).

Antibodies may be produced by any of a number of techniques. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express antibodies in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies disclosed herein include Chinese Hamster Ovary (CHO cells) (including dhfr– CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the disclosure. For example, it may be desirable to transfect a host cell with DNA encoding functional fragments of either the light chain and/or the heavy chain of an antibody. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the disclosure. In addition, bifunctional antibodies may be produced in which one heavy and one light chain are an antibody of the disclosure and the other heavy and light chain are specific for an antigen other than the antigens of interest by cross-linking an antibody of the disclosure to a second antibody by standard chemical crosslinking methods.

In a preferred system for recombinant expression of an antibody, or antigen binding portion thereof, a recombinant expression vector encoding both the antibody heavy chain and the antibody light chain is introduced into dhfr– CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the disclosure provides a method of synthesizing a recombinant antibody by culturing a host cell in a suitable culture medium until a recombinant antibody is synthesized. Recombinant antibodies may be produced using nucleic acid molecules corresponding to the amino acid sequences disclosed herein. In one embodiment, the nucleic acid molecules set forth in SEQ ID NOs: 165-228 are used in the production of a recombinant antibody. The method can further comprise isolating the recombinant antibody from the culture medium.

III. Anti-TMEFF1 Antibody Drug Conjugates (ADCs)

Anti-TMEFF1 antibodies described herein may be conjugated to a drug moiety to form an anti-TMEFF1 Antibody Drug Conjugate (ADC). Antibody-drug conjugates (ADCs) may increase the therapeutic efficacy of antibodies in treating disease, e.g., cancer, due to the ability of the ADC to selectively deliver one or more drug moiety(s) to target tissues or cells, e.g., TMEFF1 expressing tumors or TMEFF1 expressing cells. Thus, in certain embodiments, the disclosure provides anti-TMEFF1 ADCs for therapeutic use, e.g., treatment of cancer.

Anti-TMEFF1 ADCs comprise an anti-TMEFF1 antibody, i.e., an antibody that specifically binds to TMEFF1, linked to one or more drug moieties. The specificity of the ADC is defined by the specificity of the antibody, i.e., anti-TMEFF1. In one embodiment, an anti-TMEFF1 antibody is linked to one or more cytotoxic drug(s) which is delivered internally to a cancer cell expressing TMEFF1.

Examples of drugs that may be used in the anti-TMEFF1 ADCs are provided below, as are linkers that may be used to conjugate the antibody and the one or more drug(s). The terms "drug," "agent," and "drug moiety" are used interchangeably herein. The terms "linked" and "conjugated" are also used interchangeably herein and indicate that the antibody and moiety are covalently linked.

In some embodiments, the ADC has the following formula (formula I):

$$Ab\text{-}(L\text{-}D)_n \qquad (I)$$

wherein Ab an anti-TMEFF1 antibody described herein, and (L-D) is a Linker-Drug moiety. The Linker-Drug moiety is made of L- which is a Linker, and -D, which is a drug moiety having, for example, cytostatic, cytotoxic, or otherwise therapeutic activity against a target cell, e.g., a cell expressing TMEFF1; and n is an integer from 1 to 20. In some embodiments, n ranges from 1 to 8, 1 to 7, 1 to 6, 1 to 5, 1 to 4, 1 to 3, 1 to 2, or is 1. The DAR of an ADC is equivalent to the "n" referred to in Formula I.

Additional details regarding drugs (D of Formula I) and linkers (L of Formula I) that may be used in the ADCs, as well as alternative ADC structures, are described below.

A. Anti-TMEFF1 ADCs: Exemplary Drugs for Conjugation

Anti-TMEFF1 antibodies may be used in ADCs to target one or more drug(s) to a cell of interest, e.g., a cell expressing TMEFF1. The anti-TMEFF1 ADCs disclosed herein provide a targeted therapy that may, for example, reduce the side effects often seen with anti-cancer therapies, as the one or more drug(s) is delivered to a specific cell. In one embodiment, the drug used in an ADC is MMAE. In another embodiment, the drug used in an ADC is maleimidocaproyl-Va-Cit-MMAE (vcMMAE).

Examples of drugs that may be used in ADCs, i.e., drugs that may be conjugated to the anti-TMEFF1 antibodies, are provided below, and include mitotic inhibitors, antitumor antibiotics, immunomodulating agents, gene therapy vectors, alkylating agents, antiangiogenic agents, antimetabolites, boron-containing agents, chemoprotective agents, hormone agents, glucocorticoids, photoactive therapeutic agents, oligonucleotides, radioactive isotopes, radiosensitizers, topoisomerase inhibitors, tyrosine kinase inhibitors, and combinations thereof.

1. Mitotic Inhibitors

In one aspect, anti-TMEFF1 antibodies may be conjugated to one or more mitotic inhibitor(s) to form an ADC for the treatment of cancer. The term "mitotic inhibitor", as used herein, refers to a cytotoxic and/or therapeutic agent that blocks mitosis or cell division, a biological process particularly important to cancer cells. A mitotic inhibitor disrupts microtubules such that cell division is prevented, often by effecting microtubule polymerization (e.g., inhibiting microtubule polymerization) or microtubule depolymerization (e.g., stabilizing the microtubule cytoskeleton against depolymrization). Thus, in one embodiment, an anti-TMEFF1 antibody of the invention is conjugated to one or more mitotic inhibitor(s) that disrupts microtubule formation by inhibiting tubulin polymerization. In another embodiment, an anti-TMEFF1 antibody of the invention is conjugated to one or more mitotic inhibitor(s) that stabilizes the microtubule cytoskeleton from deploymerization. In one embodiment, the mitotic inhibitor used in the ADCs of the invention is Ixempra (ixabepilone). Examples of mitotic inhibitors that may be used in the anti-TMEFF1 ADCs of the invention are provided below. Included in the genus of mitotic inhibitors are auristatins, described below.

a. Dolastatins

The anti-TMEFF1 antibodies of the invention may be conjugated to at least one dolastatin to form an ADC. Dolastatins are short peptidic compounds isolated from the Indian Ocean sea hare *Dolabella auricularia* (see Pettit et al., J. Am. Chem. Soc., 1976, 98, 4677). Examples of dolastatins include dolastatin 10 and dolatstin 15. Dolastatin 15, a seven-subunit depsipeptide derived from *Dolabella auricularia*, and is a potent antimitotic agent structurally related to the antitubulin agent dolastatin 10, a five-subunit peptide obtained from the same organism. Thus, in one embodiment, the anti-TMEFF1 ADC of the invention comprises an anti-TMEFF1 antibody, as described herein, and at least one dolastatin. Auristatins are synthetic derivatives of dolastatin 10.

b. Auristatins

Anti-TMEFF1 antibodies may be conjugated to at least one auristatin. Auristatins represent a group of dolastatin analogs that have generally been shown to possess anticancer activity by interfering with microtubule dynamics and GTP hydrolysis, thereby inhibiting cellular division. For example, Auristatin E (U.S. Pat. No. 5,635,483) is a synthetic analogue of the marine natural product dolastatin 10, a compound that inhibits tubulin polymerization by binding to the same site on tubulin as the anticancer drug vincristine (G. R. Pettit, Prog. Chem. Org. Nat. Prod, 70: 1-79 (1997)). Dolastatin 10, auristatin PE, and auristatin E are linear peptides having four amino acids, three of which are unique to the dolastatin class of compounds. Exemplary embodiments of the auristatin subclass of mitotic inhibitors include, but are not limited to, monomethyl auristatin D (MMAD or auristatin D derivative), monomethyl auristatin E (MMAE or auristatin E derivative), monomethyl auristatin F (MMAF or auristatin F derivative), auristatin F phenylenediamine (AFP), auristatin EB (AEB), auristatin EFP (AEFP), and 5-benzoylvaleric acid-AE ester (AEVB). The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239, 104; 6,034,065; 5,780,588; 5,665,860; 5,663,149; 5,635, 483; 5,599,902; 5,554,725; 5,530,097; 5,521,284; 5,504, 191; 5,410,024; 5,138,036; 5,076,973; 4,986,988; 4,978, 744; 4,879,278; 4,816,444; and 4,486,414, each of which is incorporated by reference herein.

In one embodiment, anti-TMEFF1 antibodies are conjugated to at least one MMAE (mono-methyl auristatin E). Monomethyl auristatin E (MMAE, vedotin) inhibits cell division by blocking the polymerization of tubulin. Because of its super toxicity, it also cannot be used as a drug itself. In recent cancer therapy developments, it is linked to a monoclonal antibody (mAb) that recognizes a specific marker expression in cancer cells and directs MMAE to the cancer cells. In one embodiment, the linker linking MMAE to the anti-TMEFF1 antibody is stable in extracellular fluid (i.e., the medium or environment that is external to cells), but is cleaved by cathepsin once the ADC has bound to the specific cancer cell antigen and entered the cancer cell, thus releasing the toxic MMAE and activating the potent antimitotic mechanism.

The structure of MMAE is provided below.

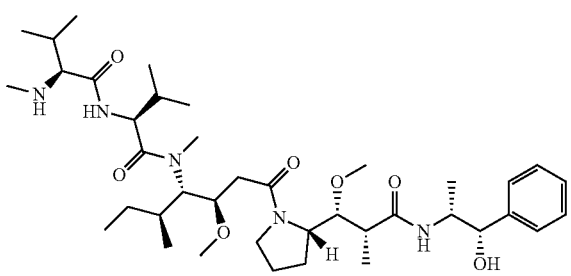

Monomethyl Auristatin E (MMAE)

In one embodiment, the antibody is coupled to a single drug and, therefore, has a DAR of 1. In certain embodiments, the ADC will have a DAR of 2 to 8, or, alternatively, 2 to 4.

c. Maytansinoids

The anti-TMEFF1 antibodies of the invention may be conjugated to at least one maytansinoid to form an ADC. Maytansinoids are potent antitumor agents that were originally isolated from members of the higher plant families Celastraceae, Rhamnaceae, and Euphorbiaceae, as well as some species of mosses (Kupchan et al, J. Am. Chem. Soc. 94:1354-1356 [1972]; Wani et al, J. Chem. Soc. Chem. Commun. 390: [1973]; Powell et al, J. Nat. Prod. 46:660-666 [1983]; Sakai et al, J. Nat. Prod. 51:845-850 [1988]; and Suwanborirux et al, Experientia 46:117-120 [1990]). Evidence suggests that maytansinoids inhibit mitosis by inhibiting polymerization of the microtubule protein tubulin, thereby preventing formation of microtubules (see, e.g., U.S. Pat. No. 6,441,163 and Remillard et al., Science, 189, 1002-1005 (1975)). Maytansinoids have been shown to inhibit tumor cell growth in vitro using cell culture models, and in vivo using laboratory animal systems. Moreover, the cytotoxicity of maytansinoids is 1,000-fold greater than conventional chemotherapeutic agents, such as, for example, methotrexate, daunorubicin, and vincristine (see, e.g., U.S. Pat. No. 5,208,020).

Maytansinoids to include maytansine, maytansinol, C-3 esters of maytansinol, and other maytansinol analogues and derivatives (see, e.g., U.S. Pat. Nos. 5,208,020 and 6,441,163, each of which is incorporated by reference herein). C-3 esters of maytansinol can be naturally occurring or synthetically derived. Moreover, both naturally occurring and synthetic C-3 maytansinol esters can be classified as a C-3 ester with simple carboxylic acids, or a C-3 ester with derivatives of N-methyl-L-alanine, the latter being more cytotoxic than the former. Synthetic maytansinoid analogues are described in, for example, Kupchan et al., J. Med. Chem., 21, 31-37 (1978).

Suitable maytansinoids for use in ADCs of the invention can be isolated from natural sources, synthetically produced, or semi-synthetically produced. Moreover, the maytansinoid can be modified in any suitable manner, so long as sufficient cytotoxicity is preserved in the ultimate conjugate molecule. In this regard, maytansinoids lack suitable functional groups to which antibodies can be linked. A linking moiety desirably is utilized to link the maytansinoid to the antibody to form the conjugate, and is described in more detail in the linker section below. The structure of an exemplary maytansinoid, mertansine (DM1), is provided below.

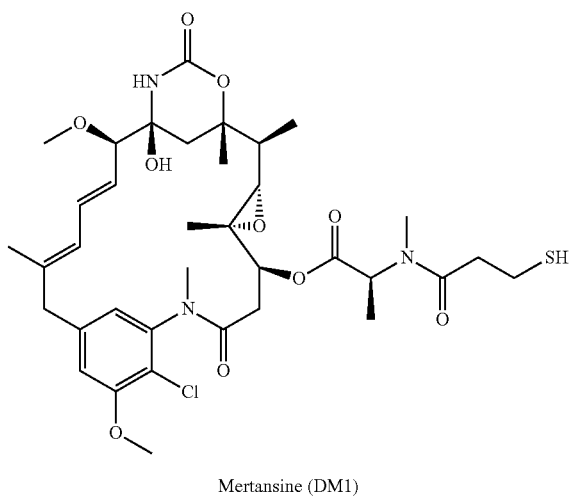

Mertansine (DM1)

Representative examples of maytansinoids include, but are not limited, to DM1 ($N^{2'}$-deacetyl-$N^{2'}$-(3-mercapto-1-oxopropyl)-maytansine; also referred to as mertansine, drug maytansinoid 1; ImmunoGen, Inc.; see also Chari et al. (1992) Cancer Res 52:127), DM2, DM3 ($N^{2'}$-deacetyl-$N^{2'}$-(4-mercapto-1-oxopentyl)-maytansine), DM4 (4-methyl-4-mercapto-1-oxopentyl)-maytansine), and maytansinol (a synthetic maytansinoid analog). Other examples of maytansinoids are described in U.S. Pat. No. 8,142,784, incorporated by reference herein.

Ansamitocins are a group of maytansinoid antibiotics that have been isolated from various bacterial sources. These compounds have potent antitumor activities. Representative examples include, but are not limited to ansamitocin P1, ansamitocin P2, ansamitocin P3, and ansamitocin P4.

In one embodiment of the invention, an anti-TMEFF1 antibody is conjugated to at least one DM1. In one embodiment, an anti-TMEFF1 antibody is conjugated to at least one DM2. In one embodiment, an anti-TMEFF1 antibody is conjugated to at least one DM3. In one embodiment, an anti-TMEFF1 antibody is conjugated to at least one DM4.

2. Antitumor Antibiotics

Anti-TMEFF1 antibodies may be conjugated to one or more antitumor antibiotic(s) for the treatment of cancer. As used herein, the term "antitumor antibiotic" means an antineoplastic drug that blocks cell growth by interfering with DNA and is made from a microorganism. Often, antitumor antibiotics either break up DNA strands or slow down or stop DNA synthesis. Examples of antitumor antibiotics that may be included in the anti-TMEFF1 ADCs include, but are not limited to, actinomycines (e.g., pyrrolo[2,1-c][1,4]benzodiazepines), anthracyclines, calicheamicins, and duocarmycins. In addition to the foregoing, additional antitumor antibiotics that may be used in the anti-TMEFF1 ADCs include bleomycin (Blenoxane, Bristol-Myers Squibb), mitomycin, and plicamycin (also known as mithramycin).

3. Immunomodulating Agents

In one aspect, anti-TMEFF1 antibodies may be conjugated to at least one immunomodulating agent. As used herein, the term "immunomodulating agent" refers to an agent that can stimulate or modify an immune response. In one embodiment, an immunomodulating agent is an immunostimuator which enhances a subject's immune response. In another embodiment, an immunomodulating agent is an immunosuppressant which prevents or decreases a subject's immune response. An immunomodulating agent may modulate myeloid cells (monocytes, macrophages, dendritic cells, megakaryocytes and granulocytes) or lymphoid cells (T cells, B cells and natural killer (NK) cells) and any further differentiated cell thereof. Representative examples include, but are not limited to, bacillus calmette-guerin (BCG) and levamisole (Ergamisol). Other examples of immunomodulating agents that may be used in the ADCs include, but are not limited to, cancer vaccines, and cytokines.

As used herein, the term "cancer vaccine" refers to a composition (e.g., a tumor antigen and a cytokine) that elicits a tumor-specific immune response. The response is elicited from the subject's own immune system by administering the cancer vaccine, or, in the case of the instant disclosure, administering an ADC comprising an anti-TMEFF1 antibody and a cancer vaccine. In preferred embodiments, the immune response results in the eradication of tumor cells in the body (e.g., primary or metastatic tumor cells). The use of cancer vaccines generally involves the administration of a particular antigen or group of antigens that are, for example, present on the surface a particular cancer cell, or present on the surface of a particular infectious agent shown to facilitate cancer formation. In some embodiments, the use of cancer vaccines is for prophylactic purposes, while in other embodiments, the use is for therapeutic purposes. Non-limiting examples of cancer vaccines that may be used in the anti-TMEFF1 ADCs include, recombinant bivalent human papillomavirus (HPV) vaccine types 16 and 18 vaccine (Cervarix, GlaxoSmithKline), recombinant quadrivalent human papillomavirus (HPV) types 6, 11, 16, and 18 vaccine (Gardasil, Merck & Company), and sipuleucel-T (Provenge, Dendreon). Thus, in one embodiment, the anti-TMEFF1 antibody is conjugated to at least one cancer vaccine that is either an immunostimulator or is an immunosuppressant.

The anti-TMEFF1 antibodies may be conjugated to at least one cytokine. The term "cytokine" generally refers to proteins released by one cell population which act on another cell as intercellular mediators. Cytokines directly stimulate immune effector cells and stromal cells at the tumor site and enhance tumor cell recognition by cytotoxic effector cells (Lee and Margolin (2011) Cancers 3:3856). Numerous animal tumor model studies have demonstrated that cytokines have broad anti-tumor activity and this has been translated into a number of cytokine-based approaches for cancer therapy (Lee and Margoli, supra). Recent years have seen a number of cytokines, including GM-CSF, IL-7, IL-12, IL-15, IL-18 and IL-21, enter clinical trials for patients with advanced cancer (Lee and Margoli, supra).

Examples of cytokines that may be used in the ADCs include, but are not limited to, parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor; mullerian-inhibiting substance; mouse gonadotropin-associated peptide; inhibin; activin; vascular endothelial growth factor; integrin; thrombopoietin (TPO); nerve growth factors such as NGF; platelet-growth factor; transforming growth factors (TGFs); insulin-like growth factor-I and -II; erythropoietin (EPO); osteoinductive factors; interferons such as interferon α, β, and γ, colony stimulating factors (CSFs); granulocyte-macrophage-C-SF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; tumor necrosis factor; and other polypeptide factors including LIF and kit ligand (KL). As used herein, the term cytokine includes proteins from natural sources or from recombinant cell culture and biologically active equivalents of the native sequence cytokines. Thus, in one embodiment, the disclosure provides an ADC comprising an anti-TMEFF1 antibody described herein and a cytokine.

The anti-TMEFF1 antibodies may be conjugated to at least one colony stimulating factor (CSF). Colony stimulating factors (CSFs) are growth factors that assist the bone marrow in making red blood cells. Because some cancer treatments (e.g., chemotherapy) can affect white blood cells (which help fight infection), colony-stimulating factors may be introduced to help support white blood cell levels and strengthen the immune system. Colony-stimulating factors may also be used following a bone marrow transplant to help the new marrow start producing white blood cells. Representative examples of CSFs that may be used in the anti-TMEFF1 ADCs include, but are not limited to erythropoietin (Epoetin), filgrastim (Neopogen (also known as granulocyte colony-stimulating factor (G-CSF); Amgen, Inc.), sargramostim (leukine (granulocyte-macrophage colony-stimulating factor and GM-CSF); Genzyme Corporation), promegapoietin, and Oprelvekin (recombinant IL-11; Pfizer, Inc.). Thus, in one embodiment, an ADC may comprise an anti-TMEFF1 antibody described herein and a CSF.

4. Alkylating Agents

The anti-TMEFF1 antibodies may be conjugated to one or more alkylating agent(s). Alkylating agents are a class of antineoplastic compounds that attaches an alkyl group to DNA. Examples of alkylating agents that may be used in the ADCs include, but are not limited to, alkyl sulfonates, pyrrolobenzodiazepines or PBDs, ethylenimimes, methylamine derivatives, epoxides, nitrogen mustards, nitrosoureas, triazines and hydrazines.

DNA Alkylating Agents

The term "DNA alkylating agent", as used herein, includes a family of DNA alkylating agents including indolino-benzodiazepines (IGNs). IGNs represent a chemical class of cytotoxic molecules with high in vitro potency ($IC_{50}$ values in the low pmol/L range) toward cancer cells. Examples of IGN DNA alkylating agents that can be used as a cytotoxic payload in an ADC are described in Miller et al. (2016) *Molecular Cancer Therapeutics*, 15(8)). The IGN compounds described in Miller et al. bind to the minor groove of DNA followed by covalent reaction of guanine residues with the two imine functionalities in the molecule resulting in cross-linking of DNA. The structure of an exemplary IGN is provided below.

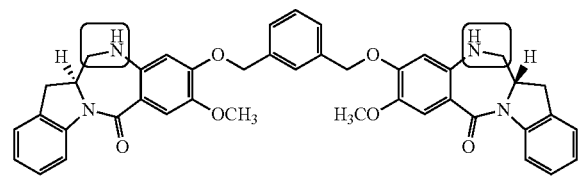

2

DNA alkylating agents also include pyrrolobenzodiazepines or PBDs, a class of natural products with antibiotic or anti-tumor properties, which are produced by various actinomycetes (a broad group of bacteria that form thread-like filaments in the soil). PBDs are a family of sequence-selective DNA minor-groove binding agents that form a covalent aminal bond between their C11-position and the C2-$NH_2$ groups of guanine bases. As a class of DNA-crosslinking agents, they are significantly more potent than systemic chemotherapeutic drugs. As DNA minor groove binding agents, pyrrolobenzodiazepines bind and cross-link specific sites of DNA of the cancer cell, blocking cancer cell division without distorting its DNA helix, thus potentially avoiding the common phenomenon of emergent drug resistance.

The first example of a PBD monomer, the natural product anthramycin, was discovered in the 1960s, and the best known PBD dimer, SJG-136 (also known as SG2000, NSC 694501 or BN2629), was synthesized in the 1990s and has recently completed Phase II clinical trials in patients with leukaemia and ovarian cancer. Other agents belonging to the pyrrolo(1,4)benzodiazepine antibiotic group include abbeymycin, chicamycin, DC-81, mazethramycin, neothramycins A and B, porothramycin prothracarcin, sibanomicin (DC-102) sibiromycin, tomamycin and derivatives thereof, and anthramycin. See, for example, Mantaj et al., *Angewe Chem Int Ed Engl.* 2017; 56(2):462-488, the contents of which are expressly incorporated herein by reference in their entirety.

Dimeric pyrrolobenzodiazepines can be used as the cytotoxic drug payloads in antibody-drug conjugates, including vadastuximab talirine (Seattle Genetics), which is being developed for the treatment of patients acute myeloid leukemia (AML), and rovalpituzumab tesirine. Kolltan Pharmaceuticals and Genentech/Roche are developing antibody-drug conjugates with pyrrolobenzodiazepine as the cytotoxic drug payload. Kolltan Pharmaceuticals' preclinical agent, KTN0182A, is an anti-KIT, PBD-containing antibody-drug conjugate which demonstrated potent anti-tumor activity in vitro and in vivo against a broad range of tumor types. ADCs conjugated with PBD are also described in, for example, Rios-Doria, J. et al. (2017) *Cancer Res.* 77(10); 2686 and Mantaj, J. et al. (2017) *Angew Chem Int Ed Engl.* January 9; 56(2): 462-488, the contents of which are incorporated herein by reference.

5. Antiangiogenic Agents

In one aspect, the anti-TMEFF1 antibodies described herein are conjugated to at least one antiangiogenic agent. Antiangiogenic agents inhibit the growth of new blood vessels. Antiangiogenic agents exert their effects in a variety of ways. In some embodiments, these agents interfere with the ability of a growth factor to reach its target. For example, vascular endothelial growth factor (VEGF) is one of the primary proteins involved in initiating angiogenesis by binding to particular receptors on a cell surface. Thus, certain antiangiogenic agents, that prevent the interaction of VEGF with its cognate receptor, prevent VEGF from initiating angiogenesis. In other embodiments, these agents interfere with intracellular signaling cascades. For example, once a particular receptor on a cell surface has been triggered, a cascade of other chemical signals is initiated to promote the growth of blood vessels. Thus, certain enzymes, for example, some tyrosine kinases, that are known to facilitate intracellular signaling cascades that contribute to, for example, cell proliferation, are targets for cancer treatment. In other embodiments, these agents interfere with intercellular signaling cascades. Yet, in other embodiments, these agents disable specific targets that activate and promote cell growth or by directly interfering with the growth of blood vessel cells. Angiogenesis inhibitory properties have been discovered in more than 300 substances with numerous direct and indirect inhibitory effects.

Representative examples of antiangiogenic agents that may be used in the ADCs include, but are not limited to, angiostatin, ABX EGF, C1-1033, PKI-166, EGF vaccine, EKB-569, GW2016, ICR-62, EMD 55900, CP358, PD153035, AG1478, IMC-C225 (Erbitux, ZD1839 (Iressa), OSI-774, Erlotinib (tarceva), angiostatin, arrestin, endostatin, BAY 12-9566 and w/fluorouracil or doxorubicin, canstatin, carboxyamidotriozole and with paclitaxel, EMD121974, S-24, vitaxin, dimethylxanthenone acetic acid, IM862, Interleukin-12, Interleukin-2, NM-3, HuMV833, PTK787, RhuMab, angiozyme (ribozyme), IMC-1C11, Neovastat, marimstat, prinomastat, BMS-275291, COL-3, MM1270, SU101, SU6668, SU11248, SU5416, with paclitaxel, with gemcitabine and cisplatin, and with irinotecan and cisplatin and with radiation, tecogalan, temozolomide and PEG interferon a2b, tetrathiomolybdate, TNP-470, thalidomide, CC-5013 and with taxotere, tumstatin, 2-methoxyestradiol, VEGF trap, mTOR inhibitors (deforolimus, everolimus (Afinitor, Novartis Pharmaceutical Corporation), and temsirolimus (Torisel, Pfizer, Inc.)), tyrosine kinase inhibitors (e.g., erlotinib (Tarceva, Genentech, Inc.), imatinib (Gleevec, Novartis Pharmaceutical Corporation), gefitinib (Iressa, AstraZeneca Pharmaceuticals), dasatinib (Sprycel, Brystol-Myers Squibb), sunitinib (Sutent, Pfizer, Inc.), nilotinib (Tasigna, Novartis Pharmaceutical Corporation), lapatinib (Tykerb, GlaxoSmithKline Pharmaceuticals), sorafenib (Nexavar, Bayer and Onyx), phosphoinositide 3-kinases (PI3K).

6. Antimetabolites

The anti-TMEFF1 antibodies may be conjugated to at least one antimetabolite. Antimetabolites are types of chemotherapy treatments that are very similar to normal substances within the cell. When the cells incorporate an antimetabolite into the cellular metabolism, the result is negative for the cell, e.g., the cell is unable to divide. Antimetabolites are classified according to the substances with which they interfere. Examples of antimetabolies that may be used in the ADCs include, but are not limited to, a folic acid antagonist (e.g., methotrexate), a pyrimidine antagonist (e.g., 5-Fluorouracil, Foxuridine, Cytarabine, Capecitabine, and Gemcitabine), a purine antagonist (e.g., 6-Mercaptopurine and 6-Thioguanine) and an adenosine deaminase inhibitor (e.g., Cladribine, Fludarabine, Nelarabine and Pentostatin), as described in more detail below.

7. Boron-Containing Agents

The anti-TMEFF1 antibody may be conjugated to at least one boron containing agent. Boron-containing agents comprise a class of cancer therapeutic compounds which interfere with cell proliferation. Representative examples of boron containing agents include, but are not limited, to borophycin and bortezomib (Velcade, Millenium Pharmaceuticals).

8. Chemoprotective Agents

The anti-TMEFF1 antibodies may be conjugated to at least one chemoprotective agent. Chemoprotective drugs are a class of compounds, which help protect the body against specific toxic effects of chemotherapy. Chemoprotective agents may be administered with various chemotherapies in order to protect healthy cells from the toxic effects of chemotherapy drugs, while simultaneously allowing the cancer cells to be treated with the administered chemotherapeutic. Representative chemoprotective agents include, but are not limited to amifostine (Ethyol, Medimmune, Inc.), which is used to reduce renal toxicity associated with cumulative doses of cisplatin, dexrazoxane (Totect, Apricus Pharma; Zinecard), for the treatment of extravasation caused by the administration of anthracycline (Totect), and for the treatment of cardiac-related complications caused by the administration of the antitumor antibiotic doxorubicin (Zinecard), and mesna (Mesnex, Bristol-Myers Squibb), which is used to prevent hemorrhagic cystitis during chemotherapy treatment with ifocfamide.

9. Photoactive Therapeutic Agents

The anti-TMEFF1 antibodies may be conjugated to at least one photoactive therapeutic agent. Photoactive therapeutic agents include compounds that can be deployed to kill treated cells upon exposure to electromagnetic radiation of a particular wavelength. Therapeutically relevant compounds absorb electromagnetic radiation at wavelengths which penetrate tissue. In preferred embodiments, the compound is administered in a non-toxic form that is capable of producing a photochemical effect that is toxic to cells or tissue upon sufficient activation. In other preferred embodiments, these compounds are retained by cancerous tissue and are readily cleared from normal tissues. Non-limiting examples include various chromagens and dyes.

10. Radionuclide Agents (Radioactive Isotopes)

The anti-TMEFF1 antibodies may be conjugated to at least one radionuclide agent. Radionuclide agents comprise agents that are characterized by an unstable nucleus that is capable of undergoing radioactive decay. The basis for successful radionuclide treatment depends on sufficient concentration and prolonged retention of the radionuclide by the cancer cell. Other factors to consider include the radionuclide half-life, the energy of the emitted particles, and the maximum range that the emitted particle can travel. In preferred embodiments, the therapeutic agent is a radionuclide selected from the group consisting of $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I $^{32}$P, $^{33}$P, $^{47}$Sc, $^{111}$Ag, $^{67}$Ga, $^{142}$Pr, $^{153}$Sm, $^{61}$Tb, $^{166}$Dy, $^{166}$Ho, $^{86}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{09}$Pd, $^{143}$Pr, $^{149}$Pm, $^{169}$Er, $^{194}$Ir, $^{198}$Au, $^{199}$Au, and $^{211}$Pb. Also preferred are radionuclides that substantially decay with Auger-emitting particles. For example, Co-58, Ga-67, Br-80m, Tc-99m, Rh-103m, Pt-109, In-ill 1, Sb-119, 1-125, Ho-161, Os-189m and Ir-192. Decay energies of useful beta-particle-emitting nuclides are preferably Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Or, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

11. Radiosensitizers

The anti-TMEFF1 antibodies may be conjugated to at least one radiosensitizer. The term "radiosensitizer," as used herein, is defined as a molecule, preferably a low molecular weight molecule, administered to animals in therapeutically effective amounts to increase the sensitivity of the cells to be radiosensitized to electromagnetic radiation and/or to promote the treatment of diseases that are treatable with electromagnetic radiation. Radiosensitizers are agents that make cancer cells more sensitive to radiation therapy, while typically having much less of an effect on normal cells. Thus, the radiosensitizer can be used in combination with a radiolabeled antibody or ADC. The addition of the radiosensitizer can result in enhanced efficacy when compared to treatment with the radiolabeled antibody or antibody fragment alone. Radiosensitizers are described in D. M. Goldberg (ed.), Cancer Therapy with Radiolabeled Antibodies, CRC Press (1995). Examples of radiosensitizers include gemcitabine, 5-fluorouracil, taxane, and cisplatin.

Radiosensitizers may be activated by the electromagnetic radiation of X-rays. Representative examples of X-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same. Alternatively, radiosensitizers may be activated using photodynamic therapy (PDT). Representative examples of photodynamic radiosensitizers include, but are not limited to, hematoporphyrin derivatives, Photofrin(r), benzoporphyrin derivatives, NPe6, tin etioporphyrin (SnET2), pheoborbide a, bacteriochlorophyll a, naphthalocyanines, phthalocyanines, zinc phthalocyanine, and therapeutically effective analogs and derivatives of the same.

12. Topoisomerase Inhibitors

The anti-TMEFF1 antibodies may be conjugated to at least one topoisomerase inhibitor. Topoisomerase inhibitors are chemotherapy agents designed to interfere with the action of topoisomerase enzymes (topoisomerase I and II), which are enzymes that control the changes in DNA structure by catalyzing then breaking and rejoining of the phosphodiester backbone of DNA strands during the normal cell cycle. Representative examples of DNA topoisomerase I inhibitors include, but are not limited to, camptothecins and its derivatives irinotecan (CPT-11, Camptosar, Pfizer, Inc.) and topotecan (Hycamtin, GlaxoSmithKline Pharmaceuticals). Representative examples of DNA topoisomerase II inhibitors include, but are not limited to, amsacrine, daunorubicin, doxotrubicin, epipodophyllotoxins, ellipticines, epirubicin, etoposide, razoxane, and teniposide.

13. Tyrosine Kinase Inhibitors

The anti-TMEFF1 antibodies may be conjugated to at least one tyrosine kinase inhibitor. Tyrosine kinases are enzymes within the cell that function to attach phosphate groups to the amino acid tyrosine. By blocking the ability of protein tyrosine kinases to function, tumor growth may be inhibited. Examples of tyrosine kinases that may be used on the ADCs include, but are not limited to, Axitinib, Bosutinib, Cediranib, Dasatinib, Erlotinib, Gefitinib, Imatinib, Lapatinib, Lestaurtinib, Nilotinib, Semaxanib, Sunitinib, and Vandetanib.

14. Other Agents

Examples of other agents that may be used in the ADCs include, but are not limited to, abrin (e.g. abrin A chain), alpha toxin, *Aleurites fordii* proteins, amatoxin, crotin, curcin, dianthin proteins, diptheria toxin (e.g. diphtheria A chain and nonbinding active fragments of diphtheria toxin), deoxyribonuclease (Dnase), gelonin, mitogellin, modeccin A chain, *Momordica charantia* inhibitor, neomycin, oncoase, phenomycin, *Phytolaca americana* proteins (PAPI, PAPII, and PAP-S), pokeweed antiviral protein, *Pseudomonas* endotoxin, *Pseudomonas* exotoxin (e.g. exotoxin A chain (from *Pseudomonas aeruginosa*)), restrictocin, ricin A chain, ribonuclease (Rnase), *Sapaonaria officinalis* inhibitor, saporin, alpha-sarcin, Staphylcoccal enterotoxin-A, tetanus toxin, cisplatin, carboplatin, and oxaliplatin (Eloxatin, Sanofi Aventis), proteasome inhibitors (e.g. PS-341 [bortezomib or Velcade]), HDAC inhibitors (vorinostat (Zolinza, Merck & Company, Inc.)), belinostat, entinostat, mocetinostat, and panobinostat), COX-2 inhibitors, substituted ureas, heat shock protein inhibitors (e.g. Geldanamycin and its numerous analogs), adrenocortical suppressants, and the tricothecenes. (See, for example, WO 93/21232). Other agents also include asparaginase (Espar, Lundbeck Inc.), hydroxyurea, levamisole, mitotane (Lysodren, Bristol-Myers Squibb), and tretinoin (Renova, Valeant Pharmaceuticals Inc.).

It should be noted that the aforementioned groups of drug moieties that may be used in the anti-TMEFF1 ADCs are not exclusive, in that certain examples of drugs may be found in more than one category, e.g., ansamitocins are both mitotic inhibitors and antitumor antibiotics.

All stereoisomers of the above drug moieties are contemplated for use herein, i.e. any combination of R and S configurations at the chiral carbons of D.

The above agents (i.e., naked agents not conjugated to an antibody) may also be used in combination therapies with the anti-TMEFF1 antibodies described herein. In one embodiment, anti-TMEFF1 antibodies or ADCs are used with any of the foregoing agents in a combination therapy to treat cancer, where the agent is administered prior to, at the same time as, or following administration of the anti-TMEFF1 antibody or ADC to the subject.

B. Anti-TMEFF1 ADCs: Exemplary Linkers

An anti-TMEFF1 ADC comprises an anti-TMEFF1 antibody and at least one drug(s), whereby the antibody and the at least one drug are conjugated by a linker. The term "linker," as used herein, refers to a chemical moiety that may be bifunctional or multifunctional, and is used to attach an antibody to a drug moiety. A linker may include one conjugating component or may include multiple components. For example, the linker may include a spacer, which is a moiety that extends the drug linkage to avoid, for example, shielding the active site of the antibody or improving the solubility of the ADC. Other examples of components of linkers include a stretcher unit and an amino acid unit.

Two methods are commonly used for conjugating drugs to antibodies: alkylation of reduced interchain cysteine disulfides through an enzymatically non-cleavable maleimido or simple and cleavable disulfide linker, and acylation of lysines by cleavable linear amino acids.

In one aspect, a linker covalently attaches an antibody to a drug moiety. An ADC is prepared using a linker having reactive functionality for binding to the antibody and the drug. For example, a cysteine thiol, or an amine, e.g., N-terminus or amino acid side chain such as lysine, of the antibody may form a bond with a functional group of the linker.

In one aspect, a linker has a functionality that is capable of reacting with a free cysteine present on an antibody to form a covalent bond. Nonlimiting exemplary such reactive functionalities include maleimide, haloacetamides, Q-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), Bioconjugate Chemistry 15(4):765-773.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

Suitable linkers include, for example, cleavable and non-cleavable linkers. A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020). A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit) or a phenylalanine-lysine (phe-lys) linker.

Linkers are preferably stable extracellularly in a sufficient manner to be therapeutically effective. Before transport or delivery into a cell, the ADC is preferably stable and remains intact, i.e. the antibody remains conjugated to the drug moiety. Linkers that are stable outside the target cell may be cleaved at some efficacious rate once inside the cell. Thus, an effective linker will: (i) maintain the specific binding properties of the antibody; (ii) allow delivery, e.g., intracellular delivery, of the drug moiety; and (iii) maintain the therapeutic effect, e.g., cytotoxic effect, of a drug moiety.

In one embodiment, the linker is cleavable under intracellular conditions, such that cleavage of the linker sufficiently releases the drug from the antibody in the intracellular environment to be therapeutically effective. In some embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264: 14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyloxycarbonyl-alpha-methyl-alpha-(2-pyridyl-dithio)toluene), SPDB and SMPT. (See, e.g., Thorpe et al., 1987, Cancer Res. 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.).

In some embodiments, the linker is cleavable by a cleaving agent, e.g., an enzyme, that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Most typical are peptidyl linkers that are cleavable by enzymes that are present in TMEFF1-expressing cells. Examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10): 1305-12).

In yet other embodiments, the linker unit is not cleavable and the drug is released, for example, by antibody degradation. See U.S. Publication No. 20050238649 incorporated by reference herein in its entirety. An ADC comprising a non-cleavable linker may be designed such that the ADC remains substantially outside the cell and interacts with certain receptors on a target cell surface such that the binding of the ADC initiates (or prevents) a particular cellular signaling pathway.

In some embodiments, the linker is substantially hydrophilic linker (e.g., PEG4Mal and sulfo-SPDB). A hydrophilic linker may be used to reduce the extent to which the drug may be pumped out of resistant cancer cells through MDR (multiple drug resistance) or functionally similar transporters.

In other embodiments, upon cleavage, the linker functions to directly or indirectly inhibit cell growth and/or cell proliferation. For example, in some embodiments, the linker, upon cleavage, can function as an intercalating agent, thereby inhibiting macromolecular biosynthesis (e.g. DNA replication, RNA transcription, and/or protein synthesis).

In other embodiments, the linker is designed to facilitate bystander killing (the killing of neighboring cells) through diffusion of the linker-drug and/or the drug alone to neighboring cells. In other, embodiments, the linker promotes cellular internalization.

The presence of a sterically hindered disulfide can increase the stability of a particular disulfide bond, enhancing the potency of the ADC. Thus, in one embodiment, the linker includes a sterically hindered disulfide linkage. A sterically hindered disulfide refers to a disulfide bond present within a particular molecular environment, wherein the environment is characterized by a particular spatial arrangement or orientation of atoms, typically within the same molecule or compound, which prevents or at least partially inhibits the reduction of the disulfide bond. Thus, the presence of bulky (or sterically hindering) chemical moieties and/or bulky amino acid side chains proximal to the disulfide bond prevents or at least partially inhibits the disulfide bond from potential interactions that would result in the reduction of the disulfide bond.

Notably, the aforementioned linker types are not mutually exclusive. For example, in one embodiment, the linker used in the anti-TMEFF1 ADCs described herein is a non-cleavable linker that promotes cellular internalization.

In some embodiments, the ADC has the following formula (formula I):

Ab-(L-D)$_n$              (I)

or a pharmaceutically acceptable salt or solvate thereof; wherein Ab is the antibody, e.g., anti-TMEFF1 antibody, and (L-D) is a Linker-Drug moiety. The Linker-Drug moiety is made of L-which is a Linker, and -D, which is a drug moiety having, for example, cytostatic, cytotoxic, or otherwise therapeutic activity against a target cell, e.g., a cell expressing TMEFF1; and n is an integer from 1 to 20.

In some embodiments, n ranges from 1 to 8, 1 to 7, 1 to 6, 1 to 5, 1 to 4, 1 to 3, 1 to 2, or is 1.

In some embodiments, the -D moieties are the same. In yet another embodiment, the -D moieties are different.

In some embodiments, a linker component comprises an "amino acid unit." In some such embodiments, the amino acid unit allows for cleavage of the linker by a protease, thereby facilitating release of the drug from the immunoconjugate upon exposure to intracellular proteases, such as lysosomal enzymes (Doronina et al. (2003) Nat. Biotechnol. 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline Amino acid units can be designed and optimized for enzymatic cleavage by a particular enzyme, for example, a tumor-associated protease, cathepsin B, C and D, or a plasmin protease.

In one embodiment, the amino acid unit is valine-citrulline (vc or val-cit). In another aspect, the amino acid unit is phenylalanine-lysine (i.e., fk). In yet another aspect of the amino acid unit, the amino acid unit is N-methylvaline-citrulline. In yet another aspect, the amino acid unit is 5-aminovaleric acid, homo phenylalanine lysine, tetraisoquinolinecarboxylate lysine, cyclohexylalanine lysine, isopecotic acid lysine, beta-alanine lysine, glycine serine valine glutamine and isonepecotic acid.

Another approach for the generation of ADCs involves the use of heterobifunctional cross-linkers which link the anti-TMEFF1 antibody to the drug moiety. Examples of cross-linkers that may be used include N-succinimidyl 4-(5-nitro-2-pyridyldithio)-pentanoate or the highly water-soluble analog N-sulfosuccinimidyl 4-(5-nitro-2-pyridyldithio)-pentanoate, N-succinimidyl-4-(2-pyridyldithio) butyrate (SPDB), N-succinimidyl-4-(5-nitro-2-pyridyldithio) butyrate (SNPB), and N-sulfosuccinimidyl-4-(5-nitro-2-pyridyldithio) butyrate (SSNPB), N-succinimidyl-4-methyl-4-(5-nitro-2-pyridyldithio)pentanoate (SMNP), N-succinimidyl-4-(5-N,N-dimethylcarboxamido-2-pyridyldithio) butyrate (SCPB) or N-sulfosuccinimidyl4-(5-N,N-dimethylcarboxamido-2-pyridyldithio) butyrate (SSCPB)). The antibodies may be modified with the cross-linkers N-succinimidyl 4-(5-nitro-2-pyridyldithio)-pentanoate, N-sulfosuccinimidyl 4-(5-nitro-2-pyridyldithio)-pentanoate, SPDB, SNPB, SSNPB, SMNP, SCPB, or SSCPB can then react with a small excess of a particular drug that contains a thiol moiety to give excellent yields of an ADC (see also U.S. Pat. No. 6,913,748, incorporated by reference herein).

In one embodiment, charged linkers (also referred to as pro-charged linkers) are used to conjugate anti-TMEFF1 antibodies to drugs to form ADCs. Charged linkers include linkers that become charged after cell processing. The presence of a charged group(s) in the linker of a particular ADC or on the drug after cellular processing provides several advantages, such as (i) greater water solubility of the ADC, (ii) ability to operate at a higher concentration in aqueous solutions, (iii) ability to link a greater number of drug molecules per antibody, potentially resulting in higher potency, (iv) potential for the charged conjugate species to be retained inside the target cell, resulting in higher potency, and (v) improved sensitivity of multidrug resistant cells, which would be unable to export the charged drug species from the cell. Examples of some suitable charged or pro-charged cross-linkers and their synthesis are shown in FIGS. 1 to 10 of U.S. Pat. No. 8,236,319, and are incorporated by reference herein. Preferably, the charged or pro-charged cross-linkers are those containing sulfonate, phosphate, carboxyl or quaternary amine substituents that significantly increase the solubility of the ADCs, especially for ADCs with 2 to 20 conjugated drugs. Conjugates prepared from linkers containing a pro-charged moiety would produce one or more charged moieties after the conjugate is metabolized in a cell.

Additional examples of linkers that can be used with the compositions and methods include valine-citrulline; maleimidocaproyl; amino benzoic acids; p-aminobenzylcarbamoyl (PAB); lysosomal enzyme-cleavable linkers; maleimidocaproyl-polyethylene glycol (MC(PEG)6-OH); N-methyl-valine citrulline; N-succinimidyl 4-(N-maleimidomethyl)cyclohexane-1-carboxylate (SMCC); N-Succinimidyl 4-(2-pyridyldithio)butanoate (SPDB); and N-Succinimidyl 4-(2-pyridylthio)pentanoate (SPP) (See also US 2011/0076232). Another linker for use includes an avidin-biotin linkage to provide an avidin-biotin-containing ADC (See also U.S. Pat. No. 4,676,980, PCT publication Nos. WO1992/022332A2, WO1994/016729A1, WO1995/015770A1, WO1997/031655A2, WO1998/035704A1, WO1999/019500A1, WO2001/09785A2, WO2001/090198A1, WO2003/093793A2, WO2004/050016A2, WO2005/081898A2, WO2006/083562A2, WO2006/089668A1, WO2007/150020A1, WO2008/135237A1, WO2010/111198A1, WO2011/057216A1, WO2011/058321A1, WO2012/027494A1, and EP77671B1), wherein some such linkers are resistant to biotinidase cleavage. Additional linkers that may be used include a cohesin/dockerin pair to provide a cohesion-dockerin-containing ADC (See PCT publication Nos. WO2008/097866A2, WO2008/097870A2, WO2008/103947A2, and WO2008/103953A2).

Additional linkers may contain non-peptide polymers (examples include, but are not limited to, polyethylene glycol, polypropylene glycol, polyoxyethylated polyols, polyvinyl alcohol, polysaccharides, dextran, polyvinyl ethyl ether, PLA (poly(lactic acid)), PLGA (poly(lactic acid-glycolic acid)), and combinations thereof, wherein a preferred polymer is polyethylene glycol) (See also PCT publication No. WO2011/000370). Additional linkers are also described in WO 2004-010957, U.S. Publication No. 20060074008, U.S. Publication No. 20050238649, and U.S. Publication No. 20060024317, each of which is incorporated by reference herein in its entirety).

For an ADC comprising a maytansinoid, many positions on maytansinoids can serve as the position to chemically link the linking moiety. In one embodiment, maytansinoids comprise a linking moiety that contains a reactive chemical group are C-3 esters of maytansinol and its analogs where the linking moiety contains a disulfide bond and the chemical reactive group comprises a N-succinimidyl or N-sulfo-succinimidyl ester. For example, the C-3 position having a hydroxyl group, the C-14 position modified with hydroxymethyl, the C-15 position modified with hydroxy and the C-20 position having a hydroxy group are all useful. The linking moiety most preferably is linked to the C-3 position of maytansinol.

The conjugation of the drug to the antibody via a linker can be accomplished by any technique known in the art. A number of different reactions are available for covalent attachment of drugs and linkers to antibodies. This may be accomplished by reaction of the amino acid residues of the antibody, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody. Also available for attachment of drugs to antibodies is the Schiff base reaction. This method involves the periodate oxidation of a drug that contains glycol or hydroxy groups, thus forming an aldehyde which is then reacted with the binding agent. Attachment occurs via formation of a Schiff base with amino groups of the antibody. Isothiocyanates can also be used as coupling agents for covalently attaching drugs to antibodies. Other techniques are known to the skilled artisan and within the scope of the disclosure.

In certain embodiments, an intermediate, which is the precursor of the linker, is reacted with the drug under appropriate conditions. In certain embodiments, reactive groups are used on the drug or the intermediate. The product of the reaction between the drug and the intermediate, or the derivatized drug, is subsequently reacted with the anti-TMEFF1 antibody under appropriate conditions. The synthesis and structure of exemplary linkers, stretcher units, amino acid units, self-immolative spacer units are described in U.S. Patent Application Publication Nos. 20030083263, 20050238649 and 20050009751, each if which is incorporated herein by reference.

Stability of the ADC may be measured by standard analytical techniques such as mass spectroscopy, HPLC, and the separation/analysis technique LC/MS.

IV. Uses of Anti-TMEFF1 Antibodies and Anti-TMEFF1 ADCs

The antibodies and antibody portions (and ADCs) preferably are capable of neutralizing human TMEFF1 activity both in vivo and in vitro. Accordingly, such antibodies, ADCs, and antigen-binding portions can be used to inhibit TMEFF1 activity, e.g., in a cell culture containing hTMEFF1, in human subjects or in other mammalian subjects having TMEFF1 with which an antibody disclosed herein cross-reacts. In one embodiment, the disclosure provides a method for inhibiting hTMEFF1 activity comprising contacting hTMEFF1 with an antibody, ADC, or antigen-binding portion such that hTMEFF1 activity is inhibited. For example, in a cell culture containing, or suspected of containing hTMEFF1, an antibody, ADC, or antigen-binding portion can be added to the culture medium to inhibit hTMEFF1 activity in the culture.

In another embodiment, disclosed herein is a method for reducing hTMEFF1 activity in a subject, advantageously from a subject suffering from a TMEFF1 associated disorder, e.g., cancer such as lung cancer, e.g., small cell lung cancer (SCLC), ovarian cancer or TNBC or a disorder in which TMEFF1 activity is detrimental. The disclosure provides methods for reducing TMEFF1 activity in a subject suffering from such a disease or disorder, which method comprises administering to the subject an antibody or antibody portion of the disclosure such that TMEFF1 activity in the subject is reduced. Preferably, the TMEFF1 is human TMEFF1, and the subject is a human subject. Alternatively, the subject can be a mammal expressing a TMEFF1 to which antibodies of the disclosure are capable of binding. Still further the subject can be a mammal into which TMEFF1 has been introduced (e.g., by administration of TMEFF1 or by expression of a TMEFF1 transgene). Antibodies of the disclosure can be administered to a human subject for therapeutic purposes. Moreover, antibodies of the disclosure can be administered to a non-human mammal expressing a TMEFF1 with which the antibody is capable of binding for veterinary purposes or as an animal model of human disease. Regarding the latter, such animal models may be useful for evaluating the therapeutic efficacy of antibodies of the disclosure (e.g., testing of dosages and time courses of administration).

As used herein, the term "a disorder in which TMEFF1 activity is detrimental" is intended to include diseases and other disorders in which the presence of TMEFF1 in a subject suffering from the disorder has been shown to be or is suspected of being either responsible for the pathophysiology of the disorder or a factor that contributes to a worsening of the disorder. Accordingly, a disorder in which TMEFF1 activity is detrimental is a disorder in which reduction of TMEFF1 activity is expected to alleviate the symptoms and/or progression of the disorder. Such disorders may be evidenced, for example, by an increase in the concentration of TMEFF1 in a biological cell, fluid or tissue of a subject suffering from the disorder (e.g., an increase in the concentration of TMEFF1 in a tumor, serum, plasma, synovial fluid, etc. of the subject), which can be detected, for example, using an anti-TMEFF1 antibody as described above.

Non-limiting examples of disorders that can be treated with the antibodies, ADCs, or antigen binding portions thereof, include those disorders discussed below. For example, suitable disorders include, but are not limited to, a variety of cancers including, but not limited to, lung cancer, e.g., small cell lung cancer, ovarian cancer and TNBC.

Other examples of cancers that may be treated using the compositions and methods disclosed herein include, but are not limited to carcinoma, lymphoma, blastoma, sarcoma, and leukemia or lymphoid malignancies. More particular examples of such cancers include but are not limited to breast cancer (Luminal A, TNBC, Ductal), prostate cancer, squamous cell tumors, squamous cell carcinoma (e.g., squamous cell lung cancer or squamous cell head and neck cancer), neuroendocrine tumors, urothelial cancer, vulvar cancer, mesothelioma, liver cancer, bone cancer, pancreatic cancer, skin cancer, cancer of the head or neck, non-small cell lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers. PVNS, acute myeloid leukemia, adrenocortico carcinoma, bladder urothelial carcinoma, cervical squamous cell carcinoma, endocervical adenocarcinoma, diffuse large B cell lymphoma, glioblastoma multiforme, chronic lymphocytic leukemia, brain lower grade glioma, head and neck squamous cell carcinoma, hepatocellular carcinoma, lung adenocarcinoma, large squamous cell carcinoma, cutaneous melanoma, ovarial serous cystadenocarcinoma, gastric cancer, soft tissue sarcoma, testicular germ cell cancer, thymoma, thyroid carcinoma, uterine corpus endometrial carcinoma, uterine carcinosarcoma, kidney renal clear cell carcinoma, and kidney renal papillary cell carcinoma. The present invention is also applicable to treatment of metastatic cancers.

In one embodiment, the antibodies and ADCs, and antigen-binding portions thereof, disclosed herein are used to treat a solid tumor, e.g., inhibit growth of or decrease size of a solid tumor, overexpressing TMEFF1 or which is TMEFF1 positive. In one embodiment, the antibodies and ADCs, and antigen-binding portions thereof, disclosed herein are used to treat lung cancer, e.g., small cell lung cancer, ovarian cancer and TNBC. Diseases and disorders described herein may be treated by anti-TMEFF1 antibodies or ADCs, or antigen-binding portions thereof, as well as pharmaceutical compositions comprising such anti-TMEFF1 antibodies or ADCs, or antigen-binding portions thereof.

In certain embodiments, the antibodies and ADCs, and antigen-binding portions thereof, disclosed herein are administered to a subject in need thereof in order to treat advanced solid tumor types likely to exhibit elevated levels of TMEFF1.

In certain embodiments, the disclosure includes a method for inhibiting or decreasing solid tumor growth in a subject having a solid tumor, said method comprising administering an anti-TMEFF1 antibody or ADC, or antigen-binding portions thereof, described herein, to the subject having the solid tumor, such that the solid tumor growth is inhibited or decreased. In certain embodiments, the solid tumor is a lung tumor, a breast tumor, or an ovarian tumor. In further embodiments, the solid tumor is an TMEFF1 expressing solid tumor. In certain embodiments the anti-TMEFF1 antibodies or ADCs, or antigen-binding portions thereof, described herein are administered to a subject having lung cancer, e.g., small cell lung cancer, ovarian cancer or TNBC, alone or in combination with an additional agent, e.g., radiation and/or chemotherapy, or an immune checkpoint inhibitor.

In certain embodiments, the disclosure includes a method for inhibiting or decreasing solid tumor growth in a subject having a solid tumor which was identified as an TMEFF1 expressing or TMEFF1 expressing tumor, said method comprising administering an anti-TMEFF1 antibody or ADC described herein, to the subject having the solid tumor, such that the solid tumor growth is inhibited or decreased. Methods for identifying TMEFF1 expressing tumors are known in the art, and include FDA-approved tests and validation assays. For example, these assays may use primers that are specific for the TMEFF1 gene and/or cDNA and result in the amplification of the TMEFF1 gene/cDNA, or a portion thereof. The amplified PCR products may be subsequently analyzed, for example, by gel electrophoresis using standard methods known in the art to determine the size of the PCR products. Such tests may be used to identify tumors that may be treated with the methods and compositions described herein.

In another aspect, this application features a method of treating (e.g., curing, suppressing, ameliorating, delaying or preventing the onset of, or preventing recurrence or relapse of) or preventing a TMEFF1-associated disorder, in a subject. The method includes: administering to the subject an TMEFF1 binding agent (particularly an antagonist), e.g., an anti-TMEFF1 antibody or portion thereof as described herein, in an amount sufficient to treat or prevent the TMEFF1-associated disorder. The TMEFF1 antagonist, e.g., the anti-TMEFF1 antibody, ADC, or portion thereof, can be administered to the subject, alone or in combination with other therapeutic modalities as described herein.

Antibodies or ADCs, or antigen binding portions thereof, can be used alone or in combination to treat such diseases.

It should be understood that the antibodies or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody. The additional agent also can be an agent that imparts a beneficial attribute to the therapeutic composition, e.g., an agent which affects the viscosity of the composition.

It should further be understood that the combinations which are to be included within this disclosure are those combinations useful for their intended purpose. The agents set forth below are illustrative for purposes and not intended to be limited. The combinations, which are part of this disclosure, can be the antibodies of the disclosure and at least one additional agent selected from the lists below. The combination can also include more than one additional agent, e.g., two or three additional agents if the combination is such that the formed composition can perform its intended function.

The combination therapy can include one or more TMEFF1 antagonists, e.g., anti-TMEFF1 antibodies, ADCs, or portions thereof, formulated with, and/or co-administered with, one or more additional therapeutic agents, e.g., one or more cytokine and growth factor inhibitors, immunosuppressants, anti-inflammatory agents (e.g., systemic anti-inflammatory agents), anti-fibrotic agents, metabolic inhibitors, enzyme inhibitors, and/or cytotoxic or cytostatic agents, mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, or radiosensitizers, as described in more detail herein.

In a particular embodiment, the anti-TMEFF1 antibodies or ADCs disclosed herein are used in combination with an anti-cancer agent or an antineoplastic agent. The terms "anti-cancer agent" and "antineoplastic agent" refer to drugs used to treat malignancies, such as cancerous growths. In one embodiment, the anti-TMEFF1 antibodies or ADCs of the invention are administered in combination with one or more immune checkpoint inhibitors (e.g., antibody or small molecule immune checkpoint inhibitors) for the treatment of a cancer. In some embodiments, the immune checkpoint inhibitor is an inhibitor (e.g., antibody) of Programmed Death-Ligand 1 (PD-L1, also known as B7-H1, CD274), Programmed Death 1 (PD-1), CTLA-4, PD-L2 (B7-DC, CD273), LAG3, TIM3, 2B4, 4-1BB, A2aR, B7H1, B7H3, B7H4, BTLA, CD2, CD6, CD27, CD28, CD30, CD38, CD39, CD40, CD47, CD70, CD73, CD80, CD86, CD137, CD160, CD166, CD200, CD200R1, CD226, CD276, DR3, GAL9, GITR, HAVCR2, HVEM, IDO1, IDO2, ICOS (inducible T cell costimulator), KIR, LAG3, LAIR1, TREM2, LILRB1, LILRB2, LILRB3, LIGHT, MARCO (macrophage receptor with collageneous structure), PS (phosphatidylserine), OX-40, SLAM, SIRPA, CSF1R, CD47, SIRPA, TIGHT, TGFβ, VISTA, VTCN1, or any combinations thereof.

In some embodiments, the immune checkpoint inhibitor is an anti-CTLA-4, PD-L1, or PD-1 antibody therapy such as, but not limited to Yervoy® (ipilimumab: Bristol-Myers Squibb), Opdivo® (nivolumab; Bristol-Myers Squibb), Keytrada® (pembrolizumab; Merck), and Tecentriq® (atezolizumab; Roche).

In other embodiments, the immune checkpoint inhibitor is an anti-CD38 antibody therapy such as isatuximab (Sanofi), Darzalex® (daratumumab; Genmab A/S and Janssen Biotech), MOR202 (MorphoSys AG), and Tusk Therapeutics Ltd.'s anti-CD38 monoclonal antibody.

In some embodiments, the checkpoint inhibitor is an antibody or small molecule currently undergoing clinical testing, including, for example, an antibody against IDO (Epacadostat and Indoximod and BMS-986205), 4-1BB/CD137 (Utomilumab and Urelumab), KIR (Lirilulmab), CD40 (CP-870,893), CD27 (Varlilumab), LAG-3 (Relatilimab), MHCII (Eftilagimod Alpha).

In one embodiment, the anti-TMEFF1 antibodies or ADCs of the invention are administered in combination with one checkpoint inhibitor, e.g., an anti-CTLA-4, CD38, PD-L1, or PD-1 antibody.

In other embodiments, the anti-TMEFF1 antibodies or ADCs of the invention are administered in combination with more than one checkpoint inhibitor, e.g., an an anti-TMEFF1 antibody or ADC of the invention in combination with an anti-CD38 antibody and an anti-PD-L1 antibody, or an anti-TMEFF1 antibody or ADC of the invention in combination with an anti-CD38 antibody and an anti-PD-1 antibody.

Drug therapy may be used alone, or in combination with other treatments such as surgery or radiation therapy. Several classes of drugs may be used in cancer treatment, depending on the nature of the organ involved. For example, breast cancers are commonly stimulated by estrogens, and may be treated with drugs which inactive the sex hormones. Similarly, prostate cancer may be treated with drugs that inactivate androgens, the male sex hormone.

In particular embodiments, the anti-TMEFF1 antibodies or ADCs can be administered alone or with another anti-cancer agent which acts in conjunction with or synergistically with the antibody to treat the disease associated with TMEFF1 activity. Such anti-cancer agents include, for example, agents well known in the art (e.g., cytotoxins, chemotherapeutic agents, small molecules and radiation). Provided herein are methods for treating cancer, e.g., small cell lung cancer (SCLC), ovarian cancer or TNBC, or a disorder in which TMEFF1 activity is detrimental, in a patient comprising administering to the patient an anti-TMEFF1 antibody, or fragment thereof, or an ADC of the invention wherein the combination therapy exhibits synergy, e.g., therapeutic synergy, in the subject. As used herein, "synergy" or "therapeutic synergy" refers to a phenomenon where treatment of patients with a combination of therapeutic agents manifests a therapeutically superior outcome to the outcome achieved by each individual constituent of the combination used at its optimum dose (Corbett, T. H. et al., Cancer Treatment Reports, 66:1187 (1982)). For example, a therapeutically superior outcome is one in which the patients either a) exhibit fewer incidences of adverse events while receiving a therapeutic benefit that is equal to or greater than that where individual constituents of the combination are each administered as monotherapy at the same dose as in the combination, or b) do not exhibit dose-limiting toxicities while receiving a therapeutic benefit that is greater than that of treatment with each individual constituent of the combination when each constituent is administered in at the same doses in the combination(s) as is administered as individual components.

In one embodiment, the administration to a subject of an effective amount of anti-TMEFF1 antibody, or fragment thereof, or an anti-TMEFF1 ADC of the invention, in combination with a second therapeutic agent, such as a PARP inhibitor or a DNA alkylating agent, has a synergistic effect on decreasing or inhibiting cancer, tumor cellular proliferation or tumor growth, or tumor invasion or metastasis, in the subject.

In one embodiment, agents which have a synergistic effect with an anti-TMEFF1 antibody or ADC of the invention include, but are not limited to, chemotherapeutic agents such as a poly ADP-ribose polymerase (PARP) inhibitor (e.g., niraparib (Zejula)), a DNA alkylating agent (e.g., cisplatin and/or tomaymycin, or derivative thereof), or a topoisomerase inhibitor (e.g., etoposide (Etopophos®)) (see Example 7). In one embodiment, the ADC is an anti-TMEFF1 antibody conjugated to a DNA alkylating agent, e.g., PBD.

Other examples of anti-cancer agents which may have a synergistic effect or an additive effect with an anti-TMEFF1 antibody or ADC of the invention include Panorex (Glaxo-Welcome), Rituxan (IDEC/Genentech/Hoffman la Roche), Mylotarg (Wyeth), Campath (Millennium), Zevalin (IDEC and Schering AG), Bexxar (Corixa/GSK), Erbitux (Imclone/BMS), Avastin (Genentech) and Herceptin (Genentech/Hoffman la Roche). Other anti-cancer agents include, but are not limited to, those disclosed in U.S. Pat. No. 7,598,028 and International Publication No. WO2008/100624, the contents of which are hereby incorporated by reference. One or more anti-cancer agents may be administered either simultaneously or before or after administration of an antibody or antigen binding portion thereof.

In particular embodiments of the invention, the anti-TMEFF1 antibodies or ADCs described herein can be used in a combination therapy, which may have a synergistic effect or an additive effect, with an inhibitor of NAMPT (see examples of inhibitors in US 2013/0303509; AbbVie, Inc., incorporated by reference herein) to treat a subject in need thereof. NAMPT (also known as pre-B-cell-colony-enhancing factor (PBEF) and visfatin) is an enzyme that catalyzes the phosphoribosylation of nicotinamide and is the rate-limiting enzyme in one of two pathways that salvage NAD. In one embodiment, anti-TMEFF1 antibodies and ADCs described herein are administered in combination with a NAMPT inhibitor for the treatment of cancer in a subject.

In particular embodiments, the anti-TMEFF1 antibodies or ADCs described herein can be used in a combination therapy with a topoisomerase inhibitor, e.g., SN-38, which is the active metabolite of the topoisomerase inhibitor irinotecan, and/or the topoisomerase inhibitor exatecan, or derivatives thereof (see Ogitani, et al., 2016 *Bioorganic & Medicinal Chemistry Letters,* 26(20; 5069, the contents of which are incorporated herein by reference), which may result in a synergistic effect or an additive effect.

In particular embodiments, the anti-TMEFF1 antibodies or ADCs described herein can be used in a combination therapy with an RNA polymerase II inhibitor such as alpha-amantin, or a derivative thereof (see Ogitani, et al., 2016 *Clinical Cancer Research October* 15; 22(20):5097-5108, the contents of which are incorporated herein by reference) which may result in a synergistic effect or an additive effect.

The pharmaceutical compositions may include a "therapeutically effective amount" or a "prophylactically effective amount" of an antibody or antibody portion. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an ADC, an antibody or antibody portion is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In another aspect, this application provides a method for detecting the presence of TMEFF1 in a sample in vitro (e.g., a biological sample, such as serum, plasma, tissue, biopsy). The subject method can be used to diagnose a disorder, e.g., a cancer. The method includes: (i) contacting the sample or a control sample with the anti-TMEFF1 antibody or portion thereof as described herein; and (ii) detecting formation of a complex between the anti-TMEFF1 antibody or portion thereof, and the sample or the control sample, wherein a statistically significant change in the formation of the complex in the sample relative to the control sample is indicative of the presence of TMEFF1 in the sample.

Given their ability to bind to human TMEFF1, the anti-human TMEFF1 antibodies, or portions thereof, (as well as ADCs thereof) can be used to detect human TMEFF1 (e.g., in a biological sample, such as serum or plasma), using a conventional immunoassay, such as an enzyme linked immunosorbent assays (ELISA), an radioimmunoassay (RIA) or tissue immunohistochemistry. In one aspect, the disclosure provides a method for detecting human TMEFF1 in a biological sample comprising contacting a biological sample with an antibody, or antibody portion, and detecting either the antibody (or antibody portion) bound to human TMEFF1 or unbound antibody (or antibody portion), to thereby detect human TMEFF1 in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}H$, $^{14}C$, $^{35}S$, $^{90}Y$, $^{99}Tc$, $^{111}In$, 125I, $^{131}I$, $^{177}Lu$, 166Ho, or $^{153}Sm$.

Alternative to labeling the antibody, human TMEFF1 can be assayed in biological fluids by a competition immunoassay utilizing rhTMEFF1 standards labeled with a detectable substance and an unlabeled anti-human TMEFF1 antibody. In this assay, the biological sample, the labeled rhTMEFF1 standards and the anti-human TMEFF1 antibody are combined and the amount of labeled rhTMEFF1 standard bound to the unlabeled antibody is determined. The amount of human TMEFF1 in the biological sample is inversely proportional to the amount of labeled rhTMEFF1 standard bound to the anti-TMEFF1 antibody. Similarly, human TMEFF1 can also be assayed in biological fluids by a competition immunoassay utilizing rhTMEFF1 standards labeled with a detectable substance and an unlabeled anti-human TMEFF1 antibody.

In yet another aspect, this application provides a method for detecting the presence of TMEFF1 in vivo (e.g., in vivo imaging in a subject). The subject method can be used to diagnose a disorder, e.g., a TMEFF1-associated disorder. The method includes: (i) administering the anti-TMEFF1 antibody or portion thereof as described herein to a subject or a control subject under conditions that allow binding of the antibody or portion to TMEFF1; and (ii) detecting formation of a complex between the antibody or portion and TMEFF1, wherein a statistically significant change in the formation of the complex in the subject relative to the control subject is indicative of the presence of TMEFF1.

V. Pharmaceutical Compositions

The disclosure also provides pharmaceutical compositions comprising an antibody, ADC, or antigen binding portion thereof, and a pharmaceutically acceptable carrier. The pharmaceutical compositions comprising antibodies or ADCs are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies. In another embodiment, the pharmaceutical composition comprises one or more antibodies or ADCs and one or more prophylactic or therapeutic agents other than antibodies or ADCs for treating a disorder in which TMEFF1 activity is detrimental. Preferably, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The antibodies and antibody-portions or ADCs can be incorporated into pharmaceutical compositions suitable for administration to a subject. Typically, the pharmaceutical composition comprises an antibody or antibody portion and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion or ADC.

Various delivery systems are known and can be used to administer one or more antibodies or ADCs or the combination of one or more antibodies and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody portion, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290, 540, and 4,880,078; and PCT Publication Nos. WO 92/19244, WO 97/32572, WO 97/44013, WO 98/31346, and WO 99/66903, each of which is incorporated herein by reference their entireties. In one embodiment, an antibody, combination therapy, or a composition is administered using Alkermes AIR® pulmonary drug delivery technology (Alkermes, Inc., Cambridge, Mass.). In a specific embodiment, prophylactic or therapeutic agents are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies antagonists is administered locally to the affected area to a subject to prevent, treat, manage, and/or ameliorate a disorder or a symptom thereof. In another embodiment, an effective amount of one or more antibodies is administered locally to the affected area in combination with an effective amount of one or more therapies (e.g., one or more prophylactic or therapeutic agents) other than an antibody of a subject to prevent, treat, manage, and/or ameliorate a disorder or one or more symptoms thereof.

A pharmaceutical composition is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

If the method of the disclosure comprises oral administration, compositions can be formulated orally in the form of tablets, capsules, cachets, gel caps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the disclosure also provides that one or more of the prophylactic or therapeutic agents, or pharmaceutical compositions is packaged in a hermetically sealed container such as an ampoule or sachette indicating the quantity of the agent. In one embodiment, one or more of the prophylactic or therapeutic agents, or pharmaceutical compositions is supplied as a dry sterilized lyophilized powder or water free concentrate in a hermetically sealed container and can be reconstituted (e.g., with water or saline) to the appropriate concentration for administration to a subject. The antibodies and antibody-portions or ADCs can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

It will be readily apparent to those skilled in the art that other suitable modifications and adaptations of the methods of the invention described herein are obvious and may be made using suitable equivalents without departing from the scope of the invention or the embodiments disclosed herein. Having now described the invention in detail, the same will be more clearly understood by reference to the following examples, which are included for purposes of illustration only and are not intended to be limiting.

Examples

Example 1. TMEFF1 is Expressed in Cancer Cell Lines

A panel of SCLC cell lines were examined on their surface for TMEFF1 expression using two human monoclonal anti-TMEFF1 antibodies conjugated to fluorochrome PE (30C10-PE and 31B7-PE). Flow cytometry analysis was performed for eleven SCLC cell lines H1876, DMS79, H1930, H69, H446, H378, H1048, H526, H209, H524 and SW1271 using 30C10-PE and 31B7-PE. TMEFF1-negative cell line SW1271 was used as a negative control.

Antigen density (number of TMEFF1 molecules on the surface of each cell) was also calculated in NTERA2 (an embryonal carcinoma cell line), HCC1187 (a triple negative breast cancer (TNBC) cell line) and PA-1 (an ovarian cancer cell line). Antigen density was determined using BD Quantibrite™ Beads PE Fluorescence Quantitation Kit (BD Bioscience, Cat. #340495)

TMEFF1 was found to be expressed at different copy numbers in all SCLC cell lines tested and in the ovarian, TNBC and embryonal carcinoma cell line. Cell surface TMEFF1 density ranged from 16175 to 1713 for the panel of cancer cell lines tested (see Table 1).

TABLE 1

Antigen density of TMEFF1 in a panel of cancer cell lines.

| Cell Line | Cell Surface Antigen Density | |
|---|---|---|
| | 30C10-PE | 31B7-PE |
| H1876 | 5147 | 4565 |
| DMS79 | 5134 | 5231 |
| H1930 | 4857 | 4754 |
| H69 | 4507 | 4422 |
| H446 | 3682 | 2986 |
| H378 | 3084 | 3127 |
| H1048 | 2675 | 2085 |
| H526 | 2385 | 2504 |
| H209 | 2296 | 1946 |
| H524 | 1713 | 1779 |
| SW1271 | 188 | 219 |
| HCC1187 | 16175 | 14431 |
| PA-1 | 3897 | 2415 |
| NTERA2 | 5777 | 4416 |

Example 2. Generation of Human Monoclonal Antibodies Against the TMEFF1 Extracellular Domain (ECD)

Experiments were performed to generate fully human antibodies against the TMEFF1 extracellular domain (TMEFF1-ECD). The following methods were used in this Example.

Methods

Immunizations in Humanized Mice

Monoclonal antibodies were obtained by immunizing Harbour H2L2 mice with CHO cell lines expressing full-length TMEFF1 tagged with MYC-DDK at the C-terminus. H2L2 mice were engineered with the capacity to produce human immunoglobulins at the variable region. Mice received 5 rounds of CHO-hTMEFF1 cells by tail vein injection and allowed to rest for one month. Mice were boosted 5 and 3 days prior to fusion of the spleen with rabbit splenocytes expressing full length hTMEFF1 or with recombinant protein of the extracellar domain (ECD) of hTMEFF1. hTMEFF1-ECD recombinant protein was made and secreted by CHO cells internally or purchased from Abcam (ab156353, Cambridge, Mass.).

Monoclonal antibodies were also obtained by immunization of H2L2 mice by Rapid immunization. Briefly TMEFF1-ECD was injected at the footpad twice/week and popliteal/inguinal lymph nodes were collected for fusion.

Recombinant TMEFF1 Cloning

Human TMEFF1 cDNA was purchased from Origene (RC207212, Rockville, Md.) and named BBP156. The encoded protein aligns 100% with GenBank TMEFF1_HUMAN. Mouse TMEFF1 cDNA was also purchased from Origine (MR205737).

Ectodomains of human, monkey (BBP196), rat and mouse were cloned by either PCR (human and mouse) or synthetic genes (monkey and rat). The synthetic genes were based on GenBank sequences (see Table 2). All DNA sequences were cloned into appropriate CMV-based expression vectors with non-native signal peptides and C-terminal histidine tags for purification.

TABLE 2

Source of TMEFF1 protein sequences

| Species | GenBank Protein Reference |
|---|---|
| Human | TMEFF1_HUMAN |
| Macaca fascicularis | XP_015292416 |
| Rat | NP_075409 |
| Mouse | TMEFF1_MOUSE |

The Origene BBP156 construct was used to express full-length human TMEFF1 protein (M1-V380) on the surface of HEK-293 or CHO cells (see Table 3). Mouse and monkey TMEFF1 were also expressed on the surface of HEK-293.

TABLE 3

TMEFF1 cell-surface expression vectors

| Plasmid name | Species | Sequence feature | Comment |
|---|---|---|---|
| BBP156 | Human | M1-V380 (Plus Myc-DDK) | Full construct |
| BBP196 | Macaca fascicularis | M1-A404 (Plus Myc-DDK) | Full construct |

A series of TMEFF1 constructs of human, mouse, monkey and rat were generated to secrete the ECD from CHO cells to assist with biophysical evaluations. In addition, a series of human TMEFF1 constructs containing deletions of different domains were generated to secrete portions of the ECD to screen antibody binding properties and epitopes (see Table 4).

TABLE 4

TMEFF1 ectodomain expression vectors

| Plasmid name | Species | Sequence feature (with N-terminal signal peptide and C-terminal 8xHis) | Comment |
|---|---|---|---|
| BBP377 | Homo sapiens | S40-V330 | Full Human ectodomain |
| BBP480 | Macaca fascicularis | S40-V330 | Full Monkey ectodomain |
| BBP481 | Rattus norvegicus | A36-V323 | Full rat ectodomain |
| BBP482 | Mus musculus | S36-V322 | Full mouse ectodomain |
| BBP483 | Homo sapiens | S40-V76/Y144-V330 | ΔFS1; Follistatin Domain 1 |
| BBP484 | Homo sapiens | S40-K169/T236-V330 | ΔFS2; Follistatin Domain 2 |
| BBP485 | Homo sapiens | S40-V76/T236-V330 | ΔFS1,2; Follistatin Domain 1&2 |

Cloning VH and VL Sequences from Hybridomas

For determination of CDR sequences, total RNA was isolated from hybridoma cells using an RNeasy® kit (Qiagen, Hilden, Germany). First and second-strand cDNA synthesis was performed using a OneTaq® One-Step RT-PCR kit (New England BioLabs, Ipswich, Mass.). Several primer sets were used (Table 5). PCR products were separated by agarose electrophoresis and fragments were excised and purified by a QIAquick® gel extraction kit (Qiagen, Hilden, Germany). Fragments were cloned directly into expression vectors with BspQI (New England BioLabs, Ipswich, Mass.) by Golden Gate cloning techniques. Four colonies from each reaction were scaled up for miniprep-scale plasmid purification by SequeMid® DNA Purification Kit (Aline Biosciences, Woburn, Mass.).

TABLE 5

Oligonucleotide Sequences

| SEQ ID NO | Oligonucleotide Sequence | Oligonucleotide Purpose |
|---|---|---|
| 230 | ATAGCTCTTCAGGGaccATGAARCAYCTGTGGTTCTTCCT | IGHV4 leader |
| 231 | ATAGCTCTTCAGGGaccATGGACATACTTTGTTCCACGC | IGHV2 leader |
| 232 | ATAGCTCTTCAGGGaccATGGACACACTTTGCTACACAC | IGHV2-26 leader |
| 233 | ATAGCTCTTCAGGGaccATGTCTGTCTCCTTCCTCATCT | IGHV6 leader |
| 234 | ATAGCTCTTCAGGGaccATGGACTGGACCTGGAGVATC | IGHV1 leader |
| 235 | ATAGCTCTTCAGGGaccATGGACTGGATTTGGAGGRTC | IGHV1-58 leader |
| 236 | ATAGCTCTTCAGGGaccATGGACTGCACCTGGAGGATC | IGHV1-24 leader |
| 237 | ATAGCTCTTCAGGGaccATGGACTGGACCTGGAGGKTC | IGHV1-69/1-46/7-4-1 leader |
| 238 | ATAGCTCTTCAGGGaccATGGAGTTKGGRCTGAGCTGG | IGHV3 leader |
| 239 | ATAGCTCTTCAGGGaccATGGAGTTTKGGCTKAGCTGG | IGHV3-53/3-49 leader |
| 240 | ATAGCTCTTCAGGGaccATGGAACTGGGGCTCCGCTGG | IGHV3-21 leader |
| 241 | ATAGCTCTTCAGGGaccATGGARTTGGGGCTGWGCTGG | IGHV3-48/3-7 leader |
| 242 | ATAGCTCTTCAGGGaccATGGGGTCAACCGCCATCCTC | IGHV5 leader |
| 243 | ATAGCTCTTCAGGGaccATGGACATGAGGGTSCCYGCTCAGCTC | IgkV1a leader |
| 244 | ATAGCTCTTCAGGGaccATGGACATGAGRGTCCTCGCTCAGCTC | IgkV1b leader |
| 245 | ATAGCTCTTCAGGGaccATGGAAGCCCCAGCDCAGCTTCTC | IgkV3 leader |
| 246 | ATAGCTCTTCAGGGaccATGGAAACCCCAGCGCAGCTTCTC | IgkV3-20 leader |
| 247 | ATAGCTCTTCAGGGaccATGGTGTTGCAGACCCAGGTCTTC | IgkV4 leader |
| 248 | ATAGCTCTTCAGGGaccATGGGGTCCCAGGTTCACCTCCTC | IgkV5 leader |
| 249 | ATAGCTCTTCAGGGaccATGAGGCTCCYTGCTCAGCTCCTG | IgkV2 leader |
| 250 | ATAGCTCTTCTTCGTTTGATCTCCASCTTGGTC | Kappa FW4 |
| 251 | ATAGCTCTTCTTCGTTTAATCTCCAGTCGTGTC | Kappa FW4 |
| 252 | ATAGCTCTTCTGGCTGAGGAGACGGTGACC | Heavy FW4 |
| 253 | ATAGCTCTTCATGTGACGCTGTTGTGACTCAGGA | VL-FOR L1 |
| 254 | ATAGCTCTTCATGTGACCYTGTGCTCACTCAGTC | VL-FOR L2 |
| 255 | GATGCTCTTCTGGGCTGGCCTAGGACAGTCAMCYTGG | VL-REV L |

Identification of Functional, Recombinant VH and VL Sequences

For each hybridoma, each plasmid was sent for Sanger Sequencing. These plasmids were subjected to DNA sequence determination and analysis. Unique recombinant heavy chains were paired with unique recombinant light chains. These plasmid pairs were transfected into CHO cells in 24-well plates. Ten days later conditioned medium from each pairing was screened by FLOW™ or Octet™ for binding to TMEFF1.

Transient Expression System of Medium Scale Antibody Production or Recombinat Proteins The TMEFF1 recombinant proteins and anti-TMEFF1 antibodies were expressed in Chinese hamster ovary (CHO) cells in a 100 ml volume flask using recommended transfection and media components of the ExpiCHO™ system (Invitrogen, Carlsbad, Calif.). Cell culture supernatants were harvested 14 days post-transfection, centrifuged, and filtered (0.22 um).

Purification of Recombinant His-Tagged Proteins

Conditioned medium from CHO cell cultures was clarified, filtered, and loaded onto an AKTAprime Plus™ system with a 5 mL HisTrap™ FF column (GE Healthcare). Fractions were collected, analyzed by SDS-PAGE, pooled, and dialyzed against PBS.

Antibody Purification

Conditioned medium from CHO cell cultures was clarified, filtered, and purified by loading onto an AKTA Pure™ system with a 5mLMabSelect SuRe® column (GE Healthcare). Antibodies were eluted with 100 mM glycine, pH 3.5 and neutralized with 1M Tris-C1, pH 8.5.

Recombinant Antibody Analyses

Concentration: Concentration of recombinant antibodies was determined on a Fortebio Octet Red™ (Pall ForteBio, Fremont, Calif.) instrument using Protein A tips and a human IgG1 antibody for the standard curve.

Purity Testing by SDS-PAGE:

Purity testing was performed by sodium dodecyl sulfate polyacrylamide gel electrophoresis (SDS-PAGE) of reduced and non-reduced samples. Samples (10 ug) were mixed with loading buffer (+/−β-mercaptoethanol), heated, and electrophoresed on a 4-20% gel (Invitrogen, Carlsbad, Calif.). Bands were visualized by Coomassie InstantBlue™ (Expedeon, San Diego, Calif.) staining.

Purity Testing by Endotoxin:

Endotoxin concentrations were measured by the Limulus amoebocyte lysate (LAL) kinetic turbidometric method using the Endosafe-PTS™ system (Charles River Laboratories, Wilmington, Mass.).

Purity Testing by HPLC-SEC:

Samples were screened for aggregation or other forms of antibody on a 1260 Infinity System™ (Agilent, Santa Clara, Calif.) with a TSKgel UltraSW Aggregate Guard™ column and HPLC column (Tosoh Bioscience). Samples and standards were detected by absorbance at 280 nm. Comparison against the standard curve provided the molar mass of sample components.

Affinity:

The affinity of antibodies to various recombinant TMEFF1 protein was determined on an Octet Red™ instrument. After loading reagents into a 96-well plate, the Octet Red™ with Protein A-conjugated biosensors was programmed as follows: 30 seconds for baseline #1; 120 seconds to immobilize the antibody; 30 seconds for baseline #2; 300 seconds for association of antibody to recombinant TMEFF1; and 300-600 seconds for dissociation of recombinant TMEFF1 from the antibody.

Binding Competition Binning:

Binding competition among different antibodies was determined using a real-time, interferometry assay on an Octet Red™ instrument with Protein A-conjugated biosensors. To assess whether two antibodies competed for binding to a recombinant TMEFF1 protein, the assay was performed as follows. Protein A biosensors were first submerged into wells containing 10 ug/mL of individual monoclonal antibodies for 5 minutes. Following the capture step, the biosensors were dipped briefly (15 seconds) into buffer and then any unoccupied sites on the biosensor were saturated by submerging them for 5 minutes into wells containing 100 ug/mL of an irrelevant monoclonal antibody. The Octet biosensors were then dipped briefly (15 seconds) in buffer before immersion for 1 minute into wells containing recombinant TMEFF1. The biosensors were dipped briefly (15 seconds) in buffer before immersion for 1 minute into wells containing a second recombinant antibody.

For the control case where the second antibody was the same as the first, there was no increase in signal, because there was no additional binding to the recombinant target.

For the control case where buffer was used instead of the first antibody, no recombinant target bound the non-quenching antibody on the biosensor and no second antibody bound the biosensor.

For cases where a boost in signal was seen with the second antibody, the two antibodies were determined not to compete.

For cases where no boost in signal was seen with the second antibody, the two antibodies were determined to compete for binding.

Binding Domain Determination:

TMEFF1 recombinant proteins expressing 3 different deletion mutants, AFS1 (AFollistatin Domain 1), AFS2 (AFollistatin Domain 2) or AFS1&FS2 were used to identify binding domains among different antibodes using an Octet Red instrument with Anti-Penta-His (HIS 1K) biosensors. Expression of the 3 deletion mutants was confirmed by WB analysis. 100 ngs of purified TMEFF1 ECD was run along with unpurified supernatant of transfected CHO cells with the different deletion mutants. HIS 1K biosensors were loaded by submerging the biosensors into wells containing 10 ug/ml of full length TMEFF1 or one of 3 different deletion mutants (AFS1, AFS2 or AFS1&FS2) for 60 seconds. Following the loading step, the biosensors were then dipped for 30 seconds in PBS before immersion for 30 seconds in 200 ul of unpurified recombinant antibodies for 30 seconds. The biosensors were then dipped briefly (30 seconds) in PBS to observe any dissociation. Samples were determined to show binding or no binding by comparing to a control well that contained no recombinant antibody. Differential binding to the deletion mutants allowed for determination of binding sites on TMEFF1 recombinant protein. For cases where the antibody bound all 3 recombinant proteins, the binding is outside of the deleted domains. For the case where binding is observed only on full length TMEFF1 and AFS2, the antibody is binding in the ΔFS1 domain.

Immunofluorescence (IF) Based High Content Screening (HCS)

High content immunofluorescence was used to identify wells that contain immunoglobulin that preferentially bound TMEFF1. Briefly, 293 cells and 293-hTMEFF1 cells seeded 24 hours before the assay were incubated for 120 minutes at 37° C. with hybridoma supernatant diluted 2-fold in DMEM+10% fetal bovine serum (FBS). After incubation, cells were fixed in 4% formaldehyde, washed with PBS, permeabilized with 0.3% Triton-X-100, and labeled with anti-rat Alexa 488 (at hybridoma stage) or anti-human Alexa 488 secondary antibodies (with recombinant TMEFF1 antibodies) for 1 hour at room temperature. Unbound secondary antibody was removed with PBS washes, and cells were stained with DNA dye (propidium iodide and Hoechst 33342).

Potential hits were initially identified via low-resolution, high throughput screening using a TTP Labtech Acumen eX3™ (TTP Labtech, Cambridge, Mass.), quantifying the fluorescence differential for each sample on both positive and negative cell lines. Those hits were subsequently verified and the subcellular localization of each sample was characterized using a Thermo ArrayScan VTi™ (Thermo Fisher Scientific, Waltham, Mass.) to obtain high-resolution images of both cell lines.

Flow Cytometry

Supernatant from hybridoma wells after having undergone cellular subcloning, containing TMEFF1 specific antibodies, were re-tested on parental 293 cells and 293-hTMEFF1, 293 cells over-expressing mouse TMEFF1 and 293 cells overexpressing monkey TMEFF1 and on cancer cell lines. Cells were collected, pelleted and transferred to 96-V bottom polypropylene plates. Cells were resuspended with hybridoma supernatant diluted 2-fold and labeled with anti-rat 488 secondary antibodies for 45 min at 4° C. Cells were resuspended in 200 μL of flow buffer containing PI to identify dead cells and remove from analysis. Cells were run on a MACSQuant Analyzer 10™ flow cytometer (Miltenyi Bioted, Bergisch Gladbach, Germany) and analysis was performed with FlowJo™ software (FlowJo, Ashland, Oreg.).

Results

Fully human antibodies against TMEFF1-ECD were generated by hybridoma procedures. Briefly H2L2 mice were immunized with CHO cells over-expressing TMEFF1 and boosted with Rabbit splenocytes expressing human TMEFF1 or with ECD TMEFF1 recombinant protein. Splenocytes were fused with the mouse myeloma cell line X63-Ag8.653. For mice receiving recombinant TMEFF1-ECD at the foot pad by rapid immunization, popliteal and inguinal limph nodes were collected and fused. Clones from H2L2 mice receiving whole cell immunizations producing antibodies against TMEFF1-ECD were identified by immunofluorescence (IF) based high content screening (HCS) on 293 cells overexpressing hTMEFF1 and parental 293 cells not expressing TMEFF1. From H2L2 mice receiving whole cell immunizations, 170 hits that showed MFI ratio >2 in 293-hTMEFF1 vs. parental 293 cells were identified. From H2L2 mice receiving recombinant hTMEFF1-ECD by rapid immunization, 307 hits with MFI higher than baseline signal from single cell sorting and Flow analyses were identified. 170 hits from whole cell immunizations and 40 hits from recombinant protein immunizations were cryopreserved and stored in liquid nitrogen. 48 clones were selected for molecular cloning and 32 antibodies with unique CDR3 variable regions were converted to recombinant human IgG1 antibodies against TMEFF1-ECD.

Complete amino acid sequences of the heavy and light chains from these 32 antibodies are set forth in Table 6, below, and as SEQ ID NOs: 1-164. The nucleic acid sequences of the heavy and light chains from the 32 antibodies are set forth as SEQ ID NOs: 165-228, as listed in the Sequence Summary, below and in the Sequence Listing.

TABLE 6

Variable region sequencs of human antibodies

| SEQ ID NO: | Clone Name | Protein Domain | Sequence |
| --- | --- | --- | --- |
| 1 | 34B7 | VH | QVQLVESGGGVVQPGRSLRLSCAASGFTFTSYGMHWVRQAPGKGLEWV AVVWYEGNSKFYIDSVKGRFIISRDNSKNTLYLQMNSLRAEDTAVYYCA RAYCGDDCYPFDYWGQGTLVTVSS |
| 2 | 34B7 | CDR-H1 | GFTFTSYGMH |
| 3 | 34B7 | CDR-H2 | VVWYEGNSKFYIDSVKG |
| 4 | 34B7 | CDR-H3 | AYCGDDCYPFDY |
| 5 | 34B7 | VL | DIQMTQSPSSLSASVGDRVTITCRASQGISNYLAWYQQKPGKVPKLLIYA ASTLQSGVPSRFSGSGSGTDFTLTISSLQPEDVATYYCQKYNSAPWTFGQ GTKLEIK |
| 6 | 34B7 | CDR-L1 | RASQGISNYLA |
| 7 | 34B7 | CDR-L2 | AASTLQS |
| 8 | 34B7 | CDR-L3 | QKYNSAPWT |
| 9 | M1F1 | VH | QVQLQESGPGLVKPSETLSLTCAVSGYSISSGYFWGWIRQPPGKKLEWIG SIYHSGSTYYNPSLKSRVTMSVDTSKNQFSLKLSSVTAADTAVYYCAREG DCSGGICYWYFDLWGRGTLVTVSS |
| 10 | M1F1 | CDR-H1 | GYSISSGYFWG |
| 11 | M1F1 | CDR-H2 | SIYHSGSTYYNPSLKS |
| 12 | M1F1 | CDR-H3 | EGDCSGGICYWYFDL |
| 13 | M1F1 | VL | EIVMTQSPATLSVSPGERATLSCRASQSVSSNLAWYQQKPGQAPRLLIYG ASTRATGIPARFSGSGSGTEVTLTISSLQSEDFAVYYCQQYNKWPLTFGG GTKVEIK |
| 14 | M1F1 | CDR-L1 | RASQSVSSNLA |
| 15 | M1F1 | CDR-L2 | GASTRAT |
| 16 | M1F1 | CDR-L3 | QQYNKWPLT |
| 17 | 31B7 | VH | QVQLVESGGGVVQPGRSLRLSCAASGFTFSSYGMHWVRQAPGKGLEWV AVIWYNGINKYYADSVKGRFTISRDASKNTLYLQMNSLRAEDTAVYYCA REGLLWFGGMDVWGQGTTVTVSS |
| 18 | 31B7 | CDR-H1 | GFTFSSYGMH |
| 19 | 31B7 | CDR-H2 | VIWYNGINKYYADSVKG |
| 20 | 31B7 | CDR-H3 | EGLLWFGGMDV |

TABLE 6-continued

Variable region sequencs of human antibodies

| SEQ ID NO: | Clone Name | Protein Domain | Sequence |
|---|---|---|---|
| 21 | 31B7 | VL | EIVLTQSPLSLPVTPGEPASISCRSSQSLLHSNGYNYLHWYLQKPGQSPQL LIYLGSNRASGVPDRFSGSRSGTDFTLKIIRVEAEDVGVYYCMQALQTPY TFGQGTKLEIK |
| 22 | 31B7 | CDR-L1 | RSSQSLLHSNGYNYLH |
| 23 | 31B7 | CDR-L2 | LGSNRAS |
| 24 | 31B7 | CDR-L3 | MQALQTPYT |
| 25 | M3 | VH | QVLLVESGGGVVQPGRSLRLSCAASGFTFKRYGMHWVRQAPGRGLEWV AVIWSDGNKKHYADSVKGRFTISRDNSKNTLYLQMNSLRAEDTAVYYC ARENYGSGSYYNGGMDVWGQGTTVTVSS |
| 26 | M3 | CDR-H1 | GFTFKRYGMH |
| 27 | M3 | CDR-H2 | VIWSDGNKKHYADSVKG |
| 28 | M3 | CDR-H3 | ENYGSGSYYNGGMDV |
| 29 | M3 | VL | DIQMTQSPSTLSASVGDRVTITCRASQSISSWLAWYQQKPGKAPKLLIYK ASSLESGVPSRFSGSGSGTEFTLTISSLQPDDFATYYCQQYNSYSWTFGQG TKLEIK |
| 30 | M3 | CDR-L1 | RASQSISSWLA |
| 31 | M3 | CDR-L2 | KASSLES |
| 32 | M3 | CDR-L3 | QQYNSYSWT |
| 33 | 24F10 | VH | QVQLVESGGGVVQPGRSLRLSCAASGFTFSSYGMHWVRQAPGKGLEWV AVIWYDGSDKYYTDSVKGRFTISRDNSKNTLYLQMNSLRAEDTAVYYC ARESMVRGIVITFFDYWGQGTLVTVSS |
| 18 | 24F10 | CDR-H1 | GFTFSSYGMH |
| 34 | 24F10 | CDR-H2 | VIWYDGSDKYYTDSVKG |
| 35 | 24F10 | CDR-H3 | ESMVRGIVITFFDY |
| 36 | 24F10 | VL | EIVMTQSPATLSVSPGERATLSCRASQSVSSNLAWYQQKPGQAPRLLIYG ASTRATGIPARFSGSGSGTEFTLTISSLQSEDFAVYSCQHYNNWPPTFGGG TKVEIK |
| 14 | 24F10 | CDR-L1 | RASQSVSSNLA |
| 15 | 24F10 | CDR-L2 | GASTRAT |
| 37 | 24F10 | CDR-L3 | QHYNNWPPT |
| 38 | 30C10 | VH | QVQLVESGGGVVQPGRSLRLSCAASGFTFSSYGMHWVRQAPGKGLEWV AVIWYDGSDKYYADSVKGRFTISRDNSKKTLYLQMNSLRAEDTAVYFC ARETIFRGLTITFFDHWGQGTLVTVSS |
| 18 | 30C10 | CDR-H1 | GFTFSSYGMH |
| 39 | 30C10 | CDR-H2 | VIWYDGSDKYYADSVKG |
| 40 | 30C10 | CDR-H3 | ETIFRGLTITFFDH |
| 41 | 30C10 | VL | EIVMTQSPATLSVSPGERATLSCRASQSVSSNLAWYQQKPGQAPRLLIYG ASTRATGIPARFSGSGSGTEFTLTISSLQSEDFAVYYCQQYNNWPPTFGGG TKLEIK |
| 14 | 30C10 | CDR-L1 | RASQSVSSNLA |
| 15 | 30C10 | CDR-L2 | GASTRAT |
| 42 | 30C10 | CDR-L3 | QQYNNWPPT |
| 43 | 36H6 | VH | QVQLVESGGGVVQPGRSLRLSCAASGFTFSDYGMHWVRQAPGKGLEWV AVIWYEGGNKYYTDSVKGRFTISRDNSKNTLYLQMNSLRAEDTAVYYC ARILLWFGESYGMDVWGQGTTVTVSS |
| 44 | 36H6 | CDR-H1 | GFTFSDYGMH |

TABLE 6-continued

Variable region sequencs of human antibodies

| SEQ ID NO: | Clone Name | Protein Domain | Sequence |
|---|---|---|---|
| 45 | 36H6 | CDR-H2 | VIWYEGGNKYYTDSVKG |
| 46 | 36H6 | CDR-H3 | ILLWFGESYGMDV |
| 47 | 36H6 | VL | DIQMTQSPSSLSASVGDRVTITCRASQGISNYLAWYQQKPGKVPKLLIYA ASTLQSGVPSRFSGSGSGTDFTLTISSLQPEDVATYYCQKYNNAPWTFGQ GTKVEIK |
| 6 | 36H6 | CDR-L1 | RASQGISNYLA |
| 7 | 36H6 | CDR-L2 | AASTLQS |
| 48 | 36H6 | CDR-L3 | QKYNNAPWT |
| 49 | 43A12H | VH | QVQLVESGGGVVQPGRSLRLSCAASGFTFRSYGMHWVRQAPGKGLEWV AVIWYDGSIKYYADSVKGRFTISRDNSKNTLYVQMNSLRAEDTAVYYCA RDRDYFGSGYYSNVRYYYYGMDVWGQGTTVTVSS |
| 50 | 43A12H | CDR-H1 | GFTFRSYGMH |
| 51 | 43A12H | CDR-H2 | VIWYDGSIKYYADSVKG |
| 52 | 43A12H | CDR-H3 | DRDYFGSGYYSNVRYYYYGMDV |
| 53 | 43A12H | VL | DIQMTQSPSSLSASVGDRVTITCRASQSISSYLNWYQQKPGKPKLLIYAA SSLQSGVPSRFSGSGSGTDFTLTISSLQPEDFATYYCQQSYSTPPLTFGGGT KVEIK |
| 54 | 43A12H | CDR-L1 | RASQSISSYLN |
| 7 | 43A12H | CDR-L2 | AASSLQS |
| 55 | 43A12H | CDR-L3 | QQSYSTPPLT |
| 56 | 6C11 | VH | QVQLQQSGPGLVKPSQTLSLTCAISGDSVSSNSAAWNWIRQSPSRGLEWL GRTYYRSKWYNDYPVSVKSRITINPDTSKNQVSLQLNPVTPEDTAVYYC TREQGYSSSRYYYYYGMDVWGQGTTVTVSS |
| 57 | 6C11 | CDR-H1 | GDSVSSNSAAWN |
| 58 | 6C11 | CDR-H2 | RTYYRSKWYNDYPVSVKS |
| 59 | 6C11 | CDR-H3 | EQGYSSSRYYYYYGMDV |
| 60 | 6C11 | VL | DIVMTQSPLSLPVTPGEPASISCRSSQSLLHINGYNYLDWYLQKPGQSPQL LIYLGSNRASGVPDRFSGSGSGTDFTLKISRVEAEDVGVYYCMQALQTPY TFGQGTKVEIK |
| 61 | 6C11 | CDR-L1 | RSSQSLLHINGYNYLD |
| 23 | 6C11 | CDR-L2 | LGSNRAS |
| 24 | 6C11 | CDR-L3 | MQALQTPYT |
| 62 | 19H1 | VH | QVQLQQSGPGLVKPSQTLSLTCAISGDSVSSNSAAWNWIRQSPSRGLEWL GRTYYRSQWYNDYPVSVKSRITINPDTSKNQVSLQLNPVTPEDTAVYYC AREQGYSSSRYYYYYGMDVWGQGTTVTVSS |
| 57 | 19H1 | CDR-H1 | GDSVSSNSAAWN |
| 63 | 19H1 | CDR-H2 | RTYYRSQWYNDYPVSVKS |
| 59 | 19H1 | CDR-H3 | EQGYSSSRYYYYYGMDV |
| 64 | 19H1 | VL | DIVMTQSPLSLPVTPGEPASISCRSSQSLLHSNGYNYLDWYLQKPGQSPQL LIYLGSNRASGVPDRFSGSGSGTDFTLKISRVEAEDVGVYYCMQALQTPY TFGQGTKVEIK |
| 65 | 19H1 | CDR-L1 | RSSQSLLHSNGYNYLD |
| 23 | 19H1 | CDR-L2 | LGSNRAS |
| 24 | 19H1 | CDR-L3 | MQALQTPYT |

TABLE 6-continued

Variable region sequences of human antibodies

| SEQ ID NO: | Clone Name | Protein Domain | Sequence |
|---|---|---|---|
| 66 | 35B1 | VH | QVQLVESGGGVVQPGRSLRLSCAASGFTFTTYGMHWVRQAPGKGLEWV AVVWFEGNSKFYIDSVKGRFIISRDNSKNTLFLQMNSLRAEDTAVYYCAR ANCGADCYPFDYWGQGTLVTVSS |
| 67 | 35B1 | CDR-H1 | GFTFTTYGMH |
| 68 | 35B1 | CDR-H2 | VVWFEGNSKFYIDSVKG |
| 69 | 35B1 | CDR-H3 | ANCGADCYPFDY |
| 70 | 35B1 | VL | DIQMTQSPSSLSASVGDRVTITCRASQGISNYLAWYQQKPGKVPKLLIYA ASTLQSGVPSRFSGSGSGTDFSLTISSLRPEDVATYYCQKYNSAPWTFGQ GTKVEIK |
| 6 | 35B1 | CDR-L1 | RASQGISNYLA |
| 7 | 35B1 | CDR-L2 | AASTLQS |
| 8 | 35B1 | CDR-L3 | QKYNSAPWT |
| 79 | M17 | VH | QVQLVESGGGVVQPGRSLRLSCAASGFTFRSYGMHWVRQAPGKGLEWV ALIWYDGGDQYYADSVKGRFTISRDSSKSTLYLQMNSLRAEDTAVYYCA RAQCGDDCYPFDYWGQGTLVTVSS |
| 50 | M17 | CDR-H1 | GFTFRSYGMH |
| 80 | M17 | CDR-H2 | LIWYDGGDQYYADSVKG |
| 81 | M17 | CDR-H3 | AQCGDDCYPFDY |
| 82 | M17 | VL | DIQMTQSPSSLSASVGDRVTITCRASQGIYNYLAWYQQKPGKVPKLLIYA ASTLQSGVPSRFSGSGSGTDFTLTISSLQPEDVATYYCQKYNSDPWTFGQ GTKLEIK |
| 83 | M17 | CDR-L1 | RASQGIYNYLA |
| 7 | M17 | CDR-L2 | AASTLQS |
| 84 | M17 | CDR-L3 | QKYNSDPWT |
| 85 | 37G7 | VH | QVQLVESGGGVVQPGRSLRLSCAASGFTFTSYGMHWVRQAPGKGLEWV AVVWYEGSSKFYVDSVKGRFIISRDNSKNTLYLQMNSLRAEDTAVYYCA RAYCGGDCYPFDYWGQGTLVTVSS |
| 2 | 37G7 | CDR-H1 | GFTFTSYGMH |
| 86 | 37G7 | CDR-H2 | VVWYEGSSKFYVDSVKG |
| 87 | 37G7 | CDR-H3 | AYCGGDCYPFDY |
| 88 | 37G7 | VL | DIQMTQSPSSLSASVGDRVTITCRASQGISNYLAWYQQKPGKVPKLLIYA ASTLQSGVPSRFSGSGSGTDFTLTISSLQPEDVATYYCQKYNSAPWTFGQ GTKVEIK |
| 6 | 37G7 | CDR-L1 | RASQGISNYLA |
| 7 | 37G7 | CDR-L2 | AASTLQS |
| 8 | 37G7 | CDR-L3 | QKYNSAPWT |
| 89 | 18C2 | VH | QVQLVESGGGVVQPGRSLRLSCAASGFTFSIYGMHWVRQAPGMGLEWV AIIRYDGSNKYYADSVKGRFTISRDNSKNTLYLRMNSLRAEDTAVYYCA RDPFTSSLDYWGQGTLVTVSS |
| 90 | 18C2 | CDR-H1 | GFTFSIYGMH |
| 91 | 18C2 | CDR-H2 | IIRYDGSNKYYADSVKG |
| 92 | 18C2 | CDR-H3 | DPFTSSLDY |
| 93 | 18C2 | VL | DIQLTQSPSFLSASVGDRVTITCRASQGISSYLAWYQQKPGKAPKLLIYAA STLQSGVPSRFSGSGSGTEFTLTISSLQPEDFATYYCQQLNSYPLTFGGGT KLEIK |
| 94 | 18C2 | CDR-L1 | RASQGISSYLA |

TABLE 6-continued

Variable region sequencs of human antibodies

| SEQ ID NO: | Clone Name | Protein Domain | Sequence |
|---|---|---|---|
| 7 | 18C2 | CDR-L2 | AASTLQS |
| 95 | 18C2 | CDR-L3 | QQLNSYPLT |
| 96 | 10C10 | VH | QVQLVESGGGVVQPGRSLRLSCATSGFTFSIYGMHWVRQAPGKGLEWV AIIWYDGNKKYYADSVKGRFTISRDNSKNTLYLQMNSLRAEDTAVYYCA RDPYTSSLDYWGQGTLVTVSS |
| 90 | 10C10 | CDR-H1 | GFTFSIYGMH |
| 97 | 10C10 | CDR-H2 | IIWYDGNKKYYADSVKG |
| 98 | 10C10 | CDR-H3 | DPYTSSLDY |
| 93 | 10C10 | VL | DIQLTQSPSFLSASVGDRVTITCRASQGISSYLAWYQQKPGKAPKLLIYAA STLQSGVPSRFSGSGSGTEFTLTISSLQPEDFATYYCQQLNSYPLTFGGGT KLEIK |
| 94 | 10C10 | CDR-L1 | RASQGISSYLA |
| 7 | 10C10 | CDR-L2 | AASTLQS |
| 95 | 10C10 | CDR-L3 | QQLNSYPLT |
| 99 | 19D9 | VH | QVQLVESGGGVVQPGRSLRLSCAASGFTFSIYGMHWVRQAPGKGLEWV ANIWYDGSKKYYADSVKGRFTISRDNSKNTLYLQMNSLRAEDTSVYYC ARDPYTSSLDYWGQGTLVTVSS |
| 90 | 19D9 | CDR-H1 | GFTFSIYGMH |
| 100 | 19D9 | CDR-H2 | NIWYDGSKKYYADSVKG |
| 98 | 19D9 | CDR-H3 | DPYTSSLDY |
| 101 | 19D9 | VL | DIQLTQSPSFLSASVGDRVTITCRASQGISSYLAWYQQKPGKAPKLLIYTA STLQSGVPSRFSGSGSGTEFTLTISSLQPEDFATYYCQQLNSYPLTFGGGT KLEIK |
| 94 | 19D9 | CDR-L1 | RASQGISSYLA |
| 102 | 19D9 | CDR-L2 | TASTLQS |
| 95 | 19D9 | CDR-L3 | QQLNSYPLT |
| 103 | 7F12 | VH | QVQLVESGGGVVQPGRSLRLSCAASGFTFSIYGMHWVRQAPGKGLEWV AIIWYDGSDKYYADSVKGRFTISRDNSKNTLYLQMNSLRAEDTAVYYCA RDPYTTSLDYWGQGTLVTVSS |
| 90 | 7F12 | CDR-H1 | GFTFSIYGMH |
| 104 | 7F12 | CDR-H2 | IIWYDGSDKYYADSVKG |
| 105 | 7F12 | CDR-H3 | DPYTTSLDY |
| 106 | 7F12 | VL | DIQLTQSPSFLSASVGDRVTITCRASQGISSYLAWYQQKPGKAPKLLIYAA STLQSGVPSRFSGSGSGTEFTLTISSLQPEDFATYYCQQLNSYPLTFGGGT KVEIK |
| 94 | 7F12 | CDR-L1 | RASQGISSYLA |
| 7 | 7F12 | CDR-L2 | AASTLQS |
| 95 | 7F12 | CDR-L3 | QQLNSYPLT |
| 107 | 9D1 | VH | QVQLVESGGGVVQPGRSLRLSCAASGFTFSSYGMHWVRQAPGKGLEWV AVIWYDGSNKYADSVKGRFTLSRDNSKNTLYLQMNSLRAEDTAVYYC ARDSTGSSWSYYYYYGMDVWGQGTTVTVSS |
| 18 | 9D1 | CDR-H1 | GFTFSSYGMH |
| 108 | 9D1 | CDR-H2 | VIWYDGSNKYYADSVKG |
| 109 | 9D1 | CDR-H3 | DSTGSSWSYYYYYGMDV |

TABLE 6-continued

Variable region sequencs of human antibodies

| SEQ ID NO: | Clone Name | Protein Domain | Sequence |
|---|---|---|---|
| 110 | 9D1 | VL | DAVVTQESALTTSPGETVTLTCRSSTGAVTTSNYANWVQEKPDHLFTGLI GGTNNRAPGVPARFSGSLIGDKAALTITGAQTEDEAIYFCALWYSNHLVF GGGTKLTVLG |
| 111 | 9D1 | CDR-L1 | RSSTGAVTTSNYAN |
| 112 | 9D1 | CDR-L2 | GTNNRAP |
| 113 | 9D1 | CDR-L3 | ALWYSNHLV |
| 9 | M1H1 | VH | QVQLQESGPGLVKPSETLSLTCAVSGYSISSGYFWGWIRQPPGKKLEWIG SIYHSGSTYYNPSLKSRVTMSVDTSKNQFSLKLSSVTAADTAVYYCAREG DCSGGICYWYFDLWGRGTLVTVSS |
| 10 | M1H1 | CDR-H1 | GYSISSGYFWG |
| 11 | M1H1 | CDR-H2 | SIYHSGSTYYNPSLKS |
| 12 | M1H1 | CDR-H3 | EGDCSGGICYWYFDL |
| 78 | M1H1 | VL | DIQMTQSPSSLSASVGDRVTITCRASQGISNYLAWYQQKPGKVPKLLIYA ASTLQSGVPSRFSGSGSGTDFTLTISSLQPEDFAVYYCQQYNKWPLTFGG GTKLEIK |
| 6 | M1H1 | CDR-L1 | RASQGISNYLA |
| 7 | M1H1 | CDR-L2 | AASTLQS |
| 16 | M1H1 | CDR-L3 | QQYNKWPLT |
| 9 | M33F | VH | QVQLQESGPGLVKPSETLSLTCAVSGYSISSGYFWGWIRQPPGKKLEWIG SIYHSGSTYYNPSLKSRVTMSVDTSKNQFSLKLSSVTAADTAVYYCAREG DCSGGICYWYFDLWGRGTLVTVSS |
| 10 | M33F | CDR-H1 | GYSISSGYFWG |
| 11 | M33F | CDR-H2 | SIYHSGSTYYNPSLKS |
| 12 | M33F | CDR-H3 | EGDCSGGICYWYFDL |
| 141 | M33F | VL | DIQMTQSPSSLSASVGDRVTITCRASQGISNYLAWYQQKPGKVPKLLIYA ASTLQSGVPSRFSGSGSGTEVTLTISSLQSEDFAVYYCQQYNKWPLTFGG GTKLEIK |
| 6 | M33F | CDR-L1 | RASQGISNYLA |
| 7 | M33F | CDR-L2 | AASTLQS |
| 16 | M33F | CDR-L3 | QQYNKWPLT |
| 124 | M10 | VH | QVQLVESGGGGVQPGRSLRLSCAASGFTFSRYGMHWVRQAPGKGLEWV AVIWYDGSDEYYADSVKGRFTISRDNSKNTLYLQMNSLRAEDTAVYYC ARETMGRGIIISYFDYWGQGTPVTVSS |
| 125 | M10 | CDR-H1 | GFTFSRYGMH |
| 126 | M10 | CDR-H2 | VIWYDGSDEYYADSVKG |
| 127 | M10 | CDR-H3 | ETMGRGIIISYFDY |
| 128 | M10 | VL | EIVMTQSPATLSVSPGERATLSCRASQSVSSNLAWYQQKPGQAPRLLIYG ASTRATGIPARFSGSGSGTEFTLTISSLQSEDFAVYYCQQYNNWPPTFGQG TKLEIK |
| 14 | M10 | CDR-L1 | RASQSVSSNLA |
| 15 | M10 | CDR-L2 | GASTRAT |
| 42 | M10 | CDR-L3 | QQYNNWPPT |
| 129 | 45D8 | VH | EVQLLESGGGLVQPGGSLRLSCAASGFTFSSYAMSWVRQAPGKGLEWVS TISGSGGSTYYADSVKGRFTISRDNSKNTLYLQMNSLRAEDTAIYYCAKF GVRGVIITNWFDPWGQGTLVTVSS |
| 130 | 45D8 | CDR-H1 | GFTFSSYAMS |

TABLE 6-continued

Variable region sequences of human antibodies

| SEQ ID NO: | Clone Name | Protein Domain | Sequence |
|---|---|---|---|
| 131 | 45D8 | CDR-H2 | TISGSGGSTYYADSVKG |
| 132 | 45D8 | CDR-H3 | FGVRGVIITNWFDP |
| 133 | 45D8 | VL | EIVMTQSPATLSVSPGERATLSCRASQSVSSNLAWYQQKPGQAPRLLIYG ASTRATGIPARFSGSGSGTEFTLTISSLQSEDFAVYYCQQYNNWPLTFGGG TKLEIK |
| 14 | 45D8 | CDR-L1 | RASQSVSSNLA |
| 15 | 45D8 | CDR-L2 | GASTRAT |
| 16 | 45D8 | CDR-L3 | QQYNKWPLT |
| 71 | 11F9 | VH | EVQLVESGGGLVKPGGSLRLSCAASGFTFSYAWMSWVRQAPGKGLEWV GRIKSKTDGGTTDYAAPVKGRFTISRDDSKNTLYLQLNSLKIEDTAVYYC TTGRIAAAGFDYWAQGTLVTVSS |
| 72 | 11F9 | CDR-H1 | GFTFSYAWMS |
| 73 | 11F9 | CDR-H2 | RIKSKTDGGTTDYAAPVKG |
| 74 | 11F9 | CDR-H3 | GRIAAAGFDY |
| 75 | 11F9 | VL | DAVVTQESALTTSPGETVTLTCRSSTGTVTTSNYANWVQEKPDHLFTGLI AGTNNRAPGVPARFSGSLIGDKAVLTITGAQTEDEAIYFCALWYSNHWV FGGGTKLTVLG |
| 76 | 11F9 | CDR-L1 | RSSTGTVTTSNYAN |
| 112 | 11F9 | CDR-L2 | GTNNRAP |
| 77 | 11F9 | CDR-L3 | ALWYSNHWV |
| 114 | 3H9 | VH | EVQLVESGGGLVKPGGSLRLSCAASGFVFSYAWMNWVRQAPGKGLEW VGRIKSKTEGGTTDNAAPVKGRFTISREDSKNTLYLQLNSLKIEDTAVYY CTTGRIAAAGFDYWGQGTLVTVSS |
| 115 | 3H9 | CDR-H1 | GFVFSYAWMN |
| 116 | 3H9 | CDR-H2 | RIKSKTEGGTTDNAAPVKG |
| 74 | 3H9 | CDR-H3 | GRIAAAGFDY |
| 117 | 3H9 | VL | DAVVTQESALTTSPGETVTLTCRSSTGTVTTSNYANWVQEKPDHLFTGLI AGTNNRAPGVPARFSGSLIGDKAALTITGAQTEDEAIYFCALWYSNHWV FGGGTKLTVLG |
| 76 | 3H9 | CDR-L1 | RSSTGTVTTSNYAN |
| 112 | 3H9 | CDR-L2 | GTNNRAP |
| 77 | 3H9 | CDR-L3 | ALWYSNHWV |
| 134 | M35hA10 | VH | QVQLQESGPGLVKPSGTLSLTCAVSGGSISSSNWWSWVRQPPGKGLEWI GEIYHSGSTNYNPSLKSRVTISVDKSKNQFSLKLSSVTAADTAVYYCATM VRGRYYYYGMDVWGQGTTVTVSS |
| 135 | M35hA10 | CDR-H1 | GGSISSSNWWS |
| 136 | M35hA10 | CDR-H2 | EIYHSGSTNYNPSLKS |
| 137 | M35hA10 | CDR-H3 | MVRGRYYYYGMDV |
| 138 | M35hA10 | VL | DIVMTQSPLSLPVTPGEPASISCRSSQSLLHSDGYNFLDWYLQKPGQSPQF LIYLGSNRASGVPDRFSGVGSGTDFTLQISRVEAEDFGVYYCMQALQAP WTFGQGTKLEIK |
| 139 | M35hA10 | CDR-L1 | RSSQSLLHSDGYNFLD |
| 23 | M35hA10 | CDR-L2 | LGSNRAS |
| 140 | M35hA10 | CDR-L3 | MQALQAPWT |

TABLE 6-continued

Variable region sequencs of human antibodies

| SEQ ID NO: | Clone Name | Protein Domain | Sequence |
|---|---|---|---|
| 118 | 29C4 | VH | QVQLVESGGGVVQPGRSLRLSCAASGFTFSNYGMHWVRQAPGKGLEWV AVIWYDGGPKFYADSVKGRFTISRDNSKNTLYLQMNSLRAEDTAVYYC ARSYCGGDCYPFDYWGQGDLVTVSS |
| 119 | 29C4 | CDR-H1 | GFTFSNYGMH |
| 120 | 29C4 | CDR-H2 | VIWYDGGPKFYADSVKG |
| 121 | 29C4 | CDR-H3 | SYCGGDCYPFDY |
| 122 | 29C4 | VL | DIQMTQSPSSLSASVGDRVTITCRASQGISNYLAWYQQKPGKVPKLLIYA ASTLQSGVPSRFSGSGSGTDFTLTISSLQPEDVATYYCQKYYSAPWTFGQ GTKVEIK |
| 6 | 29C4 | CDR-L1 | RASQGISNYLA |
| 7 | 29C4 | CDR-L2 | AASTLQS |
| 123 | 29C4 | CDR-L3 | QKYYSAPWT |
| 142 | 43B2_56A6 | VH | EVQLLESGGGLVQPGGSLRLSCAASGFTFSSYAMSWVRQAPGKGLEWVS TISGSGDSTYYADSVKGRFTISRDNSKNTLYLQMNSLRAEDTAIYYCAKF GVRGVIITNWFDPWGQGTLVTVSS |
| 130 | 43B2_56A6 | CDR-H1 | GFTFSSYAMS |
| 143 | 43B2_56A6 | CDR-H2 | TISGSGDSTYYADSVKG |
| 132 | 43B2_56A6 | CDR-H3 | FGVRGVIITNWFDP |
| 133 | 43B2_56A6 | VL | EIVMTQSPATLSVSPGERATLSCRASQSVSSNLAWYQQKPGQAPRLLIYG ASTRATGIPARFSGSGSGTEFTLTISSLQSEDFAVYYCQQYNNWPLTFGGG TKLEIK |
| 14 | 43B2_56A6 | CDR-L1 | RASQSVSSNLA |
| 15 | 43B2_56A6 | CDR-L2 | GASTRAT |
| 16 | 43B2_56A6 | CDR-L3 | QQYNNWPLT |
| 144 | 50B4_56B2 | VH | EVQLLESGGGLVQPGGSLRLSCAASGFTFSSYAMSWVRQAPGKGLEWVS TISGSGDSTYYADSVKGRFTISRDNSKNTLYLQMNSLRVEDTAIYYCAKF GVRGVIITNWFDPWGQGTLVTVSS |
| 130 | 50B4_56B2 | CDR-H1 | GFTFSSYAMS |
| 145 | 50B4_56B2 | CDR-H2 | TISGSGDSTYYADSVKG |
| 132 | 50B4_56B2 | CDR-H3 | FGVRGVIITNWFDP |
| 146 | 50B4_56B2 | VL | EIVMTQSPATLSVSPGERATLSCRASQSVSSNLAWYQQKPGQVPRLLIYG ASTRATGIPARFSGSGSGTEFTLTISSLQSEDFAVYYCQQYNNWPLTFGGG TKVEIK |
| 14 | 50B4_56B2 | CDR-L1 | RASQSVSSNLA |
| 15 | 50B4_56B2 | CDR-L2 | GASTRAT |
| 16 | 50B4_56B2 | CDR-L3 | QQYNNWPLT |
| 147 | 3A6_56A1 | VH | QVQLQQSGPGLVKPSQTLSLTCAISGDSVSNNSATWNWIRQSPSRGLEWL GRTYYRSKWYNDYPVSVKSRISINPDTSKNQVSLQLNPVTPEDTAVYYC AREQGYSSSRYYYYYGMDVWGQGTTVTVSS |

TABLE 6-continued

Variable region sequencs of human antibodies

| SEQ ID NO: | Clone Name | Protein Domain | Sequence |
|---|---|---|---|
| 148 | 3A6_56A1 | CDR-H1 | GDSVSNNSATWN |
| 58 | 3A6_56A1 | CDR-H2 | RTYYRSKWYNDYPVSVKS |
| 59 | 3A6_56A1 | CDR-H3 | EQGYSSSRYYYYYGMDV |
| 149 | 3A6_56A1 | VL | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQPLQTPYTFGQGTKLEIK |
| 65 | 3A6_56A1 | CDR-L1 | RSSQSLLHSNGYNYLD |
| 23 | 3A6_56A1 | CDR-L2 | LGSNRAS |
| 150 | 3A6_56A1 | CDR-L3 | MQPLQTPYT |
| 151 | 46G4_60A5 | VH | QVQLVESGGGVVQPGRSLRLSCAASGFTFSSYGMHWVRQAPGKGLEWVAVIWFDGSKKYYADSVKGRVTISRDNSRNTLFLQMNSLRAEDTAVYYCAREDYFGSGTYSTDAFDIWGQGTMVTVSS |
| 18 | 46G4_60A5 | CDR-H1 | GFTFSSYGMH |
| 152 | 46G4_60A5 | CDR-H2 | VIWFDGSKKYYADSVKG |
| 153 | 46G4_60A5 | CDR-H3 | EDYFGSGTYSTDAFDI |
| 154 | 46G4_60A5 | VL | DIQLTQSPSFLSASVGDRVTITCRASQGISSYLAWYQQKPGKAPKLLIYAASTLHSGVPSRFSGSGSGTEFTLTIRSLQPEDFATYYCQQLNSYPLFAFGPGTKVDIK |
| 94 | 46G4_60A5 | CDR-L1 | RASQGISSYLA |
| 155 | 46G4_60A5 | CDR-L2 | AASTLHS |
| 156 | 46G4_60A5 | CDR-L3 | QQLNSYPLFA |
| 157 | 34E1_56A4 | VH | QVQLVESGGGVVQPGRSLRLSCAASGLTFSRYAMHWVRQAPGKGLEWVAVIWYDGSNKYYADSVKGRFTISRDTSKNTLYLQMNSLRAEDTAVYYCAREGLLWFGGMDVWGQGTTVTVSS |
| 158 | 34E1_56A4 | CDR-H1 | GLTFSRYAMH |
| 108 | 34E1_56A4 | CDR-H2 | VIWYDGSNKYYADSVKG |
| 20 | 34E1_56A4 | CDR-H3 | EGLLWFGGMDV |
| 159 | 34E1_56A4 | VL | DIVLTQSPLSLPVTPGEPASISCRSSQSLLHSNGYNYLHWYLQKPGQSPQLLIYLGSNRASGVPDRFSGSGSGTDFTLKISRVEAEDVGLYYCMQALQTPYTFGQGTKLEIK |
| 22 | 34E1_56A4 | CDR-L1 | RSSQSLLHSNGYNYLH |
| 23 | 34E1_56A4 | CDR-L2 | LGSNRAS |
| 24 | 34E1_56A4 | CDR-L3 | MQALQTPYT |

TABLE 6-continued

Variable region sequences of human antibodies

| SEQ ID NO: | Clone Name | Protein Domain | Sequence |
|---|---|---|---|
| 160 | 27G5_56A2 | VH | QVQLQESGPGLVKPSETLSLTCAVSDYSISSGYYWGWIRQPPGKGLEWIG SIYHSGSTYYNPSLKSRVTISVDMSKNQFSLKLSSVTAADTAVYYCARDR DSVSWNGGRDYYYYGMDVWGQGTTVTVSS |
| 161 | 27G5_56A2 | CDR-H1 | DYSISSGYYWG |
| 11 | 27G5_56A2 | CDR-H2 | SIYHSGSTYYNPSLKS |
| 162 | 27G5_56A2 | CDR-H3 | DRDSVSWNGGRDYYYYGMDV |
| 163 | 27G5_56A2 | VL | DIQMTQSPSSLSASVGDRVTITCRASQSISSYLNWYQQKPGKAPKLLIYAA SSLQSGVPSRFSGSGSGTDFTLTISSLQPEDFATYYCQQSFSTPYTFGQGTK VEIK |
| 54 | 27G5_56A2 | CDR-L1 | RASQSISSYLN |
| 7 | 27G5_56A2 | CDR-L2 | AASSLQS |
| 164 | 27G5_56A2 | CDR-L3 | QQSFSTPYT |

26 of the identified antibodies were checked for epitope domain binding by Octet™ using the hTMEFF1-ECD recombinant deletion mutants (see Table 7, below).

TABLE 7

Epitope domain binding.

| Parent Ab | Immunization | Binding region |
|---|---|---|
| 10C10 | WCI | FS1 |
| 11F9 | WCI | other |
| 18C2 | WCI | FS1 |
| 19D9 | WCI | FS1 |
| 19H1 | WCI | FS1 |
| 24F10 | WCI | FS1 |
| 29C4 | WCI | FS1 |
| 30C10 | WCI | FS1 |
| 3H9 | WCI | other |
| 6C11 | WCI | FS1 |
| 7F12 | WCI | FS1 |
| 9D1 | WCI | undetermined |
| 31B7 | WCI | other |
| 34B7 | WCI | FS1 |
| 35B1 | WCI | FS1 |
| 36H6 | WCI | FS1 |
| 37G7 | WCI | FS1 |
| 43A12H | WCI | FS1 |
| 45D8 | WCI | FS1 |
| M1F1 | TMEFF1-ECD | Other |
| M3 | TMEFF1-ECD | FS2 |
| M10 | TMEFF1-ECD | FS1 |
| M17 | TMEFF1-ECD | FS1 |
| M33F | TMEFF1-ECD | other |
| M35 | TMEFF1-ECD | FS1 |
| M1H1 | TMEFF1_ECD | other |

FS1—follistatin domain 1
FS2—follistatin domain 2

11 recombinant human monoclonal antibodies were selected for further biological characterization. Biological characterization of these antibodies include live cell binding to human and *Macaca fascicularis*, secondary antibody drug conjugate, epitope competition binning, aggregation, and sequence liabilities.

Live cell flow shows all ten antibodies bind human, mouse and monkey TMEFF1. These antibodies also showed binding in cancer cell lines expressing endogenous levels of TMEFF1 (H69 (small cell lung cancer cell line), HCC1187 (TNBC cell line), PA-1 (ovarian cancer cell line)) and were negative in the TMEFF1 negative cell line SW1271.

Competition binning using Octet™ was done with seven antibodies and 3 separate bins were identified. Antibodies 24F10, 30C10, 34B7 and 36H6 compete with each other and bind FS1. 31B7 and M1F1 bind a region different from FS1 or FS2 and compete with each other. The third bin includes M3, which binds to FS2.

Aggregation was assessed by HPLC-SEC and all ten antibodies tested showed <5% higher-order aggregates.

Amino acid sequences of the variable domains of ten antibodies were assessed for potential liabilities. The significance of the findings in Table 8 are provided in the table footer.

TABLE 8

Identified sequence liabilities

| Parent Ab | VH | VL |
|---|---|---|
| 19H1 | N-terminal Gln<br>CDR-1 Asn-Ser, Trp<br>CDR-2 Trp<br>CDR-3 Met | CDR-1 Asn-Gly<br>CDR-3 Met |
| 24F10 | N-terminal Gln<br>CDR-1 Met<br>CDR-2 Trp<br>CDR-3 Met | CDR-3 Trp |
| 30C10 | N-terminal Gln<br>CDR-1 Met<br>CDR-2 Trp | CDR-3 Trp |
| 6C11 | N-terminal Gln<br>CDR-1 Asn-Ser, Trp<br>CDR-2 Trp<br>CDR-3 Met | CDR-1 Asn-Gly<br>CDR-3 Met |

TABLE 8-continued

Identified sequence liabilities

| Parent Ab | VH | VL |
|---|---|---|
| 31B7 | N-terminal Gln<br>CDR-1 Met<br>CDR-2 Asn-Gly, Trp<br>CDR-3 Met, Trp | CDR-1 Asn-Gly<br>CDR-3 Met |
| 34B7 | N-terminal Gln<br>CDR-1 Met<br>CDR-2 Asn-Ser, Trp<br>CDR-3 2 non-canonical Cys | CDR-3 Asn-Ser, Trp |
| 36H6 | N-terminal Gln<br>CDR-1 Met<br>CDR-2 Trp<br>CDR-3 Met, Trp | CDR-3 Trp |
| 43A12H | N-terminal Gln<br>CDR-1 Met<br>CDR-2 Trp<br>CDR-3 Met | |
| M1F1 | N-terminal Gln<br>CDR-1 Trp<br>CDR-3 2 non-canonical Cys, Trp | CDR-3 Trp |
| M3 | N-terminal Gln<br>CDR-1 Met<br>CDR-2 Trp<br>CDR-3 Asn-Gly, Met | CDR-1 Trp<br>CDR-3 Asn-Ser, Trp |
| 3A6_56A1 | N-terminal Gln<br>CDR-1 N-linked glycosylation<br>CDR-2 Trp | CDR-3 Met |

N-terminal Gln, possible pyroglutamate formation.
Asn-Gly, Asn-Ser, possible deamidation site.
Non-canonical Cys, possible misfolding and/or aggregation.
Met or Trp, possible oxidation site.
Asn-Xxx-Ser/Thr, N-linked glycosylation Affinity of thirteen antibodies was calculated using hTMEFF1 ECD recombinant protein by Octet™. Values ranged from 4 nM to >500 nM (see Table 9, below).

TABLE 9

$K_D$ (human) values for anti-TMEFF1 Antibodies

| Sample | KD (human) |
|---|---|
| 24F10 | 50 nM |
| 30C10 | 4 nM |
| 31B7 | 43 nM |
| 34B7 | 20 nM |
| M3 | 15 nM |
| 36H6 | 51 nM |
| M1F1 | 19 nM |
| M10 | 9 nM |
| 43B2_56A6 | 39 nM |
| 50B4_56B2 | 52 nM |
| 3A6_56A1 | 62 nM |
| 34E1_56A4 | 98 nM |
| 27G5_56A2 | 69 nM |

Affinity of 7 antibodies was calculated using cyTMEFF1 ECD recombinant protein by Octet™. Values ranged from 7 nM to 101 nM (see Table 10, below).

TABLE 10

$K_D$ (cynomolgus) values for anti-TMEFF1 Antibodies

| Sample | KD (monkey) |
|---|---|
| 24F10 | 65 nM |
| 30C10 | 7 nM |
| 31B7 | 101 nM |
| 34B7 | 22 nM |

TABLE 10-continued $K_D$ (cynomolgus) values for anti-TMEFF1 Antibodies

| Sample | KD (monkey) |
|---|---|
| M10 | 7 nM |
| 36H6 | 96 nM |
| M1F1 | 27 nM |

Example 3. Internalization of Anti-TMEFF1 Antibodies in 293-hTMEFF1 Cells

Experiments were performed to characterize anti-TMEFF1 antibody internalization in 293-hTMEFF1 cells. The following methods were used in the example.

Methods

For Flow based internalization assay, 293-hTMEFF1 cells were collected and either fixed with 4% paraformaldehyde (PFA) for 20 minutes at 37° C. or kept live on ice. Cells were then incubated on ice for 40 minutes with anti-TMEFF1 antibody at 1 ug/ml, washed 2× with ice cold PBS, resuspended in complete warm media and incubated at 37° C. for 30, 60 or 120 minutes. Live cells were then fixed at those time points, washed 2× with PBS and labeled with fluorescent conjugated secondary antibody for 30 minutes on ice.

Results

Figure 1B:
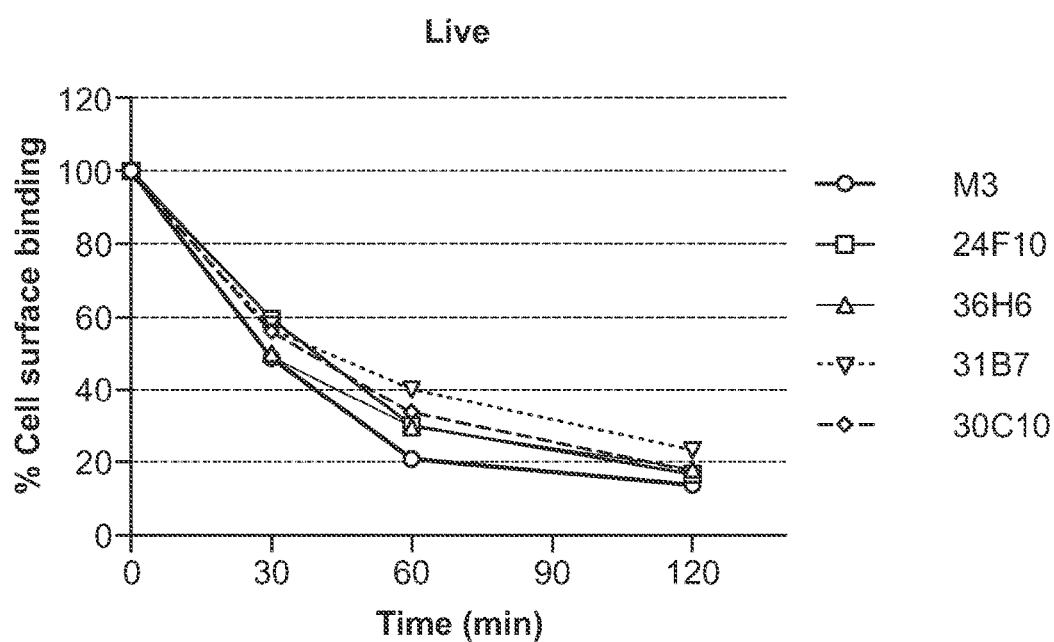
Figure 2A:
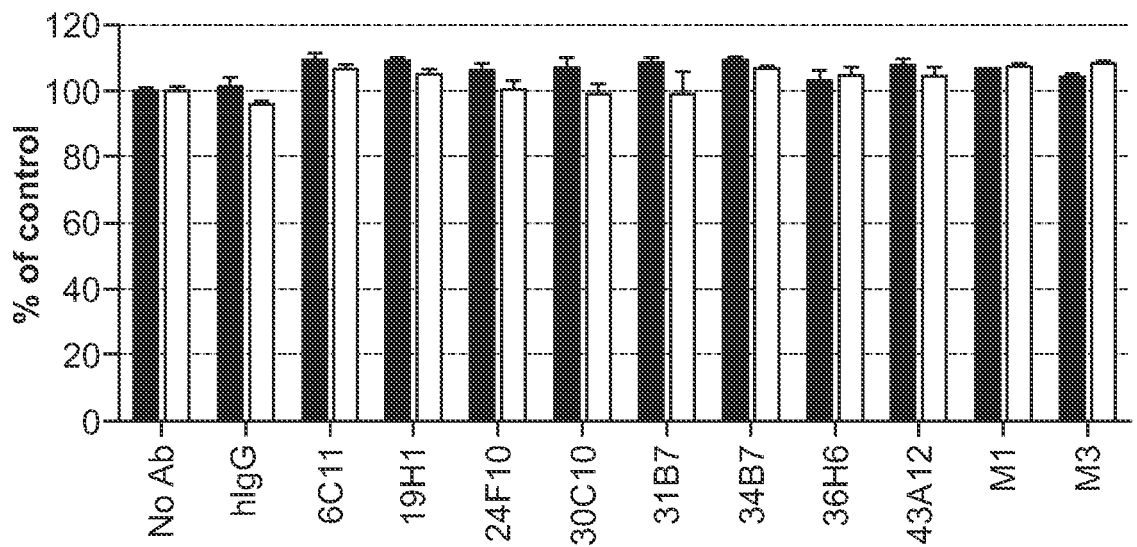
FIGS. 2A-2E illustrate cell killing by 10 nonconjugated anti-TMEFF1-ECD antibodies with an anti-human secondary IgG conjugated to MMAE in (A) parental 293 cells; (B) growing 293-hTMEFF1 cells; (C) cancer cell line H69 (small cell lung cancer), in vitro; (D) cancer cell line NTERA2 (embryonal carcinoma); and (E) cancer cell line HCC1187 (TNBC). hIgG1 (anti-HBV surface Ag antibody) conjugated antibody was included as negative controls.
Figure 2B:
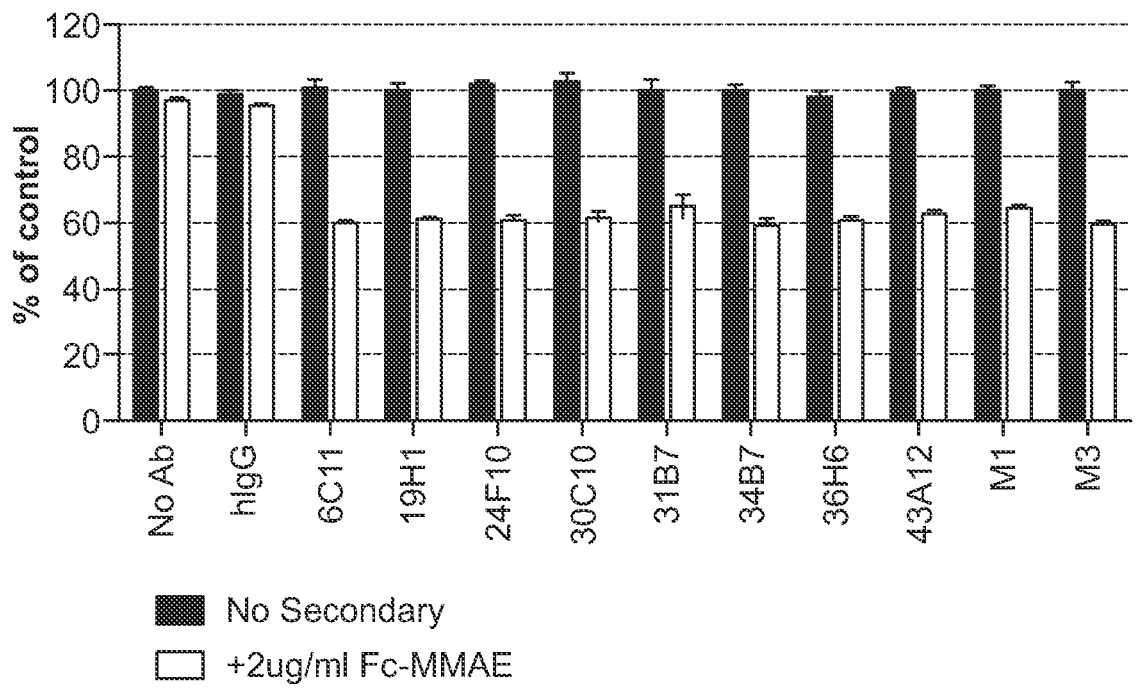
Figure 2C:
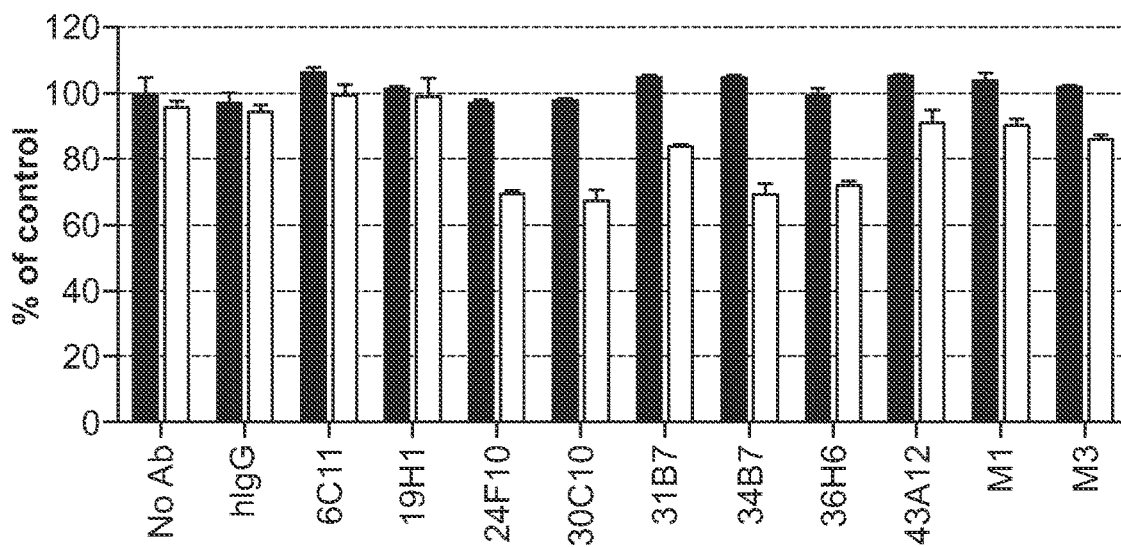
Figure 2D:
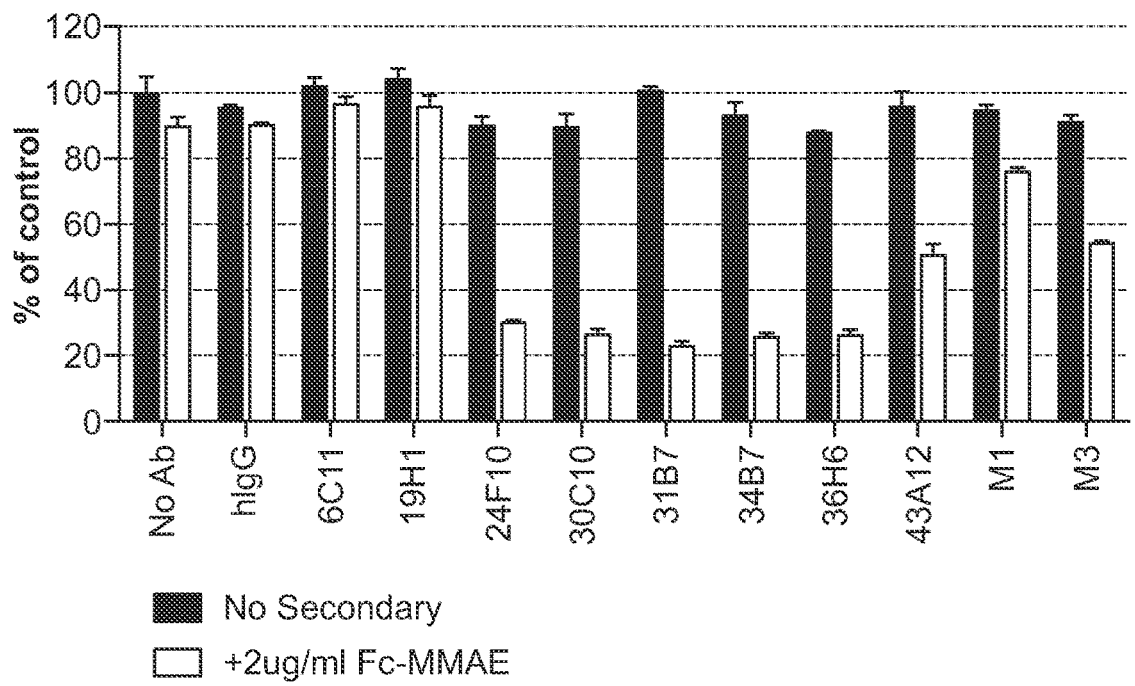
Figure 2E:
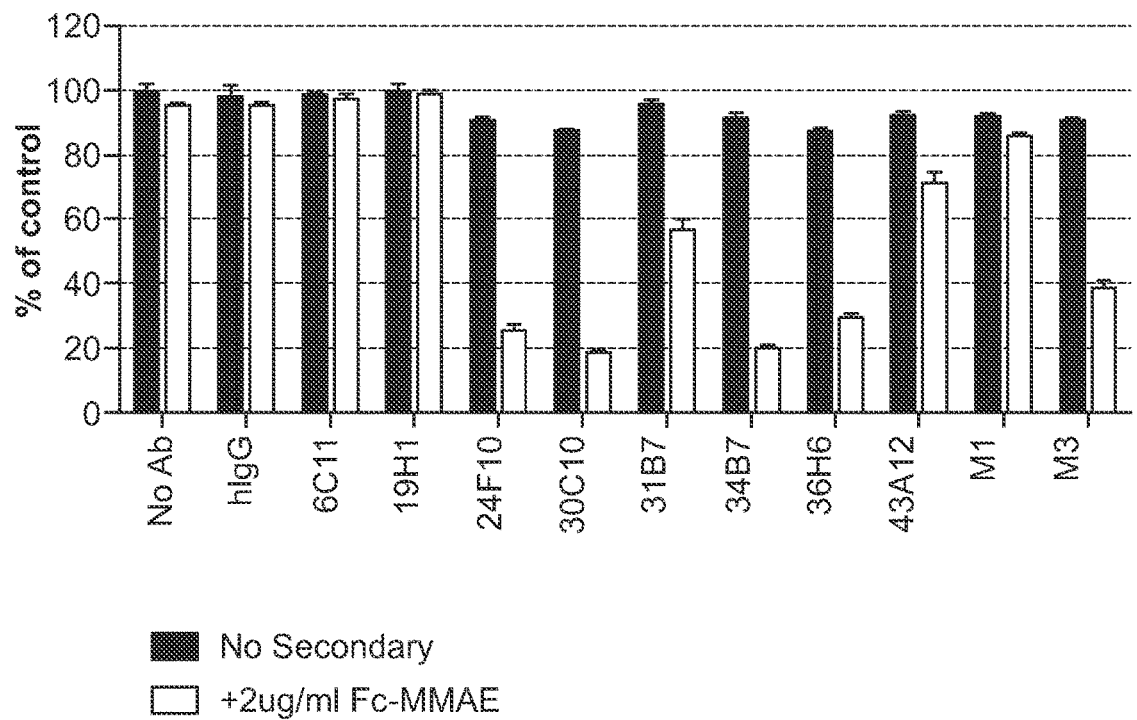
Figure 3A:
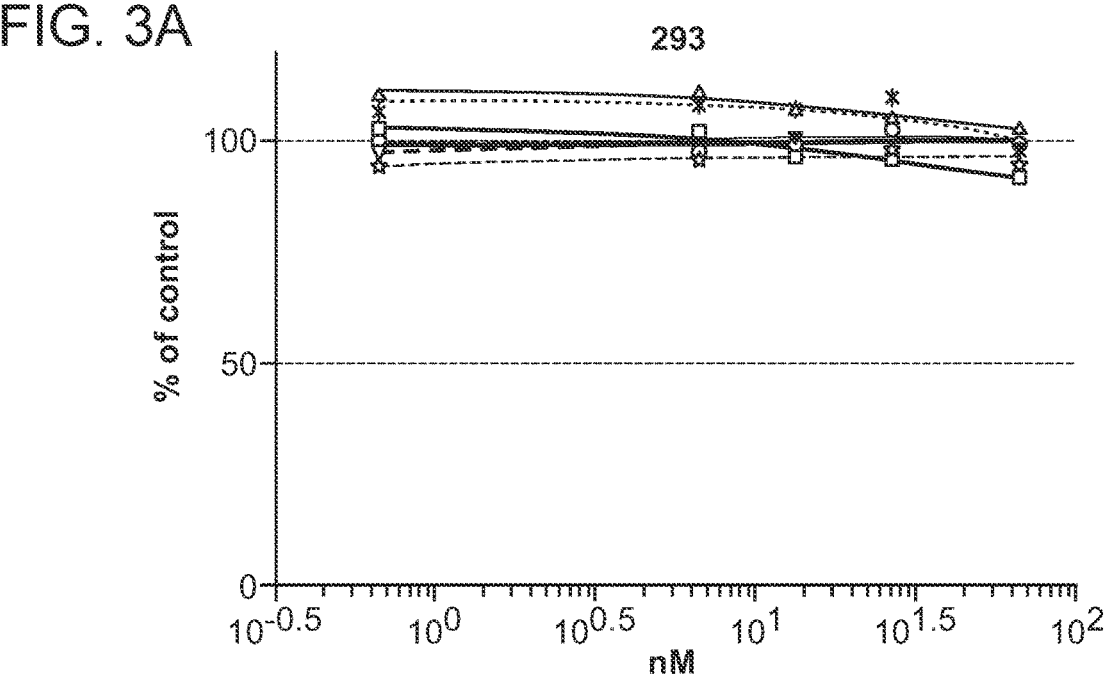
FIGS. 3A-3F illustrate in vitro efficacy of anti-TMEFF1-vcMMAE in (A) parental 293 cells; (B) 293-hTMEFF1 cells; (C) HCC1187 (TNBC) cells; (D) H69 cells; (E) H526 cells; and (F) SW1271 cells. hIgG1 (anti-HBV surface Ag antibody) conjugated antibody was included as negative controls.
Figure 3B:
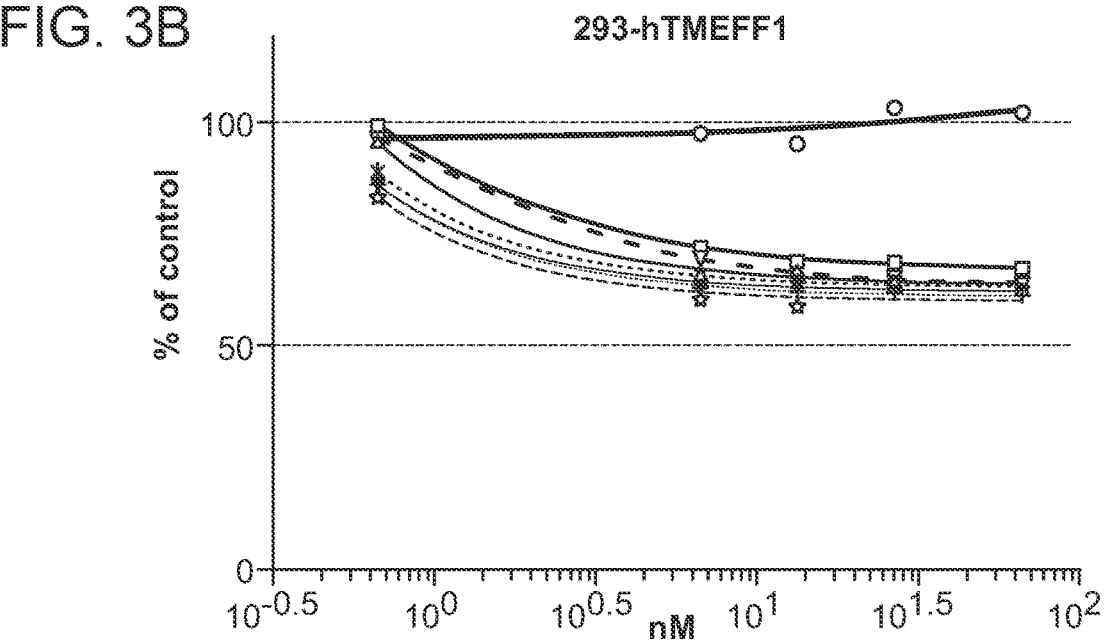
Figure 3C:
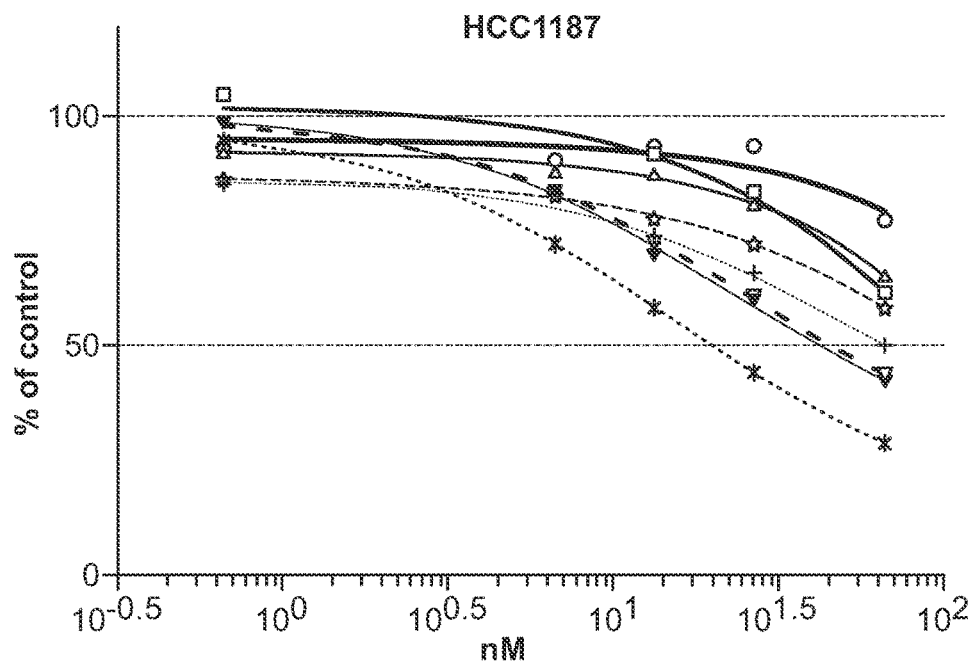
Figure 3D:
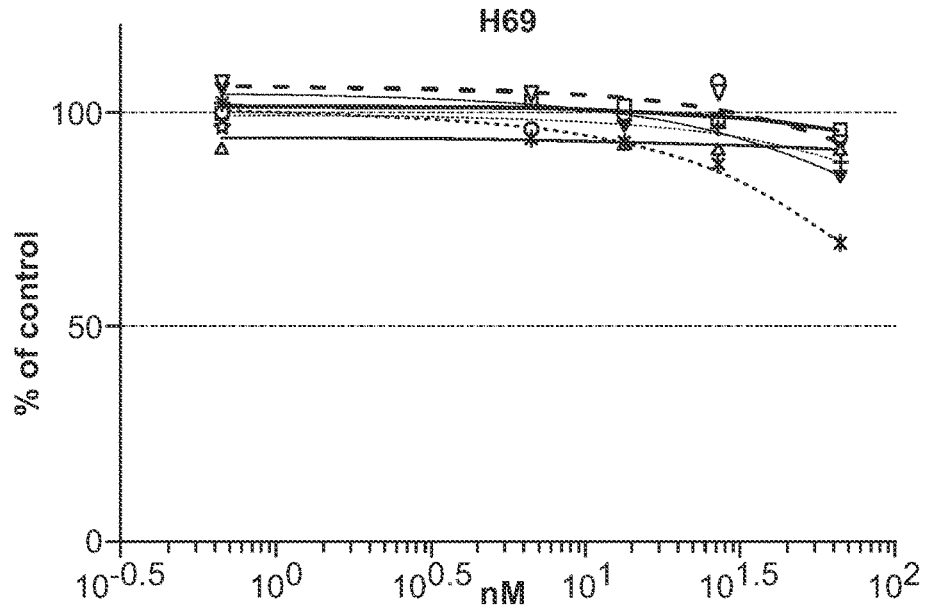
Figure 3E:
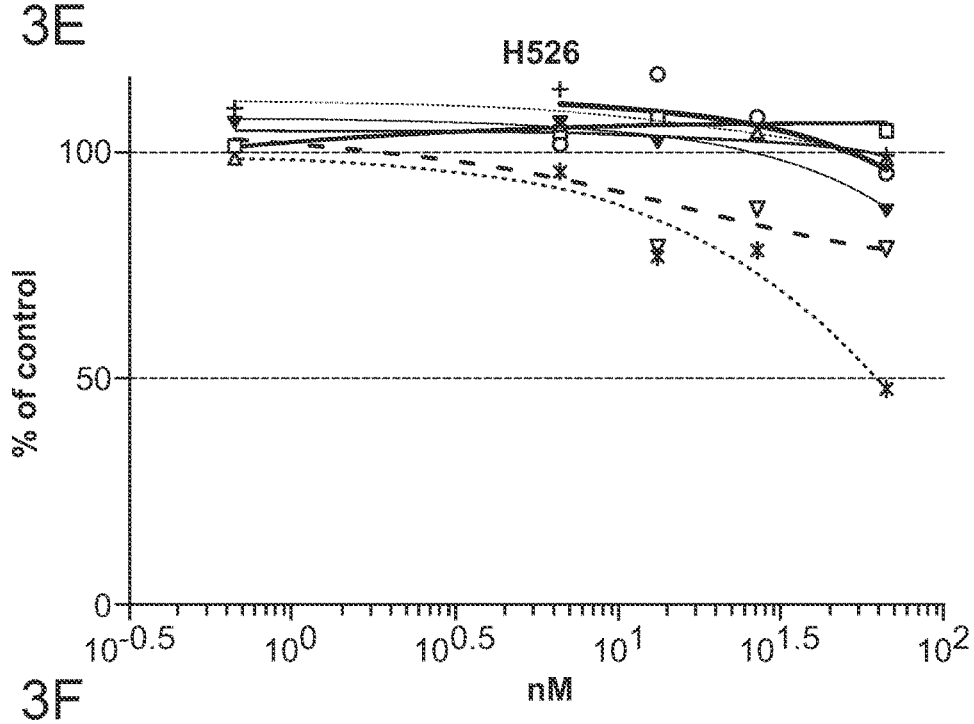
Figure 3F:
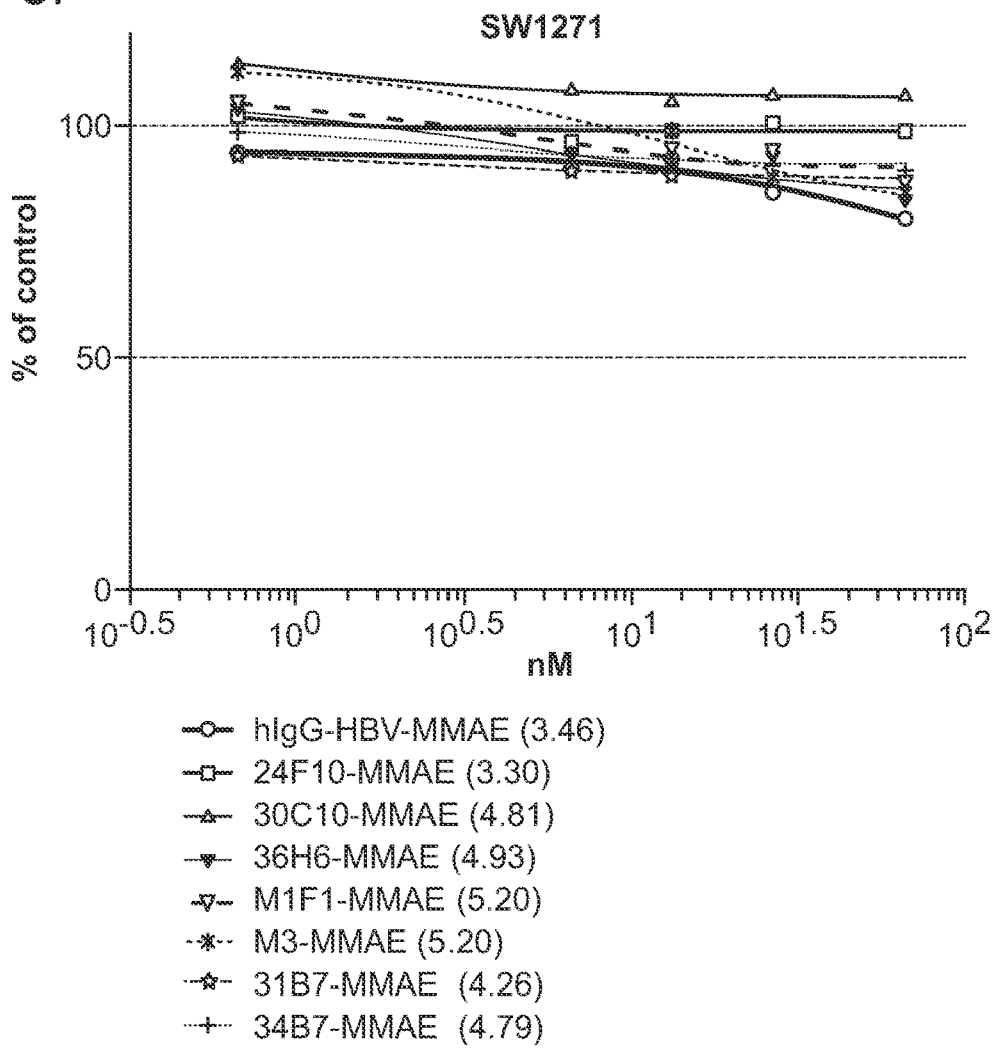

Antibody mediated TMEFF1 internalization was evaluated by Flow cytometry with five human anti-TMEFF1 antibodies in 293-hTMEFF1 cells. Fixed cells were treated with the antibody as a control of antibody loss due to detachment rather than internalization which would result in reduce signal. Thus a constant signal over time in fixed cells and a loss of signal in live cells would indicate antibody internalization. It was observed that M3 had some reduced binding in fix cells over the duration of the experiment, however the other 4 antibodies tested, 24F10, 36H6, 31B7 and 30C10 show consistent cell surface binding in fix cells for the duration of the assay (FIG. 1A). In live cells, it was observed that most antibodies show about a 50% internalization by 30 min of treatment (FIG. 1B). Thus treatment of 293-hTMEFF1 cells with our antibodies resulted in target loss from the membrane due to internalization.

Example 4. In Vitro Secondary Antibody Drug Conjugate Assay to vcMMAE

Unconjugated human antibodies were tested for their effect on growing 293-hTMEFF1 versus parental 293 cells and on HCC1187 (Triple Negative Breast Cancer (TNBC)), H69 (small cell lung cancer), and NTERA2 (embryonal carcinoma) cell lines in vitro with an anti-human secondary IgG conjugated to MMAE. Primary antibody concentration was used at 1 ug/ml and secondary anti-human Fc-IgG-MMAE at 2 ug/ml. Cells were seeded onto 96 well plates at 3000-7500 cells/well 24 hours prior to treatment for attached cells or same day of treatment for suspension cells. Primary antibody was added 5 minutes prior to secondary antibody treatment and cell viability was measured 72 hours later by CellTiter Glo® Luminescent Cell viability Assay™ (Promega, Madison, Wis.) according to manufacturer's instructions. Cell viability was graphed by Prism™ using ratio of cell viability of test conditions to that of control wells that were incubated with growth medium. All 10 anti-TMEFF1-ECD antibodies tested promoted 40% killing in 293-hTMEFF1 compared to parental 293 cells. In endogenous cells, 8 antibodies (24F10, 30C10, 31B7, 34B7, 36H6, 43A12H, M1F1 and M3) showed different degrees of killing ranging from 80% to 10% killing (see FIGS. 2A-E).

Example 5. In Vitro Primary Antibody Drug Killing with Conjugated Human Antibodies to vcMMAE Seven human monoclonal antibodies against TMEFF1 were selected to be conjugated to vcMMAE in order to test primary antibody drug conjugate efficacy against 293-hTMEFF1 or cancer cell lines. The antibodies conjugated to MMAE were 34B7, 31B7, M3, M1F1, 36H6, 30C10 and 24F10. They were tested in 293, 293-hTMEFF1, HCC1187, H69, H526 and SW1271 cell lines.

Methods

The methods for antibody conjugation were described, e.g., in Doronina, Svetlana O., et al. "Development of potent monoclonal antibody auristatin conjugates for cancer therapy." Nature Biotechnology 21.7 (2003): 778-784; and Francisco, Joseph A., et al. "cAC10-vcMMAE, an anti-CD30-monomethyl auristatin E conjugate with potent and selective antitumor activity." Blood 102.4 (2003): 1458-1465, the entire contents of which are expressly incorporated herein by reference.

Briefly, each antibody was mixed with dithiothreitol (DTT) at room temperature for 30 minutes, and the buffer was exchanged by Amicon spin columns (30 kDa) into PBS pH 7.0 with 2 mM EDTA. The antibody concentration was quantified by absorbance at 280 nm (A280). They were then diluted to 1.5 mg/ml in PBS pH 7.0 and 2 mM EDTA. Molar excess of maleimidocaproyl-Val-Cit-MMAE (vcMMAE) was then added to the reduced antibody at room temperature for 1 hour. The reaction mixture was then dialyzed against IX PBS pH 8.0 and filter sterilized. The drug:tmAb ratio (DAR) was then calculated based on spec readings at A280 and A248 on an absorption spectroscopy. The method of calculating DAR is described in Hamblett, Kevin J., et al. "Effects of drug loading on the antitumor activity of a monoclonal antibody drug conjugate," *Clinical Cancer Research* 10.20 (2004): 7063-7070, the entire contents of which are expressly incorporated herein by reference.

Cells were seeded onto 96 well plates at 2000-5000 cells/well 24 hrs prior to treatment. Cells were treated with Ab-vcMMAE bearing a drug antibody ratio (DAR) of 3.3-5.2 in complete culture medium so that the final Ab-vcMMAE concentration in the well is 0.1, 1.0, 2.0, 4.0 and 10 ug/ml. Each treatment was replicated in 2-3 wells. 72 hours later, cell viability was measured by CellTiter Glo® Luminescent Cell viability assay (Promega, Madison, Wis.) according to manufacturer's instructions. Cell viability was graphed by Prism™ using ratio of cell viability of test conditions to that of control wells that were incubated with growth medium.

Results

All seven Abs conjugated to vcMMAE showed a 40% cell killing effect compared to control treatment using hIgG-HBV-vcMMAE antibody in 293 over-expressing hTMEFF1 (see FIGS. 3A-F). Parental 293 cells did not show any killing with all seven antibodies. Killing ranging from 60% to 10% was observed with the different antibodies tested at 4 ug/ml final concentration in cancer cell lines. No killing was observed in the SW1271 TMEFF1 negative cancer cell line.

Example 6. In Vitro Efficacy by Primary Antibody Drug Conjugate to PBD

Experiments were performed to characterize the ability of anti-TMEFF1-PBD conjugated antibodies in in vitro efficacy. The following methods were used.

Methods

Antibody Drug Conjugation

Human monoclonal antibodies were conjugated to the valine-alanine-pyrrolobenzodiazepine, MA-PEG8-VA-PAB-SG3199 (PBD) as previously described (Stefano J. E., Busch M., Hou L., Park A., Gianolio D. A. (2013) Micro- and Mid-Scale Maleimide-Based Conjugation of Cytotoxic Drugs to Antibody Hinge Region Thiols for Tumor Targeting. In: Ducry L. (eds) Antibody-Drug Conjugates. Methods in Molecular Biology (Methods and Protocols), vol 1045. Humana Press, Totowa, N.J.). Briefly, each antibody was partially reduced with an appropriate molar amount of TCEP for 2 hrs at 37° C. After incubation, the antibodies were cooled to room temperature and a 6-fold molar excess of PBD was added to the partially reduced antibody for 1 hour. After this incubation, the entire mixture was run over a gel filtration column to remove free drug. A fraction of the eluate was then used for concentration and DAR determination using A280 and HIC respectively. The drug to antibody ratio for 30C10-PBD and 36H6-PBD was 1.7 and 1.9, respectively. The drug to antibody ratio for control human IgG1-PBD (Ctrl) was 3.0.

In Vitro Efficacy

Cells were seeded onto 96 well plate at 2000-4000 cells/well. Anti-TMEFF1-PBD antibodies were added to the wells in complete culture medium in a serial dilution. Each treatment was replicated in 2 wells. 4-5 days later, cell viability was measured by CellTiter Glo Luminescent Cell viability assay (Promega) according to manufacturer's instructions. Cell viability was graphed by Prism using ratio of cell viability of test conditions to that of control wells that are treated with growth medium only.

Results

Figure 4A:
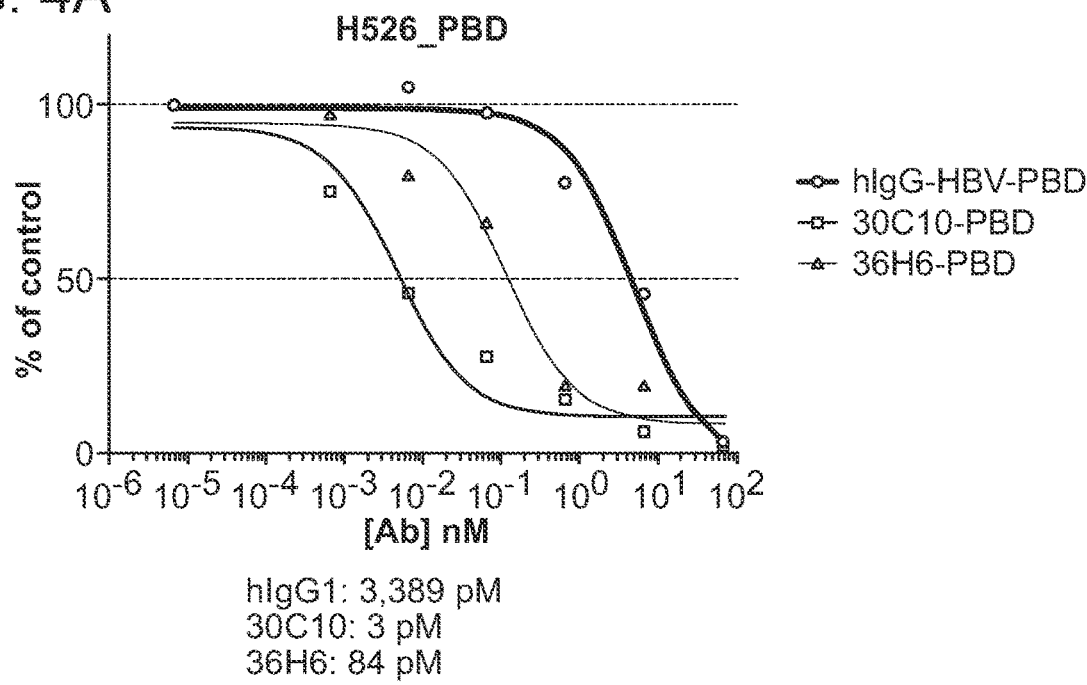
FIGS. 4A-4H illustrate in vitro efficacy of anti-TMEFF1-PBD in SCLC cell lines. (A) H526 cells; (B) H1048 cells; (C) DMS79 cells; (D) H1963 cells; (E) H1930 cells; (F) H1876 cells; (G) NTERA2 cells; (H) SW1271 cells. hIgG1 (anti-HBV surface Ag antibody) conjugated antibody was included as negative controls. IC50 values are listed at the bottom of each graph.
Figure 4B:
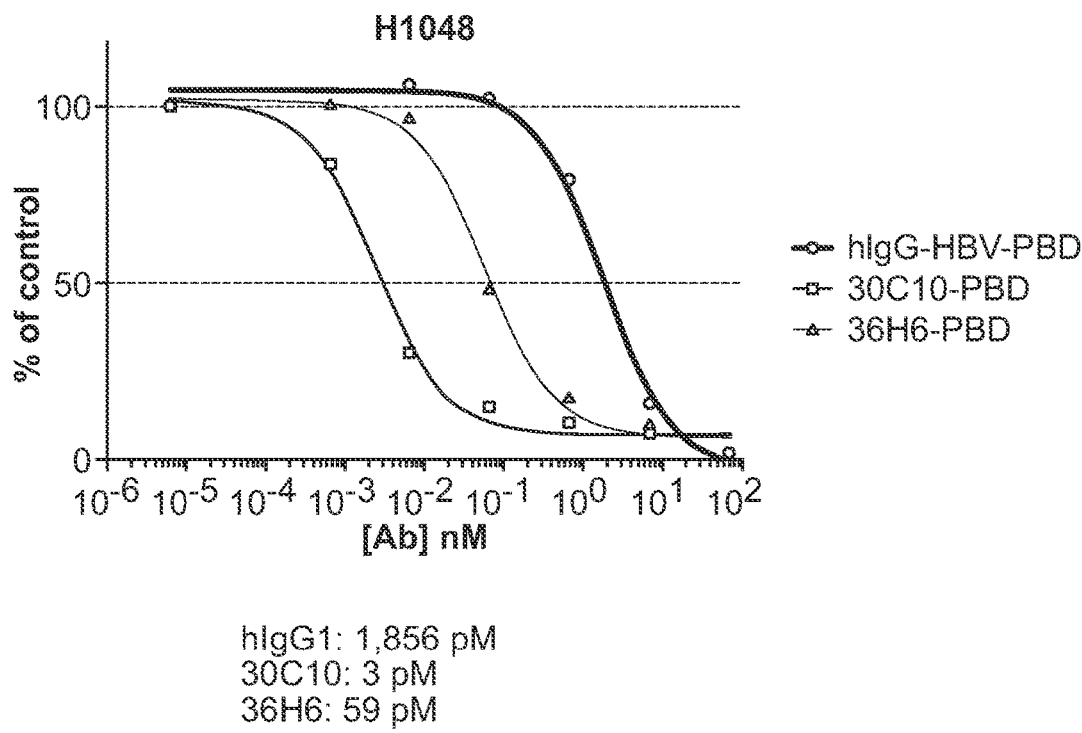
Figure 4C:
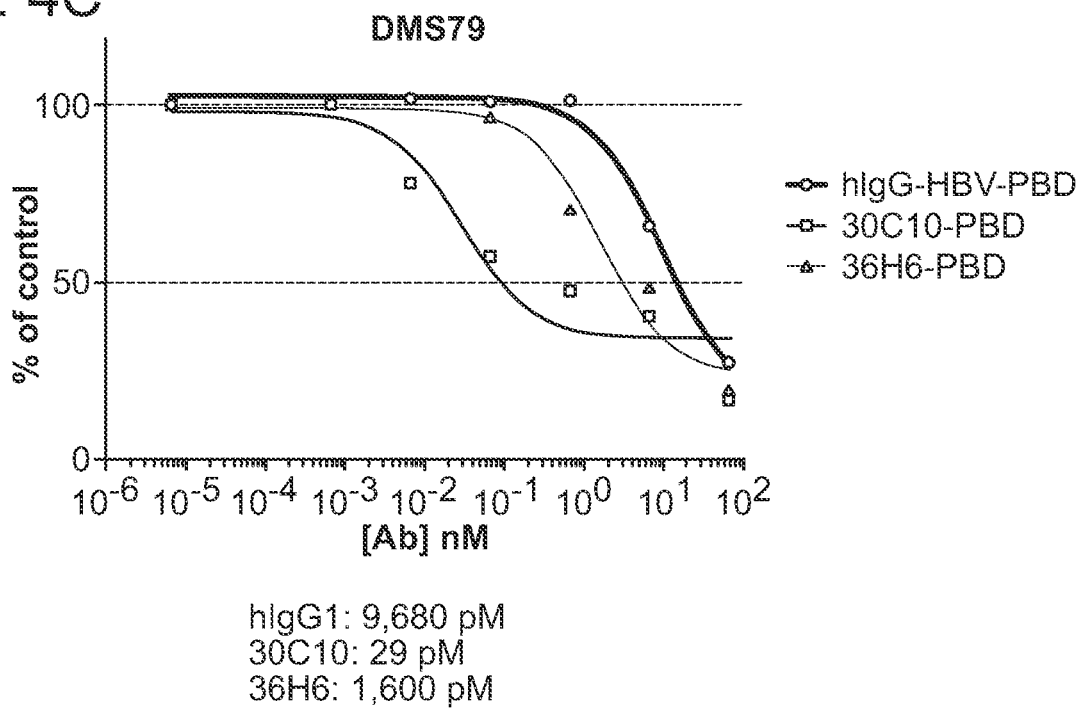
Figure 4D:
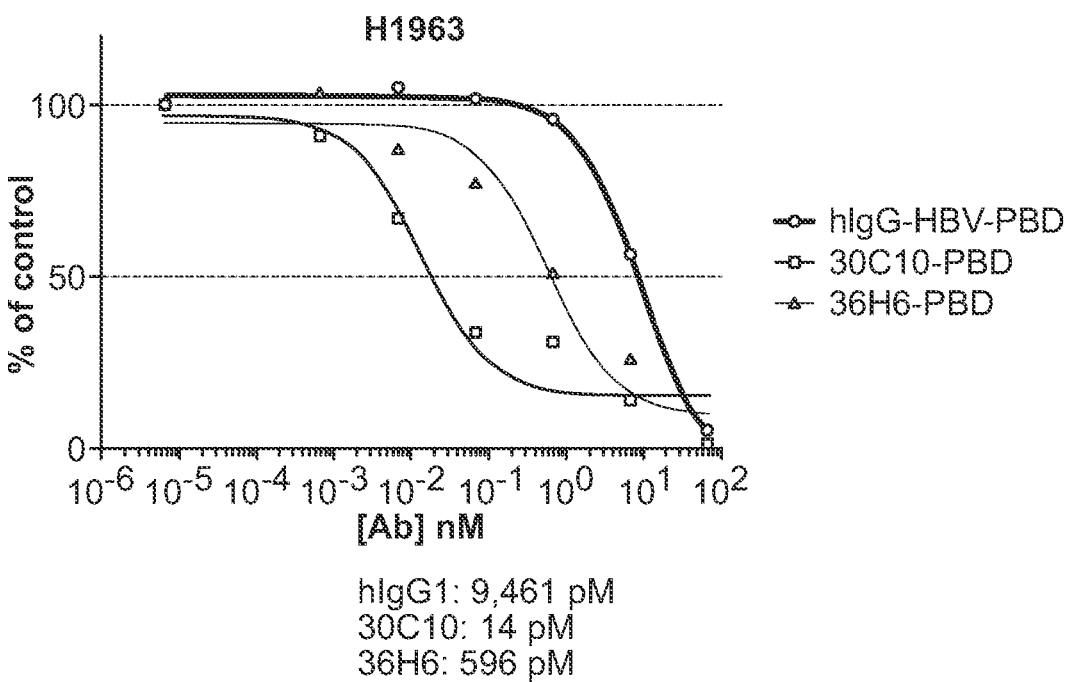
Figure 4E:
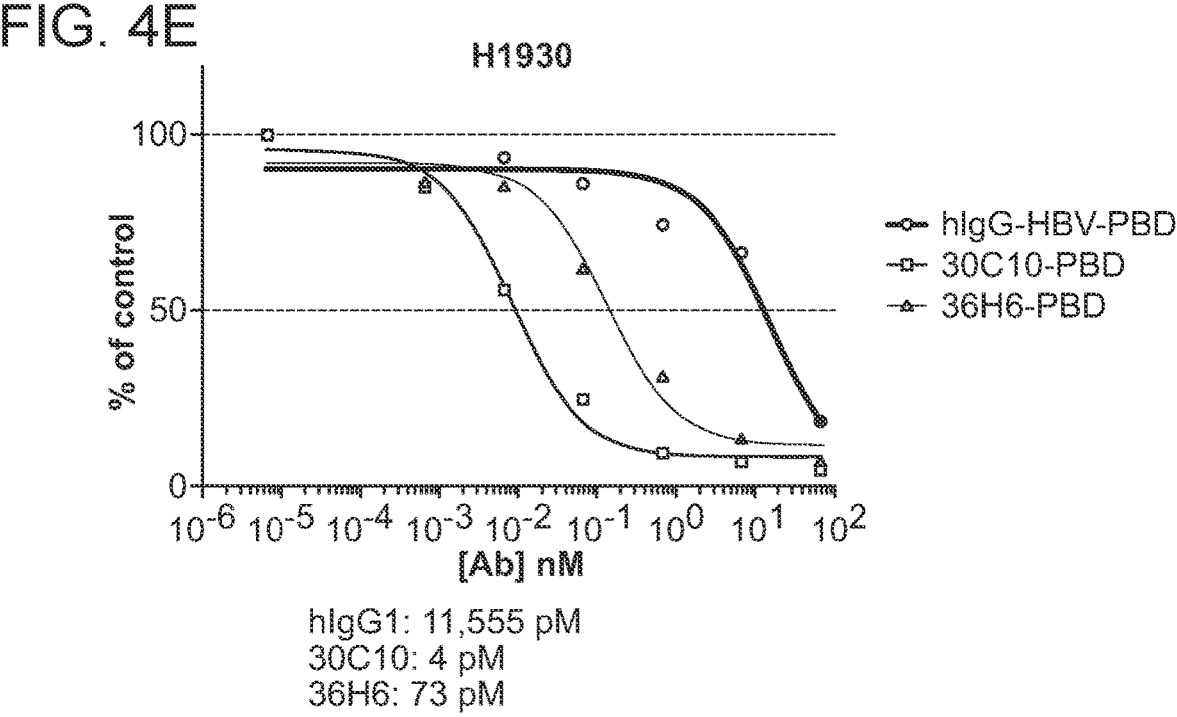
Figure 4F:
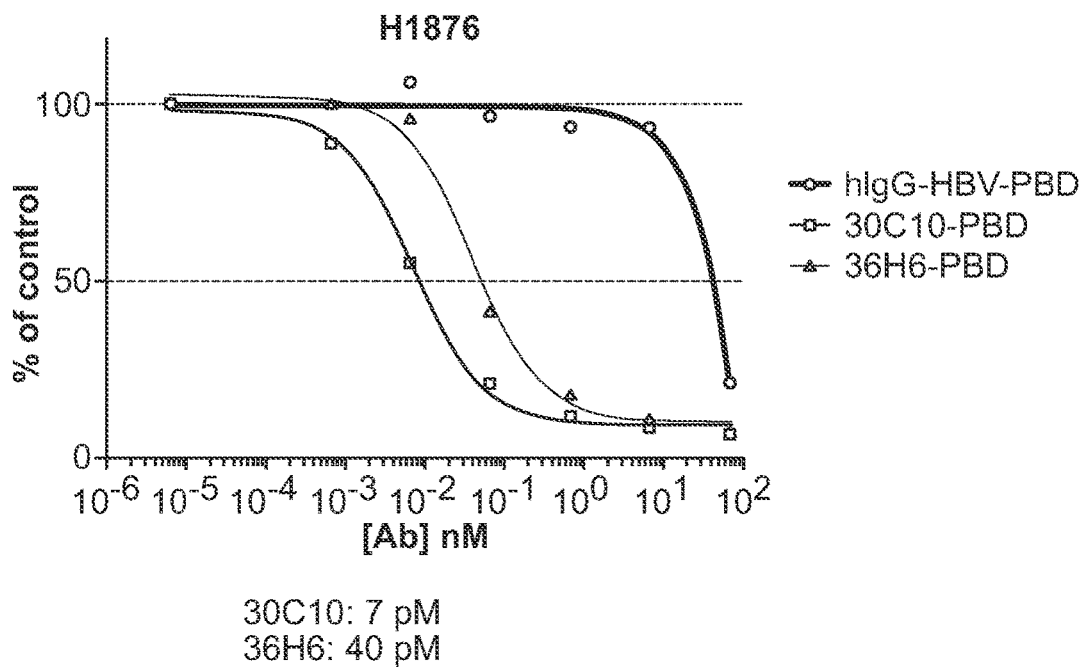
Figure 4G:
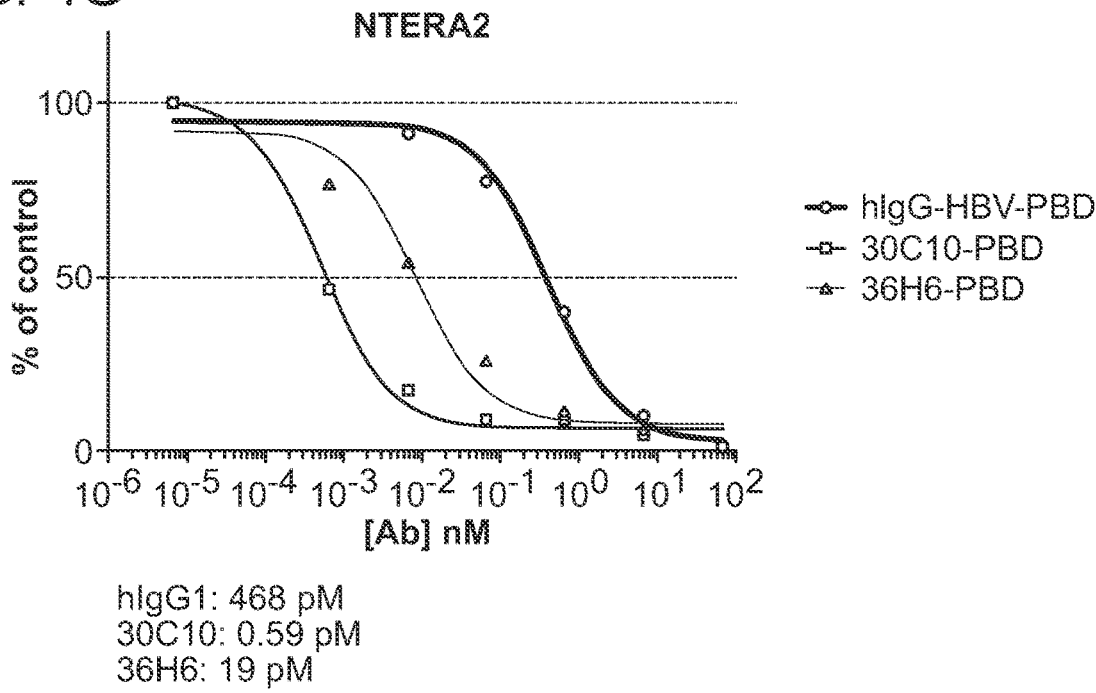
Figure 4H:
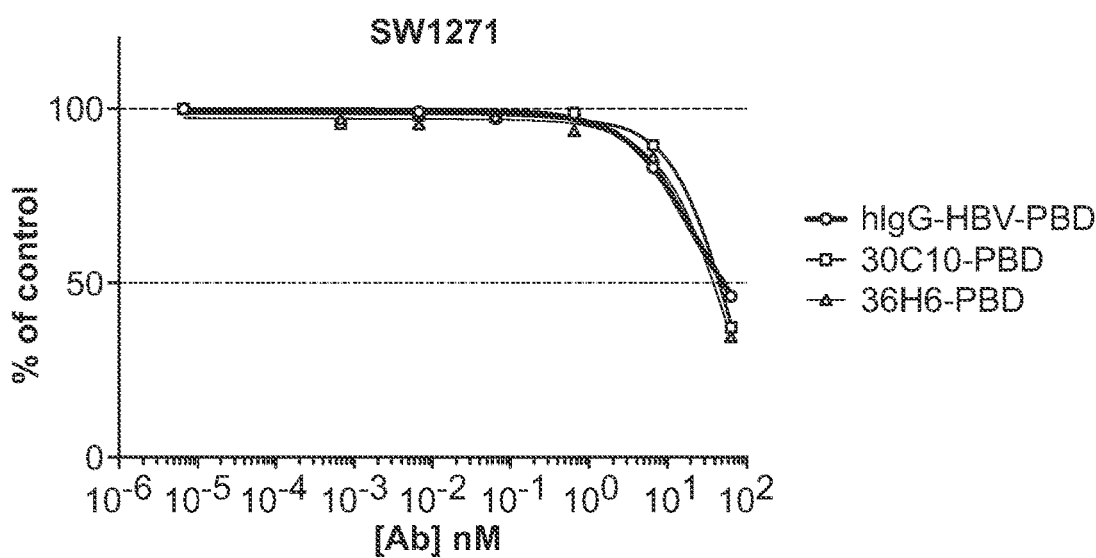
Figure 5A:
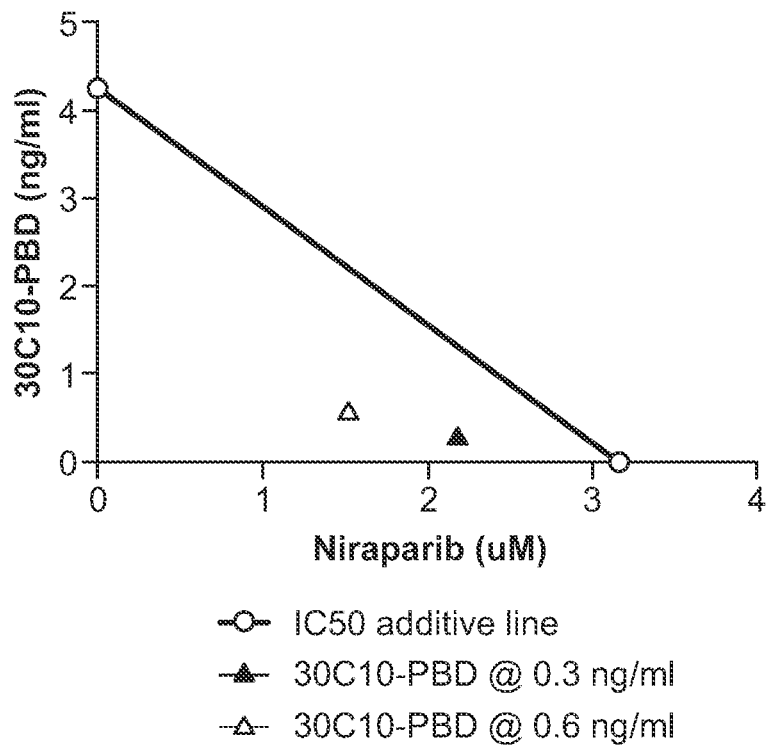
FIGS. 5A-5F illustrate results of isobolograms analysis of combination treatments of 30C10-PBD with niraparib, etoposide or cisplatin. (A) niraparib and H526 cells; (B) etoposide and H526 cells; (C) cisplatin and H526 cells; (D) niraparib and H1048 cells; (E) etoposide and H1048 cells; (F) cisplatin and H1048 cells. Cells were seeded in 96 well plates and treated with 30C10-PBD, niraparib, cisplatin or etoposide alone for 5 days. Combination treatments were also performed with a constant concentration of 30C10-PBD and titrating doses of niraparib, cisplatin or etoposide. IC50 values were recorded for single treatments or combinations to calculate Isobologram points.
Figure 5B:
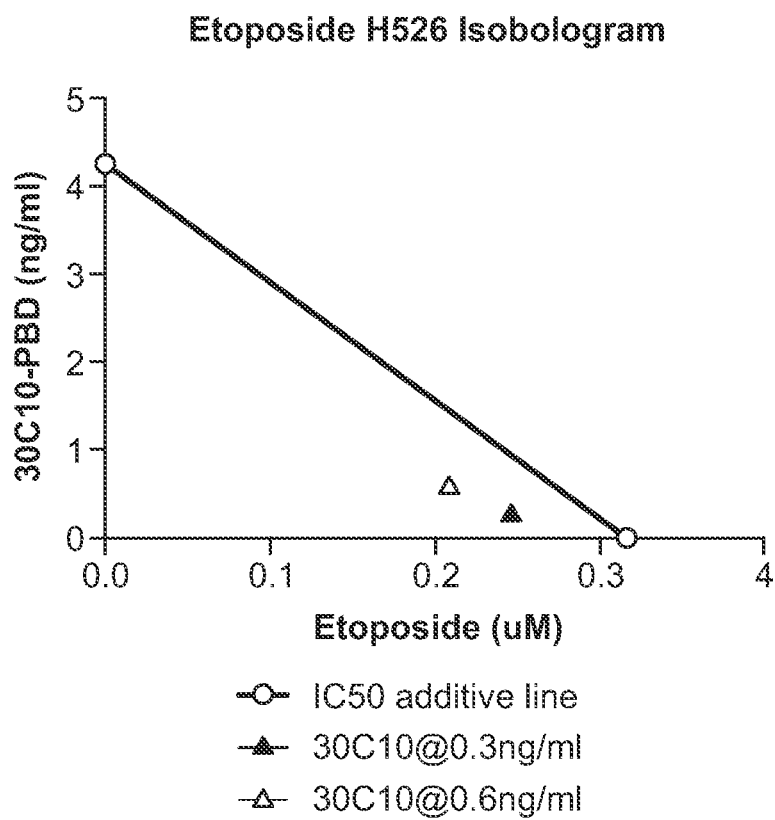
Figure 5C:
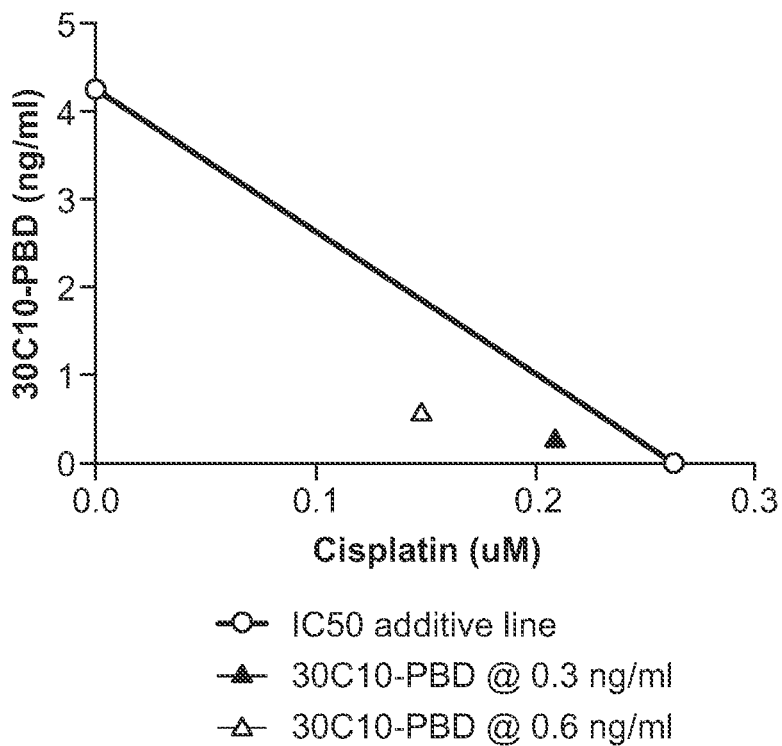
Figure 5D:
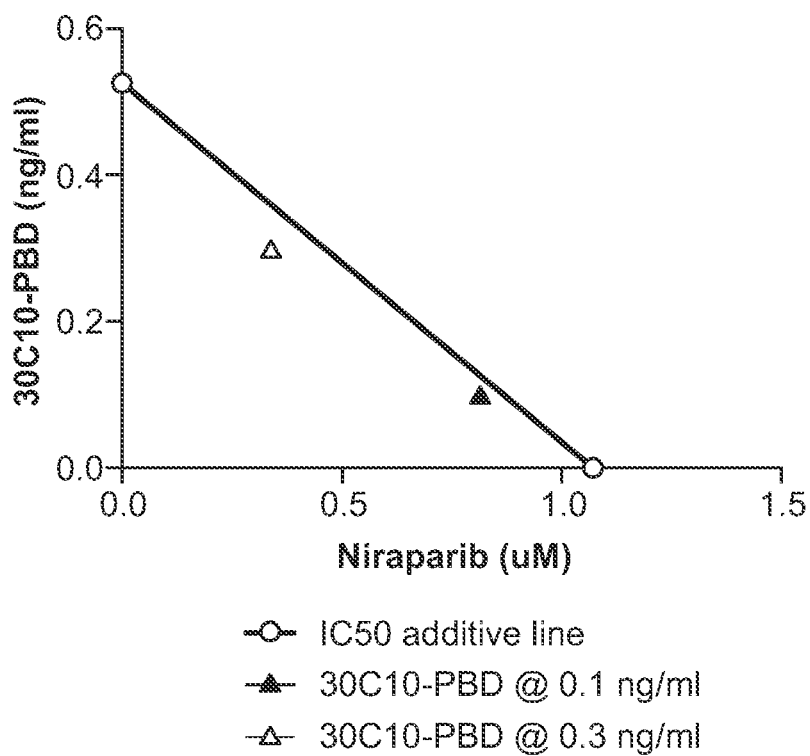
Figure 5E:
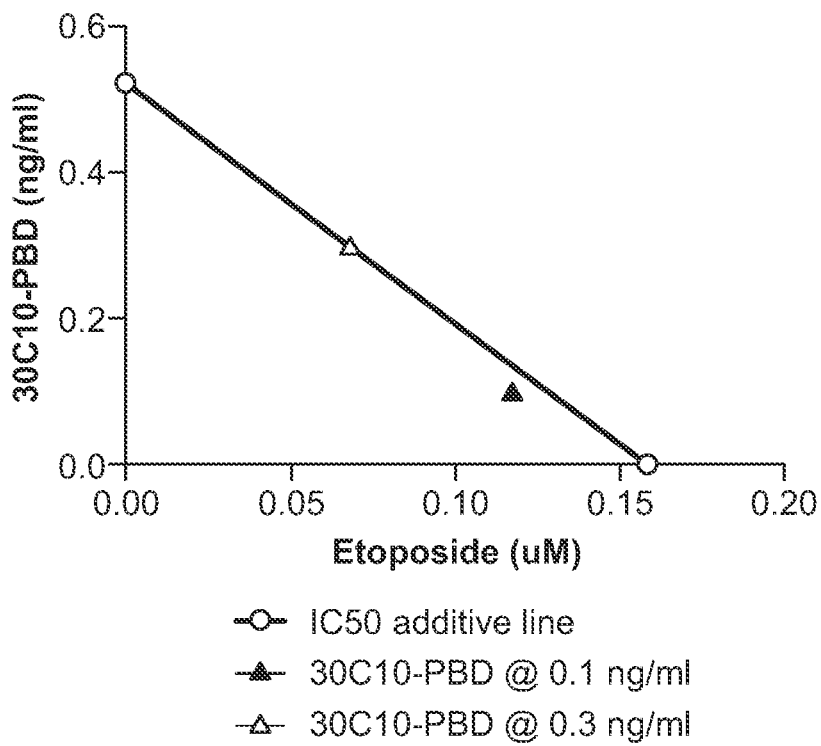
Figure 5F:
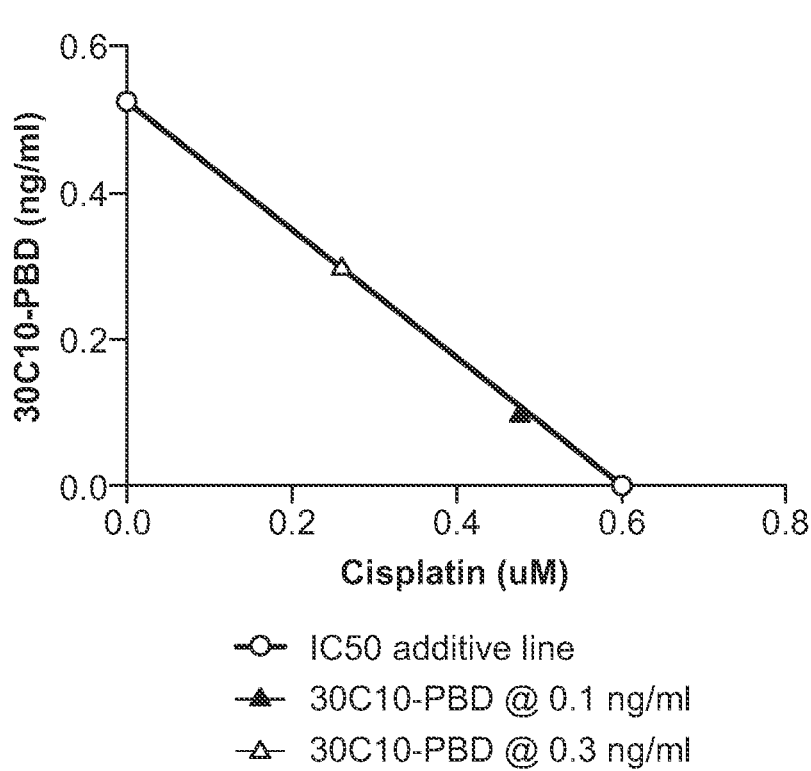
Figure 6A:
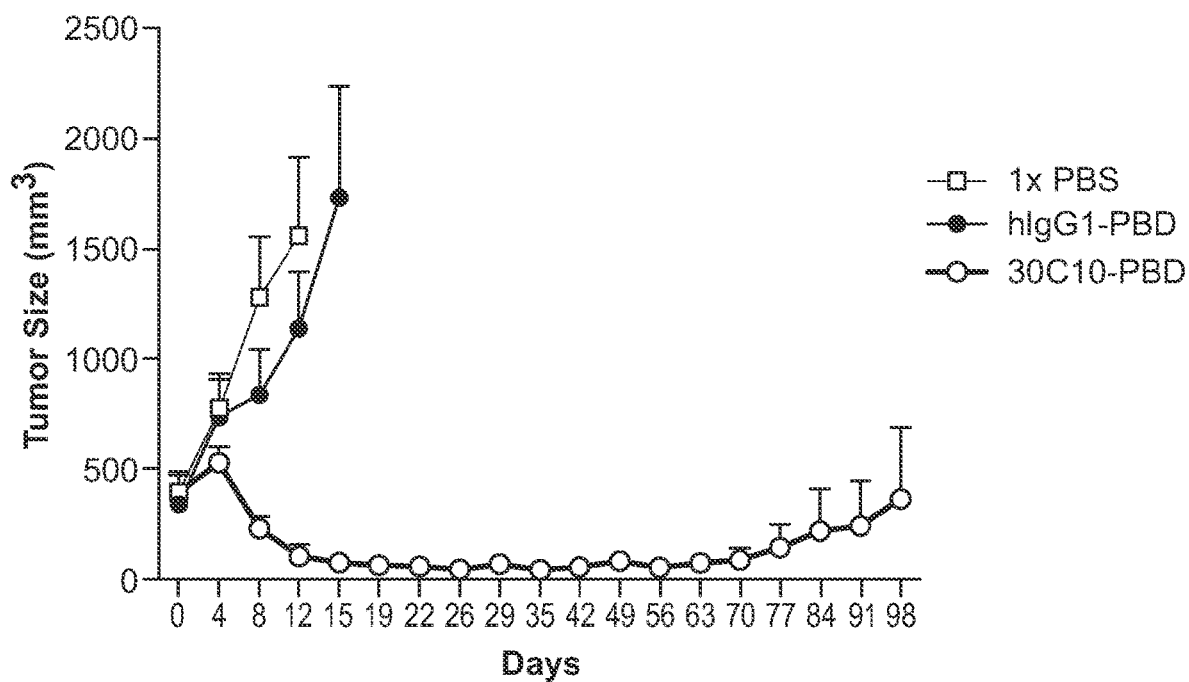
FIGS. 6A-6C illustrate that tesirine PBD conjugated antibodies inhibit tumor growth in vivo. Graph depicts efficacy of 30C10 conjugated to PBD in H526 xenograft model. (A) depicts tumor volume of H526 xenografts; (B) depicts Kaplan-Meier survival curve of the study; and (C) depicts the mice body weight of the study.
Figure 6B:
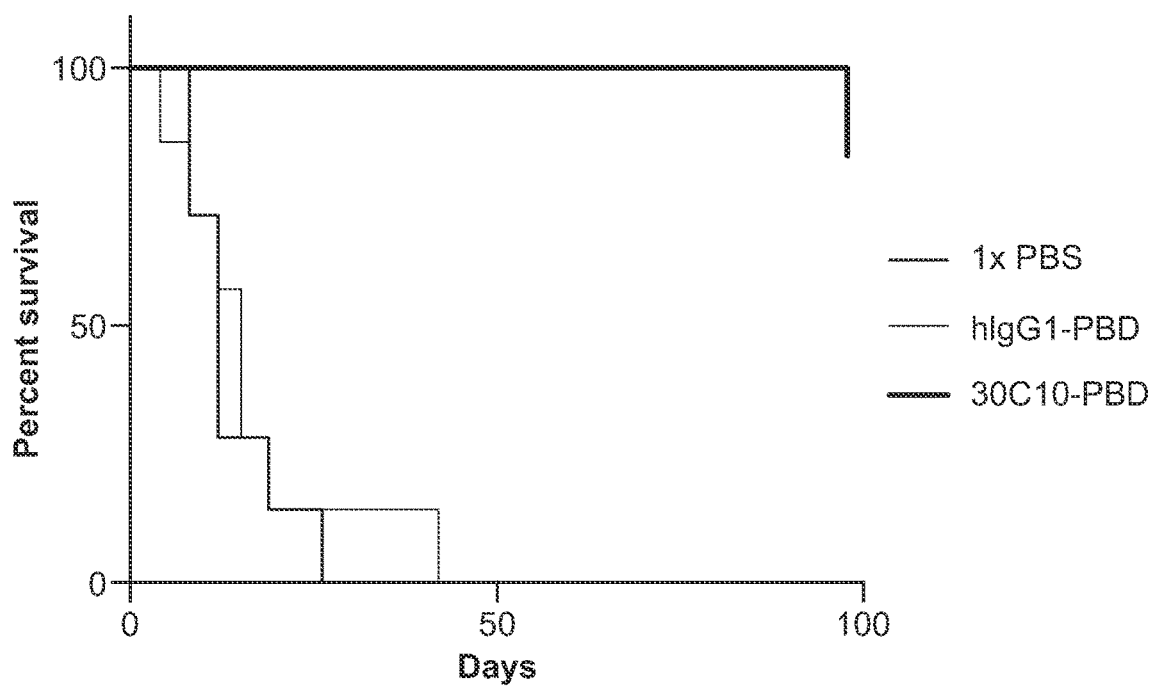
Figure 6C:
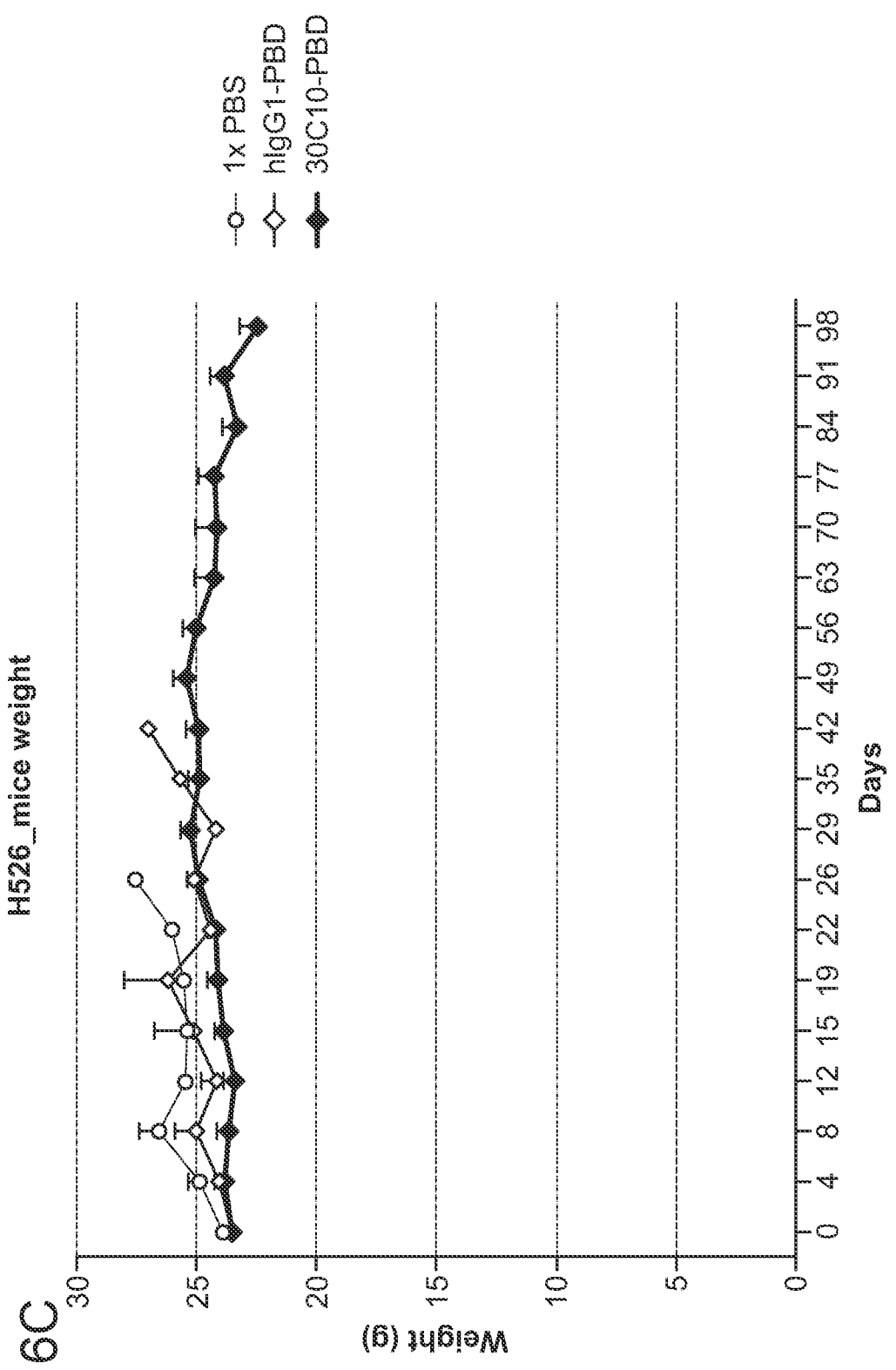

Antibodies 30C10 and 36H6 were conjugated to Tesirine PBD, a DNA damage agent. Primary conjugated antibodies were evaluated for in vitro efficacy against a panel of cancer cell lines. PBD conjugated antibodies showed efficacy with picomolar $IC_{50}$ values (FIGS. 4A-G). SW1271 served as a negative control cell line (FIG. 4H).

Example 7: In Vitro Efficacy of an Anti-TMEFF1-PBD Antibody Combined with Niraparib, Etoposide or Cisplatin Cisplatin and etoposide have been used as first line treatment for SCLC patients. Thus, the combination of an anti-TMEFF1 antibody conjugated to PBD (30C10-PBD) with cisplatin or etoposide was tested. Furthermore, Poly [ADP-ribose] polymerase 1 (PARP1) was identified to be highly expressed at the mRNA and protein level in SCLC (Byers, L. A., et al, Proteomic Profiling Identifies Dysregulated Pathways in Small Cell Lung Cancer and Novel Therapeutic Targets Including PARP1, *Cancer Discov.,* 2012) thus, PARP inhibitor, niraparib, with 30C10-PBD were combined to determine the effect on growth in H526 and H1048 SCLC cell lines in vitro.

Methods

Two SCLC cell lines H526 and H1048, which expresses ~2,500 copies of TMEFF1 on the cell surface per cell, were seeded onto 96 well plates at 2,000 cells/well on the day of treatment. To distinguish synergy from additivity of the combination of 30C10-PBD with niraparib (selleckchem, Cat # S2741), etoposide (Cell Signaling Technology, Cat #2200S) or cisplatin (Sigma, Cat # P4394), for each combination, a specific isobologram was constructed and the combination-index was calculated as described by Chou, TC and Talalay P (Quanttative analysis of dose-effect relationships: the combined effects of multiple drugs or enzyme inhibitors, *Adv Enzyme Regul,* 1984). IC50 value was defined as the drug concentration reducing by 50% the growth of treated cells compared with control. IC50 values of each drug was determined by plating H526 or H1048 cells and adding 30C10-PBD, niraparib, etoposide or cisplatin at 10-fold dilutions spanning their probable range of activity. Concentrations ranging from 0.0001-1 ug/ml were used for 30C10-PBD, from 0.01 to 100 uM for Niraparib, from 0.001-10 uM for etoposide and from 0.01-100 uM for cisplatin. Cell viability was measured 5 days later by Cell-Titer Glo® Luminescent Cell viability Assay™ (Promega, Madison, Wis.) according to manufacturer's instructions. Each IC50 was graphically derived from the growth curve graphed by Prism™ showing percent survival vs log drug concentrations.

Combination-index (CI) was defined as follows: $CI=[C]_{A50}/IC50_A+[C]_{B50}/IC50_B$, where $[C]_{A50}$ and $[C]_{B50}$ are the concentrations in combination inducing the IC50 effect. A CI of less than, equal to, or more than 1 indicates, respectively, synergy, additivity, or antagonism.

The 50% growth-inhibitory activity of the drug combinations was measured after 5 days of treatment. The line of additivity for the isobologram was constructed by interpolating the two points corresponding to the IC50 of the two drugs alone. Graphically, synergy, additivity, and antagonism are indicated by a point plotted below, on, or above the line of additivity, respectively.

Results

The IC50 value of 30C10-PBD, niraparib, etoposide and cisplatin alone were determined in H526 and H1048 cell lines. The IC50 of 30C10-PBD was 4.27 ng/ml and 0.53 ng/ml in H526 and H1048, respectively. The IC50 of niraparib was 3.24 uM and 1.07 uM in H526 and H1048, respectively. The IC50 of etoposide was 0.33 uM and 0.16 uM in H526 and H1048, respectively. The IC50 of cisplatin was 0.24 uM and 0.62 uM in H526 and H1048 respectively. An isobologram analysis of the combination of 30C10-PBD at 0.3 or 0.6 ng/ml for H526 and at 0.1 or 0.3 ng/ml for H1048 was performed with titrating concentrations of niraparib, etoposide or cisplatin (see FIGS. 5A-F). It was then assessed if the combination results in additive or synergistic effect based on the isobologram or the calculated CI (table 11).

Synergistic effect was observed when 30C10-PBD was combined with niraparib in H526 and H1048 cells. 30C10-PBD also showed synergistic effect when combined with etoposide in H526 cells. In H1048 cell lines, 30C10-PBD showed synergistic effect at 0.1 ng/ml of 30C10-PBD and additive effect at 0.3 ng/ml of 30C10-PBD. 30C10-PBD also had synergistic effects when combined with cisplatin in H526 cell lines and additive effects in H1048 cells.

TABLE 11

Combination Index of H526 and H1048 cells

| Cell line | Drug 1 | 30C10-PBD (ng/ml) | CI | effect |
|---|---|---|---|---|
| H526 | Niraparib | 0.3 | 0.762 | synergy |
| H526 | Niraparib | 0.6 | 0.619 | synergy |
| H526 | Etoposide | 0.3 | 0.847 | synergy |
| H526 | Etoposide | 0.6 | 0.801 | synergy |
| H526 | Cisplatin | 0.3 | 0.865 | synergy |
| H526 | Cisplatin | 0.6 | 0.703 | synergy |
| H1048 | Niraparib | 0.1 | 0.949 | synergy |
| H1048 | Niraparib | 0.3 | 0.888 | synergy |
| H1048 | Etoposide | 0.1 | 0.932 | synergy |

TABLE 11-continued

Combination Index of H526 and H1048 cells

| Cell line | Drug 1 | 30C10-PBD (ng/ml) | CI | effect |
|---|---|---|---|---|
| H1048 | Etoposide | 0.3 | 0.998 | additive |
| H1048 | Cisplatin | 0.1 | 0.985 | additive |
| H1048 | Cisplatin | 0.3 | 1.008 | additive |

Example 8. In Vivo Efficacy by Primary Antibody Drug Conjugates to PBD

Experiments were performed to characterize in vivo efficacy of drug conjugated antibodies against H526, a SCLC cell line. The following methods were used in the examples.

Methods

Antibody Drug Conjugation

Human monoclonal antibodies were conjugated to the valine-alanine-pyrrolobenzodiazepine, MA-PEG8-VA-PAB-SG3199 (PBD) as previously described (Stefano J. E., Busch M., Hou L., Park A., Gianolio D. A. (2013) Micro- and Mid-Scale Maleimide-Based Conjugation of Cytotoxic Drugs to Antibody Hinge Region Thiols for Tumor Targeting. In: Ducry L. (eds) Antibody-Drug Conjugates. Methods in Molecular Biology (Methods and Protocols), vol 1045. Humana Press, Totowa, N.J.). Briefly, each antibody was partially reduced with an appropriate molar amount of TCEP for 2 hours at 37° C. After incubation, the antibodies were cooled to room temperature and a 6-fold molar excess of PBD was added to the partially reduced antibody for 1 hour. After this incubation, the entire mixture was run over a gel filtration column to remove free drug. A fraction of the eluate was then used for concentration and DAR determination using A280 and HIC respectively. The drug to antibody ratio for 30C10-PBD was 1.7. The drug to antibody ratio for control human IgG1-PBD (Ctrl) was 3.0.

Tumor IMPLANTATION

For efficacy studies with antibody drug conjugates, 6-8 weeks old female Nu/Nu mice (Taconic) were inoculated subcutaneously in the dorsal right flank with 2.5 million H526 cells in 1× PBS with equal volume of Matrigel (Corning, Cat #356234). When tumor volumes reached 200-400 mm3 (day 0), animals were randomized into 3 groups of 6-7 each and administered 3× IV injections every 4 days (IV/Q4Dx3) of anti-TMEFF1-PBD or hIgG-PBD control antibody at 1 mg/kg or PBS (vehicle) control. Tumor volumes were determined using digital calipers (Fred V. Fowler Company, Inc.) using the formula (length×width$^2$)× 0.52. Measurement was performed twice weekly for the first 30 days after initial dosing, then once a week until the end of the study.

Endpoint

Each animal was euthanized when its tumor reached the endpoint size of 1500 mm$^3$ or on the final day of the study (Day 98), whichever came first. The time to endpoint (TTE) for each mouse was defined as the time elapsed for an animal to be removed from the study. Animals that did not reach the endpoint are assigned a TTE value equal to the length of the study (98 days). Animals classified as NTR (nontreatment-related) deaths due to unknown causes were excluded from TTE calculations (and all further analyses).

Treatment outcome was determined from percent tumor growth inhibition (TGI) and tumor growth delay (TGD).

TGI is defined as the percent decrease in average tumor volume of treated versus control group and calculated from the following equation:

$$TGI = \left(1 - \frac{TV_{tx}\text{Day}x - TV_{tx}\text{Day}0}{TV_{veh}\text{Day}x - TV_{veh}\text{Day}0}\right) \times 100\%$$

Where $TV_{tx}$ Day X=Average tumor volume of treated group on Day X; $TV_{tx}$ Day 0=Average tumor volume of treated group on Day 0; $TV_{veh}$ Day X=Average tumor volume of control group on Day X; $TV_{veh}$ Day 0=Average tumor volume of control group on Day 0.

TGI of the treatment group was assessed when 50% of animals in control group has reached their TTE, which is on Day 15 on this study.

TGD or T-C is defined by difference between median TTE of treated (T) versus control (C) groups and calculated from the following equation:

TGD=Median of $TTE_{tx}$−Median of $TTE_{veh}$

Where Median of $TTE_{tx}$=median of TTE of treated group; Median of $TTE_{veh}$=median of TTE of vehicle group.

Mice were monitored for regression responses. An animal with a complete tumor regression at the termination of the study was classified as a tumor free survivor (TFS).

Toxicity

Animals were weighed weekly for the study. The mice were observed frequently for overt signs of any adverse, treatment-related side effects, and clinical signs of toxicity were recorded when observed. Acceptable toxicity is defined as a group mean body-weight loss of less than 15% during the study and not more than one treatment-related (TR) death among ten treated animals. Any dosing regimen that results in greater toxicity is considered above the maximum tolerated dose (MTD). A death is classified as TR if attributable to treatment side effects as evidenced by clinical signs and/or necropsy or if due to unknown causes during the dosing period or within 10 days of the last dose. A death is classified as an NTR if there is no evidence that death was related to treatment side effects.

Results

30C10-PBD and hIgG-PBD were dosed at 1 mg/kg, 3 times every 4 days. Day 0 was the day treatments started and Day 98 was the end of the study. TGI of 30C10-PBD treated group compared to hIgG-PBD control group at Day 15 was 123.8%. TGD was 83 days. 30C10-PBD showed tumor regression, excellent efficacy and survival advantage over the control groups (see FIGS. 6A and 6B). Little or no mice body weight loss was observed for the study (see FIG. 6C). 5 out of 6 mice were TFS at the end of the study.

SEQUENCE SUMMARY

| SEQ ID NO: | Description |
|---|---|
| 1 | 34B7 VH amino acid sequence |
| 2 | 34B7, 37G7 VH CDR1 amino acid sequence |
| 3 | 34B7 VH CDR2 amino acid sequence |
| 4 | 34B7 VH CDR3 amino acid sequence |
| 5 | 34B7 VL amino acid sequence |
| 6 | 34B7, 36H6, 35B1, 37G7, M1H1, M33F, 29C4 VL CDR1 amino acid sequence |
| 7 | 34B7, 36H6, 43A12H, 35B1, M17, 37G7, 18C2, 10C10, 7F12, M1H1, M33F, 29C4, 27G5_56A2 VL CDR2 amino acid sequence |
| 8 | 34B7, 35B1, 37G7 VL CDR3 amino acid sequence |
| 9 | M1F1, M1H1, M33F VH amino acid sequence |
| 10 | M1F1, M1H1, M33F VH CDR1 amino acid sequence |
| 11 | M1F1, M1H1, M33F, 27G5_56A2 VH CDR2 amino acid sequence |
| 12 | M1F1, M1H1, M33F VH CDR3 amino acid sequence |
| 13 | M1F1 VL amino acid sequence |
| 14 | M1F1, 24F10, 30C10, M10, 45D8, 43B2_56A6, 50B4_56B2 VL CDR1 amino acid |
| 15 | M1F1, 24F10, 30C10, M10, 45D8, 43B2_56A6, 50B4_56B2 VL CDR2 amino acid |
| 16 | M1F1, M1H1, M33F, 45D8, 43B2_56A6, 50B4_56B2 VL CDR3 amino acid sequence |
| 17 | 31B7 VH amino acid sequence |
| 18 | 31B7, 24F10, 30C10, 9D1, 46G4_60A5 VH CDR1 amino acid sequence |
| 19 | 31B7 VH CDR2 amino acid sequence |
| 20 | 31B7, 34E1_56A4 VH CDR3 amino acid sequence |
| 21 | 31B7 VL amino acid sequence |
| 22 | 31B7, 34E1_56A4 VL CDR1 amino acid sequence |
| 23 | 31B7, 6C11, 19H1, M35hA10, 3A6_56A1, 34E1_56A4 VL CDR2 amino acid sequence |
| 24 | 31B7, 6C11, 19H1, 34E1_56A4 VL CDR3 amino acid sequence |
| 25 | M3 VH amino acid sequence |
| 26 | M3 VH CDR1 amino acid sequence |
| 27 | M3 VH CDR2 amino acid sequence |
| 28 | M3 VH CDR3 amino acid sequence |
| 29 | M3 VL amino acid sequence |
| 30 | M3 VL CDR1 amino acid sequence |
| 31 | M3 VL CDR2 amino acid sequence |
| 32 | M3 VL CDR3 amino acid sequence |
| 33 | 24F10 VH amino acid sequence |
| 34 | 24F10 VH CDR2 amino acid sequence |
| 35 | 24F10 VH CDR3 amino acid sequence |
| 36 | 24F10 VL amino acid sequence |
| 37 | 24F10 VL CDR3 amino acid sequence |
| 38 | 30C10 VH amino acid sequence |
| 39 | 30C10 VH CDR2 amino acid sequence |
| 40 | 30C10 VH CDR3 amino acid sequence |
| 41 | 30C10 VL amino acid sequence |

SEQUENCE SUMMARY

SEQ ID NO: Description

| | |
|---|---|
| 42 | 30C10, M10 VL CDR3 amino acid sequence |
| 43 | 36H6 VH amino acid sequence |
| 44 | 36H6 VH CDR1 amino acid sequence |
| 45 | 36H6 VH CDR3 amino acid sequence |
| 46 | 36H6 VH CDR3 amino acid sequence |
| 47 | 36H6 VL amino acid sequence |
| 48 | 36H6 VL CDR3 amino acid sequence |
| 49 | 43A12H VH amino acid sequence |
| 50 | 43A12H, M17 VH CDR1 amino acid sequence |
| 51 | 43A12H VH CDR2 amino acid sequence |
| 52 | 43A12H VH CDR3 amino acid sequence |
| 53 | 43A12H VL amino acid sequence |
| 54 | 43A12H, 27G5_56A2 VL CDR1 amino acid sequence |
| 55 | 43A12H VL CDR3 amino acid sequence |
| 56 | 6C11 VH amino acid sequence |
| 57 | 6C11, 19H1 VH CDR1 amino acid sequence |
| 58 | 6C11, 3A6_56A1 VH CDR2 amino acid sequence |
| 59 | 6C11, 19H1, 3A6_56A1 VH CDR3 amino acid sequence |
| 60 | 6C11 VL amino acid sequence |
| 61 | 6C11 VL CDR1 amino acid sequence |
| 62 | 19H1 VH amino acid sequence |
| 63 | 19H1 VH CDR2 amino acid sequence |
| 64 | 19H1 VL amino acid sequence |
| 65 | 19H1, 3A6_56A1 VL CDR1 amino acid sequence |
| 66 | 35B1 VH amino acid sequence |
| 67 | 35B1 VH CDR1 amino acid sequence |
| 68 | 35B1 VH CDR2 amino acid sequence |
| 69 | 35B1 VH CDR3 amino acid sequence |
| 70 | 35B1 VL amino acid sequence |
| 71 | 11F9 VH amino acid sequence |
| 72 | 11F9 VH CDR1 amino acid sequence |
| 73 | 11F9 VH CDR2 amino acid sequence |
| 74 | 11F9, 3H9 VH CDR3 amino acid sequence |
| 75 | 11F9 VL amino acid sequence |
| 76 | 11F9, 3H9 VL CDR1 amino acid sequence |
| 77 | 11F9, 3H9 VL CDR3 amino acid sequence |
| 78 | M1H1 VL amino acid sequence |
| 79 | M17 VH amino acid sequence |
| 80 | M17 VH CDR2 amino acid sequence |
| 81 | M17 VH CDR3 amino acid sequence |
| 82 | M17 VL amino acid sequence |
| 83 | M17 VL CDR1 amino acid sequence |
| 84 | M17 VL CDR3 amino acid sequence |
| 85 | 37G7 VH amino acid sequence |
| 86 | 37G7 VH CDR2 amino acid sequence |
| 87 | 37G7 VH CDR3 amino acid sequence |
| 88 | 37G7 VL amino acid sequence |
| 89 | 18C2 VH amino acid sequence |
| 90 | 18C2, 10C10, 19D9, 7F12 VH CDR1 amino acid sequence |
| 91 | 18C2 VH CDR2 amino acid sequence |
| 92 | 18C2 VH CDR3 amino acid sequence |
| 93 | 18C2, 10C10 VL amino acid sequence |
| 94 | 18C2, 10C10, 19D9, 7F12, 46G4_60A5 VL CDR1 amino acid sequence |
| 95 | 18C2, 10C10, 19D9, 7F12 VL CDR3 amino acid sequence |
| 96 | 10C10 VH amino acid sequence |
| 97 | 10C10 VH CDR2 amino acid sequence |
| 98 | 10C10, 19D9 VH CDR3 amino acid sequence |
| 99 | 19D9 VH amino acid sequence |
| 100 | 19D9 VH CDR2 amino acid sequence |
| 101 | 19D9 VL amino acid sequence |
| 102 | 19D9 VL CDR2 amino acid sequence |
| 103 | 7F12 VH amino acid sequence |
| 104 | 7F12 VH CDR2 amino acid sequence |
| 105 | 7F12 VH CDR3 amino acid sequence |
| 106 | 7F12 VL amino acid sequence |
| 107 | 9D1 VH amino acid sequence |
| 108 | 9D1, 34E1_56A4 VH CDR2 amino acid sequence |
| 109 | 9D1 VH CDR3 amino acid sequence |
| 110 | 9D1 VL amino acid sequence |
| 111 | 9D1 VL CDR1 amino acid sequence |
| 112 | 9D1, 11F9, 3H9 VL CDR2 amino acid sequence |
| 113 | 9D1 VL CDR3 amino acid sequence |
| 114 | 3H9 VH amino acid sequence |
| 115 | 3H9 VH CDR1 amino acid sequence |
| 116 | 3H9 VH CDR2 amino acid sequence |

-continued

SEQUENCE SUMMARY

| SEQ ID NO: | Description |
|---|---|
| 117 | 3H9 VL amino acid sequence |
| 118 | 29C4 VH amino acid sequence |
| 119 | 29C4 VH CDR1 amino acid sequence |
| 120 | 29C4 VH CDR2 amino acid sequence |
| 121 | 29C4 VH CDR3 amino acid sequence |
| 122 | 29C4 VL amino acid sequence |
| 123 | 29C4 VL CDR3 amino acid sequence |
| 124 | M10 VH amino acid sequence |
| 125 | M10 VH CDR1 amino acid sequence |
| 126 | M10 VH CDR2 amino acid sequence |
| 127 | M10 VH CDR3 amino acid sequence |
| 128 | M10 VL amino acid sequence |
| 129 | 45D8 VH amino acid sequence |
| 130 | 45D8, 43B2_56A6, 50B4_56B2 VH CDR1 amino acid sequence |
| 131 | 45D8 VH CDR2 amino acid sequence |
| 132 | 45D8, 43B2_56A6, 50B4_56B2 VH CDR3 amino acid sequence |
| 133 | 45D8, 43B2_56A6 VL amino acid sequence |
| 134 | M35hA10 VH amino acid sequence |
| 135 | M35hA10 VH CDR1 amino acid sequence |
| 136 | M35hA10 VH CDR2 amino acid sequence |
| 137 | M35hA10 VH CDR3 amino acid sequence |
| 138 | M35hA10 VL amino acid sequence |
| 139 | M35hA10 VL CDR1 amino acid sequence |
| 140 | M35hA10 VL CDR3 amino acid sequence |
| 141 | M33F VL amino acid sequence |
| 142 | 43B2_56A6 VH amino acid sequence |
| 143 | 43B2_56A6 CDR-H2 amino acid sequence |
| 144 | 50B4_56B2 VH amino acid sequence |
| 145 | 50B4_56B2 CDR-H2 amino acid sequence |
| 146 | 50B4_56B2 VL amino acid sequence |
| 147 | 3A6_56A1 VH amino acid sequence |
| 148 | 3A6_56A1 CDR-H1 amino acid sequence |
| 149 | 3A6_56A1 VL amino acid sequence |
| 150 | 3A6_56A1 CDR-L3 amino acid sequence |
| 151 | 46G4_60A5 VH amino acid sequence |
| 152 | 46G4_60A5 CDR-H2 amino acid sequence |
| 153 | 46G4_60A5 CDR-H3 amino acid sequence |
| 154 | 46G4_60A5 VL amino acid sequence |
| 155 | 46G4_60A5 CDR-L2 amino acid sequence |
| 156 | 46G4_60A5 CDR-L3 amino acid sequence |
| 157 | 34E1_56A4 VH amino acid sequence |
| 158 | 34E1_56A4 CDR-H1 amino acid sequence |
| 159 | 34E1_56A4 VL amino acid sequence |
| 160 | 27G5_56A2 VH amino acid sequence |
| 161 | 27G5_56A2 CDR-H1 amino acid sequence |
| 162 | 27G5_56A2 CDR-H3 amino acid sequence |
| 163 | 27G5_56A2 VL amino acid sequence |
| 164 | 27G5_56A2 CDR-L3 amino acid sequence |
| 165 | 34B7 VH nucleic acid sequence |
| 166 | 34B7 VL nucleic acid sequence |
| 167 | M1F1 VH nucleic acid sequence |
| 168 | M1F1 VL nucleic acid sequence |
| 169 | 31B7 VH nucleic acid sequence |
| 170 | 31B7 VL nucleic acid sequence |
| 171 | M3 VH nucleic acid sequence |
| 172 | M3 VL nucleic acid sequence |
| 173 | 24F10 VH nucleic acid sequence |
| 174 | 24F10 VL nucleic acid sequence |
| 175 | 30C10 VH nucleic acid sequence |
| 176 | 30C10 VL nucleic acid sequence |
| 177 | 36H6 VH nucleic acid sequence |
| 178 | 36H6 VL nucleic acid sequence |
| 179 | 43A12H8 VH nucleic acid sequence |
| 180 | 43A12H VL nucleic acid sequence |
| 181 | 6C11 VH nucleic acid sequence |
| 182 | 6C11 VL nucleic acid sequence |
| 183 | 19H1 VH nucleic acid sequence |
| 184 | 19H1 VL nucleic acid sequence |
| 185 | 35B1 VH nucleic acid sequence |
| 186 | 35B1 VL nucleic acid sequence |
| 187 | M17 VH nucleic acid sequence |
| 188 | M17 VL nucleic acid sequence |
| 189 | 37G7 VH nucleic acid sequence |
| 190 | 37G7 VL nucleic acid sequence |
| 191 | 18C2 VH nucleic acid sequence |

SEQUENCE SUMMARY

| SEQ ID NO: | Description |
|---|---|
| 192 | 18C2 VL nucleic acid sequence |
| 193 | 10C10 VH nucleic acid sequence |
| 194 | 10C10 VL nucleic acid sequence |
| 195 | 19D9 VH nucleic acid sequence |
| 196 | 19D9 VL nucleic acid sequence |
| 197 | 7F12 VH nucleic acid sequence |
| 198 | 7F12 VL nucleic acid sequence |
| 199 | 9D1 VH nucleic acid sequence |
| 200 | 9D1 VL nucleic acid sequence |
| 201 | M1H1 VH nucleic acid sequence |
| 202 | M1H1 VL nucleic acid sequence |
| 203 | M33F VH nucleic acid sequence |
| 204 | M33F VL nucleic acid sequence |
| 205 | M10 VH nucleic acid sequence |
| 206 | M10 VL nucleic acid sequence |
| 207 | 45D8 VH nucleic acid sequence |
| 208 | 45D8 VL nucleic acid sequence |
| 209 | 11F9 VH nucleic acid sequence |
| 210 | 11F9 VL nucleic acid sequence |
| 211 | 3H9 VH nucleic acid sequence |
| 212 | 3H9 VL nucleic acid sequence |
| 213 | M35hA10 VH nucleic acid sequence |
| 214 | M35hA10 VL nucleic acid sequence |
| 215 | 29C4 VH nucleic acid sequence |
| 216 | 29C4 VL nucleic acid sequence |
| 217 | 43B2_56A6 VH nucleic acid sequence |
| 218 | 43B2_56A6 VL nucleic acid sequence |
| 219 | 50B4_56B2 VH nucleic acid sequence |
| 220 | 50B4_56B2 VL nucleic acid sequence |
| 221 | 3A6_56A1 VH nucleic acid sequence |
| 222 | 3A6_56A1 VL nucleic acid sequence |
| 223 | 46G4_60A5 VH nucleic acid sequence |
| 224 | 46G4_60A5 VL nucleic acid sequence |
| 225 | 34E1_56A4 VH nucleic acid sequence |
| 226 | 34E1_56A4 VL nucleic acid sequence |
| 227 | 27G5_56A2 VH nucleic acid sequence |
| 228 | 27G5_56A2 VL nucleic acid sequence |
| 229 | Human TMEFF1 amino acid sequence (with signal sequence) |
| 230-255 | Primers |

INCORPORATION BY REFERENCE

The contents of all references, patents, pending patent applications and published patents, Sequence Listing, and Accession Numbers, cited throughout this application are hereby expressly incorporated by reference.

EQUIVALENTS

Those skilled in the art will recognize, or be able to ascertain using no more than routine experimentation, many equivalents to the specific embodiments of the invention described herein.

Such equivalents are intended to be encompassed by the following claims.

The invention claimed is:

1. An anti-TMEFF1 (Transmembrane Protein With EGF Like And Two Follistatin Like Domains 1) antibody, or antigen-binding portion thereof, comprising a heavy chain variable region comprising a CDR3domain comprising the amino acid sequence of SEQ ID NO: 40, a CDR2 domain comprising the amino acid sequence of SEQ ID NO: 39, and a CDR1 domain comprising the amino acid sequence of SEQ ID NO: 18 and a light chain variable region comprising a CDR3 domain comprising the amino acid sequence of SEQ ID NO: 42, a CDR2 domain comprising the amino acid sequence of SEQ ID NO: 15, and a CDR1 domain comprising the amino acid sequence of SEQ ID NO: 14;
  a heavy chain variable region comprising a CDR3 domain comprising the amino acid sequence of SEQ ID NO: 127, a CDR2 domain comprising the amino acid sequence of SEQ ID NO: 126, and a CDR1 domain comprising the amino acid sequence of SEQ ID NO: 125 and a light chain variable region comprising a CDR3 domain comprising the amino acid sequence of SEQ ID NO: 42, a CDR2 domain comprising the amino acid sequence of SEQ ID NO: 15, and a CDR1 domain comprising the amino acid sequence of SEQ ID NO: 14;
  a heavy chain variable region comprising a CDR3 domain comprising the amino acid sequence of SEQ ID NO: 20, a CDR2 domain comprising the amino acid sequence of SEQ ID NO: 19, and a CDR1 domain comprising the amino acid sequence of SEQ ID NO: 18, and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 22; or
  a heavy chain variable region comprising a CDR3 domain comprising the amino acid sequence of SEQ ID NO: 46, a CDR2 domain comprising the amino acid sequence of SEQ ID NO: 45, and a CDR1 domain comprising the amino acid sequence of SEQ ID NO: 44 and a light chain variable region comprising a CDR3 domain comprising the amino acid sequence of SEQ ID NO: 48, a CDR2 domain comprising the amino acid sequence of SEQ ID NO: 7, and a CDR1 domain comprising the amino acid sequence of SEQ ID NO: 6.

2. The anti-TMEFF1 antibody, or antigen-binding portion thereof, of claim 1, comprising
  a heavy chain variable region comprising the amino acid sequence of SEQ ID NO: 38 and a light chain variable region comprising the amino acid sequence of SEQ ID NO: 41;
  a heavy chain variable region comprising the amino acid sequence of SEQ ID NO: 124 and a light chain variable region comprising the amino acid sequence of SEQ ID NO: 128;
  a heavy chain variable region comprising the amino acid sequence of SEQ ID NO: 17 and a light chain variable region comprising the amino acid sequence of SEQ ID NO: 21; or
  a heavy chain variable region comprising the amino acid sequence of SEQ ID NO: 43 and a light chain variable region comprising the amino acid sequence of SEQ ID NO: 47.

3. The anti-TMEFF1 antibody, or antigen-binding portion thereof, of claim 1, wherein the antibody, or antigen-binding portion thereof, is an IgG isotype.

4. The anti-TMEFF1 antibody, or antigen-binding portion thereof, of claim 1, wherein the antibody, or antigen-binding portion thereof, has a $K_D$ of 200 nM or less.

5. An anti-TMEFF1 (Transmembrane Protein With EGF Like And Two Follistatin Like Domains 1) antibody, or antigen-binding portion thereof, comprising
  a heavy chain comprising an amino acid sequence having at least 90%, 95%, 96%, 97%, 98%, or 99% identity to SEQ ID NO: 38, and a light chain comprising an amino acid sequence having at least 90%, 95%, 96%, 97%, 98%, or 99% identity to SEQ ID NO: 41;

a heavy chain comprising an amino acid sequence having at least 90%, 95%, 96%, 97%, 98%, or 99% identity to SEQ ID NO: 124, and a light chain comprising an amino acid sequence having at least 90%, 95%, 96%, 97%, 98%, or 99% identity to SEQ ID NO: 128;

a heavy chain comprising an amino acid sequence having at least 90%, 95%, 96%, 97%, 98%, or 99% identity to SEQ ID NO: 17, and a light chain comprising an amino acid sequence having at least 90%, 95%, 96%, 97%, 98%, or 99% identity to SEQ ID NO: 21; or a heavy chain comprising an amino acid sequence having at least 90%, 95%, 96%, 97%, 98%, or 99% identity to SEQ ID NO: 43, and a light chain comprising an amino acid sequence having at least 90%, 95%, 96%, 97%, 98%, or 99% identity to SEQ ID NO: 47.

6. A pharmaceutical composition comprising the anti-TMEFF1 antibody, or antigen-binding portion thereof, of claim 1, and a pharmaceutically acceptable carrier.

7. An isolated nucleic acid encoding the anti-TMEFF1 antibody, or antigen-binding portion thereof, of claim 1.

8. The anti-TMEFF1 antibody, or antigen-binding portion thereof, of claim 1, conjugated to at least one drug.

9. A method for treating cancer in a subject, comprising administering a therapeutically effective amount of the anti-TMEFF1 antibody or antigen-binding portion thereof, of claim 1 to the subject, thereby treating the cancer.

10. The method of claim 9, wherein the cancer is a solid tumor, and wherein the solid tumor growth is inhibited or decreased.

11. The method of claim 9, wherein the anti-TMEFF1 antibody or antigen-binding portion thereof is administered in combination with an additional agent or an additional therapy.

12. The method of claim 11, wherein the additional agent is an immune checkpoint inhibitor.

13. The method of claim 9, further comprising administering a poly (ADP-ribose) polymerase (PARP) inhibitor, a DNA alkylating agent, or a topoisomerase inhibitor to the subject.

14. The method of claim 9, wherein the cancer is small cell lung cancer, triple negative breast cancer, or ovarian cancer.

* * * * *

SEQUENCE LISTING

<160> NUMBER OF SEQ ID NOS: 255

<210> SEQ ID NO 1
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 1

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Thr Ser Tyr
            20                  25                  30

Gly Met His Val Arg Gln Ala Pro Gly Lys Gly Leu Glu Trp Val
        35                  40                  45

Ala Val Val Trp Tyr Glu Gly Asn Ser Lys Phe Tyr Ile Asp Ser Val
50                  55                  60

Lys Gly Arg Phe Ile Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Tyr Cys Gly Asp Asp Cys Tyr Pro Phe Asp Tyr Trp Gly
            100                 105                 110

Gln Gly Thr Leu Val Thr Val Ser Ser
        115                 120

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Phe Thr Phe Thr Ser Tyr Gly Met His
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Val Trp Tyr Glu Gly Asn Ser Lys Phe Tyr Ile Asp Ser Val Lys
1               5                   10                  15

Gly

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Tyr Cys Gly Asp Asp Cys Tyr Pro Phe Asp Tyr
1               5                   10

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Trp
                85                  90                  95

Thr Phe Gly Gln Gly Thr Lys Leu Glu Ile Lys
            100                 105

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Ser Gln Gly Ile Ser Asn Tyr Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Ala Ser Thr Leu Gln Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Lys Tyr Asn Ser Ala Pro Trp Thr
1               5

<210> SEQ ID NO 9
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Glu Ser Gly Pro Gly Leu Val Lys Pro Ser Glu
1               5                   10                  15
```

```
Thr Leu Ser Leu Thr Cys Ala Val Ser Gly Tyr Ser Ile Ser Ser Gly
            20                  25                  30

Tyr Phe Trp Gly Trp Ile Arg Gln Pro Pro Gly Lys Lys Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Gly Asp Cys Ser Gly Gly Ile Cys Tyr Trp Tyr Phe Asp
            100                 105                 110

Leu Trp Gly Arg Gly Thr Leu Val Thr Val Ser Ser
        115                 120
```

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Gly Tyr Ser Ile Ser Ser Gly Tyr Phe Trp Gly
1               5                   10
```

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Ser Ile Tyr His Ser Gly Ser Thr Tyr Tyr Asn Pro Ser Leu Lys Ser
1               5                   10                  15
```

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
Glu Gly Asp Cys Ser Gly Gly Ile Cys Tyr Trp Tyr Phe Asp Leu
1               5                   10                  15
```

<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30
```

```
Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Val Thr Leu Thr Ile Ser Ser Leu Gln Ser
65                  70                  75                  80

Glu Asp Phe Ala Val Tyr Tyr Cys Gln Gln Tyr Asn Lys Trp Pro Leu
                85                  90                  95

Thr Phe Gly Gly Gly Thr Lys Val Glu Ile Lys
            100                 105

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ala Ser Gln Ser Val Ser Ser Asn Leu Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Ala Ser Thr Arg Ala Thr
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Gln Tyr Asn Lys Trp Pro Leu Thr
1               5

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asn Gly Ile Asn Lys Tyr Tyr Ala Asp Ser Val
```

```
                50                  55                  60
Lys Gly Arg Phe Thr Ile Ser Arg Asp Ala Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Leu Leu Trp Phe Gly Gly Met Asp Val Trp Gly Gln
            100                 105                 110

Gly Thr Thr Val Thr Val Ser Ser
        115                 120
```

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

```
Gly Phe Thr Phe Ser Ser Tyr Gly Met His
 1               5                  10
```

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

```
Val Ile Trp Tyr Asn Gly Ile Asn Lys Tyr Tyr Ala Asp Ser Val Lys
 1               5                  10                  15

Gly
```

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

```
Glu Gly Leu Leu Trp Phe Gly Gly Met Asp Val
 1               5                  10
```

<210> SEQ ID NO 21
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

```
Glu Ile Val Leu Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly Tyr Asn Tyr Leu His Trp Tyr Leu Gln Lys Pro Gly Gln Ser
         35                  40                  45

Pro Gln Leu Leu Ile Tyr Leu Gly Ser Asn Arg Ala Ser Gly Val Pro
```

```
                50                  55                  60
Asp Arg Phe Ser Gly Ser Arg Ser Gly Thr Asp Phe Thr Leu Lys Ile
 65                  70                  75                  80

Ile Arg Val Glu Ala Glu Asp Val Gly Val Tyr Tyr Cys Met Gln Ala
                 85                  90                  95

Leu Gln Thr Pro Tyr Thr Phe Gly Gln Gly Thr Lys Leu Glu Ile Lys
            100                 105                 110

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ser Ser Gln Ser Leu Leu His Ser Asn Gly Tyr Asn Tyr Leu His
 1               5                  10                  15

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Gly Ser Asn Arg Ala Ser
 1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Gln Ala Leu Gln Thr Pro Tyr Thr
 1               5

<210> SEQ ID NO 25
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Leu Leu Val Glu Ser Gly Gly Gly Val Val Gln Pro Gly Arg
 1               5                  10                  15

Ser Leu Arg Leu Ser Cys Ala Ala Ser Gly Phe Thr Phe Lys Arg Tyr
                20                  25                  30

Gly Met His Trp Val Arg Gln Ala Pro Gly Arg Gly Leu Glu Trp Val
            35                  40                  45

Ala Val Ile Trp Ser Asp Gly Asn Lys Lys His Tyr Ala Asp Ser Val
        50                  55                  60

Lys Gly Arg Phe Thr Ile Ser Arg Asp Asn Ser Lys Asn Thr Leu Tyr
 65                  70                  75                  80
```

Leu Gln Met Asn Ser Leu Arg Ala Glu Asp Thr Ala Val Tyr Tyr Cys
                85                  90                  95

Ala Arg Glu Asn Tyr Gly Ser Gly Ser Tyr Tyr Asn Gly Gly Met Asp
            100                 105                 110

Val Trp Gly Gln Gly Thr Thr Val Thr Val Ser Ser
        115                 120

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Phe Thr Phe Lys Arg Tyr Gly Met His
1               5                   10

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Val Ile Trp Ser Asp Gly Asn Lys Lys His Tyr Ala Asp Ser Val Lys
1               5                   10                  15

Gly

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Asn Tyr Gly Ser Gly Ser Tyr Tyr Asn Gly Gly Met Asp Val
1               5                   10                  15

<210> SEQ ID NO 29
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Trp
            85                  90                  95

Thr Phe Gly Gln Gly Thr Lys Leu Glu Ile Lys
            100                 105

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ala Ser Gln Ser Ile Ser Ser Trp Leu Ala
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Ala Ser Ser Leu Glu Ser
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Gln Tyr Asn Ser Tyr Ser Trp Thr
1               5

<210> SEQ ID NO 33
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asp Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Met Val Arg Gly Ile Val Ile Thr Phe Phe Asp Tyr
            100                 105                 110

```
Trp Gly Gln Gly Thr Leu Val Thr Val Ser Ser
        115                 120

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Ile Trp Tyr Asp Gly Ser Asp Lys Tyr Tyr Thr Asp Ser Val Lys
1               5                   10                  15

Gly

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Glu Ser Met Val Arg Gly Ile Val Ile Thr Phe Phe Asp Tyr
1               5                   10

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Ser Cys Gln His Tyr Asn Asn Trp Pro Pro
                85                  90                  95

Thr Phe Gly Gly Gly Thr Lys Val Glu Ile Lys
            100                 105

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln His Tyr Asn Asn Trp Pro Pro Thr
1               5
```

<210> SEQ ID NO 38
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asp Lys Tyr Tyr Ala Asp Ser Val
    50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Val Tyr Phe Cys
                85                  90                  95

Ala Arg Glu Thr Ile Phe Arg Gly Leu Thr Ile Thr Phe Phe Asp His
            100                 105                 110

Trp Gly Gln Gly Thr Leu Val Thr Val Ser Ser
        115                 120

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Ile Trp Tyr Asp Gly Ser Asp Lys Tyr Tyr Ala Asp Ser Val Lys
1               5                   10                  15

Gly

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Thr Ile Phe Arg Gly Leu Thr Ile Thr Phe Phe Asp His
1               5                   10

<210> SEQ ID NO 41
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Thr Phe Gly Gly Gly Thr Lys Leu Glu Ile Lys
            100                 105

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Gln Tyr Asn Asn Trp Pro Pro Thr
1               5

<210> SEQ ID NO 43
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Val Ile Trp Tyr Glu Gly Asn Lys Tyr Tyr Thr Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Leu Leu Trp Phe Gly Glu Ser Tyr Gly Met Asp Val Trp
            100                 105                 110

Gly Gln Gly Thr Thr Val Thr Val Ser Ser
        115                 120

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Phe Thr Phe Ser Asp Tyr Gly Met His
1               5                   10

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Val Ile Trp Tyr Glu Gly Gly Asn Lys Tyr Tyr Thr Asp Ser Val Lys
1               5                   10                  15

Gly

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ile Leu Leu Trp Phe Gly Glu Ser Tyr Gly Met Asp Val
1               5                   10

<210> SEQ ID NO 47
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Asn Ala Pro Trp
                85                  90                  95

Thr Phe Gly Gln Gly Thr Lys Val Glu Ile Lys
            100                 105

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Lys Tyr Asn Asn Ala Pro Trp Thr
1               5

<210> SEQ ID NO 49
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Val Gln Met Asn Ser Leu Arg Ala Glu Asp Thr Ala Val Tyr Tyr Cys
                85                  90                  95

Ala Arg Asp Arg Asp Tyr Phe Gly Ser Gly Tyr Tyr Ser Asn Val Arg
            100                 105                 110

Tyr Tyr Tyr Tyr Gly Met Asp Val Trp Gly Gln Gly Thr Thr Val Thr
        115                 120                 125

Val Ser Ser
    130

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Phe Thr Phe Arg Ser Tyr Gly Met His
1               5                   10

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Val Ile Trp Tyr Asp Gly Ser Ile Lys Tyr Tyr Ala Asp Ser Val Lys
1               5                   10                  15

Gly

<210> SEQ ID NO 52
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

```
Asp Arg Asp Tyr Phe Gly Ser Gly Tyr Tyr Ser Asn Val Arg Tyr Tyr
1               5                   10                  15

Tyr Tyr Gly Met Asp Val
            20
```

<210> SEQ ID NO 53
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Gly Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Leu Thr Phe Gly Gly Gly Thr Lys Val Glu Ile Lys
            100                 105
```

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

```
Arg Ala Ser Gln Ser Ile Ser Ser Tyr Leu Asn
1               5                   10
```

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

```
Gln Gln Ser Tyr Ser Thr Pro Pro Leu Thr
1               5                   10
```

<210> SEQ ID NO 56
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
Gln Val Gln Leu Gln Gln Ser Gly Pro Gly Leu Val Lys Pro Ser Gln
1               5                   10                  15
```

```
Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Pro
 50                  55                  60

Val Ser Val Lys Ser Arg Ile Thr Ile Asn Pro Asp Thr Ser Lys Asn
 65                  70                  75                  80

Gln Val Ser Leu Gln Leu Asn Pro Val Thr Pro Glu Asp Thr Ala Val
                85                  90                  95

Tyr Tyr Cys Thr Arg Glu Gln Gly Tyr Ser Ser Arg Tyr Tyr Tyr
            100                 105                 110

Tyr Tyr Gly Met Asp Val Trp Gly Gln Gly Thr Thr Val Thr Val Ser
            115                 120                 125

Ser
```

```
<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Asp Ser Val Ser Ser Asn Ser Ala Ala Trp Asn
 1               5                  10

<210> SEQ ID NO 58
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Thr Tyr Tyr Arg Ser Lys Trp Tyr Asn Asp Tyr Pro Val Ser Val
 1               5                  10                  15

Lys Ser

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Glu Gln Gly Tyr Ser Ser Arg Tyr Tyr Tyr Tyr Tyr Gly Met Asp
 1               5                  10                  15

Val

<210> SEQ ID NO 60
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 60

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ile
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Val Glu Ile Lys
            100                 105                 110

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Ser Ser Gln Ser Leu Leu His Ile Asn Gly Tyr Asn Tyr Leu Asp
1               5                   10                  15

<210> SEQ ID NO 62
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Gln Trp Tyr Asn Asp Tyr Pro
    50                  55                  60

Val Ser Val Lys Ser Arg Ile Thr Ile Asn Pro Asp Thr Ser Lys Asn
65                  70                  75                  80

Gln Val Ser Leu Gln Leu Asn Pro Val Thr Pro Glu Asp Thr Ala Val
                85                  90                  95

Tyr Tyr Cys Ala Arg Glu Gln Tyr Ser Ser Ser Arg Tyr Tyr Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 63
<211> LENGTH: 18
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 63

Arg Thr Tyr Tyr Arg Ser Gln Trp Tyr Asn Asp Tyr Pro Val Ser Val
1               5                   10                  15

Lys Ser

<210> SEQ ID NO 64
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Val Glu Ile Lys
            100                 105                 110

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Ser Ser Gln Ser Leu Leu His Ser Asn Gly Tyr Asn Tyr Leu Asp
1               5                   10                  15

<210> SEQ ID NO 66
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Thr Tyr
            20                  25                  30

Gly Met His Trp Val Arg Gln Ala Pro Gly Lys Gly Leu Glu Trp Val
        35                  40                  45

Ala Val Val Trp Phe Glu Gly Asn Ser Lys Phe Tyr Ile Asp Ser Val
    50                  55                  60
```

```
Lys Gly Arg Phe Ile Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Ala Asn Cys Gly Ala Asp Cys Tyr Pro Phe Asp Tyr Trp Gly
            100                 105                 110

Gln Gly Thr Leu Val Thr Val Ser Ser
        115                 120

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Phe Thr Phe Thr Thr Tyr Gly Met His
1               5                   10

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Val Val Trp Phe Glu Gly Asn Ser Lys Phe Tyr Ile Asp Ser Val Lys
1               5                   10                  15

Gly

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Asn Cys Gly Ala Asp Cys Tyr Pro Phe Asp Tyr
1               5                   10

<210> SEQ ID NO 70
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60
```

```
Ser Gly Ser Gly Thr Asp Phe Ser Leu Thr Ile Ser Ser Leu Arg Pro
 65                  70                  75                  80

Glu Asp Val Ala Thr Tyr Tyr Cys Gln Lys Tyr Asn Ser Ala Pro Trp
                 85                  90                  95

Thr Phe Gly Gln Gly Thr Lys Val Glu Ile Lys
            100                 105

<210> SEQ ID NO 71
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Tyr Ala
                 20                  25                  30

Trp Met Ser Trp Val Arg Gln Ala Pro Gly Lys Gly Leu Glu Trp Val
             35                  40                  45

Gly Arg Ile Lys Ser Lys Thr Asp Gly Gly Thr Thr Asp Tyr Ala Ala
         50                  55                  60

Pro Val Lys Gly Arg Phe Thr Ile Ser Arg Asp Asp Ser Lys Asn Thr
 65                  70                  75                  80

Leu Tyr Leu Gln Leu Asn Ser Leu Lys Ile Glu Asp Thr Ala Val Tyr
                 85                  90                  95

Tyr Cys Thr Thr Gly Arg Ile Ala Ala Ala Gly Phe Asp Tyr Trp Ala
            100                 105                 110

Gln Gly Thr Leu Val Thr Val Ser Ser
        115                 120

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Phe Thr Phe Ser Tyr Ala Trp Met Ser
 1               5                  10

<210> SEQ ID NO 73
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Ile Lys Ser Lys Thr Asp Gly Gly Thr Thr Asp Tyr Ala Ala Pro
 1               5                  10                  15

Val Lys Gly

<210> SEQ ID NO 74
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 74

Gly Arg Ile Ala Ala Ala Gly Phe Asp Tyr
1               5                   10

<210> SEQ ID NO 75
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Asp Ala Val Val Thr Gln Glu Ser Ala Leu Thr Thr Ser Pro Gly Glu
1               5                   10                  15

Thr Val Thr Leu Thr Cys Arg Ser Ser Thr Gly Thr Val Thr Thr Ser
            20                  25                  30

Asn Tyr Ala Asn Trp Val Gln Glu Lys Pro Asp His Leu Phe Thr Gly
        35                  40                  45

Leu Ile Ala Gly Thr Asn Asn Arg Ala Pro Gly Val Pro Ala Arg Phe
    50                  55                  60

Ser Gly Ser Leu Ile Gly Asp Lys Ala Val Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu Gly
            100                 105                 110

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Arg Ser Ser Thr Gly Thr Val Thr Thr Ser Asn Tyr Ala Asn
1               5                   10

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Leu Trp Tyr Ser Asn His Trp Val
1               5

<210> SEQ ID NO 78
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 78

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Asn Lys Trp Pro Leu
                85                  90                  95

Thr Phe Gly Gly Gly Thr Lys Leu Glu Ile Lys
            100                 105

<210> SEQ ID NO 79
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Leu Ile Trp Tyr Asp Gly Asp Gln Tyr Tyr Ala Asp Ser Val
    50                  55                  60

Lys Gly Arg Phe Thr Ile Ser Arg Asp Ser Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gln Cys Gly Asp Asp Cys Tyr Pro Phe Asp Tyr Trp Gly
            100                 105                 110

Gln Gly Thr Leu Val Thr Val Ser Ser
        115                 120

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Leu Ile Trp Tyr Asp Gly Gly Asp Gln Tyr Tyr Ala Asp Ser Val Lys
1               5                   10                  15

Gly

<210> SEQ ID NO 81
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 81

Ala Gln Cys Gly Asp Asp Cys Tyr Pro Phe Asp Tyr
1               5                   10

<210> SEQ ID NO 82
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Tyr Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Asp Pro Trp
                85                  90                  95

Thr Phe Gly Gln Gly Thr Lys Leu Glu Ile Lys
            100                 105

<210> SEQ ID NO 83
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Arg Ala Ser Gln Gly Ile Tyr Asn Tyr Leu Ala
1               5                   10

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Lys Tyr Asn Ser Asp Pro Trp Thr
1               5

<210> SEQ ID NO 85
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85
```

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Ser Tyr
            20                  25                  30

Gly Met His Trp Val Arg Gln Ala Pro Gly Lys Gly Leu Glu Trp Val
        35                  40                  45

Ala Val Val Trp Tyr Glu Gly Ser Ser Lys Phe Tyr Val Asp Ser Val
50                  55                  60

Lys Gly Arg Phe Ile Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Tyr Cys Gly Gly Asp Cys Tyr Pro Phe Asp Tyr Trp Gly
            100                 105                 110

Gln Gly Thr Leu Val Thr Val Ser Ser
        115                 120

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Val Val Trp Tyr Glu Gly Ser Ser Lys Phe Tyr Val Asp Ser Val Lys
1               5                   10                  15

Gly

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ala Tyr Cys Gly Gly Asp Cys Tyr Pro Phe Asp Tyr
1               5                   10

<210> SEQ ID NO 88
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
```

```
                    65                  70                  75                  80
Glu Asp Val Ala Thr Tyr Tyr Cys Gln Lys Tyr Asn Ser Ala Pro Trp
                85                  90                  95

Thr Phe Gly Gln Gly Thr Lys Val Glu Ile Lys
            100                 105
```

<210> SEQ ID NO 89
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ile Tyr
            20                  25                  30

Gly Met His Trp Val Arg Gln Ala Pro Gly Met Gly Leu Glu Trp Val
        35                  40                  45

Ala Ile Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Arg Met Asn Ser Leu Arg Ala Glu Asp Thr Ala Val Tyr Tyr Cys
                85                  90                  95

Ala Arg Asp Pro Phe Thr Ser Ser Leu Asp Tyr Trp Gly Gln Gly Thr
            100                 105                 110

Leu Val Thr Val Ser Ser
        115
```

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

```
Gly Phe Thr Phe Ser Ile Tyr Gly Met His
1               5                   10
```

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

```
Ile Ile Arg Tyr Asp Gly Ser Asn Lys Tyr Tyr Ala Asp Ser Val Lys
1               5                   10                  15

Gly
```

<210> SEQ ID NO 92
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 92

Asp Pro Phe Thr Ser Ser Leu Asp Tyr
1               5

<210> SEQ ID NO 93
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Leu Glu Ile Lys
            100                 105

<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Ala Ser Gln Gly Ile Ser Ser Tyr Leu Ala
1               5                   10

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Gln Leu Asn Ser Tyr Pro Leu Thr
1               5

<210> SEQ ID NO 96
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96
```

Gln Val Gln Leu Val Glu Ser Gly Gly Gly Val Val Gln Pro Gly Arg
1               5                   10                  15

Ser Leu Arg Leu Ser Cys Ala Thr Ser Gly Phe Thr Phe Ser Ile Tyr
            20                  25                  30

Gly Met His Trp Val Arg Gln Ala Pro Gly Lys Gly Leu Glu Trp Val
            35                  40                  45

Ala Ile Ile Trp Tyr Asp Gly Asn Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Tyr Thr Ser Ser Leu Asp Tyr Trp Gly Gln Gly Thr
            100                 105                 110

Leu Val Thr Val Ser Ser
            115

<210> SEQ ID NO 97
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ile Ile Trp Tyr Asp Gly Asn Lys Lys Tyr Tyr Ala Asp Ser Val Lys
1               5                   10                  15

Gly

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Asp Pro Tyr Thr Ser Ser Leu Asp Tyr
1               5

<210> SEQ ID NO 99
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ile Tyr
            20                  25                  30

Gly Met His Trp Val Arg Gln Ala Pro Gly Lys Gly Leu Glu Trp Val
            35                  40                  45

Ala Asn Ile Trp Tyr Asp Gly Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ser Val Tyr Tyr Cys
                85                  90                  95

Ala Arg Asp Pro Tyr Thr Ser Ser Leu Asp Tyr Trp Gly Gln Gly Thr
            100                 105                 110

Leu Val Thr Val Ser Ser
        115

<210> SEQ ID NO 100
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Asn Ile Trp Tyr Asp Gly Ser Lys Lys Tyr Tyr Ala Asp Ser Val Lys
1               5                   10                  15

Gly

<210> SEQ ID NO 101
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Leu Glu Ile Lys
            100                 105

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Thr Ala Ser Thr Leu Gln Ser
1               5

<210> SEQ ID NO 103
<211> LENGTH: 118
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 103

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ile Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Tyr Thr Thr Ser Leu Asp Tyr Trp Gly Gln Gly Thr
            100                 105                 110

Leu Val Thr Val Ser Ser
        115

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ile Ile Trp Tyr Asp Gly Ser Asp Lys Tyr Tyr Ala Asp Ser Val Lys
1               5                   10                  15

Gly

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Asp Pro Tyr Thr Thr Ser Leu Asp Tyr
1               5

<210> SEQ ID NO 106
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly

```
                    50                  55                  60
Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Leu
                 85                  90                  95

Thr Phe Gly Gly Gly Thr Lys Val Glu Ile Lys
            100                 105

<210> SEQ ID NO 107
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
 50                  55                  60

Lys Gly Arg Phe Thr Leu Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ser Thr Gly Ser Ser Trp Ser Tyr Tyr Tyr Tyr Tyr Gly
            100                 105                 110

Met Asp Val Trp Gly Gln Gly Thr Thr Val Thr Val Ser Ser
        115                 120                 125

<210> SEQ ID NO 108
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Val Ile Trp Tyr Asp Gly Ser Asn Lys Tyr Tyr Ala Asp Ser Val Lys
 1               5                  10                  15

Gly

<210> SEQ ID NO 109
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Asp Ser Thr Gly Ser Ser Trp Ser Tyr Tyr Tyr Tyr Tyr Gly Met Asp
 1               5                  10                  15

Val
```

```
<210> SEQ ID NO 110
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Leu Val Phe Gly Gly Gly Thr Lys Leu Thr Val Leu Gly
            100                 105                 110

<210> SEQ ID NO 111
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Ser Ser Thr Gly Ala Val Thr Thr Ser Asn Tyr Ala Asn
1               5                   10

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Thr Asn Asn Arg Ala Pro
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ala Leu Trp Tyr Ser Asn His Leu Val
1               5

<210> SEQ ID NO 114
<211> LENGTH: 121
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 114

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Val Phe Ser Tyr Ala
            20                  25                  30

Trp Met Asn Trp Val Arg Gln Ala Pro Gly Lys Gly Leu Glu Trp Val
        35                  40                  45

Gly Arg Ile Lys Ser Lys Thr Glu Gly Gly Thr Thr Asp Asn Ala Ala
    50                  55                  60

Pro Val Lys Gly Arg Phe Thr Ile Ser Arg Glu Asp Ser Lys Asn Thr
65                  70                  75                  80

Leu Tyr Leu Gln Leu Asn Ser Leu Lys Ile Glu Asp Thr Ala Val Tyr
                85                  90                  95

Tyr Cys Thr Thr Gly Arg Ile Ala Ala Ala Gly Phe Asp Tyr Trp Gly
            100                 105                 110

Gln Gly Thr Leu Val Thr Val Ser Ser
        115                 120

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 115

Gly Phe Val Phe Ser Tyr Ala Trp Met Asn
1               5                   10

<210> SEQ ID NO 116
<211> LENGTH: 19
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 116

Arg Ile Lys Ser Lys Thr Glu Gly Gly Thr Thr Asp Asn Ala Ala Pro
1               5                   10                  15

Val Lys Gly

<210> SEQ ID NO 117
<211> LENGTH: 110
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 117

Asp Ala Val Val Thr Gln Glu Ser Ala Leu Thr Thr Ser Pro Gly Glu
1               5                   10                  15

Thr Val Thr Leu Thr Cys Arg Ser Ser Thr Gly Thr Val Thr Thr Ser
            20                  25                  30

Asn Tyr Ala Asn Trp Val Gln Glu Lys Pro Asp His Leu Phe Thr Gly
        35                  40                  45

```
Leu Ile Ala Gly Thr Asn Asn Arg Ala Pro Gly Val Pro Ala Arg Phe
 50                  55                  60
Ser Gly Ser Leu Ile Gly Asp Lys Ala Ala Leu Thr Ile Thr Gly Ala
 65                  70                  75                  80
Gln Thr Glu Asp Glu Ala Ile Tyr Phe Cys Ala Leu Trp Tyr Ser Asn
                 85                  90                  95
His Trp Val Phe Gly Gly Gly Thr Lys Leu Thr Val Leu Gly
                100                 105                 110
```

<210> SEQ ID NO 118
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Gln Val Gln Leu Val Glu Ser Gly Gly Gly Val Val Gln Pro Gly Arg
 1               5                   10                  15
Ser Leu Arg Leu Ser Cys Ala Ala Ser Gly Phe Thr Phe Ser Asn Tyr
                 20                  25                  30
Gly Met His Trp Val Arg Gln Ala Pro Gly Lys Gly Leu Glu Trp Val
             35                  40                  45
Ala Val Ile Trp Tyr Asp Gly Gly Pro Lys Phe Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Ser Tyr Cys Gly Gly Asp Cys Tyr Pro Phe Asp Tyr Trp Gly
                100                 105                 110
Gln Gly Asp Leu Val Thr Val Ser Ser
            115                 120
```

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

```
Gly Phe Thr Phe Ser Asn Tyr Gly Met His
 1               5                   10
```

<210> SEQ ID NO 120
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

```
Val Ile Trp Tyr Asp Gly Gly Pro Lys Phe Tyr Ala Asp Ser Val Lys
 1               5                   10                  15
Gly
```

<210> SEQ ID NO 121

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ser Tyr Cys Gly Gly Asp Cys Tyr Pro Phe Asp Tyr
1               5                   10

<210> SEQ ID NO 122
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Tyr Ser Ala Pro Trp
                85                  90                  95

Thr Phe Gly Gln Gly Thr Lys Val Glu Ile Lys
            100                 105

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gln Lys Tyr Tyr Ser Ala Pro Trp Thr
1               5

<210> SEQ ID NO 124
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Gln Val Gln Leu Val Glu Ser Gly Gly Gly Val Gln Pro Gly Arg
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asp Glu Tyr Tyr Ala Asp Ser Val
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Thr Met Gly Arg Gly Ile Ile Ile Ser Tyr Phe Asp Tyr
            100                 105                 110

Trp Gly Gln Gly Thr Pro Val Thr Val Ser Ser
        115                 120

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Phe Thr Phe Ser Arg Tyr Gly Met His
1               5                   10

<210> SEQ ID NO 126
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Val Ile Trp Tyr Asp Gly Ser Asp Glu Tyr Tyr Ala Asp Ser Val Lys
1               5                   10                  15

Gly

<210> SEQ ID NO 127
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Glu Thr Met Gly Arg Gly Ile Ile Ile Ser Tyr Phe Asp Tyr
1               5                   10

<210> SEQ ID NO 128
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
```

```
                    50                  55                  60
Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Pro
                     85                  90                  95

Thr Phe Gly Gln Gly Thr Lys Leu Glu Ile Lys
                100                 105

<210> SEQ ID NO 129
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Thr Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Ala Lys Phe Gly Val Arg Gly Val Ile Ile Thr Asn Trp Phe Asp Pro
                100                 105                 110

Trp Gly Gln Gly Thr Leu Val Thr Val Ser Ser
            115                 120

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Phe Thr Phe Ser Ser Tyr Ala Met Ser
  1               5                  10

<210> SEQ ID NO 131
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Thr Ile Ser Gly Ser Gly Gly Ser Thr Tyr Tyr Ala Asp Ser Val Lys
  1               5                  10                  15

Gly

<210> SEQ ID NO 132
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Phe Gly Val Arg Gly Val Ile Ile Thr Asn Trp Phe Asp Pro
1               5                   10

<210> SEQ ID NO 133
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Leu Glu Ile Lys
            100                 105

<210> SEQ ID NO 134
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Thr Met Val Arg Gly Arg Tyr Tyr Tyr Gly Met Asp Val Trp
            100                 105                 110

Gly Gln Gly Thr Thr Val Thr Val Ser Ser
            115                 120
```

<210> SEQ ID NO 135
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Gly Ser Ile Ser Ser Ser Asn Trp Trp Ser
1               5                   10

<210> SEQ ID NO 136
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Glu Ile Tyr His Ser Gly Ser Thr Asn Tyr Asn Pro Ser Leu Lys Ser
1               5                   10                  15

<210> SEQ ID NO 137
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Met Val Arg Gly Arg Tyr Tyr Tyr Tyr Gly Met Asp Val
1               5                   10

<210> SEQ ID NO 138
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Tyr Asn Phe Leu Asp Trp Tyr Leu Gln Lys Pro Gly Gln Ser
        35                  40                  45

Pro Gln Phe Leu Ile Tyr Leu Gly Ser Asn Arg Ala Ser Gly Val Pro
    50                  55                  60

Asp Arg Phe Ser Gly Val Gly Ser Gly Thr Asp Phe Thr Leu Gln Ile
65                  70                  75                  80

Ser Arg Val Glu Ala Glu Asp Phe Gly Val Tyr Tyr Cys Met Gln Ala
                85                  90                  95

Leu Gln Ala Pro Trp Thr Phe Gly Gln Gly Thr Lys Leu Glu Ile Lys
            100                 105                 110

<210> SEQ ID NO 139
<211> LENGTH: 16
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 139

Arg Ser Ser Gln Ser Leu Leu His Ser Asp Gly Tyr Asn Phe Leu Asp
1               5                   10                  15

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Met Gln Ala Leu Gln Ala Pro Trp Thr
1               5

<210> SEQ ID NO 141
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Val Thr Leu Thr Ile Ser Ser Leu Gln Ser
65                  70                  75                  80

Glu Asp Phe Ala Val Tyr Tyr Cys Gln Gln Tyr Asn Lys Trp Pro Leu
                85                  90                  95

Thr Phe Gly Gly Gly Thr Lys Leu Glu Ile Lys
            100                 105

<210> SEQ ID NO 142
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Ile Tyr Tyr Cys
                85                  90                  95

Ala Lys Phe Gly Val Arg Gly Val Ile Ile Thr Asn Trp Phe Asp Pro
            100                 105                 110

Trp Gly Gln Gly Thr Leu Val Thr Val Ser Ser
        115                 120

<210> SEQ ID NO 143
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Thr Ile Ser Gly Ser Gly Asp Ser Thr Tyr Tyr Ala Asp Ser Val Lys
1               5                   10                  15

Gly

<210> SEQ ID NO 144
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Ile Tyr Tyr Cys
                85                  90                  95

Ala Lys Phe Gly Val Arg Gly Val Ile Ile Thr Asn Trp Phe Asp Pro
            100                 105                 110

Trp Gly Gln Gly Thr Leu Val Thr Val Ser Ser
        115                 120

<210> SEQ ID NO 145
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Thr Ile Ser Gly Ser Gly Asp Ser Thr Tyr Tyr Ala Asp Ser Val Lys
1               5                   10                  15

Gly

<210> SEQ ID NO 146
```

```
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146
```

| | | | | | | | | | | | | | | | |
|---|---|---|---|---|---|---|---|---|---|---|---|---|---|---|---|
| Glu | Ile | Val | Met | Thr | Gln | Ser | Pro | Ala | Thr | Leu | Ser | Val | Ser | Pro | Gly |
| 1 | | | | 5 | | | | | 10 | | | | | 15 | |
| Glu | Arg | Ala | Thr | Leu | Ser | Cys | Arg | Ala | Ser | Gln | Ser | Val | Ser | Ser | Asn |
| | | | 20 | | | | | 25 | | | | | 30 | | |
| Leu | Ala | Trp | Tyr | Gln | Gln | Lys | Pro | Gly | Gln | Val | Pro | Arg | Leu | Leu | Ile |
| | | | 35 | | | | | 40 | | | | | 45 | | |
| Tyr | Gly | Ala | Ser | Thr | Arg | Ala | Thr | Gly | Ile | Pro | Ala | Arg | Phe | Ser | Gly |
| | 50 | | | | | 55 | | | | | 60 | | | | |
| Ser | Gly | Ser | Gly | Thr | Glu | Phe | Thr | Leu | Thr | Ile | Ser | Ser | Leu | Gln | Ser |
| 65 | | | | | 70 | | | | | 75 | | | | | 80 |
| Glu | Asp | Phe | Ala | Val | Tyr | Tyr | Cys | Gln | Gln | Tyr | Asn | Asn | Trp | Pro | Leu |
| | | | | 85 | | | | | 90 | | | | | 95 | |
| Thr | Phe | Gly | Gly | Gly | Thr | Lys | Val | Glu | Ile | Lys | | | | | |
| | | | 100 | | | | | 105 | | | | | | | |

```
<210> SEQ ID NO 147
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147
```

| | | | | | | | | | | | | | | | |
|---|---|---|---|---|---|---|---|---|---|---|---|---|---|---|---|
| Gln | Val | Gln | Leu | Gln | Gln | Ser | Gly | Pro | Gly | Leu | Val | Lys | Pro | Ser | Gln |
| 1 | | | | 5 | | | | | 10 | | | | | 15 | |
| Thr | Leu | Ser | Leu | Thr | Cys | Ala | Ile | Ser | Gly | Asp | Ser | Val | Ser | Asn | Asn |
| | | | 20 | | | | | 25 | | | | | 30 | | |
| Ser | Ala | Thr | Trp | Asn | Trp | Ile | Arg | Gln | Ser | Pro | Ser | Arg | Gly | Leu | Glu |
| | | | 35 | | | | | 40 | | | | | 45 | | |
| Trp | Leu | Gly | Arg | Thr | Tyr | Tyr | Arg | Ser | Lys | Trp | Tyr | Asn | Asp | Tyr | Pro |
| | 50 | | | | | 55 | | | | | 60 | | | | |
| Val | Ser | Val | Lys | Ser | Arg | Ile | Ser | Ile | Asn | Pro | Asp | Thr | Ser | Lys | Asn |
| 65 | | | | | 70 | | | | | 75 | | | | | 80 |
| Gln | Val | Ser | Leu | Gln | Leu | Asn | Pro | Val | Thr | Pro | Glu | Asp | Thr | Ala | Val |
| | | | | 85 | | | | | 90 | | | | | 95 | |
| Tyr | Tyr | Cys | Ala | Arg | Glu | Gln | Gly | Tyr | Ser | Ser | Ser | Arg | Tyr | Tyr | Tyr |
| | | | 100 | | | | | 105 | | | | | 110 | | |
| Tyr | Tyr | Gly | Met | Asp | Val | Trp | Gly | Gln | Gly | Thr | Thr | Val | Thr | Val | Ser |
| | | | 115 | | | | | 120 | | | | | 125 | | |
| Ser | | | | | | | | | | | | | | | |

```
<210> SEQ ID NO 148
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Asp Ser Val Ser Asn Asn Ser Ala Thr Trp Asn
```

<210> SEQ ID NO 149
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Pro
                85                  90                  95

Leu Gln Thr Pro Tyr Thr Phe Gly Gln Gly Thr Lys Leu Glu Ile Lys
            100                 105                 110

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Met Gln Pro Leu Gln Thr Pro Tyr Thr
1               5

<210> SEQ ID NO 151
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Phe Asp Gly Ser Lys Lys Tyr Tyr Ala Asp Ser Val
    50                  55                  60

Lys Gly Arg Val Thr Ile Ser Arg Asp Asn Ser Arg Asn Thr Leu Phe
65                  70                  75                  80

Leu Gln Met Asn Ser Leu Arg Ala Glu Asp Thr Ala Val Tyr Tyr Cys
                85                  90                  95

Ala Arg Glu Asp Tyr Phe Gly Ser Gly Thr Tyr Ser Thr Asp Ala Phe
            100                 105                 110

```
Asp Ile Trp Gly Gln Gly Thr Met Val Thr Val Ser Ser
        115                 120                 125

<210> SEQ ID NO 152
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Val Ile Trp Phe Asp Gly Ser Lys Lys Tyr Tyr Ala Asp Ser Val Lys
1               5                   10                  15

Gly

<210> SEQ ID NO 153
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Glu Asp Tyr Phe Gly Ser Gly Thr Tyr Ser Thr Asp Ala Phe Asp Ile
1               5                   10                  15

<210> SEQ ID NO 154
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu His Ser Gly Val Pro Ser Arg Phe Ser Gly
    50                  55                  60

Ser Gly Ser Gly Thr Glu Phe Thr Leu Thr Ile Arg Ser Leu Gln Pro
65                  70                  75                  80

Glu Asp Phe Ala Thr Tyr Tyr Cys Gln Gln Leu Asn Ser Tyr Pro Leu
                85                  90                  95

Phe Ala Phe Gly Pro Gly Thr Lys Val Asp Ile Lys
            100                 105

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ala Ala Ser Thr Leu His Ser
1               5
```

<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gln Gln Leu Asn Ser Tyr Pro Leu Phe Ala
1               5                   10

<210> SEQ ID NO 157
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Gln Val Gln Leu Val Glu Ser Gly Gly Gly Val Val Gln Pro Gly Arg
1               5                   10                  15

Ser Leu Arg Leu Ser Cys Ala Ala Ser Gly Leu Thr Phe Ser Arg Tyr
            20                  25                  30

Ala Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Leu Trp Phe Gly Gly Met Asp Val Trp Gly Gln
            100                 105                 110

Gly Thr Thr Val Thr Val Ser Ser
        115                 120

<210> SEQ ID NO 158
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Leu Thr Phe Ser Arg Tyr Ala Met His
1               5                   10

<210> SEQ ID NO 159
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Asp Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser

```
                    20                  25                  30

Asn Gly Tyr Asn Tyr Leu His Trp Tyr Leu Gln Lys Pro Gly Gln Ser
                35                  40                  45

Pro Gln Leu Leu Ile Tyr Leu Gly Ser Asn Arg Ala Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 160
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Gln Val Gln Leu Gln Glu Ser Gly Pro Gly Leu Val Lys Pro Ser Glu
1               5                   10                  15

Thr Leu Ser Leu Thr Cys Ala Val Ser Asp Tyr Ser Ile Ser Ser Gly
                20                  25                  30

Tyr Tyr Trp Gly Trp Ile Arg Gln Pro Pro Gly Lys Gly Leu Glu Trp
            35                  40                  45

Ile Gly Ser Ile Tyr His Ser Gly Ser Thr Tyr Tyr Asn Pro Ser Leu
        50                  55                  60

Lys Ser Arg Val Thr Ile Ser Val Asp Met Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Arg Asp Ser Val Ser Trp Asn Gly Gly Arg Asp Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 161
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Asp Tyr Ser Ile Ser Ser Gly Tyr Tyr Trp Gly
1               5                   10

<210> SEQ ID NO 162
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162
```

Asp Arg Asp Ser Val Ser Trp Asn Gly Gly Arg Asp Tyr Tyr Tyr Tyr
1               5                   10                  15

Gly Met Asp Val
            20

<210> SEQ ID NO 163
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Thr Pro Tyr
                85                  90                  95

Thr Phe Gly Gln Gly Thr Lys Val Glu Ile Lys
            100                 105

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gln Gln Ser Phe Ser Thr Pro Tyr Thr
1               5

<210> SEQ ID NO 165
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 165
caggtgcagc tggtggagtc tgggggaggc gtggtccagc ctggagggtc cctgagactc      60
tcctgtgcag cgtctggatt caccttcact agctatggca tgcactgggt ccgccaggct     120
ccaggcaagg ggctggagtg ggtggcagtt gtatggtatg agggaaatag taaattctat     180
atagactccg tgaagggccg attcatcatc tccagagaca attccaagaa cacgctatat     240
cttcaaatga acagcctgag agccgaggac acggctgtgt attactgtgc gagagcatat     300
tgtggtgatg actgctatcc ctttgactac tggggccagg gaaccctggt caccgtctcc     360
tca                                                                    363

<210> SEQ ID NO 166

<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 166

| gacatccaga tgacccagtc tccatcctcc ctgtctgcat ctgtaggaga cagagtcacc | 60 |
| atcacttgcc gggcgagtca gggcattagc aattatttag cctggtatca gcagaaacca | 120 |
| ggtaaagttc ctaagctcct gatctatgct gcatccactt tgcaatcagg ggtcccatct | 180 |
| cggttcagtg gcagtggatc tgggacagat ttcactctca ccatcagcag cctgcagcct | 240 |
| gaagatgttg caacttatta ctgtcaaaag tataacagtg ccccgtggac gttcggccaa | 300 |
| gggaccaagc tggagatcaa a | 321 |

<210> SEQ ID NO 167
<211> LENGTH: 372
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 167

| caggtgcagc tgcaggagtc gggcccagga ctggtgaagc cttcggagac cctgtccctc | 60 |
| acctgcgctg tctctggtta ctccatcagc agtggttact ctggggctg atccggcag | 120 |
| cccccaggga aaaaactgga gtggattggg agtatctatc atagtgggag cacctactac | 180 |
| aacccgtccc tcaagagtcg agtcaccatg tcagtagaca cgtccaagaa ccagttctcc | 240 |
| ctgaagctga gctctgtgac cgccgcagac acggccgtgt attactgtgc gagagagggg | 300 |
| gattgtagtg gtggtatctg ctactggtac ttcgatctct ggggccgtgg caccctggtc | 360 |
| accgtctcct ca | 372 |

<210> SEQ ID NO 168
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 168

| gaaatagtga tgacgcagtc tccagccacc ctgtctgtgt ctccagggga aagagccacc | 60 |
| ctctcctgca gggccagtca gagtgttagc agcaacttag cctggtacca gcagaaacct | 120 |
| ggccaggctc ccaggctcct catctatggt gcatccacca gggccactgg tatcccagcc | 180 |
| aggttcagtg gcagtgggtc tgggacagag gtcactctca ccatcagcag cctgcagtct | 240 |
| gaagattttg cagtttatta ctgtcagcag tataataagt ggccgctcac tttcggcgga | 300 |
| gggaccaagg tggagatcaa a | 321 |

<210> SEQ ID NO 169
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 169

```
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggaatg ggtggcagtt atatggtata tggaattaa taaatactat     180 gcagactccg tgaagggccg attcaccatc tccagagacg cttccaagaa cacgctgtat     240
ctgcaaatga acagcctgag agccgaggac acggctgtgt attactgtgc gagagaggga     300
ttactatggt tcggaggtat ggacgtctgg ggccaaggga ccacggtcac cgtctcctca     360
```

<210> SEQ ID NO 170
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 170

```
gaaattgtgc tgactcagtc tccactctcc ctgcccgtca cccctggaga gccggcctcc      60
atctcctgca ggtctagtca gagcctcctg catagtaatg gatacaacta tttgcattgg     120
tacctgcaga agccagggca gtctccacag ctcctgatct atttgggttc taatcgggcc     180
tccggggtcc ctgacaggtt cagtggcagt agatcaggca cagatttac actgaaaatc     240 atcagagtgg aggctgagga tgttggggtt tattactgca tgcaagctct acaaactccg     300
tacacttttg gccaggggac caagctggag atcaaa                                336
```

<210> SEQ ID NO 171
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 171

```
caggtgctac tggtggaatc tgggggaggc gtggtccagc ctgggaggtc cctgagactc      60
tcctgtgcag cgtctggatt caccttcaaa agatatggca tgcactgggt ccgccaggct     120
ccaggcaggg ggctggagtg ggtggcagtt atatggtctg atggaaataa aaacactat     180 gcagactccg tgaagggccg attcaccatc tccagagaca attccaagaa cacgctgtat     240
ctgcaaatga acagcctgag agccgaggac acggctgtgt attactgtgc gagagaaaac     300
tatggttcgg ggagttatta taacggcggt atggacgtct ggggccaagg gaccacggtc     360
accgtctcct ca                                                          372
```

<210> SEQ ID NO 172
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 172

```
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
```

```
gatgattttg caacttatta ctgccaacag tataatagtt attcgtggac gttcggccaa    300
gggaccaagc tggagatcaa a                                              321

<210> SEQ ID NO 173
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 173
caggtgcagc tggtggagtc tgggggaggc gtggtccagc ctgggaggtc cctgagactc     60
tcctgtgcag cgtctggatt caccttcagt agctatggca tgcactgggt ccgccaggct    120
ccaggcaagg ggctggagtg ggtggcagtt atatggtatg atggaagtga taaatactat    180
acagactccg tgaagggccg attcaccatc tccagagaca attccaagaa cacgctgtat    240
ctgcaaatga acagcctgag agccgaggac acggctgttt attactgtgc gagagaaagt    300
atggttcggg gaattgttat aacgttcttt gactactggg gccagggaac cctggtcacc    360
gtctcctca                                                            369

<210> SEQ ID NO 174
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 174
gaaatagtga tgacgcagtc tccagccacc ctgtctgtgt ctccagggga aagagccacc     60
ctctcctgca gggccagtca gagtgttagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttattc ctgtcagcac tataataact ggcctcctac tttcggcgga    300
gggaccaagg tggagatcaa a                                              321

<210> SEQ ID NO 175
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 175
caggtgcagc tggtggagtc tgggggaggc gtggtccagc ctgggaggtc cctgagactc     60
tcctgtgcag cgtctggatt caccttcagt agctatggca tgcactgggt ccgccaggct    120
ccaggcaagg ggctggagtg ggtggcagtt atatggtatg atggaagtga taaatactat    180
gcagactccg tgaagggccg attcaccatc tccagagaca attccaagaa aacgctgtat    240
ctgcaaatga acagcctgag agccgaggac acggctgtgt atttctgtgc gagagagact    300
atttttcggg gacttactat aacgttcttt gaccactggg gccagggaac cctggtcacc    360
gtctcctca                                                            369
```

<210> SEQ ID NO 176
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 176

```
gaaatagtga tgacgcagtc tccagccacc ctgtctgtgt ctccagggga aagagccacc      60
ctctcctgca gggccagtca gagtgttagc agcaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcag tataataact ggcctcctac tttcggcgga     300
gggaccaagc tggagatcaa a                                                321
```

<210> SEQ ID NO 177
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 177

```
caggtgcagc tggtggagtc tggggggaggc gtggtccagc ctgggaggtc cctgagactc     60
tcctgtgcag cgtctggatt caccttcagt gactatggca tgcactgggt ccgccaggct    120
ccaggcaagg ggctggagtg ggtggcagtt atatggtatg aaggtggtaa taaatactat    180
acagactccg tgaagggccg attcaccatc tccagagaca attccaagaa cacgctgtat    240
ctgcaaatga acagcctgag agccgaggac acggctgtgt attactgtgc gaggatatta    300
ctgtggttcg gggagtccta cggtatggac gtctggggcc aagggaccac ggtcaccgtc    360
tcctca                                                                366
```

<210> SEQ ID NO 178
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 178

```
gacatccaga tgacccagtc tccatcctcc ctgtctgcat ctgtaggaga cagagtcacc      60
atcacttgcc gggcgagtca gggcattagc aattatttgg cctggtatca gcagaaacca    120
gggaaagttc ctaagctcct gatctatgct gcatccactt gcaatcagg ggtcccatct     180
cggttcagtg gcagtggatc tgggacagat ttcactctca ccatcagcag cctgcagcct    240
gaagatgttg caacttatta ctgtcaaaag tataacaatg ccccgtggac gttcggccaa    300
gggaccaagg tggagatcaa a                                                321
```

<210> SEQ ID NO 179
<211> LENGTH: 393
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 179

```
caggtgcagc tggtggagtc tgggggaggc gtggtccagc ctgggaggtc cctgagactc    60
tcctgtgcag cgtctggatt caccttcaga agctatggca tgcactgggt ccgccaggct   120
ccaggcaagg ggctggagtg ggtggcagtt atatggtatg atggaagtat taaatactat   180
gcagactccg tgaagggccg attcaccatc tccagagaca attccaagaa cacgctgtat   240
gtgcaaatga acagcctgag agccgaggac acggctgtgt attactgtgc gagagatagg   300
gattactttg gttcggggta ttattctaac gtacggtact actactacgg tatggacgtc   360
tggggccaag ggaccacggt caccgtctcc tca                                393
```

<210> SEQ ID NO 180
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaaggcc ccaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta cccctccgct cactttcggc   300
ggagggacca aggtggagat caaa                                          324
```

<210> SEQ ID NO 181
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 181

```
caggtacagc tgcagcagtc aggtccagga ctggtgaagc cctcgcagac cctctcactc    60
acctgtgcca tctccgggga cagtgtctct agcaacagtg ctgcttggaa ctggatcagg   120
cagtccccat cgagaggcct tgagtggctg ggaaggacat actacaggtc caagtggtat   180
aatgattatc cagtatctgt gaaaagtcga ataaccatca cccagacac atccaagaac    240 caggtctccc tgcagctgaa ccctgtgact cccgaggaca cggctgtgta ttactgtaca   300
agagaacaag ggtatagcag cagcaggtac tactactact acggtatgga cgtctgggc    360 caagggacca cggtcaccgt ctcctca                                       387
```

<210> SEQ ID NO 182
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 182

```
gatattgtga tgactcagtc tccactctcc ctgcccgtca cccctggaga gccggcctcc    60
atctcctgca ggtctagtca gagcctcctg catattaatg gatacaacta tttggattgg   120
```

| | |
|---|---|
| tacctgcaga agccagggca gtctccacag ctcctgatct atttgggttc taatcgggcc | 180 |
| tccggggtcc ctgacaggtt cagtggcagt ggatcaggca cagattttac actgaaaatc | 240 |
| agcagagtgg aggctgagga tgttggggtt tattactgca tgcaagctct acaaactccg | 300 |
| tacactttg gccaggggac caaggtggag atcaaa | 336 |

<210> SEQ ID NO 183
<211> LENGTH: 387
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 183

| | |
|---|---|
| caggtacagc tgcagcagtc aggtccagga ctggtgaagc cctcgcagac cctctcactc | 60 |
| acctgtgcca tctccgggga cagtgtctct agcaacagtg ctgcttggaa ctggatcagg | 120 |
| cagtccccat cgagaggcct tgagtggctg ggaaggacat actacaggtc ccagtggtat | 180 |
| aatgattatc cagtatctgt gaaaagtcga ataaccatca cccagacac atccaagaac | 240 |
| caggtctccc tgcagctgaa ccctgtgact cccgaggaca cggctgtgta ttactgtgca | 300 |
| agagaacaag ggtatagcag cagcaggtac tactactact acggtatgga cgtctggggc | 360 |
| caagggacca cggtcaccgt ctcctca | 387 |

<210> SEQ ID NO 184
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 184

| | |
|---|---|
| gatattgtga tgactcagtc tccactctcc ctgcccgtca cccctggaga gccggcctcc | 60 |
| atctcctgca ggtctagtca gagcctcctg catagtaatg gatacaacta tttggattgg | 120 |
| tacctgcaga agccagggca gtctccacag ctcctgatct atttgggttc taatcgggcc | 180 |
| tccggggtcc ctgacaggtt cagtggcagt ggatcaggca cagattttac actgaaaatc | 240 |
| agcagagtgg aggctgagga tgttggggtt tattactgca tgcaagctct acaaactccg | 300 |
| tacactttg gccaggggac caaggtggag atcaaa | 336 |

<210> SEQ ID NO 185
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 185

| | |
|---|---|
| caggtgcagc tggtggagtc tgggggaggc gtggtccagc ctggaaggtc cctgagactc | 60 |
| tcctgtgcag cgtctggatt caccttcact acctatggca tgcactgggt ccgccaggct | 120 |
| ccaggcaagg ggctggagtg gtggcagtt gtttggtttg agggaaatag taaattctat | 180 |
| atagactccg tgaagggccg cttcatcatc tcccgagaca attccaagaa cacgctattt | 240 |
| cttcaaatga acagcctgag agccgaggac acggctgtgt attactgtgc gagagcaaat | 300 |
| tgtggtgctg actgctatcc ctttgactac tggggccagg gaaccctggt caccgtctcc | 360 | tca                                                                  363

<210> SEQ ID NO 186
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 186
gacatccaga tgacccagtc tccatcctcc ctgtctgcat ctgtaggaga cagagtcacc    60
atcacttgcc gggcgagtca gggcattagc aattatttag cctggtatca gcagaaacca   120
ggtaaagttc ctaagctcct gatctatgct gcatccactt tgcaatcagg ggtcccatct   180
cggttcagtg gcagtggatc tgggacagat ttcagtctaa ccatcagcag cctgcggcct   240
gaagatgttg caacttatta ctgtcaaaag tataacagtg ccccgtggac gttcggccaa   300
gggaccaagg tggagatcaa a                                             321

<210> SEQ ID NO 187
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 187
caggtgcagc tggtggagtc tgggggaggc gtggtccagc ctgggaggtc cctgagactc    60
tcctgtgcag cgtctggatt caccttcaga agttatggca tgcactgggt ccgccaggct   120
ccaggcaagg gactggagtg ggtggcactt atttggtatg atggaggtga tcaatactat   180
gcagactccg tgaagggccg attcaccatc tccagagaca gttccaagag cacgctatat   240
ctgcaaatga acagcctgag agccgaggac acggctgtgt attattgtgc gagagcacag   300
tgtggtgatg actgctaccc ctttgactac tggggccagg gaaccctggt caccgtctcc   360
tca                                                                 363

<210> SEQ ID NO 188
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 188
gacatccaga tgacccagtc tccatcctcc ctgtctgcat ctgtgggaga cagagtcacc    60
atcacttgcc gggcgagtca gggcatttac aattatttag cctggtatca gcagaaacca   120
gggaaagttc ctaagctcct gatctatgct gcatccactt tgcaatcagg ggtcccatct   180
cggttcagtg gcagtggatc tgggacagat ttcactctca ccatcagcag cctgcagcct   240
gaagatgttg caacttatta ctgtcaaaag tataacagtg acccgtggac gttcggccaa   300
gggaccaagc tggagatcaa a                                             321

<210> SEQ ID NO 189
<211> LENGTH: 363
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 189

```
caggtgcagc tggtggagtc tggggggaggc gtggtccagc ctggaggtc cctgagactc    60 tcctgtgcag cgtctggatt caccttcact agctatggca tgcactgggt ccgccaggct   120
ccaggcaagg ggctggagtg ggtggcagtt gtatggtatg agggaagtag taaattctat   180
gtggactccg tgaagggccg attcatcatc tccagagaca attccaagaa cacactgtat   240
cttcaaatga acagcctgag agccgaggac acggctgtgt attactgtgc gagagcatat   300
tgtggtggtg actgctatcc ctttgactac tggggccagg gaaccctggt caccgtctcc   360
tca                                                                 363
```

<210> SEQ ID NO 190
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 190

```
gacatccaga tgacccagtc tccatcctcc ctgtctgcat ctgtaggaga cagagtcacc    60
atcacttgcc gggcgagtca gggcattagc aattatttag cctggtatca gcagaaacca   120
gggaaagttc ctaagctcct gatctatgct gcatccactt tgcaatcagg ggtcccatct   180
cggttcagtg gcagtggatc tgggacagat ttcactctca ccatcagcag cctgcagcct   240
gaagatgttg caacttatta ctgtcaaaaa tataacagtg ccccgtggac gttcggccaa   300
gggaccaagg tggagatcaa a                                             321
```

<210> SEQ ID NO 191
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 191

```
caggtgcagc tggtggagtc tggggggaggc gtggtccagc ctggaggtc cctgagactc    60 tcctgtgcag cgtctggatt caccttcagt atctatggca tgcactgggt ccgccaggct   120
ccaggcatgg ggctagagtg ggtggctatt atacggtatg atggaagtaa taaatactat   180
gcggactccg tgaagggccg attcaccatc tccagagaca attccaagaa cacgctgtat   240
ctgcaaatga acagcctgag agccgaggac acggctgtgt attactgtgc gagagacccg   300
tttaccagca gccttgacta ctggggccag ggaaccctgg tcaccgtctc ctca         354
```

<210> SEQ ID NO 192
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 192

```
gacatccagt tgacccagtc tccatccttc ctgtctgcat ctgtaggaga cagagtcacc    60
atcacttgcc gggccagtca gggcattagc agttatttag cctggtatca gcaaaaacca   120
```

```
gggaaagccc ctaagctcct gatctatgct gcatccactt tgcaaagtgg ggtcccatca      180
aggttcagcg gcagtggatc tgggacagaa ttcactctca caatcagcag cctgcagcct      240
gaagattttg caacttatta ctgtcaacag cttaatagtt accctctcac tttcggcgga      300
gggaccaagc tggagatcaa a                                                321

<210> SEQ ID NO 193
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 193
caggtgcagc tggtggagtc tgggggaggc gtggtccagc ctgggaggtc cctgagactc      60
tcctgtgcaa cgtctggatt caccttcagt atctatggca tgcactgggt ccgccaggct      120
ccaggcaagg ggctggagtg ggtggctatt atatggtatg atggaaataa gaatactat      180 gcggactccg tgaagggccg attcaccatc tccagagaca attccaagaa tacgttgtat      240
ctgcaaatga acagcctgag agccgaggac acggctgtgt attactgtgc gagagacccg      300
tataccagca gccttgacta ctggggccag ggaaccctgg tcaccgtctc ctca           354

<210> SEQ ID NO 194
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 194
gacatccagt tgacccagtc tccatccttc ctgtctgcat ctgtaggaga cagagtcacc      60
atcacttgcc gggccagtca gggcattagc agttatttag cctggtatca gcaaaaacca      120
gggaaagccc ctaagctcct gatctatgct gcatccactt tgcaaagtgg ggtcccatca      180
aggttcagcg gcagtggatc tgggacagaa ttcactctca caatcagcag cctgcagcct      240
gaagattttg caacttatta ctgtcaacag cttaatagtt accctctcac tttcggcgga      300
gggaccaagc tggagatcaa a                                                321

<210> SEQ ID NO 195
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 195
caggtgcagc tggtggagtc tgggggaggc gtggtccagc ctgggaggtc cctgagactc      60
tcctgtgcag cgtctggatt caccttcagt atctatggca tgcactgggt ccgccaggct      120
ccaggcaagg ggctggagtg ggtggctaat atatggtatg atggaagtaa aaaatactat      180
gcggactccg tgaagggccg attcaccatc tccagagaca attccaagaa cacgctgtat      240
ctgcaaatga acagcctgag agccgaggac acgtctgtgt attactgtgc gagagacccg      300
tataccagca gccttgacta ctggggccag ggaaccctgg tcaccgtctc ctca           354
```

```
<210> SEQ ID NO 196
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 196
gacatccagt tgacccagtc tccatccttc ctgtctgcat ctgtaggaga cagagtcacc     60
atcacttgcc gggccagtca gggcattagc agttatttag cctggtatca gcaaaaacca    120
gggaaagccc ctaagctcct gatctatact gcatccactt tgcaaagtgg ggtcccatca    180
aggttcagcg gcagtggatc tgggacagaa ttcactctca caatcagcag cctgcagcct    240
gaagattttg caacttatta ctgtcaacag cttaatagtt accctctcac tttcggcgga    300
gggaccaagc tggagatcaa a                                              321

<210> SEQ ID NO 197
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 197
caggtgcaac tggtggagtc tgggggaggc gtggtccagc ctgggaggtc cctgagactc     60
tcctgtgcag cgtctggatt caccttcagt atctatggca tgcactgggt ccgccaggct    120
ccaggcaagg ggctggagtg ggtggctatt atatggtatg atggaagtga taaatactat    180
gcggactccg tgaagggccg attcaccatc tccagagaca attccaagaa cacgctgtat    240
ctgcaaatga acagcctgag agccgaggac acggctgttt attactgtgc gagagacccg    300
tataccacca gccttgacta ctggggccag ggaaccctgg tcaccgtctc ctca          354

<210> SEQ ID NO 198
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 198
gacatccagt tgacccagtc tccatccttc ctgtctgcat ctgtaggaga cagagtcacc     60
atcacttgcc gggccagtca gggcattagc agttatttag cctggtatca gcaaaaacca    120
gggaaagccc ctaagctcct gatctatgct gcatccactt tgcaaagtgg ggtcccatca    180
aggttcagcg gcagtggatc tgggacagaa ttcactctca caatcagcag cctgcagcct    240
gaagattttg caacttatta ctgtcaacag cttaatagtt accctctcac tttcggcgga    300
gggaccaagg tggagatcaa a                                              321

<210> SEQ ID NO 199
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 199
```

```
caggtgcagc tggtggagtc tgggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtt atatggtatg atggcagtaa taaatactat   180
gccgactccg tgaagggccg attcaccctc tccagagaca attccaagaa cacgctgtat   240
ctgcaaatga acagcctgag agccgaggac acggctgtgt attactgtgc gagagatagt   300
acgggcagca gctggtctta ctactactac tacggtatgg acgtctgggg ccaagggacc   360
acggtcaccg tctcctca                                                 378
```

<210> SEQ ID NO 200
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 200

```
gacgctgttg tgactcagga atctgcactc accacatcac ctggtgaaac agtcacactc    60
acttgtcgct caagtactgg ggctgttaca actagtaact atgccaactg ggtccaagaa   120
aaaccagatc atttattcac tggtctaata ggtggtacca caaccgagc tccaggtgtt    180 cctgccagat tctcaggctc cctgattgga gacaaggctg ccctcaccat cacaggggca   240
cagactgagg atgaggcaat atatttctgt gctctatggt acagcaacca tttggtgttc   300
ggtggaggaa ccaaactgac tgtcctaggc                                    330
```

<210> SEQ ID NO 201
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 201

```
caggtgcagc tgcaggagtc gggcccagga ctggtgaagc cttcggagac cctgtccctc    60
acctgcgctg tctctggtta ctccatcagc agtggttact ctggggctg gatccggcag    120 cccccaggga aaaaactgga gtggattggg agtatctatc atagtgggag cacctactac   180
aacccgtccc tcaagagtcg agtcaccatg tcagtagaca cgtccaagaa ccagttctcc   240
ctgaagctga gctctgtgac cgccgcagac acggccgtgt attactgtgc gagagagggg   300
gattgtagtg gtggtatctg ctactggtac ttcgatctct ggggccgtgg caccctggtc   360
accgtctcct ca                                                       372
```

<210> SEQ ID NO 202
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 202

```
gacatccaga tgacccagtc tccatcctcc ctgtctgcat ctgtaggaga cagagtcacc    60
atcacttgcc gggcgagtca gggcattagc aattatttag cctggtatca gcagaaacca   120
gggaaagttc ctaagctcct gatctatgct gcatccactt tgcaatcagg ggtcccatct   180
```

```
cggttcagtg gcagtggatc tgggacagat tcactctca ccatcagcag cctgcagcct    240
gaagattttg cagtttatta ctgtcagcag tataataagt ggccgctcac tttcggcgga    300
gggaccaagc tggagatcaa a                                              321

<210> SEQ ID NO 203
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203
caggtgcagc tgcaggagtc gggcccagga ctggtgaagc cttcggagac cctgtccctc     60
acctgcgctg tctctggtta ctccatcagc agtggttact ctggggctg gatccggcag    120 cccccaggga aaaaactgga gtggattggg agtatctatc atagtgggag cacctactac    180
aacccgtccc tcaagagtcg agtcaccatg tcagtagaca cgtccaagaa ccagttctcc    240
ctgaagctga gctctgtgac cgccgcagac acggccgtgt attactgtgc gagagagggg    300
gattgtagtg gtggtatctg ctactggtac ttcgatctct ggggccgtgg caccctggtc    360
accgtctcct ca                                                        372

<210> SEQ ID NO 204
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 204
gacatccaga tgacccagtc tccatcctcc ctgtctgcat ctgtaggaga cagagtcacc     60
atcacttgcc gggcgagtca gggcattagc aattatttag cctggtatca gcagaaacca    120
gggaaagttc ctaagctcct gatctatgct gcatccactt tgcaatcagg ggtcccatct    180
cggttcagtg gcagtggatc tgggacagag gtcactctca ccatcagcag cctgcagtct    240
gaagattttg cagtttatta ctgtcagcag tataataagt ggccgctcac tttcggcgga    300
gggaccaagc tggagatcaa a                                              321

<210> SEQ ID NO 205
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 205
caggtgcagc tggtggagtc tgggggaggc ggggtccagc ctgggaggtc cctgcgactc     60
tcctgtgcag cgtctggttt caccttcagt agatatggca tgcactgggt ccgccaggct    120
ccaggcaagg ggctggagtg ggtggcagtt atatggtatg atggaagtga tgaatactat    180
gcagactccg tgaagggccg attcaccatc tccagagaca attccaagaa cacgctgtat    240
ctgcaaatga acagcctgag agccgaggac acggctgtgt attactgtgc gagagagact    300
atgggtcggg gaattattat atcctacttt gactactggg gccagggaac cccggtcacc    360
gtctcctca                                                            369
```

<210> SEQ ID NO 206
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 206

| gaaatagtga tgacgcagtc tccagccacc ctgtctgtgt ctccagggga aagagccacc | 60 |
| ctctcctgca gggccagtca gagtgttagc agcaacttag cctggtacca gcagaaacct | 120 |
| ggccaggctc ccaggctcct catctatggt gcatccacca gggccactgg tatcccagcc | 180 |
| aggttcagtg gcagtgggtc tgggacagag ttcactctca ccatcagcag cctgcagtct | 240 |
| gaagattttg cagtttatta ctgtcagcag tataataact ggcctccgac gttcggccaa | 300 |
| gggaccaagc tggagatcaa a | 321 |

<210> SEQ ID NO 207
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 207

| gaggtgcagc tgttggagtc tgggggaggc ttggtacagc ctggggggtc cctgagactc | 60 |
| tcctgtgcag cctctggatt cacctttagc agctatgcca tgagctgggt ccgccaggct | 120 |
| ccagggaagg ggctggagtg ggtctcaact attagtggta gtggtggtag cacatactac | 180 |
| gcagactccg tgaagggccg gttcaccatc tccagagaca attccaagaa cacgctgtat | 240 |
| ctgcaaatga acagcctgag agccgaggac acggccatat attactgtgc gaagtttggg | 300 |
| gttcggggag ttattataac aaactggttc gacccctggg gccagggaac cctggtcacc | 360 |
| gtctcctca | 369 |

<210> SEQ ID NO 208
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 208

| gaaatagtga tgacgcagtc tccagccacc ctgtctgtgt ctccagggga aagagccacc | 60 |
| ctctcctgca gggccagtca gagtgttagc agcaacttag cctggtacca gcagaaacct | 120 |
| ggccaggctc ccaggctcct catctatggt gcatccacca gggccactgg tatcccagcc | 180 |
| aggttcagtg gcagtgggtc tgggacagag ttcactctca ccatcagcag cctgcagtct | 240 |
| gaagattttg cagtttatta ctgtcagcag tataataact ggcctctcac tttcggcgga | 300 |
| gggaccaagc tggagatcaa a | 321 |

<210> SEQ ID NO 209
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 209

```
gaggtgcaac tggtggagtc tgggggaggc ttggtaaagc ctgggggtc ccttagactc      60 tcctgtgcag cctctggatt cactttcagt tacgcctgga tgagctgggt ccgccaggct     120
ccagggaagg ggctggagtg ggttggccgt attaaaagca aaactgatgg tgggacaaca     180
gactacgctg cacccgtgaa aggcagattc accatctcaa gagatgattc aaaaaacacg     240
ctgtatctgc aactgaacag cctgaaaatc gaggacacag ccgtgtatta ctgtaccaca     300
ggtcgtatag cagcggctgg gtttgactac tgggcccagg gaaccctggt caccgtctcc     360
tca                                                                   363
```

<210> SEQ ID NO 210
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 210

```
gacgctgttg tgactcagga atctgcactc accacatcac ctggtgaaac agtcacactc      60
acttgtcgct caagtactgg gactgttaca actagtaact atgccaactg ggtccaagaa     120
aaaccagatc atttattcac tggtctaata gctggtacca caaccgagc tccaggtgtt     180 cctgccagat tctcaggctc cctgattgga gacaaggctg tcctcaccat cacagggggca     240 cagactgagg atgaggcaat atatttctgt gctctatggt acagcaacca ttgggtgttc     300
ggtggaggaa ccaaactgac tgtcctaggc                                       330
```

<210> SEQ ID NO 211
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 211

```
gaggtgcaac tggtggaatc tgggggaggc ttggtaaagc ctgggggtc ccttagactc       60 tcctgtgcag cctctggatt cgttttcagt tacgcctgga tgaactgggt ccgccaggct     120
ccagggaagg ggctggagtg ggttggccgt attaaaagca aaactgaagg tgggacaaca     180
gacaacgctg ctcccgtgaa aggcagattc accatctcaa gagaagactc aaaaaacacg     240
ctgtatttgc aattgaacag cctgaaaatc gaggacacag ccgtgtatta ttgtaccaca     300
ggtcgtatag cagcagctgg gtttgactac tggggccagg gaaccctggt caccgtctcc     360
tca                                                                   363
```

<210> SEQ ID NO 212
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 212

```
gacgctgttg tgactcagga atctgcactc accacatcac ctggtgaaac agtcacactc      60
acttgtcgct caagtactgg gactgttaca actagtaact atgccaactg ggtccaagaa     120
```

```
aaaccagatc atttattcac tggtctaata gctggtacca acaaccgagc tccaggtgtt    180
cctgccagat tctcaggctc cctgattgga gacaaggctg ccctcaccat cacagggca     240 cagactgagg atgaggcaat atatttctgt gctctatggt acagcaacca ttgggtgttc    300
ggtggaggaa ccaaactgac tgtcctaggc                                     330
```

<210> SEQ ID NO 213
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 213

```
caggtgcagc tgcaggagtc gggcccagga ctggtgaagc cttcggggac cctgtccctc    60
acctgcgctg tctctggtgg ctccatcagc agtagtaact ggtggagttg ggtccgccag    120
cccccaggga aggggctgga gtggattggg gaaatctatc atagtgggag caccaactac    180
aacccgtccc tcaagagtcg agtcaccata tcagtagaca gtccaagaa ccagttctcc     240 ctgaagctga gctctgtgac cgccgcggac acggccgtgt attactgtgc gactatggtt    300
cggggccgat actactacta cggtatggac gtctggggcc aagggaccac ggtcaccgtc    360
tcctca                                                               366
```

<210> SEQ ID NO 214
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 214

```
gatattgtga tgactcagtc tccactctcc ctgcccgtca cccctggaga gccggcctcc    60
atctcctgca ggtctagtca gagcctcctg catagtgatg gatacaactt tttggattgg    120
tacctgcaga agcctgggca gtctccacag ttcctgatct atttgggttc taatcgggcc    180
tccggggtcc ctgacaggtt cagtggcgtt ggatcaggca cagattttac actgcaaatc    240
agcagagtgg aggctgagga ttttggggtt tattactgca tgcaagctct acaagctccg    300
tggacgttcg gccaagggac caagctggag atcaaa                              336
```

<210> SEQ ID NO 215
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 215

```
caggtgcagc tggtggagtc tgggggaggc gtggtccagc ctgggaggtc cctgagactc    60
tcctgtgcag cgtctggatt caccttcagt aactatggca tgcactgggt ccgccaggct    120
ccaggcaagg ggctggagtg ggtggcagtt atatggtatg atggaggtcc taaattctat    180
gcagactccg tgaagggccg attcaccatc tccagagaca attccaagaa cacgctgtat    240
ctgcaaatga acagcctgag agccgaggac acggctgtgt attactgtgc gagatcctat    300
tgtggtggtg actgctaccc atttgactac tggggccagg gagacctggt caccgtctcc    360
```

-continued

| tca | 363 |

```
<210> SEQ ID NO 216
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 216

| gacatccaga tgacccaatc tccatcctcc ctgtctgcat ctgtaggaga cagagtcacc | 60 |
| atcacttgcc gggcgagtca gggcattagc aattatttag cctggtatca gcagaaacca | 120 |
| gggaaagttc ctaagctcct gatctatgct gcatccactt tgcaatcagg ggtcccatct | 180 |
| cggttcagtg gcagtggatc tgggacagat ttcactctca ccatcagcag cctgcagcct | 240 |
| gaagatgttg caacttatta ctgtcaaaag tattacagtg ccccgtggac gttcggccaa | 300 |
| gggaccaagg tggagatcaa a | 321 |

```
<210> SEQ ID NO 217
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 217

| gaggtgcagc tgttggagtc tgggggaggc ttggtacagc ctgggggtc cctgagactc | 60 |
| tcctgtgcag cctctggatt cacctttagc agctatgcca tgagctgggt ccgccaggct | 120 |
| ccagggaagg ggctggagtg ggtctcaact attagtggta gtggtgatag cacatactac | 180 |
| gcagactccg tgaagggccg gttcaccatc tccagagaca attccaagaa cacgctgtat | 240 |
| ctgcaaatga acagcctgag agccgaggac acggccatat attactgtgc gaagtttggg | 300 |
| gttcggggag ttattataac aaactggttc gaccccctggg gccagggaac cctggtcacc | 360 |
| gtctcctca | 369 |

```
<210> SEQ ID NO 218
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 218

| gaggtgcagc tgttggagtc tgggggaggc ttggtacagc ctgggggtc cctgagactc | 60 |
| tcctgtgcag cctctggatt cacctttagc agctatgcca tgagctgggt ccgccaggct | 120 |
| ccagggaagg ggctggagtg ggtctcaact attagtggta gtggtgatag cacatactac | 180 |
| gcagactccg tgaagggccg gttcaccatc tccagagaca attccaagaa cacgctgtat | 240 |
| ctgcaaatga acagcctgag agccgaggac acggccatat attactgtgc gaagtttggg | 300 |
| gttcggggag ttattataac aaactggttc gaccccctggg gccagggaac cctggtcacc | 360 |
| gtctcctca | 369 |

```
<210> SEQ ID NO 219
<211> LENGTH: 369
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 219

| | | | | | |
|---|---|---|---|---|---|
| gaggtgcagc | tgttggagtc | tgggggaggc | ttggtacagc | ctggggggtc | cctgagactc | 60 |
| tcctgtgcag | cctctggatt | cacctttagc | agctatgcca | tgagctgggt | ccgccaggct | 120 |
| ccagggaagg | ggctggagtg | ggtctcaact | attagtggta | gtggtgatag | cacatactac | 180 |
| gcagactccg | tgaagggccg | gttcaccatc | tccagagaca | attccaagaa | cacgctgtat | 240 |
| ctgcaaatga | acagcctgag | agccgaggac | acggccatat | attactgtgc | gaagtttggg | 300 |
| gttcggggag | ttattataac | aaactggttc | gaccccctggg | gccagggaac | cctggtcacc | 360 |
| gtctcctca | | | | | | 369 |

<210> SEQ ID NO 220
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 220

| | | | | | |
|---|---|---|---|---|---|
| gaggtgcagc | tgttggagtc | tgggggaggc | ttggtacagc | ctggggggtc | cctgagactc | 60 |
| tcctgtgcag | cctctggatt | cacctttagc | agctatgcca | tgagctgggt | ccgccaggct | 120 |
| ccagggaagg | ggctggagtg | ggtctcaact | attagtggta | gtggtgatag | cacatactac | 180 |
| gcagactccg | tgaagggccg | gttcaccatc | tccagagaca | attccaagaa | cacgctgtat | 240 |
| ctgcaaatga | acagcctgag | agccgaggac | acggccatat | attactgtgc | gaagtttggg | 300 |
| gttcggggag | ttattataac | aaactggttc | gaccccctggg | gccagggaac | cctggtcacc | 360 |
| gtctcctca | | | | | | 369 |

<210> SEQ ID NO 221
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 221

| | | | | | |
|---|---|---|---|---|---|
| gaggtgcagc | tgttggagtc | tgggggaggc | ttggtacagc | ctggggggtc | cctgagactc | 60 |
| tcctgtgcag | cctctggatt | cacctttagc | agctatgcca | tgagctgggt | ccgccaggct | 120 |
| ccagggaagg | ggctggagtg | ggtctcaact | attagtggta | gtggtgatag | cacatactac | 180 |
| gcagactccg | tgaagggccg | gttcaccatc | tccagagaca | attccaagaa | cacgctgtat | 240 |
| ctgcaaatga | acagcctgag | agccgaggac | acggccatat | attactgtgc | gaagtttggg | 300 |
| gttcggggag | ttattataac | aaactggttc | gaccccctggg | gccagggaac | cctggtcacc | 360 |
| gtctcctca | | | | | | 369 |

<210> SEQ ID NO 222
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 222

```
gaggtgcagc tgttggagtc tgggggaggc ttggtacagc ctgggggtc cctgagactc    60
tcctgtgcag cctctggatt caccttagc agctatgcca tgagctgggt ccgccaggct   120
ccagggaagg ggctggagtg ggtctcaact attagtggta gtggtgatag cacatactac   180
gcagactccg tgaagggccg gttcaccatc tccagagaca attccaagaa cacgctgtat   240
ctgcaaatga acagcctgag agccgaggac acggccatat attactgtgc gaagtttggg   300
gttcggggag ttattataac aaactggttc gaccctggg gccagggaac cctggtcacc   360
gtctcctca                                                          369
```

<210> SEQ ID NO 223
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 223

```
gaggtgcagc tgttggagtc tgggggaggc ttggtacagc ctgggggtc cctgagactc    60
tcctgtgcag cctctggatt caccttagc agctatgcca tgagctgggt ccgccaggct   120
ccagggaagg ggctggagtg ggtctcaact attagtggta gtggtgatag cacatactac   180
gcagactccg tgaagggccg gttcaccatc tccagagaca attccaagaa cacgctgtat   240
ctgcaaatga acagcctgag agccgaggac acggccatat attactgtgc gaagtttggg   300
gttcggggag ttattataac aaactggttc gaccctggg gccagggaac cctggtcacc   360
gtctcctca                                                          369
```

<210> SEQ ID NO 224
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 224

```
gaggtgcagc tgttggagtc tgggggaggc ttggtacagc ctgggggtc cctgagactc    60
tcctgtgcag cctctggatt caccttagc agctatgcca tgagctgggt ccgccaggct   120
ccagggaagg ggctggagtg ggtctcaact attagtggta gtggtgatag cacatactac   180
gcagactccg tgaagggccg gttcaccatc tccagagaca attccaagaa cacgctgtat   240
ctgcaaatga acagcctgag agccgaggac acggccatat attactgtgc gaagtttggg   300
gttcggggag ttattataac aaactggttc gaccctggg gccagggaac cctggtcacc   360
gtctcctca                                                          369
```

<210> SEQ ID NO 225
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 225

```
gaggtgcagc tgttggagtc tggggaggc ttggtacagc ctgggggtc cctgagactc      60 tcctgtgcag cctctggatt cacctttagc agctatgcca tgagctgggt ccgccaggct    120
ccagggaagg gctggagtg gtctcaact attagtggta gtggtgatag cacatactac     180
gcagactccg tgaagggccg gttcaccatc tccagagaca attccaagaa cacgctgtat   240
ctgcaaatga acagcctgag agccgaggac acggccatat attactgtgc gaagtttggg   300
gttcggggag ttattataac aaactggttc gaccctgggg gccagggaac cctggtcacc   360
gtctcctca                                                           369
```

<210> SEQ ID NO 226
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 226

```
gaggtgcagc tgttggagtc tggggaggc ttggtacagc ctgggggtc cctgagactc      60 tcctgtgcag cctctggatt cacctttagc agctatgcca tgagctgggt ccgccaggct    120
ccagggaagg gctggagtg gtctcaact attagtggta gtggtgatag cacatactac     180
gcagactccg tgaagggccg gttcaccatc tccagagaca attccaagaa cacgctgtat   240
ctgcaaatga acagcctgag agccgaggac acggccatat attactgtgc gaagtttggg   300
gttcggggag ttattataac aaactggttc gaccctgggg gccagggaac cctggtcacc   360
gtctcctca                                                           369
```

<210> SEQ ID NO 227
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 227

```
gaggtgcagc tgttggagtc tggggaggc ttggtacagc ctgggggtc cctgagactc      60 tcctgtgcag cctctggatt cacctttagc agctatgcca tgagctgggt ccgccaggct    120
ccagggaagg gctggagtg gtctcaact attagtggta gtggtgatag cacatactac     180
gcagactccg tgaagggccg gttcaccatc tccagagaca attccaagaa cacgctgtat   240
ctgcaaatga acagcctgag agccgaggac acggccatat attactgtgc gaagtttggg   300
gttcggggag ttattataac aaactggttc gaccctgggg gccagggaac cctggtcacc   360
gtctcctca                                                           369
```

<210> SEQ ID NO 228
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 228

```
gaggtgcagc tgttggagtc tggggaggc ttggtacagc ctgggggtc cctgagactc      60 tcctgtgcag cctctggatt cacctttagc agctatgcca tgagctgggt ccgccaggct    120
```

```
ccagggaagg ggctggagtg ggtctcaact attagtggta gtggtgatag cacatactac    180
gcagactccg tgaagggccg gttcaccatc tccagagaca attccaagaa cacgctgtat    240
ctgcaaatga acagcctgag agccgaggac acggccatat attactgtgc gaagtttggg    300
gttcggggag ttattataac aaactggttc gaccccgggg ccagggaac cctggtcacc    360 gtctcctca                                                            369
```

<210> SEQ ID NO 229
<211> LENGTH: 380
<212> TYPE: PRT
<213> ORGANISM: Homo sapiens

<400> SEQUENCE: 229

```
Met Gly Ala Ala Ala Glu Ala Pro Leu Arg Leu Pro Ala Ala Pro
 1               5                  10                  15

Pro Leu Ala Phe Cys Cys Tyr Thr Ser Val Leu Leu Leu Phe Ala Phe
                20                  25                  30

Ser Leu Pro Gly Ser Arg Ala Ser Asn Gln Pro Gly Gly Gly Gly
            35                  40                  45

Gly Ser Gly Gly Asp Cys Pro Gly Gly Lys Gly Lys Ser Ile Asn Cys
 50                  55                  60

Ser Glu Leu Asn Val Arg Glu Ser Asp Val Arg Val Cys Asp Glu Ser
 65                  70                  75                  80

Ser Cys Lys Tyr Gly Gly Val Cys Lys Glu Asp Gly Asp Gly Leu Lys
                 85                  90                  95

Cys Ala Cys Gln Phe Gln Cys His Thr Asn Tyr Ile Pro Val Cys Gly
                100                 105                 110

Ser Asn Gly Asp Thr Tyr Gln Asn Glu Cys Phe Leu Arg Arg Ala Ala
            115                 120                 125

Cys Lys His Gln Lys Glu Ile Thr Val Ile Ala Arg Gly Pro Cys Tyr
130                 135                 140

Ser Asp Asn Gly Ser Gly Ser Gly Glu Gly Glu Glu Gly Ser Gly
145                 150                 155                 160

Ala Glu Val His Arg Lys His Ser Lys Cys Gly Pro Cys Lys Tyr Lys
                165                 170                 175

Ala Glu Cys Asp Glu Asp Ala Glu Asn Val Gly Cys Val Cys Asn Ile
            180                 185                 190

Asp Cys Ser Gly Tyr Ser Phe Asn Pro Val Cys Ala Ser Asp Gly Ser
        195                 200                 205

Ser Tyr Asn Asn Pro Cys Phe Val Arg Glu Ala Ser Cys Ile Lys Gln
    210                 215                 220

Glu Gln Ile Asp Ile Arg His Leu Gly His Cys Thr Asp Thr Asp Asp
225                 230                 235                 240

Thr Ser Leu Leu Gly Lys Lys Asp Asp Gly Leu Gln Tyr Arg Pro Asp
                245                 250                 255

Val Lys Asp Ala Ser Asp Gln Arg Glu Asp Val Tyr Ile Gly Asn His
            260                 265                 270

Met Pro Cys Pro Glu Asn Leu Asn Gly Tyr Cys Ile His Gly Lys Cys
        275                 280                 285

Glu Phe Ile Tyr Ser Thr Gln Lys Ala Ser Cys Arg Cys Glu Ser Gly
    290                 295                 300

Tyr Thr Gly Gln His Cys Glu Lys Thr Asp Phe Ser Ile Leu Tyr Val
305                 310                 315                 320

Val Pro Ser Arg Gln Lys Leu Thr His Val Leu Ile Ala Ala Ile Ile
```

325                 330                 335
Gly Ala Val Gln Ile Ala Ile Val Ala Ile Val Met Cys Ile Thr
            340                 345                 350
Arg Lys Cys Pro Lys Asn Asn Arg Gly Arg Arg Gln Lys Gln Asn Leu
        355                 360                 365
Gly His Phe Thr Ser Asp Thr Ser Ser Arg Met Val
    370                 375                 380

<210> SEQ ID NO 230
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
atagctcttc agggaccatg aarcayctgt ggttcttcct                            40

<210> SEQ ID NO 231
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
atagctcttc agggaccatg gacatacttt gttccacgc                             39

<210> SEQ ID NO 232
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
atagctcttc agggaccatg gacacacttt gctacacac                             39

<210> SEQ ID NO 233
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
atagctcttc agggaccatg tctgtctcct tcctcatct                             39

<210> SEQ ID NO 234
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
atagctcttc agggaccatg gactggacct ggagvatc                              38

<210> SEQ ID NO 235
<211> LENGTH: 38

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
atagctcttc agggaccatg gactggattt ggaggrtc                              38

<210> SEQ ID NO 236
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
atagctcttc agggaccatg gactgcacct ggaggatc                              38

<210> SEQ ID NO 237
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
atagctcttc agggaccatg gactggacct ggaggktc                              38

<210> SEQ ID NO 238
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
atagctcttc agggaccatg gagttkggrc tgagctgg                              38

<210> SEQ ID NO 239
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
atagctcttc agggaccatg gagtttkggc tkagctgg                              38

<210> SEQ ID NO 240
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
atagctcttc agggaccatg gaactggggc tccgctgg                              38

<210> SEQ ID NO 241
<211> LENGTH: 38
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 241
atagctcttc agggaccatg garttggggc tgwgctgg                          38

<210> SEQ ID NO 242
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
atagctcttc agggaccatg gggtcaaccg ccatcctc                          38

<210> SEQ ID NO 243
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
atagctcttc agggaccatg gacatgaggg tsccygctca gctc                   44

<210> SEQ ID NO 244
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
atagctcttc agggaccatg gacatgagrg tcctcgctca gctc                   44

<210> SEQ ID NO 245
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
atagctcttc agggaccatg gaagcccag cdcagcttct c                       41

<210> SEQ ID NO 246
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
atagctcttc agggaccatg gaaaccccag cgcagcttct c                      41

<210> SEQ ID NO 247
<211> LENGTH: 41
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 247
atagctcttc agggaccatg gtgttgcaga cccaggtctt c        41

<210> SEQ ID NO 248
<211> LENGTH: 41
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 248
atagctcttc agggaccatg gggtcccagg ttcacctcct c        41

<210> SEQ ID NO 249
<211> LENGTH: 41
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 249
atagctcttc agggaccatg aggctccytg ctcagctcct g        41

<210> SEQ ID NO 250
<211> LENGTH: 33
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 250
atagctcttc ttcgtttgat ctccascttg gtc        33

<210> SEQ ID NO 251
<211> LENGTH: 33
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 251
atagctcttc ttcgtttaat ctccagtcgt gtc        33

<210> SEQ ID NO 252
<211> LENGTH: 30
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 252
atagctcttc tggctgagga gacggtgacc        30

<210> SEQ ID NO 253
<211> LENGTH: 34
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 253
atagctcttc atgtgacgct gttgtgactc agga                                34

<210> SEQ ID NO 254
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
atagctcttc atgtgaccyt gtgctcactc agtc                                34

<210> SEQ ID NO 255
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
gatgctcttc tgggctggcc taggacagtc amcytgg                             37
```